United States Patent
Mandell et al.

(10) Patent No.: US 12,295,937 B2
(45) Date of Patent: *May 13, 2025

(54) PSYCHOACTIVE MEDICINES AND THEIR USE FOR TREATING PSYCHIATRIC AND NEUROLOGICAL CONDITIONS AND DISORDERS

(71) Applicant: Transcend Therapeutics, Inc., New York, NY (US)

(72) Inventors: Blake Mandell, Brooklyn, NY (US); Martin Stogniew, Lakewood Ranch, FL (US); Jennifer Louise Schmidt, Garden City, NY (US); Markus Seelig, Kelseyville, CA (US)

(73) Assignee: TRANSCEND THERAPEUTICS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/790,708

(22) Filed: Jul. 31, 2024

(65) Prior Publication Data

US 2024/0390322 A1 Nov. 28, 2024

Related U.S. Application Data

(63) Continuation of application No. PCT/US2024/032615, filed on Jun. 5, 2024, and a continuation-in-part of application No. 18/215,547, filed on Jun. 28, 2023, now Pat. No. 12,059,402, and a continuation-in-part of application No. PCT/US2023/012196, filed on Feb. 2, 2023, said application No. 18/215,547 is a continuation of application No. 17/887,962, filed on Aug. 15, 2022, now Pat. No. 11,707,446, said application No. PCT/US2023/012196 is a continuation-in-part of application No. PCT/US2022/074369, filed on Aug. 1, 2022, said application No. 17/887,962 is a continuation of application No. PCT/US2022/074369, filed on Aug. 1, 2022.

(60) Provisional application No. 63/649,653, filed on May 20, 2024, provisional application No. 63/553,788, filed on Feb. 15, 2024, provisional application No. 63/607,702, filed on Dec. 8, 2023, provisional application No. 63/605,729, filed on Dec. 4, 2023, provisional application No. 63/602,904, filed on Nov. 27, 2023, provisional application No. 63/471,412, filed on Jun. 6, 2023, provisional application No. 63/437,000, filed on Jan. 4, 2023, provisional application No. 63/328,343, filed on Apr. 7, 2022, provisional application No. 63/325,757, filed on Mar. 31, 2022, provisional application No. 63/255,706, filed on Oct. 14, 2021, provisional application No. 63/240,113, filed on Sep. 2, 2021, provisional application No. 63/230,237, filed on Aug. 6, 2021.

(51) Int. Cl.
A61K 31/36 (2006.01)
A61K 45/06 (2006.01)
A61P 25/22 (2006.01)
A61P 25/24 (2006.01)

(52) U.S. Cl.
CPC .............. *A61K 31/36* (2013.01); *A61K 45/06* (2013.01); *A61P 25/22* (2018.01); *A61P 25/24* (2018.01)

(58) Field of Classification Search
CPC ........... A61K 45/06; A61P 25/22; A61P 25/24
USPC ....................................................... 514/466
See application file for complete search history.

(56) References Cited

U.S. PATENT DOCUMENTS

| | | |
|---|---|---|
| 11,707,446 B2 | 7/2023 | Mandell et al. |
| 2012/0108510 A1 | 5/2012 | Young et al. |
| 2014/0045884 A1 | 2/2014 | Schultz |
| 2014/0142140 A1 | 5/2014 | Bird |
| 2015/0306136 A1 | 10/2015 | Meloni et al. |
| 2019/0046499 A1 | 2/2019 | Segreti |
| 2023/0054211 A1 | 2/2023 | Mandell et al. |
| 2023/0218570 A1 | 7/2023 | Dariani |
| 2024/0124101 A1 | 4/2024 | MacRae et al. |
| 2024/0285576 A1 | 8/2024 | Smagin |

FOREIGN PATENT DOCUMENTS

| | | |
|---|---|---|
| WO | WO 1996/039133 | 12/1996 |
| WO | WO 2021/257500 | 12/2021 |
| WO | WO 2022/212854 | 10/2022 |
| WO | WO 2023/081403 | 5/2023 |

OTHER PUBLICATIONS

Cuijpers et al World psychiatry, 2020, 19(1), 92-107 (Year: 2020).*
International Search Report and Written Opinion, dated Oct. 29, 2024, from corresponding International Application No. PCT/US24/32615.
Li et al., "Methylone produces antidepressant-relevant actions and prosocial effects", Neuropharmacology, Jan. 2024, 242:109787.
Callaway et al., "Serotonin Release Contributes to the Locomotor Stimulant Effects of 3,4-Methylenedioxymethamphetamine in Rats", The Journal of Pharmacology and Experimental Therapeutics, Apr. 1990; 254(2):456-464.
Nagakura et al., "Biogenic amine depletion causes chronic muscular pain and tactile allodynia accompanied by depression: A putative animal model of fibromyalgia", Pain, 2009, 146:26-33.

(Continued)

*Primary Examiner* — Yevgeny Valenrod
(74) *Attorney, Agent, or Firm* — PEARL COHEN ZEDEK LATZER BARATZ LLP

(57) ABSTRACT

The invention relates to psychoactive medicines including methylone, 2C-B, MBDB, their respective salts, metabolites, isomers, enantiomers, solvates, isotopologues and isotopomers, polymorphs, prodrugs and analogs (2C-series and cathinones); their preparation, formulations, intermediates, routes of administration, dosing and schedule for medical uses for psychiatric and neurological conditions and disorders.

30 Claims, 41 Drawing Sheets

(56) References Cited

OTHER PUBLICATIONS

Jefferson et al., "5-MeO-DMT modifies innate behaviors and promotes structural neural plasticity in mice", Neuropsychopharmacology, Apr. 2023; 48:1257-1266.
Sande, M., "Characteristics of the use of 3-MMC and other new psychoactive drugs in Slovenia, and the perceived problems experienced by users", International Journal of Drug Policy, (2016) 27:65-73.
Reisman, "PTSD Treatment for Veterans: What's Working, What's New, and What's Next", P&T, Oct. 2016, 41(10):623-634.
Den Hollander et al., "Long-term cognitive and neurochemical effects of "bath salt" designer drugs methylone and mephedrone", Pharmacology, Biochemistry and Behavior (2013) 103:501-509.
Lopez-Arnau et al., "Repeated doses of methylone, a new drug of abuse, induce changes in serotonin and dopamine systems in the mouse", Psychopharmacology (2014) 231:3119-3129.
Karila et al., "The effects and risks associated to mephedrone and methylone in humans: A review of the preliminary evidences", Brain Research Bulletin (2016) 126:61-67.
Ciechomska et al., "Activity and Biotransformation of Three Synthetic "Legal Highs", Mephedrone, Methylone and 3,4-Methylenodioxypyrovalerone", Problems of Forensic Sciences (2012) 89:71-85.
Shao et al., "Psilocybin induces rapid and persistent growth of the dendritic spines in frontal cortex in vivo", Neuron, Aug. 18, 2021; 109:2535-2544.
Porsolt et al., "Depression: a new animal model sensitive to antidepressant treatments", Nature (1977) 266:730-732.
Borsini et al., "Is the forced swimming test a suitable model for revealing antidepressant activity?", Psychopharmacology (1988) 94:147-160.
Detke et al., "Active behaviors in the rat forced swimming test differentially produced by serotonergic and noradrenergic antidepressants", Psychopharmacology (1995) 121:66-72.
Hibicke et al., "Psychedelics, but Not Ketamine, Produce Persistent Antidepressant-like Effects in a Rodent Experimental System for the Study of Depression", ACS Chem. Neurosci., Mar. 2020, 11:864-871.
Yang et al., "Acute administration of ketamine in rats increases hippocampal BDNF and mTOR levels during forced swimming test", Upsala Journal of Medical Sciences, 2013, 118(1): 3-8.
Tizabi et al., "Antidepressant-Like Effects of Low Ketamine Dose is Associated with Increased Hippocampal AMPA/NMDA Receptor Density Ratio in Female Wistar-Kyoto Rats", Neuroscience (2012) 213:72-80.
Weston et al., "Repeated Dosing of Ketamine in the Forced Swim Test: Are Multiple Shots Better Than One?", Frontiers in Psychiatry, May 2021, 12:659052.
Majumder et al., "Antidepressant-like effects of 3,4-methylenedioxymethamphetamine in an animal model of depression", Behavioural Pharmacology (2011) 22:758-765.
Feduccia et al., "Discontinuation of medications classified as reuptake inhibitors affects treatment response of MDMA-assisted psychotherapy", Psychopharmacology, Nov. 2020, 238:581-588.
Wicking et al., "Deficient fear extinction memory in posttraumatic stress disorder", Neurobiology of Learning and Memory (2016) 136:116.
Pedraza et al., "Chronic fluoxetine prevents fear memory generalization and enhances subsequent extinction by remodeling hippocampal dendritic spines and slowing down system consolidation", Translational Psychiatry (2019) 9:53.
Feduccia et al., "MDMA-assisted psychotherapy for PTSD: Are memory reconsolidation and fear extinction underlying mechanisms?", Progress in Neuropsychopharmacology & Biological Psychiatry (2018) 84:221-228.
Young et al., "3,4-Methylenedioxymethamphetamine facilitates fear extinction learning", Translational Psychiatry (2015) 5:e634.

International Search Report and Written Opinion, dated Dec. 13, 2022, from corresponding International Application No. PCT/US22/74369.
Udangiu et al. "Clinical and Therapeutic Management of Acute Stress Disorder", Management in Health, XIV(2): 20-21 (2010).
Ansara et al., "Management of treatment-resistant generalized anxiety disorder", Mental Health Clinician, 2020; 10(6):326-334.
Bandelow et al., "Treatment of anxiety disorders", Dialogues in Clinical Neuroscience, 2017; 19(2):93-106.
Stefkova et al., "Pharmacokinetic, Ambulatory, and Hyperthermic Effects of 3,4-Methylenedioxy-N-Methylcathinone (Methylone) in Rats", Frontiers in Psychology, Nov. 2017; 8: 232.
Molendijk et al., "Coping with the forced swim stressor: Current state-of-the-art", Behavioural Brain Research (2019) 364:1-10.
Anyan et al., "Too Depressed to Swim or Too Afraid o Stop? A Reinterpretation of the Forced Swim Test as a Measure of Anxiety-Like Behavior", Neuropsychopharmacology (2018) 43:931-933.
International Search Report and Written Opinion, dated Jul. 10, 2023, from corresponding International Application No. PCT/US23/12196.
Gavezzotti, "Are Crystal Structures Predictable?", Acc. Chem. Res., 27(10):309-314 (1994).
Berquist et al., "In vivo effects of 3,4-methylenedioxymethamphetamine (MDMA) and its deuterated form in rodents: Drug discrimination and thermoregulation", Drug and Alcohol Dependence, Jan. 2020, 208:107850, 1-8.
Shao et al., "Psilocybin induces rapid and persistent growth of dendritic spines in frontal cortex in vivo", Neuron, Aug. 18, 2021; 109:2535-2544.
Slattery et al., "Using the rat forced swim test to assess antidepressant-like activity in rodents", Nature Protocols, May 2012; 7(6):1009-1014.
Islas et al., "Induced fit, ensemble binding space docking and Monte Carlo simulations of MDMA 'ecstasy' and 3D pharmacophore deign of MDMA derivatives on the human serotonin transporter (hSERT)", Heliyon 7 (2021) e07784.
Islas et al., "Allosteric Binding of MDMA to the Human Serotonin Transporter (hSERT) via Ensemble Binding Space Analysis with ΔG Calculations, Induced Fit Docking and Monte Carlo Simulations", Molecules, May 2022, 27:2977.
Baumann et al., "The Designer Methcathinone Analogs, Mephedrone and Methylone, are Substrates for Monoamine Transporters in Brain Tissue", Neuropsychopharmacology (2012) 37:1192-1203.
Warner-Schmidt et al., "Methylone, a rapid acting entactogen with robust anxiolytic and antidepressant-like activity", Frontiers in Psychology, Jan. 2023, 13:1041277.
Cavero et al., "Safety Pharmacology assessment of drugs with biased 5-HT2B receptor agonism mediating cardiac valvulopathy", Journal of Pharmacological and Toxicological Methods (2014) 69:150-161.
Setola et al., "3,4-Methylenedioxymethamphetamine (MDMA, "Ecstasy") Induces Fenfluramine-Like Proliferative Actions on Human Cardia Valvular Interstitial Cells in Vitro", Molecular Pharmacology (2003) 63(6):1223-1229.
Abboud et al., "Animal models of pain: diversity and benefits", Journal of Neuroscience Methods (2021) 348:108997.
Chaplan et al., "Quantitative assessment of tactile allodynia in the rat paw", Journal of Neuroscience Methods (1994) 53:55-63.
Poyatos et al., "Methylone and MDMA Pharmacokinetics Following Controlled Administration in Humans", International Journal of Molecular Sciences (2022) 23:14636.
De La Fuente Revenga et al., "Chronic clozapine treatment restrains via HDAC2 the performance of mGlu2 receptor agonism in a rodent model of antipsychotic activity", Neuropsychopharmacology (2019) 44:443-454.
Savalia et al., "A Dendrite-Focused Framework for Understanding the Actions of Ketamine and Psychedelics", Trends in Neurosciences, Apr. 2021; 44(4):260-275.
Poyatos et al., "A Comparison of Acute Pharmacological Effects of Methylone and MDMA Administration in Humans and Oral Fluid

(56) References Cited

OTHER PUBLICATIONS

Concentrations as Biomarkers of Exposure", Biology, Aug. 17, 2021; 10:788.

* cited by examiner

*Figure 2*
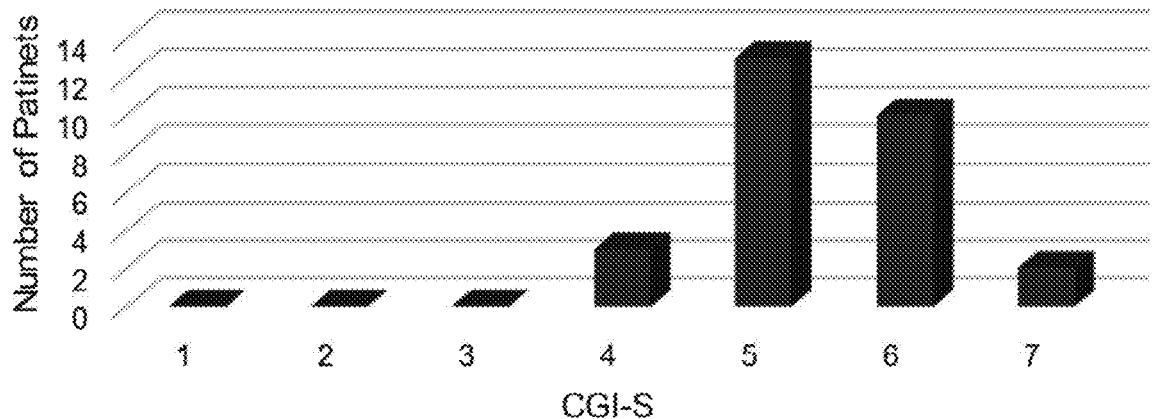
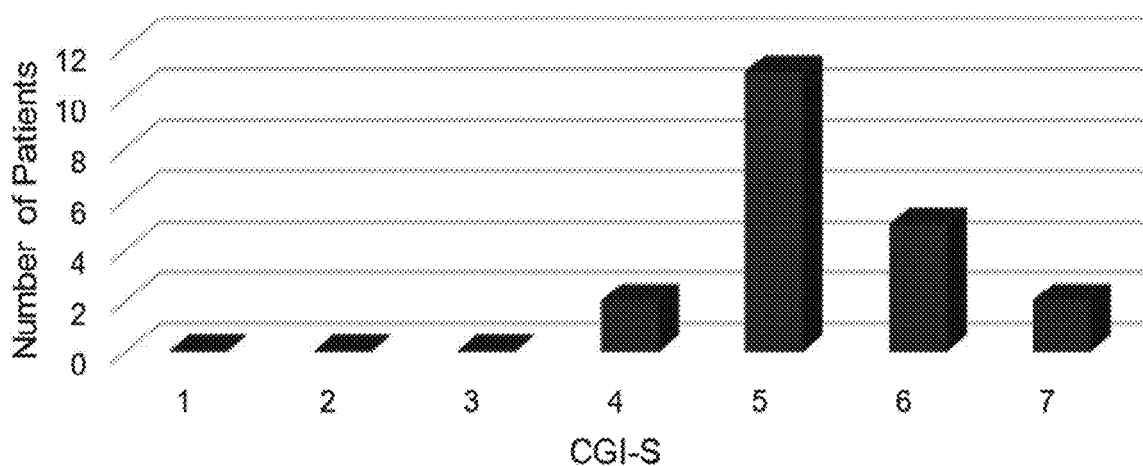
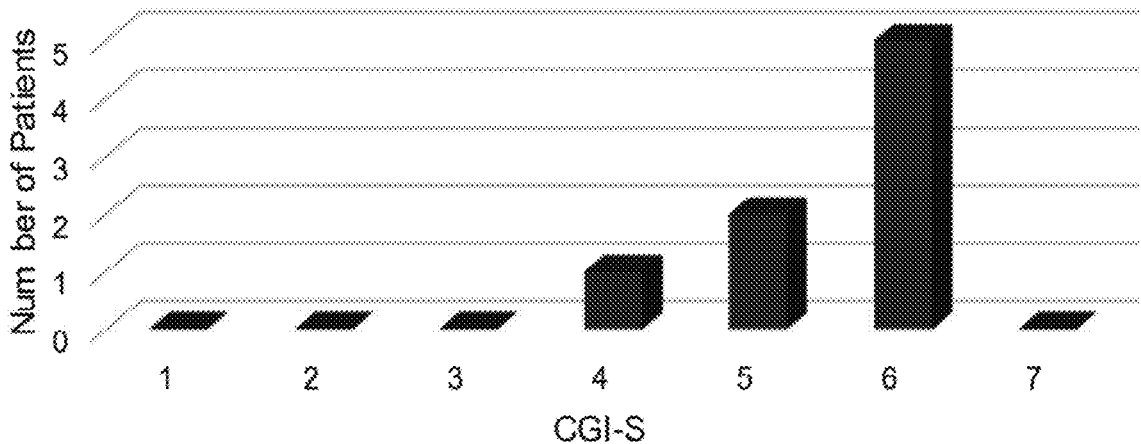

Figure 14
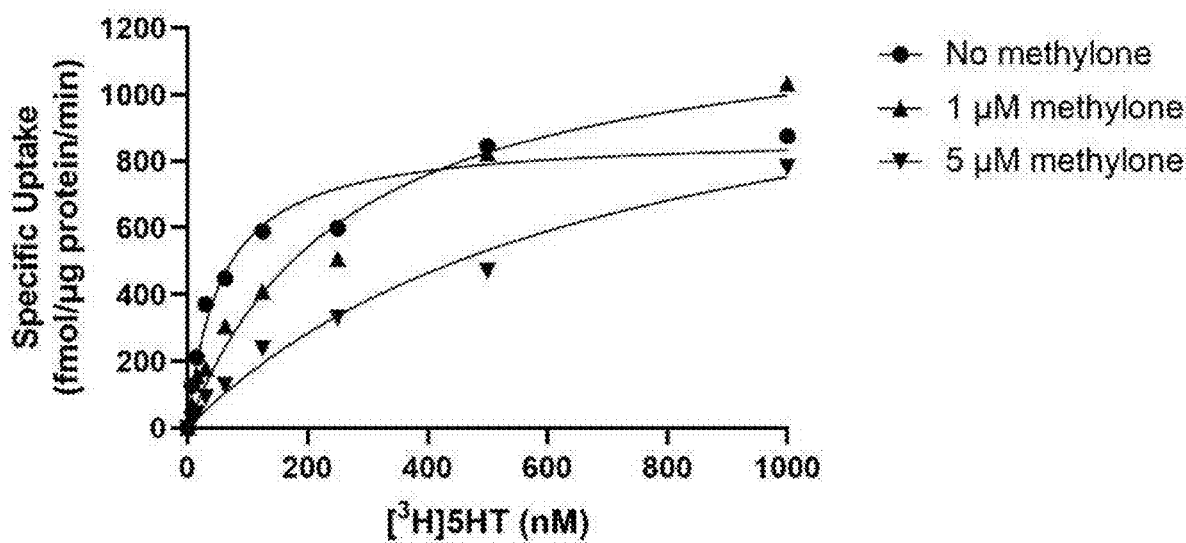
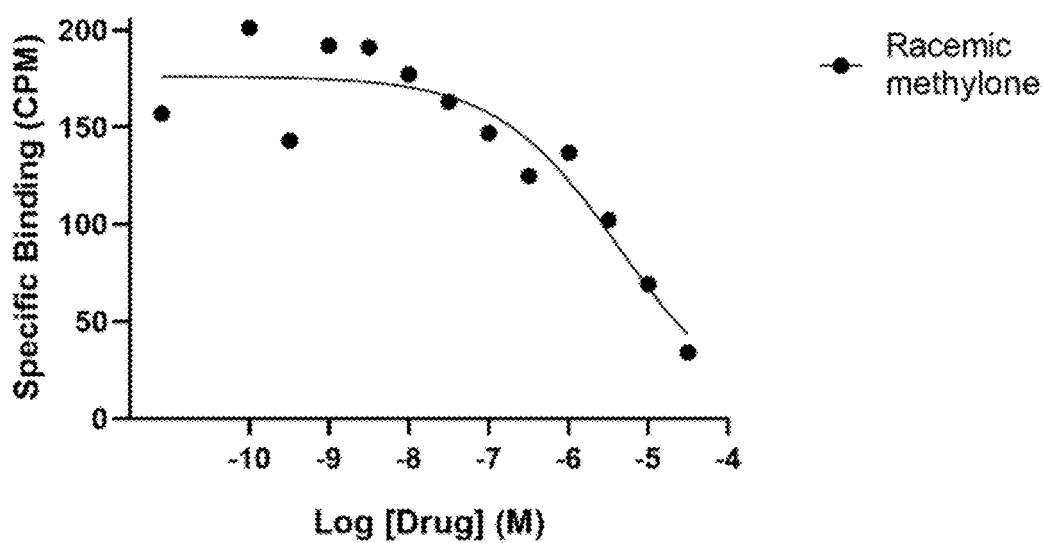
Figure 15

* p < 0.05;  p<0.001; * p<0.0001

* p < 0.05;  p<0.001; * p<0.0001

Figure 30
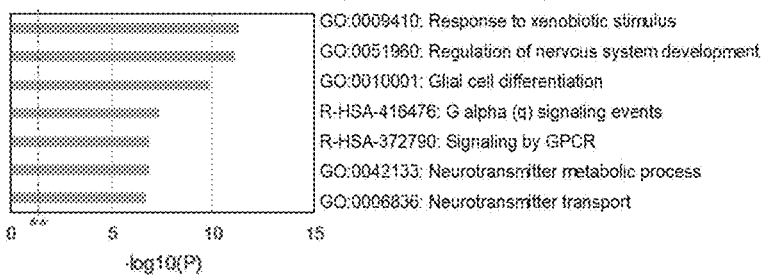
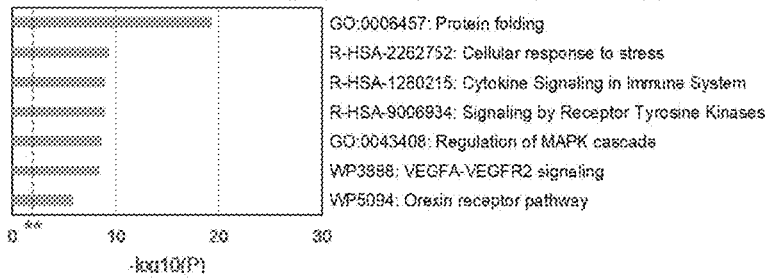
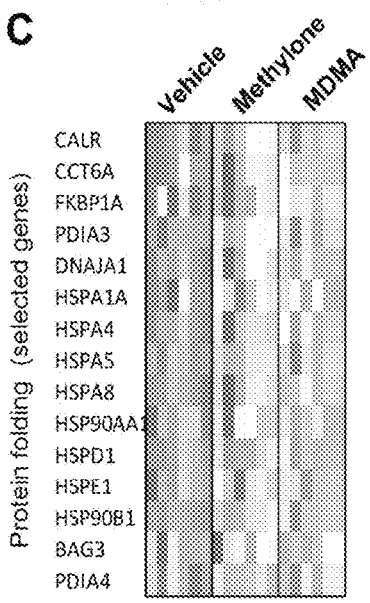
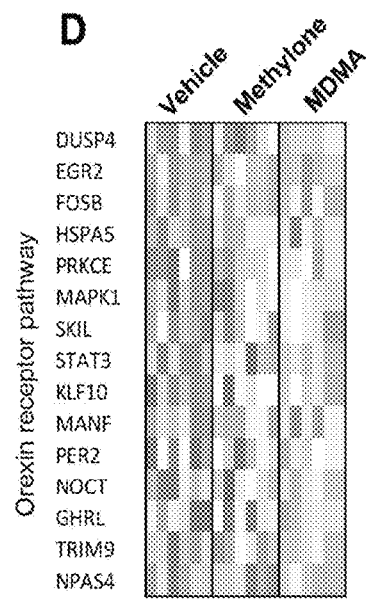
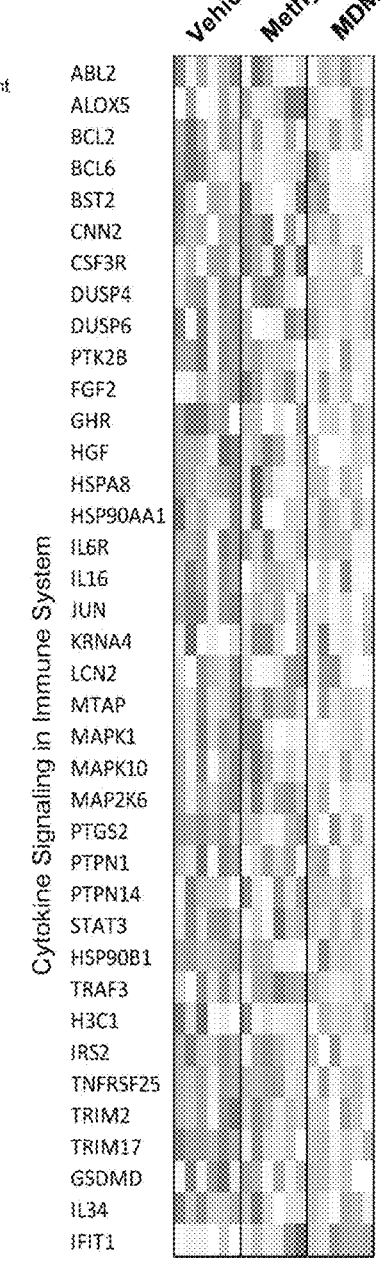

Figure 31
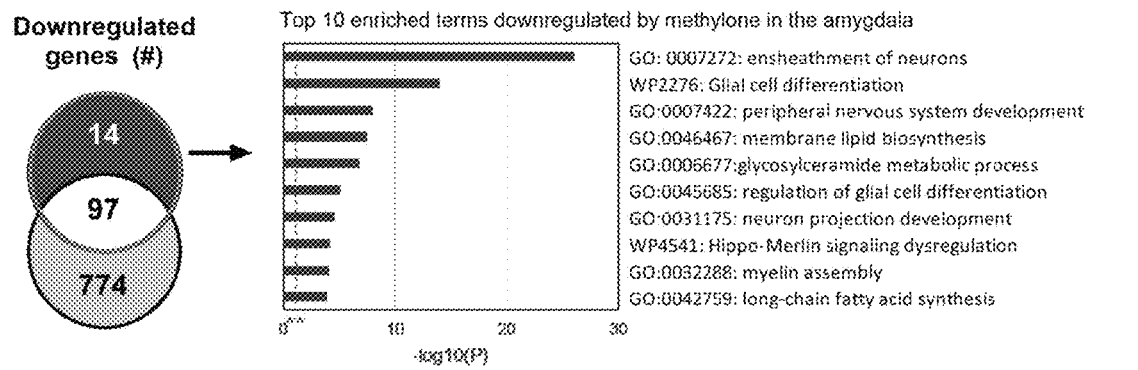
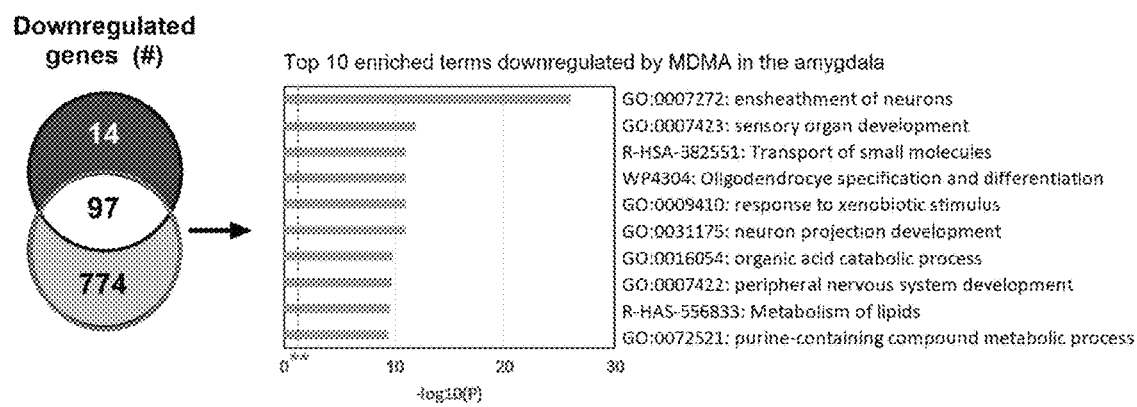
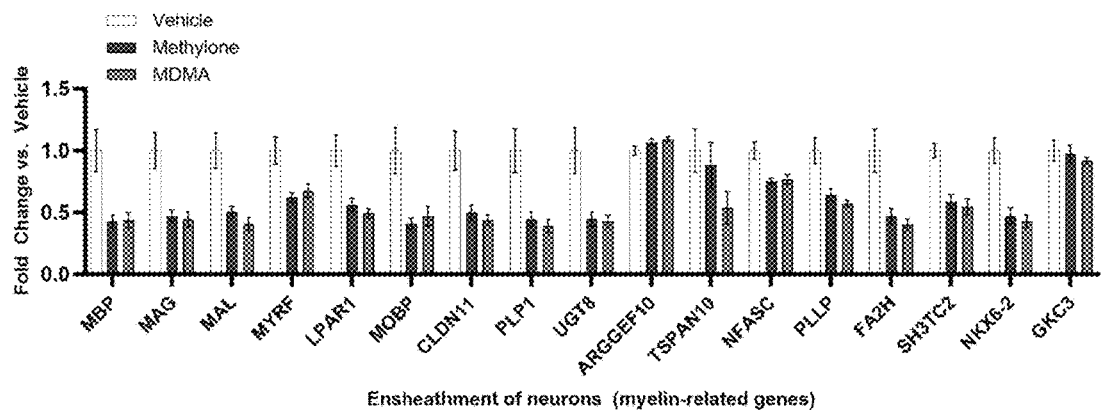

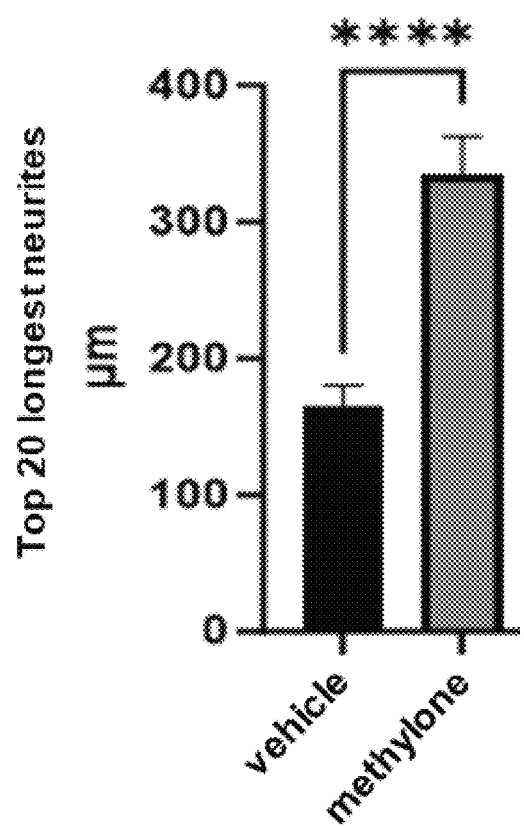

PSYCHOACTIVE MEDICINES AND THEIR USE FOR TREATING PSYCHIATRIC AND NEUROLOGICAL CONDITIONS AND DISORDERS

CROSS-REFERENCE TO RELATED APPLICATIONS

This application is a continuation of International Application No. PCT/US24/32615, filed Jun. 5, 2024, which claims the benefit of U.S. Provisional Application Nos. 63/471,412, filed Jun. 6, 2023; 63/602,904, filed Nov. 27, 2023; 63/605,729, filed Dec. 4, 2023; 63/607,702, filed Dec. 8, 2023; 63/553,788, filed Feb. 15, 2024; and 63/649,653, filed May 20, 2024. This application is also a continuation-in-part of International Application No. PCT/US23/12196, filed Feb. 2, 2023, which is a continuation-in-part of International Application No. PCT/US22/74369, filed Aug. 1, 2022, and International Application No. PCT/US23/12196 also claims benefit of U.S. Provisional Application Nos. 63/325,757, filed Mar. 31, 2022; 63/328,343, filed Apr. 7, 2022; and 63/437,000, filed Jan. 4, 2023. This application is also a continuation-in-part of U.S. patent application Ser. No. 18/215,547, filed Jun. 28, 2023, which is a continuation of U.S. patent application Ser. No. 17/887,962, filed Aug. 15, 2022 (now U.S. Pat. No. 11,707,446), which is a continuation of International Patent Application No. PCT/US22/74369, filed Aug. 1, 2022, which claims the benefit of U.S. Provisional Application Nos. 63/230,237, filed Aug. 6, 2021; 63/240,113, filed Sep. 2, 2021; 63/255,706, filed Oct. 14, 2021; 63/325,757, filed Mar. 31, 2022; and 63/328,343, filed Apr. 7, 2022; which are hereby incorporated by reference.

FIELD OF THE INVENTION

The invention relates to psychoactive medicines including methylone, 2C-B, MBDB, their respective salts, metabolites, isomers, enantiomers, solvates, isotopologues and isotopomers, polymorphs, prodrugs and analogs (2C-series and cathinones); their preparation, formulations, intermediates, routes of administration, dosing and schedule for medical uses, and for psychiatric and neurological conditions and disorders.

BACKGROUND OF THE INVENTION

Classical psychedelics are a class of mixed serotonergic-, noradrenergic-, and dopaminergic-modulating compounds, generally of ethnobotanical provenance. These heterogenous agents are psychoactive and can alter perception, mood, and numerous other cognitive and physiological processes. Anthropological study suggests their ritual use in societies ranging from the Ancient Near East, the Mediterranean Basin, and Mesoamerica. After the discovery and synthesis of the tryptamine analog lysergic acid-N,N-diethylamide (LSD) by Albert Hofmann in 1943, there followed decades of promising clinical development and therapeutic exploration. However, the entire class of compounds was restricted from mainstream scientific circles, e.g., in the United States by the "Controlled Substances Act" in 1970 and characterized as having "no medical use."

The incidence of neuropsychiatric disorders such as treatment-resistant depression, fibromyalgia, and post-traumatic stress disorder (PTSD) is growing, and there have been a dearth of new treatments that meaningfully impact patients' lives. The dissociative anesthetic ketamine, namely its enantiomer esketamine, was first approved in 2019 as Spravato for major depressive disorder (MDD) and/or suicidality. As of May 2021, there are three FDA Breakthrough Therapy designations for psychedelic medicines: 3,4-Methylenedioxymethamphetamine (MDMA) for PTSD and psilocybin for both treatment-resistant depression (TRD) and MDD. There is increasing recognition of the limited effectiveness of current pharmacological interventions, coupled with the need for new psychoactive medicines without provider-intensive safety and monitoring issues, or contraindicated in patients on existing medications such as selective-serotonin reuptake inhibitors (SSRIs) and other drug classes.

A Phase 3 trial investigating MDMA (3,4-methylenedioxy-N-methylamphetamine) in patients with severe PTSD revealed an acceptable efficacy and safety profile. There has been recent evidence for the efficacy of psilocybin in major depressive disorder (MDD). Psilocybin is a psychoactive alkaloid produced by over 200 mushroom species, with some evidence of fast-acting antidepressant properties. In recent clinical trials with psilocybin, MDD patients varied in treatment needs from a single dose to monthly doses but with similar efficacy and safety. While psilocybin and MDMA offer hope to patients without other treatment options, it is estimated that they may only benefit 5-10% of patients in need.

The identification of manipulations that reopen critical periods has been a priority for translational neuroscience. Many neuropsychiatric disease states are believed to be related developmentally to the closure of "critical periods," early intervals of the lifespan when the nervous system is more sensitive, to healthy (or harmful) environmental stimuli required for proper circuit organization and learning. The closure of critical periods limits the brains' ability to adapt even when optimal conditions are restored. The family of 5-hydroxytryptamine (5-HT) serotonin receptors agonists, including MDMA, DMT, and mescaline, increase oxytocin levels—which is involved in social function and which animal models suggest may open a critical window in cortical functioning-allowing learning of new behavioral responses. Oxytocin receptors in the nucleus accumbens (NAc) are activated via $5\text{-HT}_{1B}$ receptors in medium spiny neurons of the dorsal raphe nuclei, blockade of which prevents social reward learning.

Mescaline (3,4,5-trimethoxyphenethylamine), an ancient-precursor of modern synthetic phenethylamine 2-CB (2,5-dimethoxy-4-bromophenethylamine), is derived from the crown-buttons of the peyote cactus native to Mexico and southwestern Texas. Mescaline closely resembles the catecholamine-signaling molecules dopamine and noradrenaline after one methylation step; its psychoactive properties may stem from this structural similarity. Most novel psychoactive compounds still fit within familiar neuro-chemotype classes and have overlapping pharmacology with their classic predecessors. A long-standing hypothesis is that these agents, especially phenylalkylamines, are most selective for two receptors: $5\text{-HT}_{2A}$ and $5\text{-HT}_{2C}$, out of more than 50 neurotransmitter receptor subclasses.

MBDB (N-methyl-1-(1,3-benzodioxol-5-yl)-2-aminobutane) is the α-ethyl homolog of MDMA, which multiple medicinal chemistry groups synthesized in the 1980s. MBDB is a prototypical member of the "entactogen" class, currently not Schedule I in the United States, which combines two structural features that attenuate binding at monoamine receptors: N-methylation and α-ethylation. MBDB quickly became a recreational drug incorporated as a component of "Ecstasy" pills, along with MDMA and other synthetic cathinones. In two retrospective reports of poly-drug overdose deaths associated with MBDB (where alcohol and *cannabis* levels were also measured), blood concentration of 0.435 and 1.2 mg/L were measured. In a meta-analysis of MDMA overdose deaths, 13 of 77 deaths directly attributable to the toxic effects of MDMA alone measured blood concentrations in a range of 0.478-53.9 mg/L—which are comparable to the presumed toxic MBDB levels. Furthermore, in an animal model (±)-MBDB·HCl (25 mg/kg) was injected IP every 12 hours for 4 days, with (±)-MDMA·HCl (20 mg/kg) for comparison. Based on loss of 5-HT/5-HIAA uptake sites, the multiple dose regimen employed in this study apparently destroyed 55-60% of the serotonergic terminals in the cortex and hippocampus, without significantly altering the catecholamines or their metabolites at 2 weeks post-treatment. These results show that after multiple MBDB dosing, a decrease in indices associated with serotonergic function occurred. This neurotoxic effect was somewhat less than that seen with behaviorally equipotent MDMA doses.

Synthetic cathinones, such as methylone (3,4-methylenedioxy-N-methylcathinone), are psychomotor stimulants that exert their effects by altering the function of plasma membrane transporters for serotonin, dopamine, and norepinephrine. Individual cathinones may vary in their potencies on each of the three monoamine neurotransmitter pathways. Naturally occurring cathinone, an alkaloid structurally similar to amphetamine, was originally extracted from the fresh leaves of the *Catha edulis* or khat plant, chewed in east Africa and the Arabian Peninsula. Synthetic structural modifications of cathinone have led to a number of "designer" derivatives that are commonly sold as "bath salts" through illicit distribution. These cathinone derivatives—classified chemically as β-ketoamphetamines—include methylone, ethylone, butylone, mephedrone, and 3,4-methylenedioxypyrovalerone (MDPV), and act synergistically at the human dopamine transporter. Cathinones and the other related classes of phenethylamines both behave as Central Nervous System (CNS) stimulants; however, cathinones usually have a lower potency than the corresponding phenethylamine analog, since the β-keto group creates a more polar molecule that is less able to cross the blood-brain barrier.

Methylone's affinity for the vesicular monoamine transporter 2 (VMAT2) is about 13× lower than that of MDMA. However, there is some mixed evidence: assays for plasmalemmal and vesicular monoamine transporters in a mouse model of locomotor activity found methylone to be a more potent 5-HT and dopamine uptake inhibitor than MDMA. After intraperitoneal administration in rats, methylone peaks in brain and serum concentration in 15-30 minutes, with a half-life of about 1-2 hours. By contrast, MDMA's half-life ranges from 5-7 hours depending on the animal model used and dosing conditions.

In humans, SSRIs also diminish or prevent the therapeutic effects of MDMA due to substrate competition: side-effects such as increased blood pressure (BP) and hyperthermia are partially due to an interaction of MDMA with the serotonin carrier. This is another important consideration when thinking about use as a rapid-onset antidepressant or augmentation therapy. Previous research studies have found an association between MDMA use and symptoms of depression or anxiety. The difficulty of assessing the causation or connection between MDMA and depression is increased given that pre-existing psychiatric problems occur in people who choose to use MDMA. A meta-analysis detected an association between MDMA use and self-reported depression symptoms. The range of pharmacogenetic variation in MDMA metabolism also increases risk for depression in a sizable number of patients.

Animal studies addressing the psychological impacts of MDMA tested a 10 mg/kg dose for 10 days in rats; measures of anxiety-like behaviors, such as open-field ambulation, indicated an increase in anxious phenotypes 3 months later. A 5 mg/kg MDMA dose given to rats 4 times in 4 hours, on 2 consecutive days, diminished responses (active and passive) on the forced swim test and increased immobility up to 12 weeks post-MDMA exposure-indicating possibly long-term negative behavioral changes. Fluoxetine treatment reversed MDMA-induced anxiety in the emergence test and immobility duration in the forced swim test yet exhibited no effects on the social interaction test. This study also analyzed post-mortem levels of 5-HT and its metabolite, 5-hydroxyindoleacetic acid (5-HIAA), with both being decreased in cortical areas of MDMA-treated rats. Fluoxetine treatment did not greatly affect 5-HT levels in MDMA pretreated rats, but significantly decreased 5-HIAA levels in all brain sites examined. This can be interpreted as MDMA-induced chronic depletion of 5-HT, leading to anxious or depressed phenotypes.

Other mechanisms include acute MDMA-induced 5-HT release from serotonergic terminals, in conjunction with inhibition of 5-HT reuptake, which results in marked depletions of both 5-HT and 5-HIAA. This has been reported in postmortem human brain tissue, as well as in vivo from cerebrospinal fluid (CSF) measurements. Following the monoamine theory of depression this data is discouraging, although studies are somewhat confounded: the evidence highlights a discrepancy between acute and chronic MDMA pharmacology. While acutely, MDMA works to increase 5-HT availability, suggestive of rapid-onset antidepressant properties and positive changes to emotion, this transient effect may be accompanied by later depletions of 5-HT. There is anecdotal human experience to support depleted 5-HT stores at doses that would be used therapeutically.

Reduced levels of 5-HT and its metabolites in brain tissue and CSF have also been interpreted to indicate that MDMA is neurotoxic, assessed in vivo. Incidentally, a low serotonin transporter (SERT) density is also associated with depression. Considering reduced SERT density in animal literature, the parsimonious interpretation is that repeated exposure to MDMA in humans, even in moderate amounts, leads to damage in 5-HT neuron terminals innervating the cortex. Furthermore, alterations in mood, cognition, and impulse control associated with these changes might contribute to sustain MDMA use.

These and other discrepancies in MDMA's neurotoxicity data remain unresolved, making it unlikely that MDMA will be explored as a mainstream antidepressant; especially when 5-HT neurotransmitter circuits are implicated in both depression pathophysiology and MDMA neurotoxicity. In recent PTSD Phase 2 MDMA trials, there were cases of depression/MDD logged as adverse events at doses of 125 mg and 150 mg, some of which continued during long-term follow up. Anxiety and severe suicidal ideation were also logged. And before it progressed to Phase 3, the hypothesis that MDMA had potential efficacy as a rapid-onset antidepressant had been explored. However, MDMA, psilocybin and the other classic psychedelics mentioned have at least the following limitations in reaching the hundreds of millions of people suffering from treatment-resistant neuropsychiatric illness:

1) Safety: Given their strong serotonin agonism, they are contraindicated in patients on SSRIs and many other psychiatric medications, due to a risk of serotonin syndrome. This would prevent many, if not most, patients suffering from neuropsychiatric illness from accessing these agents. Furthermore, MDMA causes multiple forms of arrhythmia and dilated cardiomyopathy with prolonged use, potentially resulting in ventricular fibrillation and asystole, and is contraindicated in preexisting dysrhythmias or pulmonary disease.

2) Combination: Patients whose disorders are treatment-resistant have often tried SSRIs/serotonin-norepinephrine reuptake inhibitors (SNRIs)/tricyclic antidepressants (TCAs)/etc. Weaning patients off SSRIs and other antidepressant medications takes a minimum of 6 weeks. Therefore, developing psychoactive analogs which minimize adverse interactions—and are additive in therapeutic effects-would be a compelling benefit for patients in need. It would be unfortunate if those who benefit most from psychoactive medications are hindered by their past or current treatment-regimens.

3) Care delivery/Ease of Use: Psychoactive treatment is ideally administered by oneself at home or with minimal supervision. Access to MDMA and psilocybin is limited by the amount of time each administration requires, the hours of provider and safety-sitter time, and the training and licensure requirements. In addition to preparation and integration psychotherapy sessions, MDMA and psilocybin have long dosing sessions (up to 8 hours). Likewise, ketamine by IV infusion requires 3-4 hour clinic visits with physician-administration and supervision, accompanied with intensive psychotherapy.

4) Patient desirability: Many patients are unwilling to undergo treatments with classical psychedelics and entactogens like psilocybin and MDMA. For these treatments, clinical outcomes may rely on profound subjective experiences that are often challenging, discomforting, or scary.

Thus, there is a need for CNS medications, including antidepressants and PTSD treatments, with mainstream potential, better safety and efficacy, faster acting effect profile, fewer drug-drug interactions, and/or more effective in combination therapy. The prevalence of Any Mental Illness (AMI) among US adults is greater than 50 million, representing>20% of the population. The gap between the disease burden and effective treatments is widening. Despite its adverse effects, Wellbutrin (bupropion), an atypical triple-reuptake inhibitor (norepinephrine-dopamine reuptake inhibitor, nicotinic receptor antagonist), remains one of the most widely prescribed antidepressants (24 million prescriptions in 2018). Bupropion is often used in adjunct to SSRIs, and it has also been shown to have positive results in treating anxiety associated with depression compared with sertraline and fluoxetine. Bupropion is reported to be used off label in addition to other medications to treat panic disorder. However, bupropion side effects include>23% increase in chance of congenital heart defects in children in the first trimester of pregnancy, along with a constellation of neurogenic side effects such as anxiety, abdominal pain, agitation, insomnia, headache/migraine, nausea/vomiting, constipation, tremor, dizziness, excessive sweating, blurred vision, tachycardia, confusion, rash, hostility, cardiac arrhythmia, and auditory disturbance.

Accordingly, new psychopharmacological agents are needed which can solve these and other limitations and/or reach a larger cross-section of patients with neuropsychiatric pathology. Such neuropsychiatric pathology includes many difficult-to-treat mood, anxiety and personality disorders such as depression and PTSD, but also: fibromyalgia, suicidal ideation, substance use disorders (SUD), eating disorders, Borderline Personality Disorder (BPD) and other personality disorders, obsessive-compulsive disorder (OCD), palliative care/end-of-life anxiety, existential distress, chronic pain syndromes, body dysmorphia, phobias, social anxiety in autistic adults, and even sleep regulation.

SUMMARY OF THE INVENTION

In one aspect, provided herein are methods of treating and/or preventing a neuropsychiatric illness and/or ameliorating a symptom thereof in a subject in need thereof, comprising administering a therapeutically effective amount of methylone (3,4-methylenedioxy-N-methylcathinone) or a pharmaceutical composition thereof to the subject.

In another aspect, provided herein are methods of treating and/or preventing a neuropsychiatric illness and/or ameliorating a symptom thereof in a subject in need thereof, comprising administering a therapeutically effective amount of 2C-B (4-Bromo-2,5-dimethoxyphenethylamine) or a pharmaceutical composition thereof to the subject.

In another aspect, provided herein are methods of treating and/or preventing a neuropsychiatric illness and/or ameliorating a symptom thereof in a subject in need thereof, comprising administering a therapeutically effective amount of MBDB (N-methyl-1-(1,3-benzodioxol-5-yl)-2-aminobutane) or a pharmaceutical composition thereof to the subject.

In another aspect, provided herein are methods of treating and/or alleviating pain in a subject in need thereof, comprising administering a therapeutically effective amount of methylone (3,4-methylenedioxy-N-methylcathinone) or a pharmaceutical composition thereof to the subject.

In another aspect, provided herein are methods of treating and/or alleviating pain in a subject in need thereof, comprising administering a therapeutically effective amount of 2C-B (4-Bromo-2,5-dimethoxyphenethylamine) or a pharmaceutical composition thereof to the subject.

In another aspect, provided herein are methods of treating and/or alleviating pain in a subject in need thereof, comprising administering a therapeutically effective amount of MBDB (N-methyl-1-(1,3-benzodioxol-5-yl)-2-aminobutane) or a pharmaceutical composition thereof to the subject.

In another aspect, provided herein are methods of improving sleep in a subject in need thereof, comprising administering a therapeutically effective amount of methylone (3,4-methylenedioxy-N-methylcathinone) or a pharmaceutical composition thereof to the subject.

In another aspect, provided herein are methods of treating a neuropsychiatric illness, and/or ameliorating a symptom thereof in a subject in need thereof, comprising administering to the subject a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a polymorph thereof and/or a prodrug thereof in a therapeutically effective amount that results in a plasma $C_{max}$ of methylone of 15-3,020 ng/mL in the subject. Also provided herein are methods of treating a neuropsychiatric illness, and/or ameliorating a symptom thereof in a subject in need thereof, comprising administering to the subject a pharmaceutical composition comprising methylone (3,4-methylenedioxy-N-methylcathinone) and/or a methylone prodrug in a therapeutically effective amount that results in a plasma $AUC_{0-24}$ of methylone of 104-25,350 ng·h/mL in the subject.

In another aspect, provided herein are methods of treating a neuropsychiatric illness, and/or ameliorating a symptom thereof in a subject in need thereof, comprising administering to the subject a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a polymorph thereof and/or a prodrug thereof in a therapeutically effective amount that results in a plasma $C_{max}$ of methylone of 98-994 ng/mL in the subject. Also provided herein are methods of treating a neuropsychiatric illness, and/or ameliorating a symptom thereof in a subject in need thereof, comprising administering to the subject a pharmaceutical composition comprising methylone (3,4-methylenedioxy-N-methylcathinone) and/or a methylone prodrug in a therapeutically effective amount that results in a plasma $AUC_{0-24}$ of methylone of 47-10,983 ng·h/mL in the subject.

In another aspect, provided herein are methods of modulating neuroplasticity in a subject in need thereof, comprising administering to the subject a therapeutically effective amount of a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a prodrug thereof, and/or a polymorph thereof.

In another aspect, provided herein are methods of treating and/or preventing a neuropsychiatric illness and/or ameliorating a symptom thereof in a subject in need thereof, comprising administering to the subject a therapeutically effective amount of a serotonin-norepinephrine-dopamine reuptake inhibitor and releaser that lacks agonist or antagonist activity at the $5-HT_{2A}$ and $5-HT_{2B}$ receptors. In some embodiments, the serotonin-norepinephrine-dopamine reuptake inhibitor and releaser lacks agonist or antagonist activity at the 168 G-protein coupled receptors (GPCRs) set forth in Table 6.

In another aspect, provided herein are methods for screening a compound to identify whether it is a potential therapeutic for a neuropsychiatric illness. In some embodiments, the methods comprise: (a) determining whether the compound is a serotonin-norepinephrine-dopamine reuptake inhibitor and releaser; and (b) measuring agonist and antagonist activity of the compound at the $5-HT_{2A}$ and $5-HT_{2B}$ receptors, wherein a determination that the compound is a serotonin-norepinephrine-dopamine reuptake inhibitor and releaser and that the compound lacks agonist or antagonist activity at the $5-HT_{2A}$ and $5-HT_{2B}$ receptors is indicative that the compound is a potential therapeutic for the neuropsychiatric illness. In some embodiments, the methods comprise: (a) determining whether the compound is a serotonin-norepinephrine-dopamine reuptake inhibitor and releaser; and (b) measuring agonist and antagonist activity of the compound at the 168 G-protein coupled receptors (GPCRs) set forth in Table 6, wherein a determination that the compound is a serotonin-norepinephrine-dopamine reuptake inhibitor and releaser and that the compound lacks agonist or antagonist activity at the 168 GPCRs is indicative that the compound is a potential therapeutic for the neuropsychiatric illness.

Also provided herein are methods for screening a compound to identify whether it is a potential therapeutic for pain. In some embodiments, the methods comprise: (a) determining whether the compound is a serotonin-norepinephrine-dopamine reuptake inhibitor and releaser; and (b) measuring agonist and antagonist activity of the compound at the $5-HT_{2A}$ and $5-HT_{2B}$ receptors, wherein a determination that the compound is a serotonin-norepinephrine-dopamine reuptake inhibitor and releaser and that the compound lacks agonist or antagonist activity at the $5-HT_{2A}$ and $5-HT_{2B}$ receptors is indicative that the compound is a potential therapeutic for pain. In some embodiments, the methods comprise: (a) determining whether the compound is a serotonin-norepinephrine-dopamine reuptake inhibitor and releaser; and (b) measuring agonist and antagonist activity of the compound at the 168 G-protein coupled receptors (GPCRs) set forth in Table 6, wherein a determination that the compound is a serotonin-norepinephrine-dopamine reuptake inhibitor and releaser and that the compound lacks agonist or antagonist activity at the 168 GPCRs is indicative that the compound is a potential therapeutic for pain.

In another aspect, provided herein are oral dosage forms comprising methylone and a diluent/binder, a disintegrant, and a lubricant. In some embodiments, the oral dosage form further comprises a surfactant.

Other features and advantages of this invention will become apparent from the following detailed description, examples and figures. It should be understood, however, that the detailed description and the specific examples while indicating preferred embodiments are given by way of illustration only, since various changes and modifications will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 2 shows the Baseline Disease Severity in Cohort 2 of Example 4.

vehicle 1× group; ++++p<0.0001 vs. vehicle 3× group; +++ p<0.001 vs. vehicle 3× group. N=6-8 per group.

FIGS. 8A-8D: Methylone has a robust antidepressant-like effect in the Forced Swim Test. (FIG. 8A) Schematic of experimental design. Quantification of the time spent (FIG. 8B) immobile ($F_{(4,31)}$=17.05, p<0.0001), (FIG. 8C) climbing $F_{(4,31)}$=5.786, p<0.01) or (FIG. 8D) swimming ($F_{(4,31)}$=6.063, p<0.01) during a 5-min rat Forced Swim Test. Rats were subjected to a 15 minute swim 24 h before testing. Fluoxetine (10 mg/kg, IP) was administered 1, 5, and 23.5 h before testing. Methylone (5 or 15 mg/kg, IP) was administered 30 min before testing. All data are presented as means+/−SEM. *p<0.05, p<0.01, *p<0.001, ****p<0.0001 vs. Vehicle control group; +p<0.05, ++p<0.01 vs. Fluoxetine-treated group; $^a$p=0.06 vs. Fluoxetine-treated group; $^b$p=0.08 vs. Vehicle control group. N=6-8 per group.

Figure 9A:
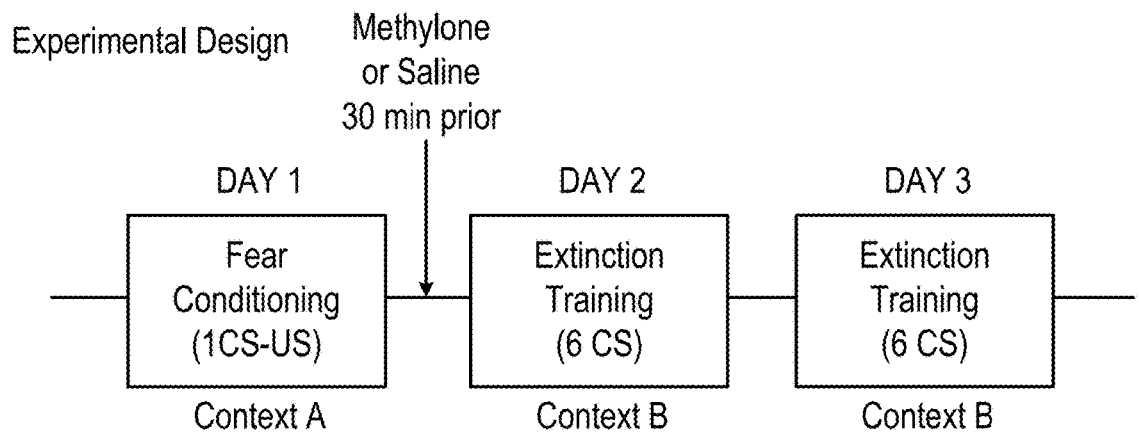
Figure 9B:
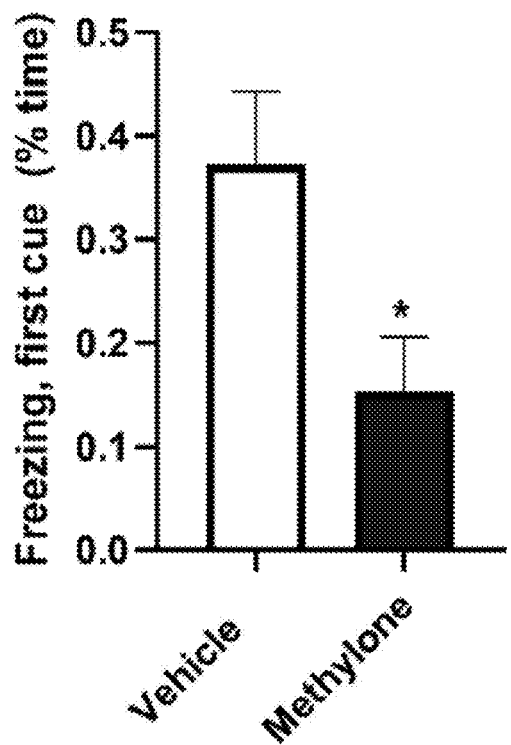
Figure 9C:
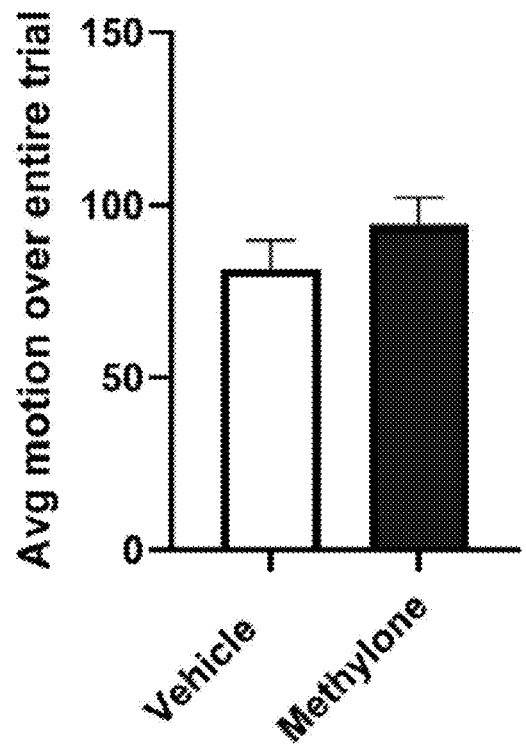

FIGS. 9A-9C: Methylone improves fear extinction recall in a PTSD mouse model. (FIG. 9A) Schematic of experimental design. A single CS-US (tone-shock) pairing on day 1 was followed by 6 CS presentations in a novel context (context B). Methylone or saline vehicle was injected 30 min before extinction training on day 2. On day 3, the time spent freezing to the CS was quantified. (FIG. 9B) Freezing time during the first cue on day 3 (extinction recall) was significantly reduced by methylone compared to saline ($t_{(26)}$=2.350, p<0.05). (FIG. 9C) No locomotor changes were observed on day 3 ($t_{(26)}$=1.073, p>0.05). Data are mean+/−SEM. N=12 for methylone group (30 mg/kg, IP) and N=16 for saline control group. *p<0.05.

Figure 10A:
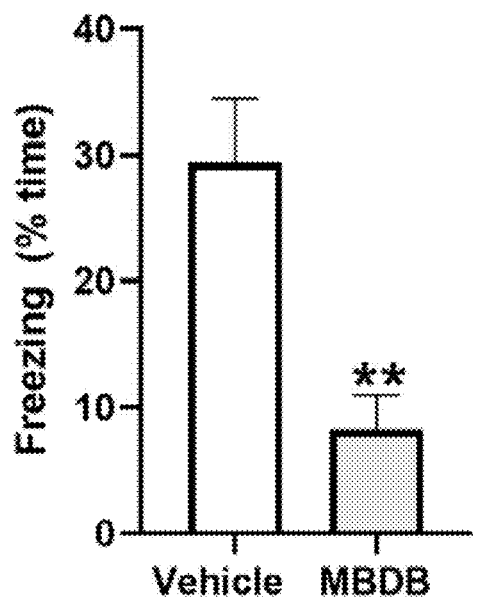
Figure 10B:
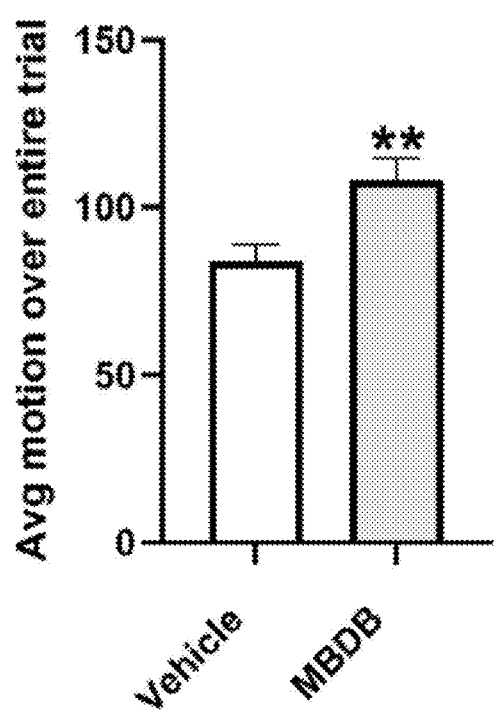

FIGS. 10A-10B: MBDB improves fear extinction in a PTSD mouse model. A single CS-US (tone-shock) pairing on day 1 was followed by 6 conditioned stimulus (CS) presentations in a novel context (context B). MBDB or saline vehicle was injected 30 min prior to extinction training on day 2. The time spent freezing to the CS was quantified on day 2. (FIG. 10A) Freezing time during the first extinction training trial on day 2 was significantly reduced by MBDB compared to saline controls (t(24)=3.095, p<0.01). (FIG. 10B) A small but significant increase in locomotor activity was also induced by MBDB on day 2 (t (24)=2.874, p<0.01). Data are mean+/−SEM. N=10 for MBDB group (5 mg/kg, IP) and N=16 for saline control group. **p<0.01 vs. vehicle control group.

Figure 11A:
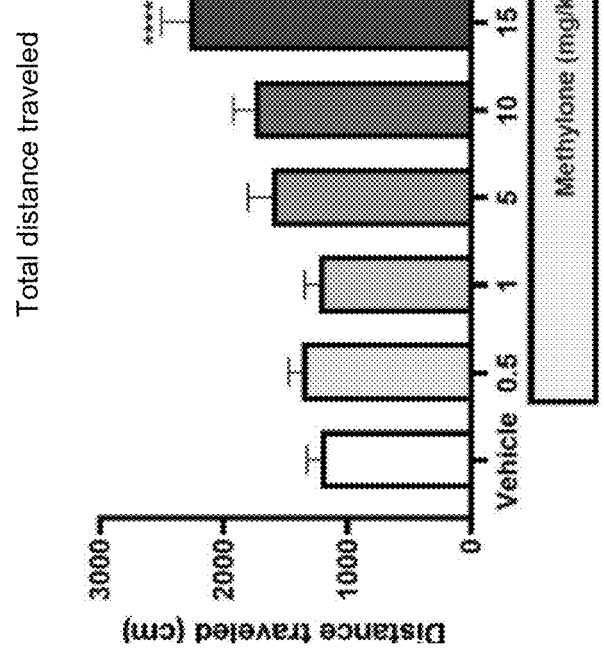
Figure 11B:
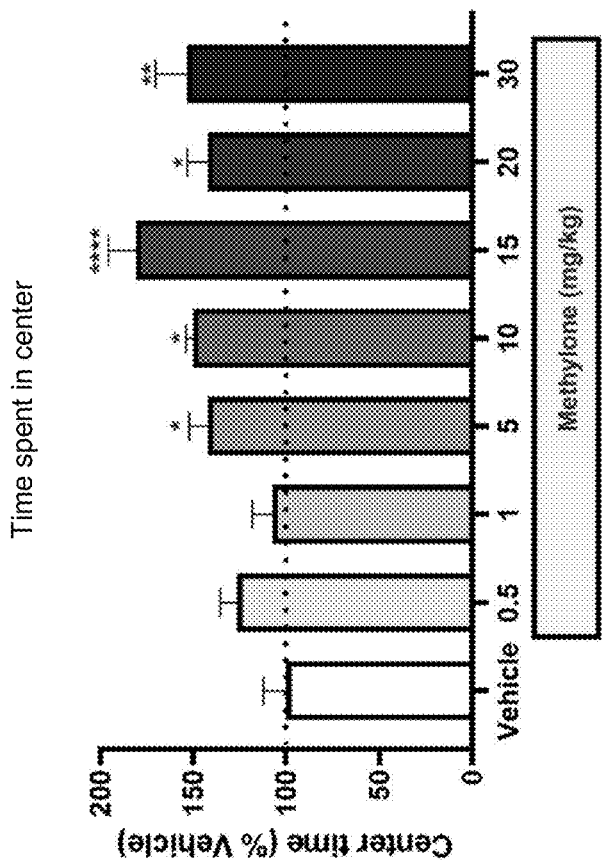

FIGS. 11A-11B: Methylone has an anti-anxiety effect in the open field test (OFT). Rats were given methylone or vehicle intraperitoneally (IP) 30 min before testing in the OFT. (FIG. 11A) More center time indicates a stronger anti-anxiety effect. Methylone significantly increased center time at doses of 5, 10, 15, 20 and 30 mg/kg. FIG. 11B shows total distance traveled. *p<0.05, p<0.01, **p<0.001 vs. vehicle. N=6-13 per group.

Figures 12A, 12B:
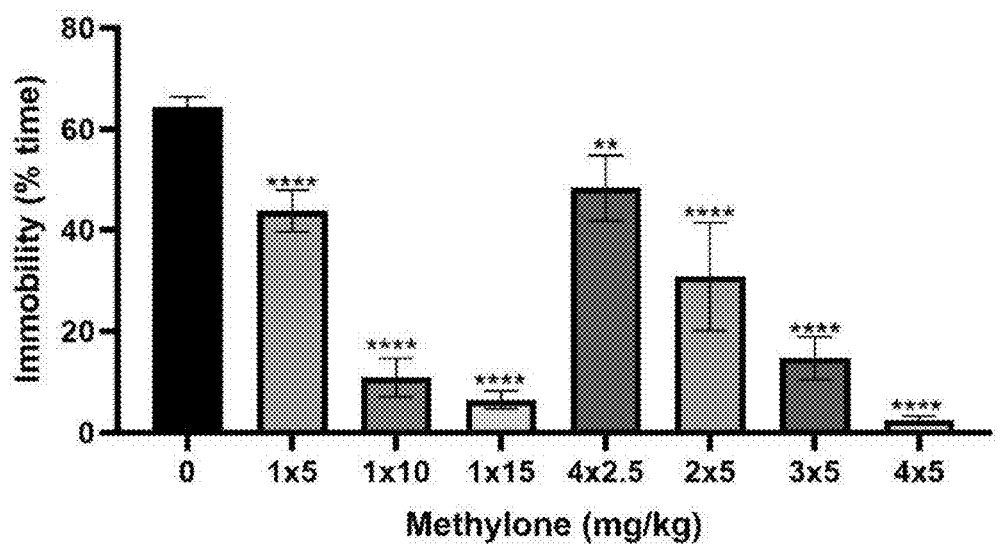

FIGS. 12A-12B: Lower methylone doses given more frequently mimic the antidepressant-like effects of a single larger dose in the rat forced swim test (FST). Rats were injected with methylone or vehicle 20.5, 8.5, 4.5 and 0.5 hours before testing in the FST as indicated in FIG. 12A. FIG. 12B shows the % time spent immobile; reduced immobility reflects antidepressant-like effects. X-axis values refer to the number of doses×the dose (mg/kg). For example, 1×5 means a single 5 mg/kg dose and 4×2.5 means four 2.5 mg/kg doses. p<0.05; **p<0.001 compared to vehicle (0 mg/kg). N=6-20 across three experiments.

Figure 13:
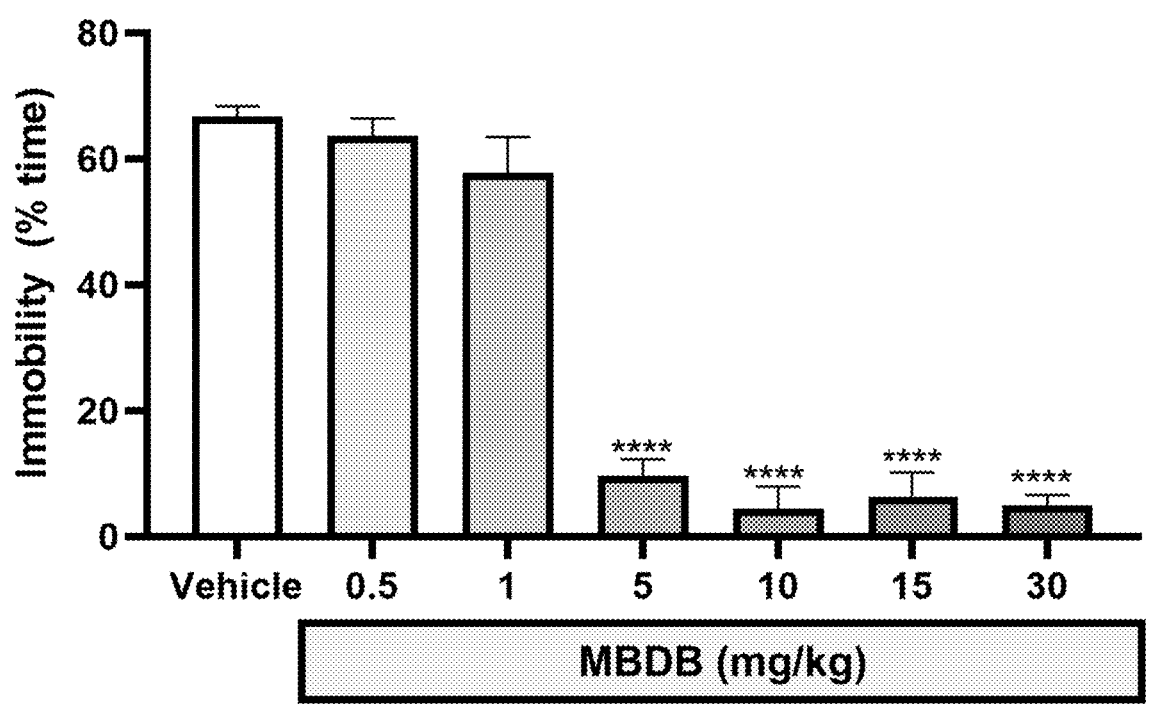

FIG. 13: MBDB or vehicle were administered 30 min before testing in the FST. Quantification of the percent time spent immobile during the 5-minute test session is shown. Data are presented as means±SEM. p<0.01, **p<0.0001 vs. Vehicle control group; Tukey's post-hoc test; N=7 per group.

FIG. 14: [$^3$H]5HT uptake in rat brain synaptosomes in the presence or absence of methylone.

FIG. 15: [$^3$H]5HT binding to $5HT_{2B}$ receptor expressing membranes.

Figure 16:
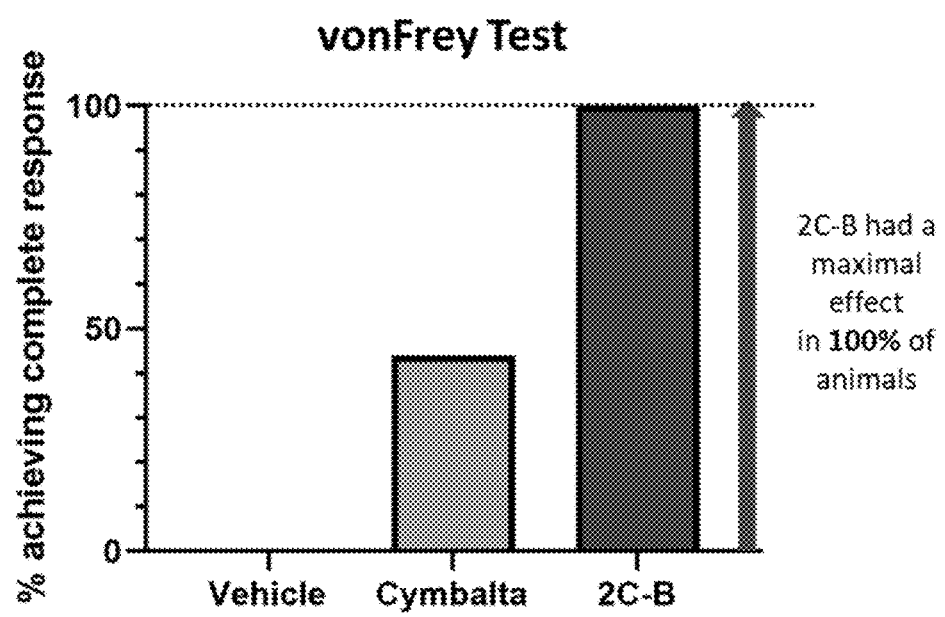

FIG. 16: 2C-B maximally reverses reserpine-induced pain sensitivity in 100% of animals in a rat model of fibromyalgia. 100% of animals given 2C-B showed maximally increased hindpaw thresholds (reduced pain sensitivity) at both doses. Duloxetine (brandname: Cymbalta), a positive control also increased thresholds but to a lesser extent than 2C-B (i.e., only 44% of animals showed maximum reversal). N=9-10 per group.

Figure 17:
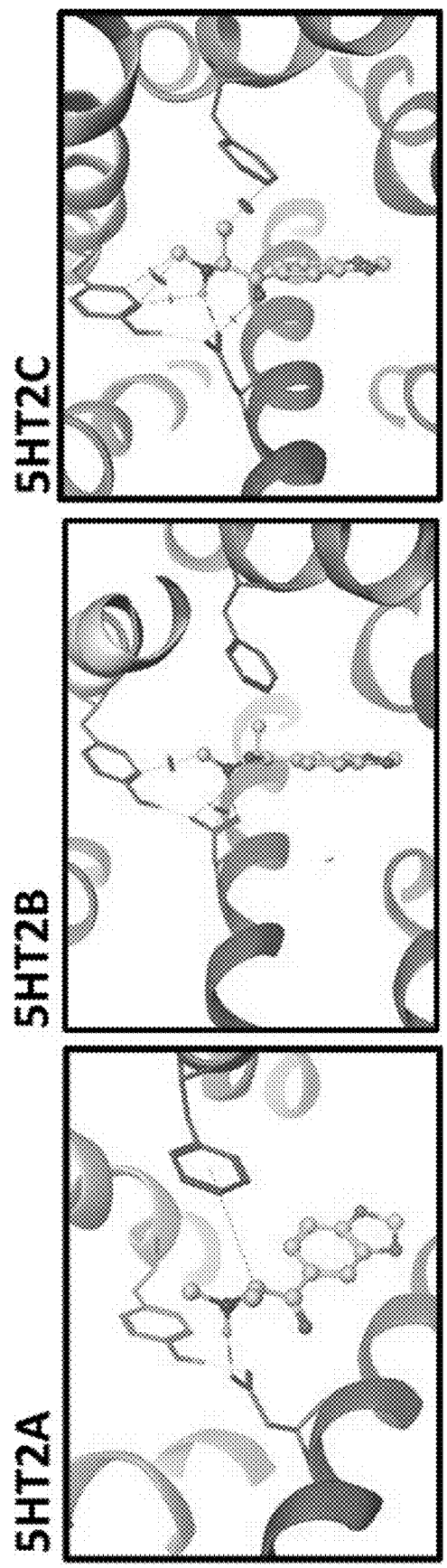

FIG. 17: Methylone is shown docking to PDB structures of $5HT_{2A}$, $5HT_{2B}$ and $5HT_{2C}$.

Figure 18:
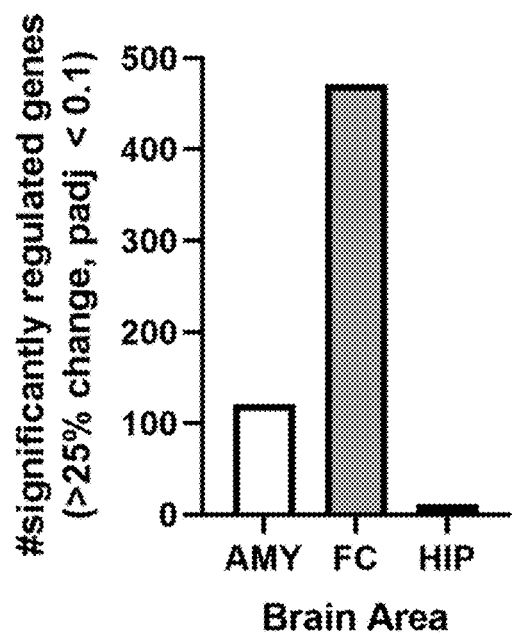

FIG. 18: RNA-sequencing study shows gene regulation by methylone in key PTSD and depression brain areas. The number of genes significantly regulated by methylone vs. vehicle 8 hours post-dose is shown. Significance was defined as gene changes>25% with padj<0.1 compared to vehicle controls. AMY=amygdala, FC=frontal cortex, HIP=hippocampus.

Figure 19:
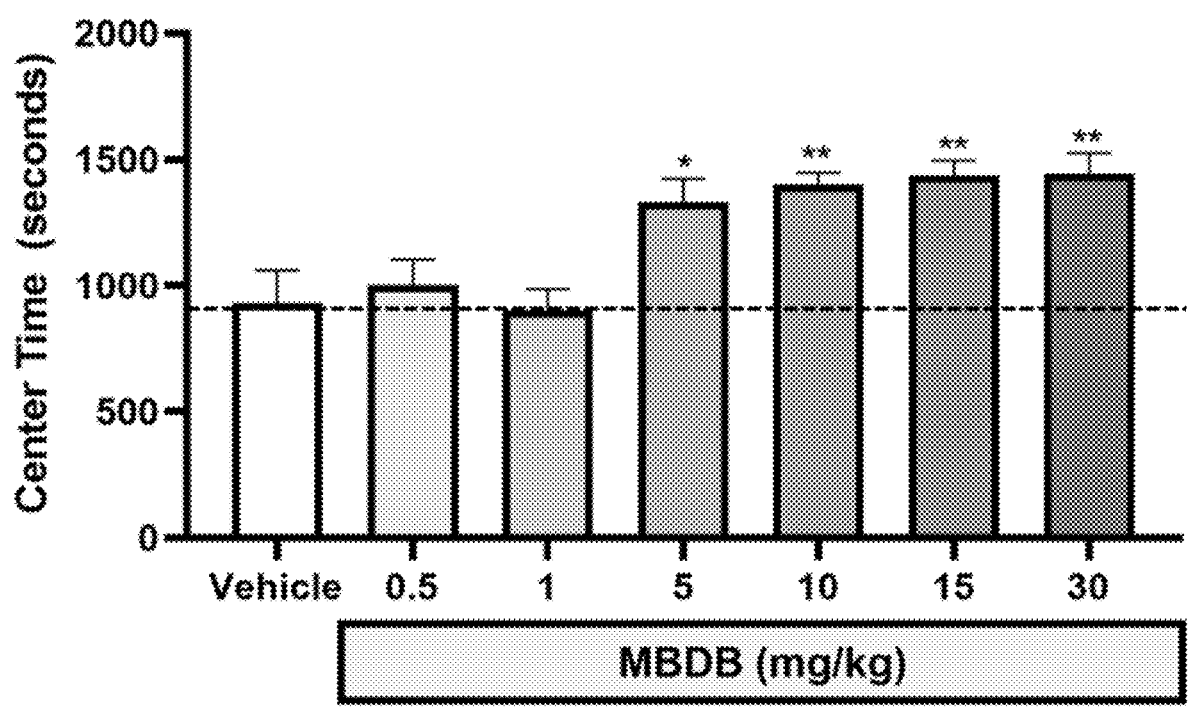

FIG. 19: MBDB has a rapid-acting and robust anxiolytic effect, increasing time spent in the center of an open field. Rats were dosed with MBDB or vehicle (IP) 30 minutes before testing in the open field for 30 minutes. The duration spent in the center is shown. All data are shown as means+/−SEM. N=8 per group. *p<0.05; **p<0.01 vs. vehicle control group. Dashed line shows baseline level of anxiety in vehicle control group.

Figure 20:
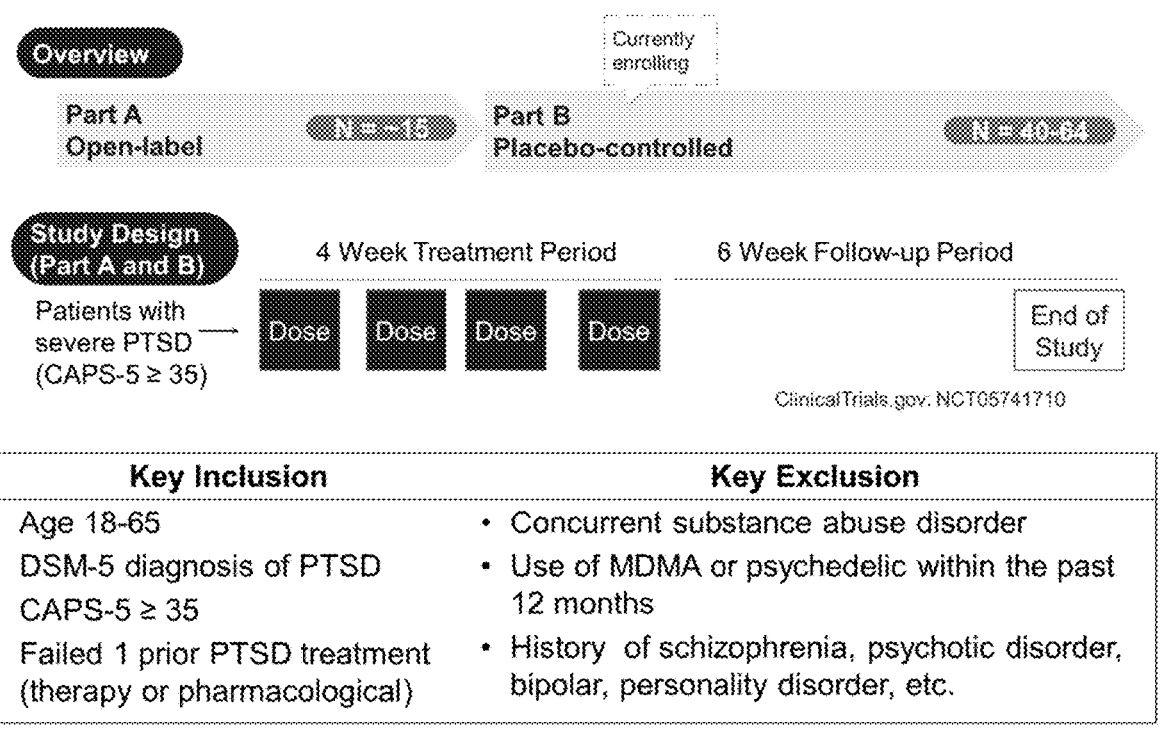

FIG. 20: Schematic for the experimental design of a study (IMPACT-1) of methylone for PTSD treatment.

Figure 21:
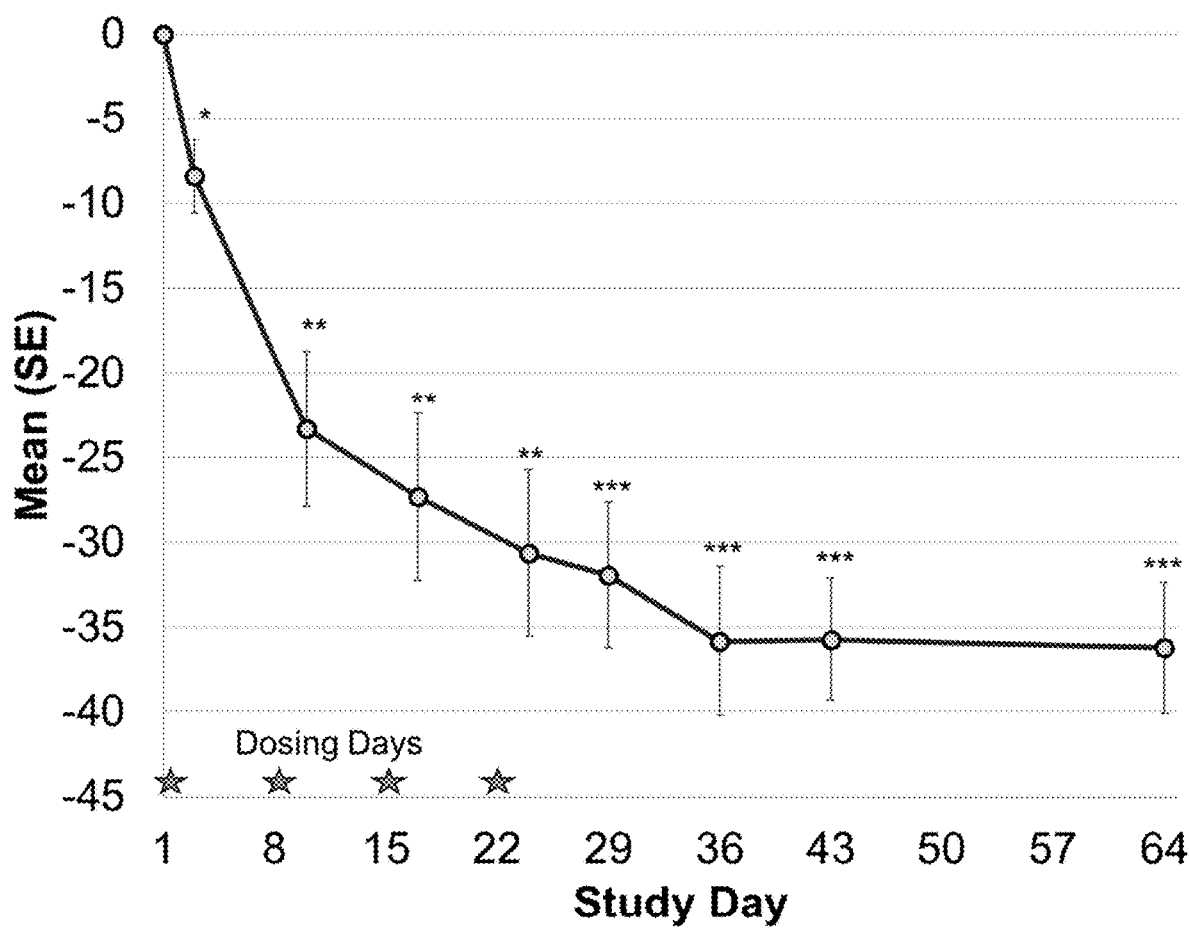

FIG. 21: Methylone produced rapid and durable improvements in Clinician-Administered PTSD Scale for DSM-5 (CAPS-5) scores in an Open-Label Study (IMPACT-1). Mean (range) at baseline: 47.8 (38-59).

Figure 22A:
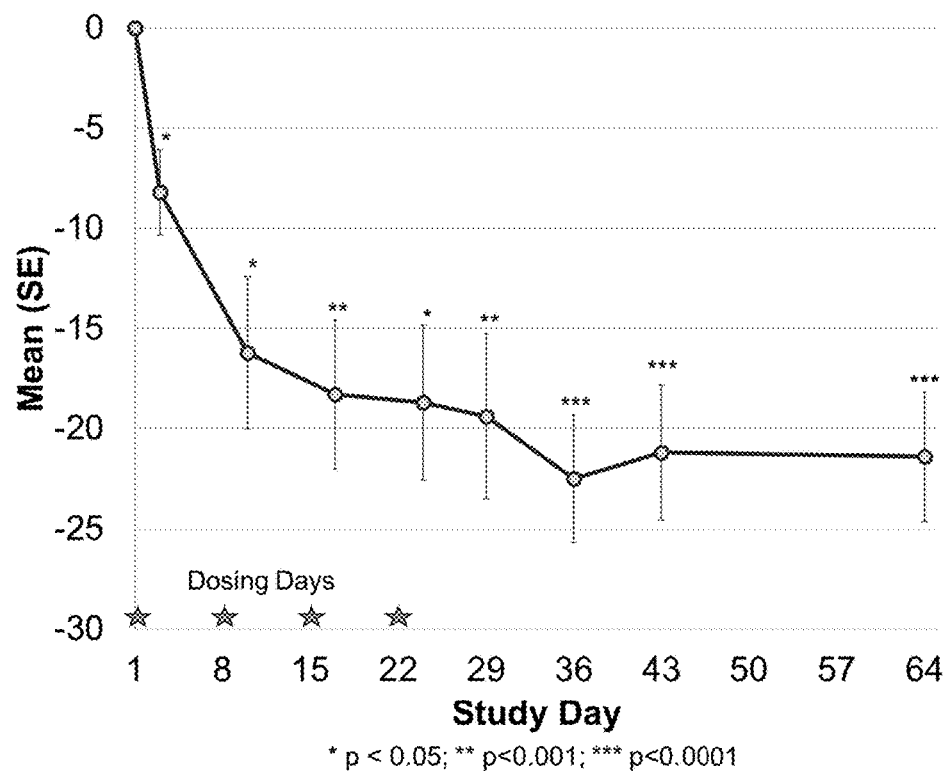
Figure 22B:
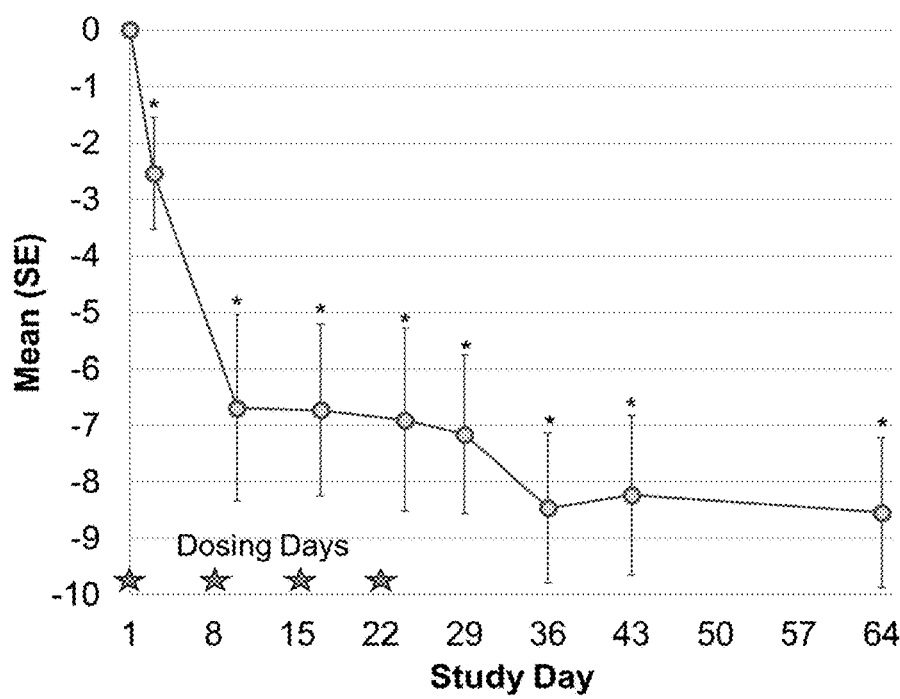

FIGS. 22A-22B: FIG. 22A shows the mean change from baseline in Montgomery-Åsberg Depression Rating Scale (MADRS) scores in an Open-Label Study (IMPACT-1) of methylone to treat PTSD. FIG. 22B shows the mean change from baseline in the Anxiety Sub-Scale of MADRS.

Figure 23:
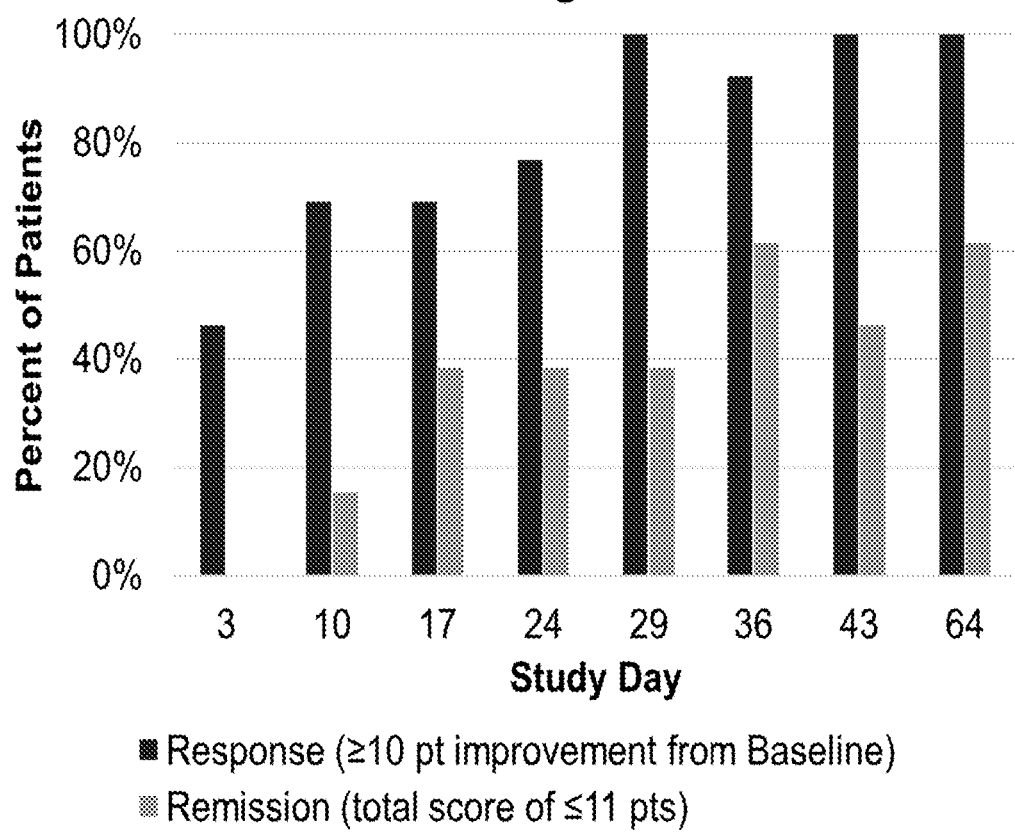

FIG. 23: Response and Remission on CAPS-5 in an Open-Label Study (IMPACT-1) of methylone for the treatment of PTSD.

Figure 24:
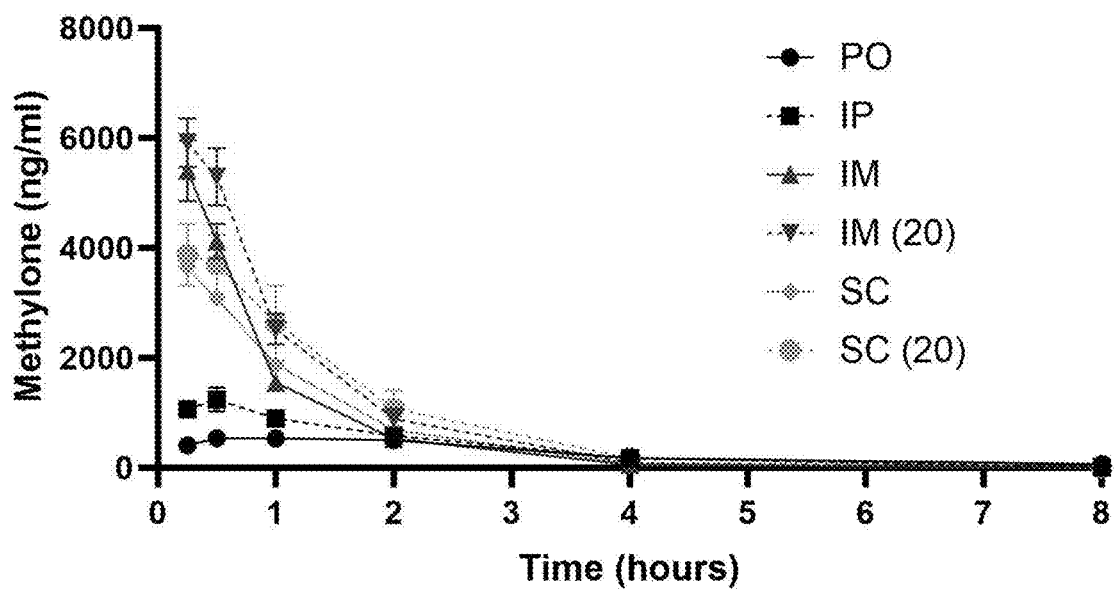

FIG. 24: Pharmacokinetic analysis of plasma in rats following oral (PO), intraperitoneal (IP), intramuscular (IM) or subcutaneous (SC) injection with methylone. Doses are 15 mg/kg unless noted (20 mg/kg).

Figure 25:
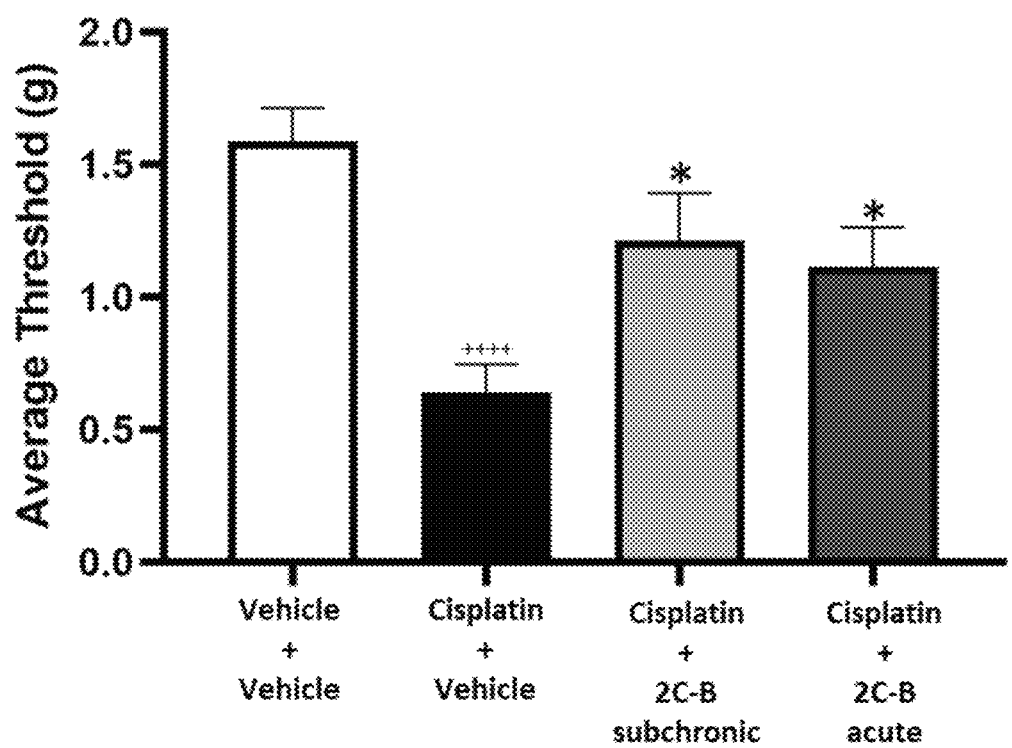

FIG. 25: 2C-B has rapid, robust effect in animal model of chemotherapy-induced peripheral neuropathy (CIPN). Pain thresholds were significantly increased in cisplatin-treated animals by 2C-B administration. Results shown are from day 17 VonFrey test, 30 min post-dose. *p≤0.05 vs. Cisplatin+Vehicle; ++++p<0.0001 vs. Vehicle/Vehicle; N=16-18 per group.

Figures 26A, 26B, 26C:
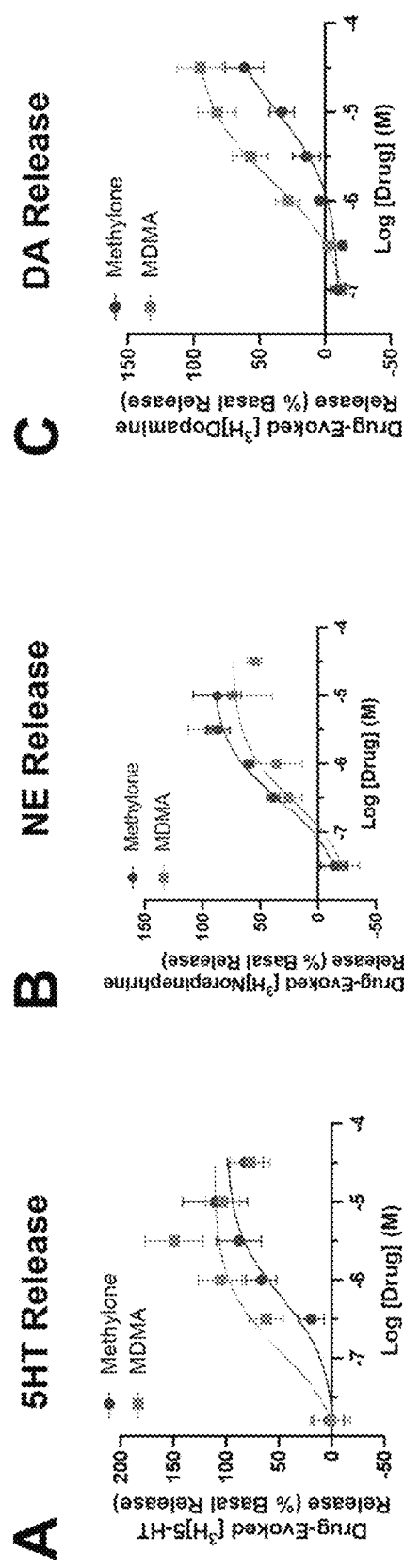

FIGS. 26A-26C: Methylone and MDMA release monoamines. Drug-evoked release of radiolabeled (FIG. 26A) 5HT, (FIG. 26B) NE or (FIG. 26C) DA by methylone or MDMA from rat brain synaptosomes was determined. Data are means+SEM. N=3 per group.

Figure 27A:
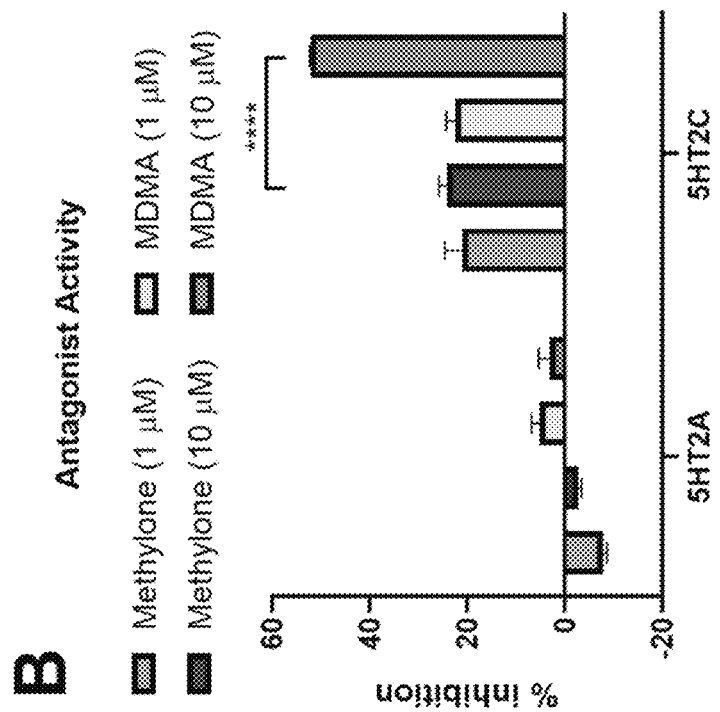
Figure 27B:
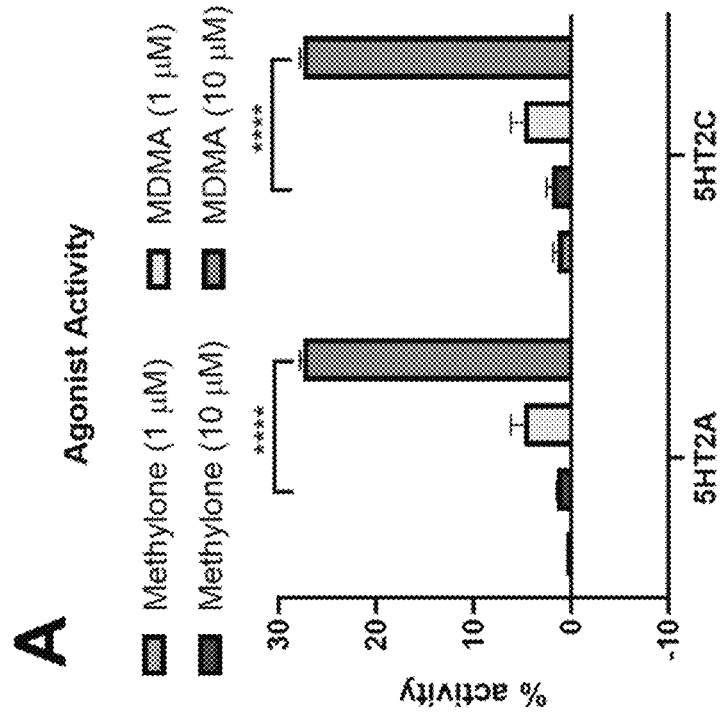

FIGS. 27A-27B: Methylone shows no agonist or antagonist activity at $5HT_{2A}$ or $5HT_2c$ receptors. Agonist or antagonist activity at GPCRs was determined using the GPCRmax high-throughput screen. Effects of methylone or MDMA (1 or 10 mM) on $5HT_{2A}$ and $5HT_{2C}$ receptor (FIG. 27A)

agonist activity or (FIG. 27B) antagonist activity are shown. Data are means±SEM. N=3 replicates per group. ****p<0.0001.

FIGS. 28A-28G: Structural differences between methylone and MDMA support differences in activity at $5HT_{2A}$ and $5HT_{2C}$ receptors. Chemical structures of (FIG. 28A) methylone or (FIG. 28B) MDMA are shown. (FIG. 28C) The diagram shows low energy conformations generated in MOE for MDMA (purple) and Methylone (blue) superimposed on the bicyclic ring system. Docking (FIG. 28D) methylone (cyan) or (FIG. 28E) MDMA (grey) to $5HT_{2A}$ receptors or (FIGS. 28F-28G) $5HT_{2C}$ receptors demonstrates that constraints in methylone's structure predict less binding to receptors. Orange disks indicate steric clashes. Blue cylinders and dashed lines illustrate hydrogen bonds.

Figure 29:
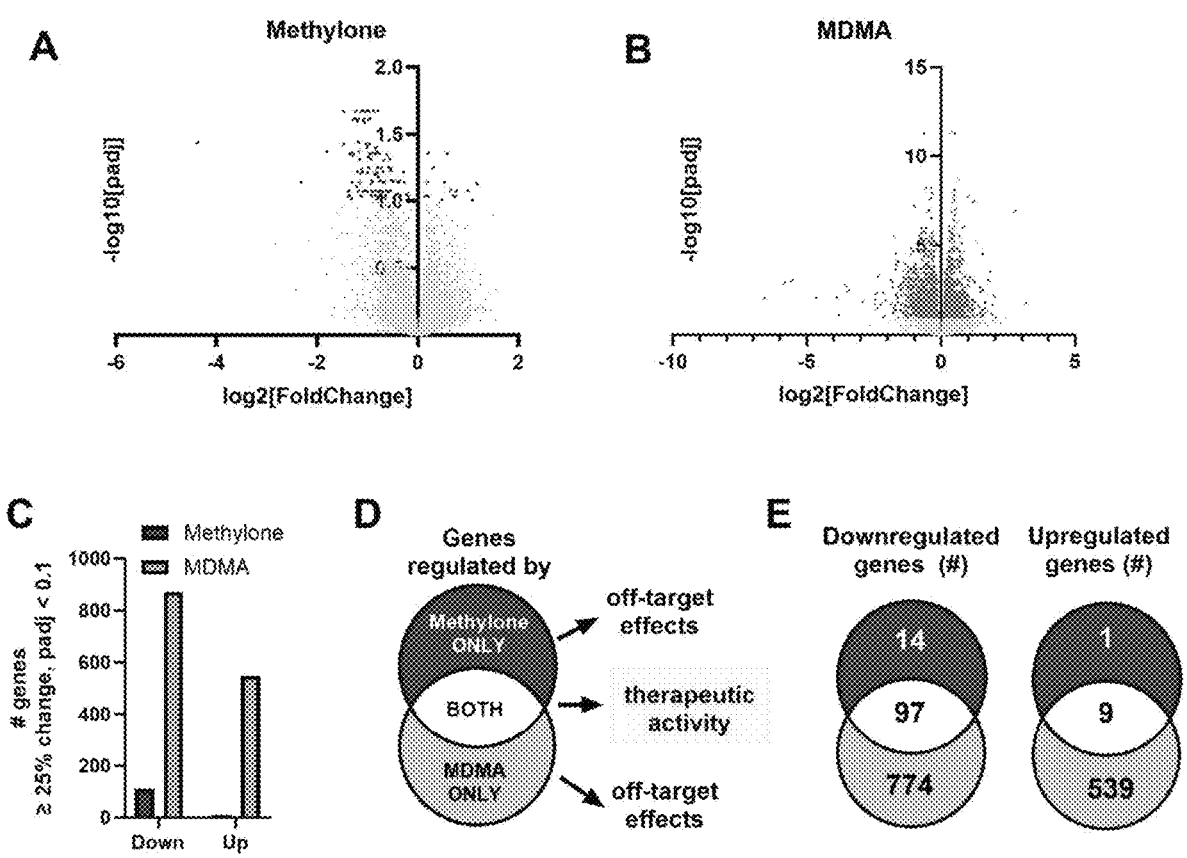

FIGS. 29A-2E: Methylone- and MDMA-induced gene expression changes in the amygdala. Volcano plots show significantly regulated genes in the amygdala after treatment with (FIG. 29A) methylone (blue dots) or (FIG. 29B) MDMA (dark grey dots) compared to vehicle-injected controls (N=6 per group). Light grey dots represent genes that were not significantly changed by either treatment. (FIG. 29C) The number of significantly down- or upregulated genes was quantified. (FIG. 29D) An illustration of the hypothesis that genes regulated by both methylone and MDMA are linked to potential therapeutic activity and that genes regulated by methylone or MDMA only are drug-specific and reflect potential off-target effects. (FIG. 29E) Venn diagrams showing the number of genes significantly regulated by methylone (blue), MDMA (gray) or both (white) reveal that 87% of genes regulated by methylone are also regulated by MDMA, but that only 7% of genes regulated by MDMA are also regulated by methylone.

FIGS. 30A-30E: Functional enrichment analysis of genes regulated only by MDMA in the amygdala. Selected enrichment terms from genes that were (FIG. 30A) downregulated or (FIG. 30B) upregulated by MDMA only are shown. All enrichment terms shown were highly statistically significant. Dashed line with ** marks the –log (P)=1 value where p=0.01. Heatmaps generated from terms in FIG. 30B confirm that MDMA regulates protein folding (FIG. 30C), the orexin receptor pathway (FIG. 30D), and cytokine signaling (FIG. 30E), and that these changes are all specific to MDMA and not regulated by methylone.

FIGS. 31A-31C: Myelin genes are downregulated in the amygdala after methylone or MDMA treatment. Functional enrichment analysis of genes downregulated by (FIG. 31A) methylone or (FIG. 31B) MDMA compared to vehicle controls show highly significant effect on genes related to the 'ensheathment of neurons.' All enrichment terms shown were highly statistically significant. Dashed line with ** marks the –log (P)=1 value where p=0.01. (FIG. 31C) Bar graph shows downregulation of myelin-related genes by methylone and MDMA (N=6 per group).

FIGS. 32A-32F: Rapid induction of myelin plasticity by methylone and MDMA and the amygdala. Representative images from immunohistochemical detection of myelin basic protein (MBP) in vehicle (FIG. 32A), methylone (FIG. 32B), MDMA (FIG. 32C) treated rats are shown. Areas in black boxes are magnified below. Quantification of MBP expression (% positive tissue) in the amygdala (FIG. 32D) basolateral nucleus (FIG. 32E; BLA, yellow dashed line), central nucleus (CeN, red dashed line), or a control region (FIG. 32F; the cortex, black arrows) is shown. Data are means±SEM. *p<0.05, N=5-6 per group.

FIGS. 33A-33D: Gene changes in the frontal cortex suggest rapid-acting neuroplasticity. Volcano plots show significantly regulated genes in the frontal cortex by (FIG. 33A) methylone (blue dots) or (FIG. 33B) MDMA compared to vehicle-injected controls (N=6 per group). Light grey dots represent genes that were not significantly changed by either treatment. Red circles highlight neuroplasticity-related genes discussed in the results section. (FIG. 33C) The top 10 enrichment terms in the frontal cortex upregulated by (FIG. 33C) methylone or (FIG. 33D) MDMA are shown. All enrichment terms shown were highly statistically significant. Red dashed line with ** marks the –log (P)=1 value where p=0.01.

Figure 34:
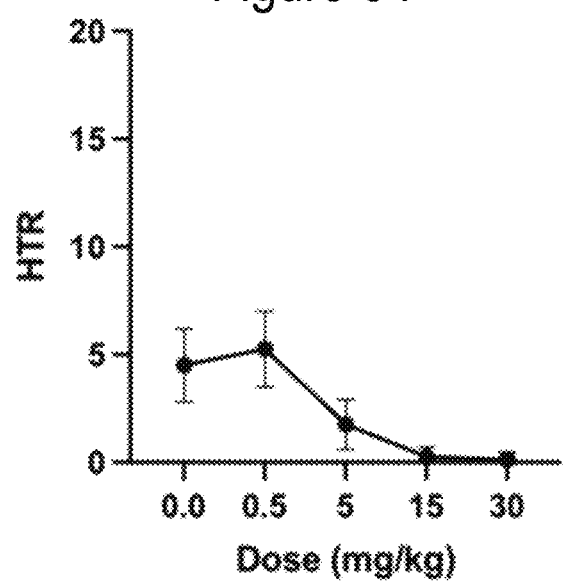

FIG. 34: Methylone shows no hallucinogenic activity in the mouse head-twitch response (HTR) test.

Figure 35:
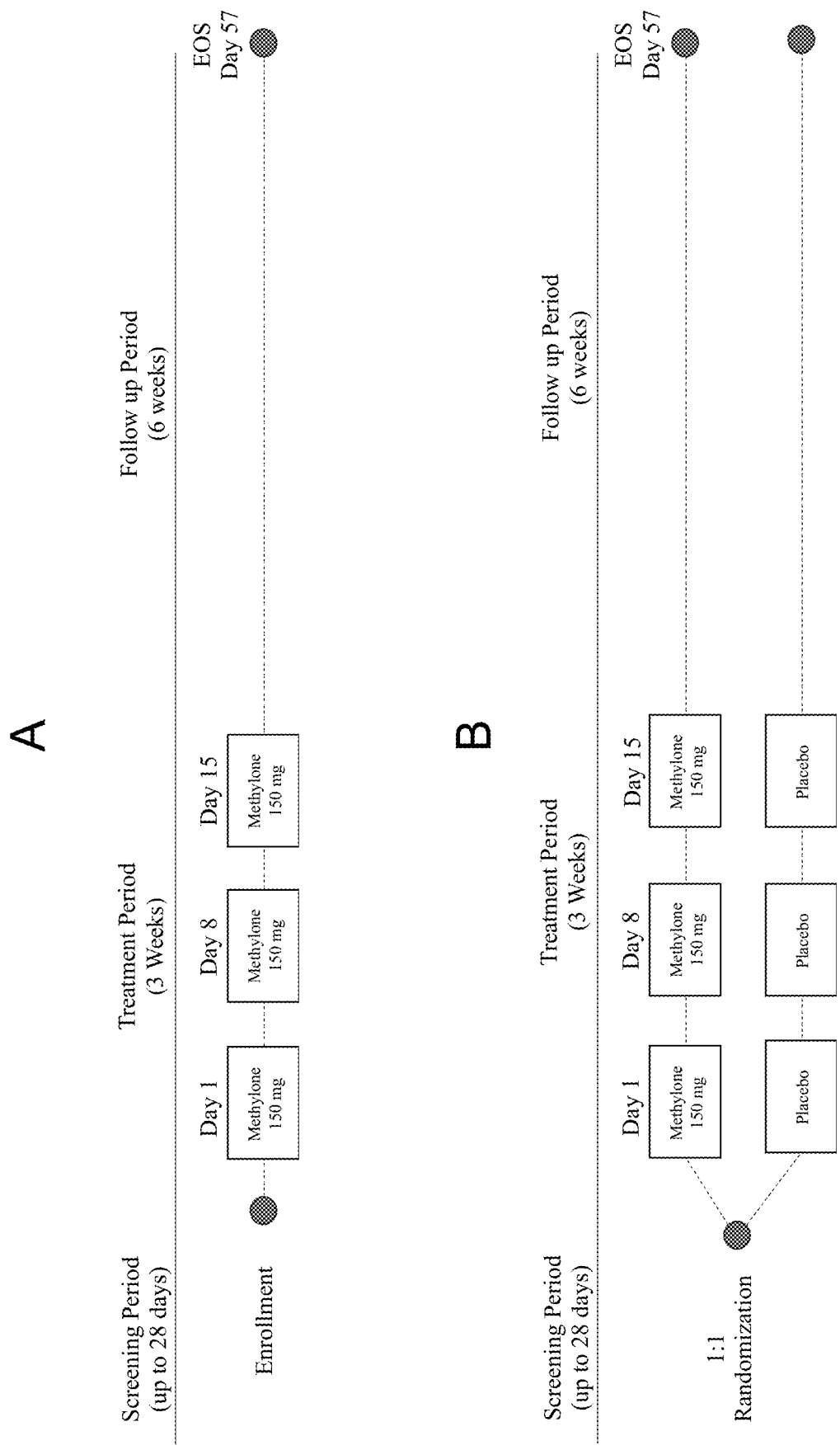

FIGS. 35A-35B: Schematic for the experimental design of a study (IMPACT-2) of methylone for the treatment of PTSD.

Figure 36:
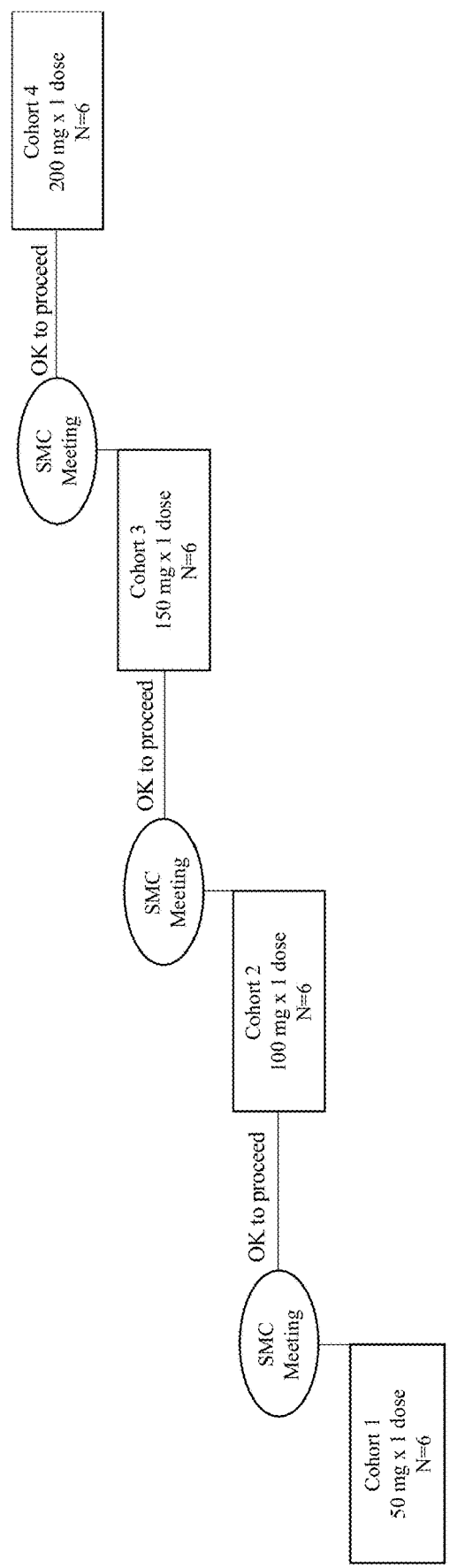

FIG. 36: Schematic for the experimental design of a an open-label, single, ascending dose study evaluating the pharmacokinetics (PK) and safety of methylone in healthy subjects.

Figure 37:
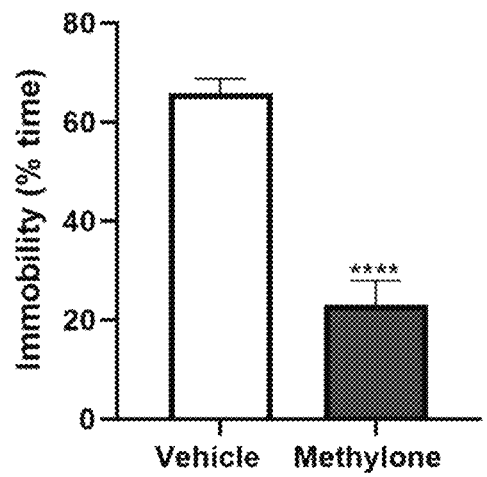

FIG. 37: Oral administration of methylone has an antidepressant-like effect in the forced swim test (FST). Rats were administered a single dose of methylone (15 mg/kg, PO) 2 hours before testing in the FST. Results show a significant antidepressant-like effect of methylone compared to vehicle controls. ****p<0.001, N=10 per group.

Figure 38:
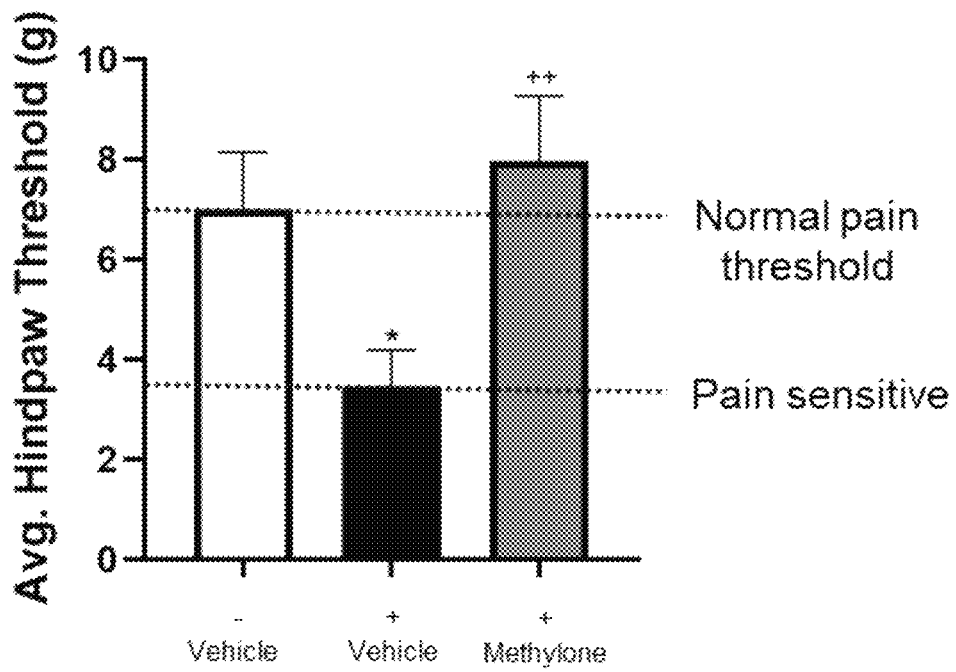

FIG. 38: Methylone has a beneficial effect in a rat fibromyalgia model. Rats were treated with reserpine for 3 days to induce pain sensitivity (+) or vehicle (–) to maintain the 'normal' pain threshold. Baseline paw withdrawal thresholds showed significant effect of reserpine vs. vehicle (not shown). On day 4, rats were given vehicle or methylone (15 mg/kg, IP) 30 min before testing in the vonFrey test for pain sensitivity. Methylone significantly increased paw withdrawal thresholds. *p<0.05 vs. '–Vehicle' group; ++p<0.01 vs. '+Vehicle' group, N=10-12 per group.

Figure 39A:
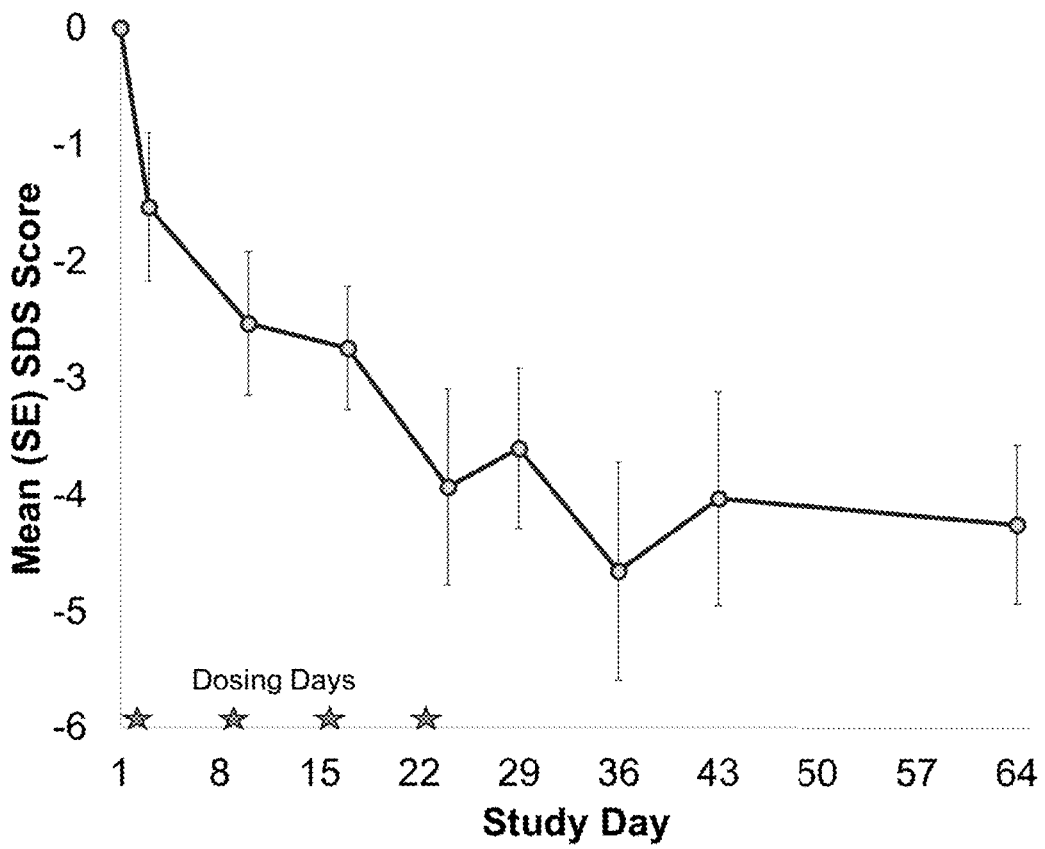
Figure 39B:
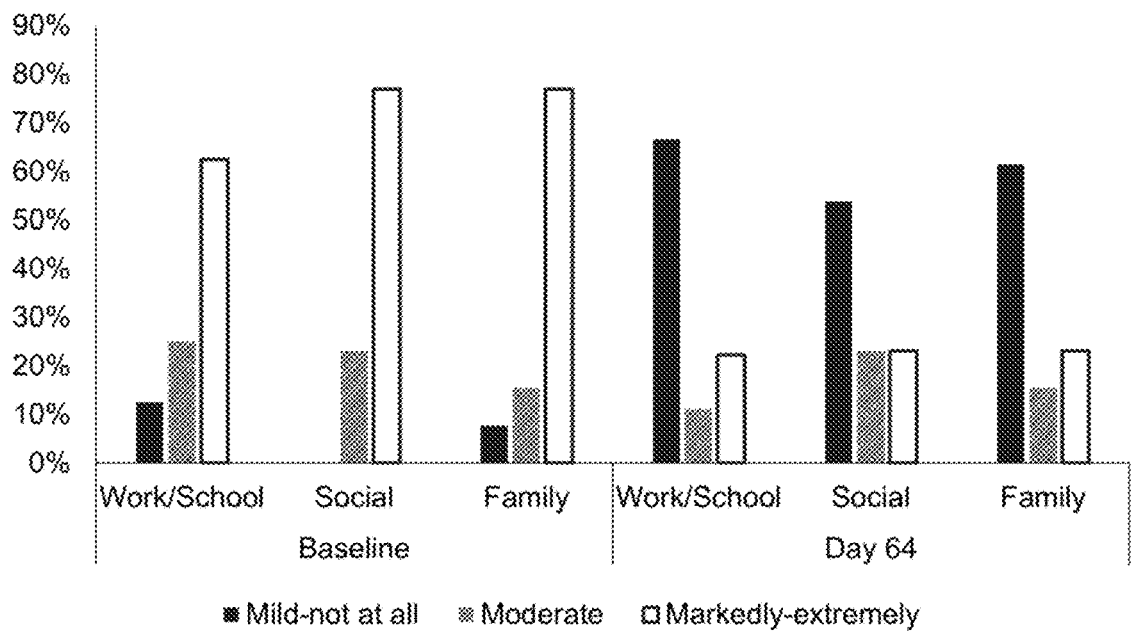

FIGS. 39A-39B: FIG. 39A shows the change from baseline in mean Sheehan Disability Scale (SDS) scores over time in an Open-Label Study (IMPACT-1) of methylone to treat PTSD. FIG. 39B is a bar graph of the percent of patients with Mild, Moderate, or Marked Severity by SDS Domain at baseline and at the end of this study.

Figure 40:
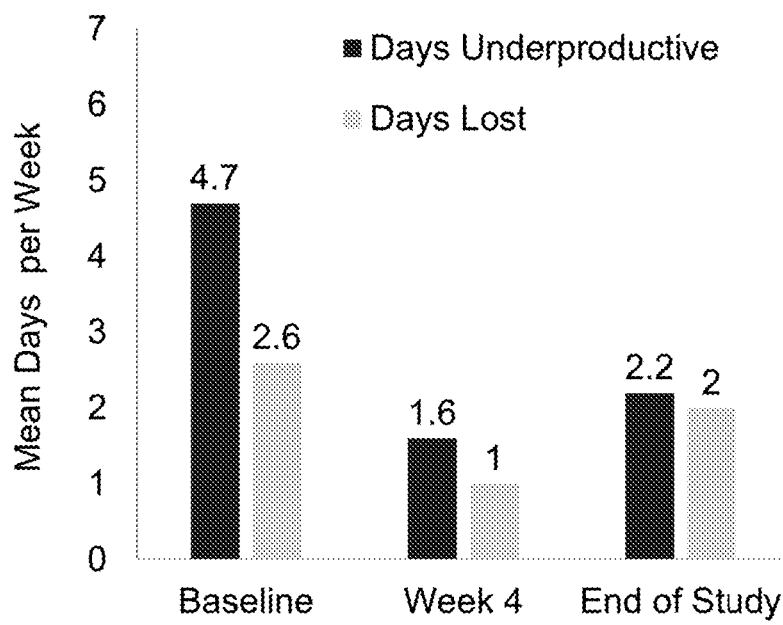

FIG. 40: Bar graph showing days per week lost and underproductive at baseline, at the end of the 4-week treatment period and at the end of the Open-Label Study (IMPACT-1) of methylone to treat PTSD.

Figure 41:
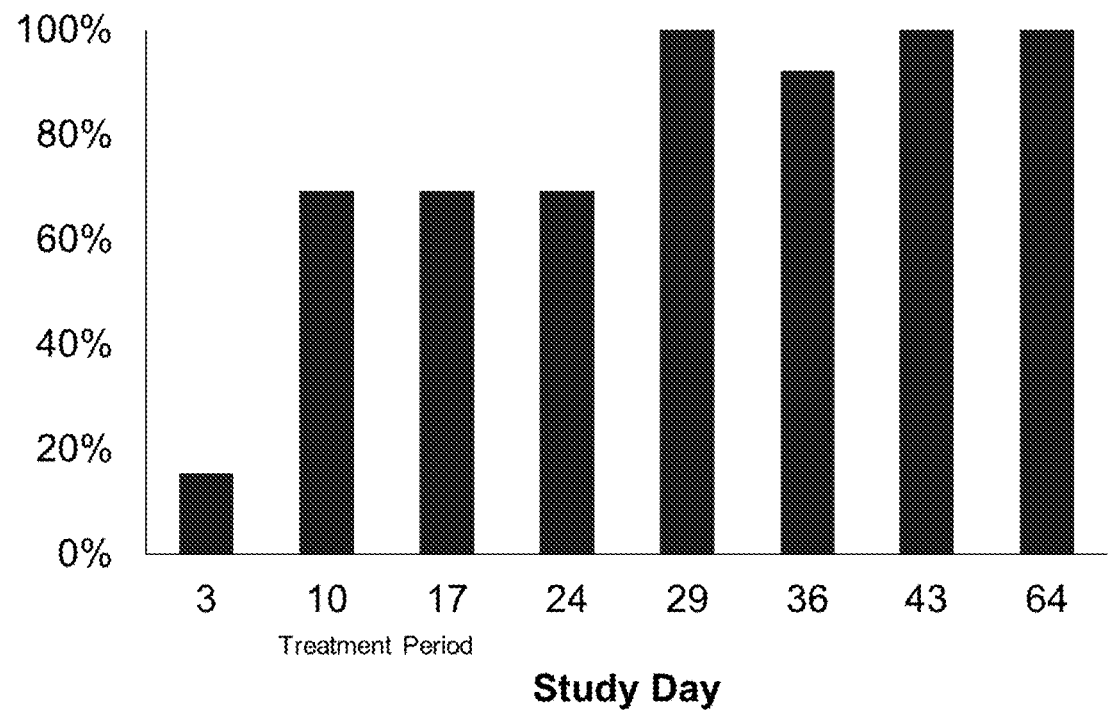

FIG. 41: Bar graph of the percent of patients who were Much or Very Much Improved on the Clinical Global Impression-improvement (CGI-I) over time for the Open-Label Study (IMPACT-1) of methylone to treat PTSD.

Figure 42A:
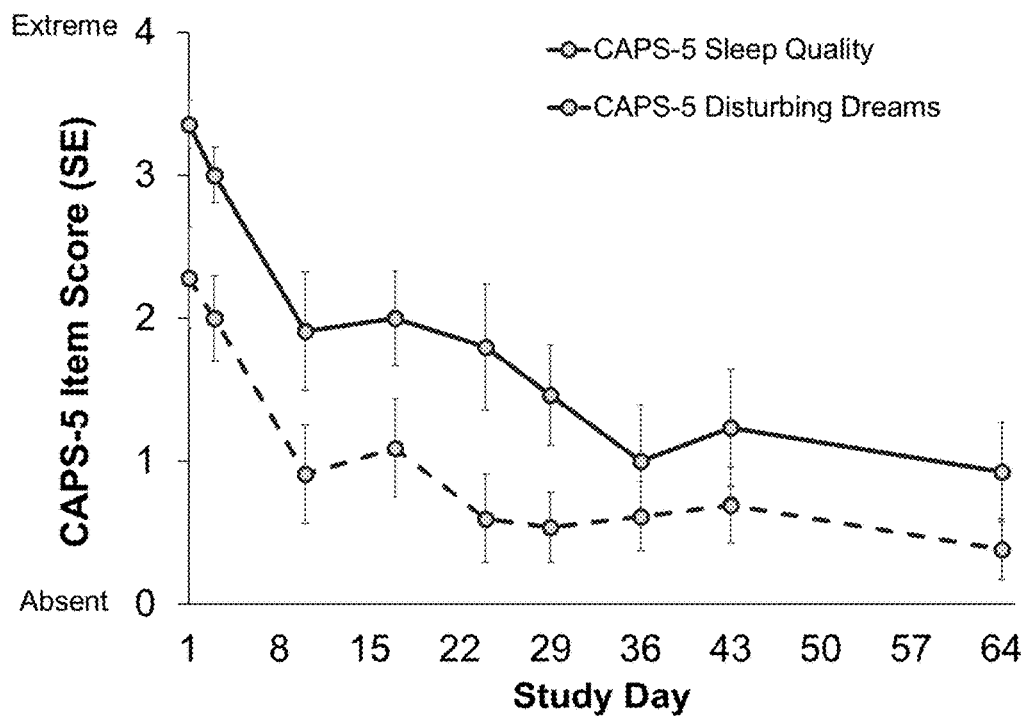
Figure 42B:
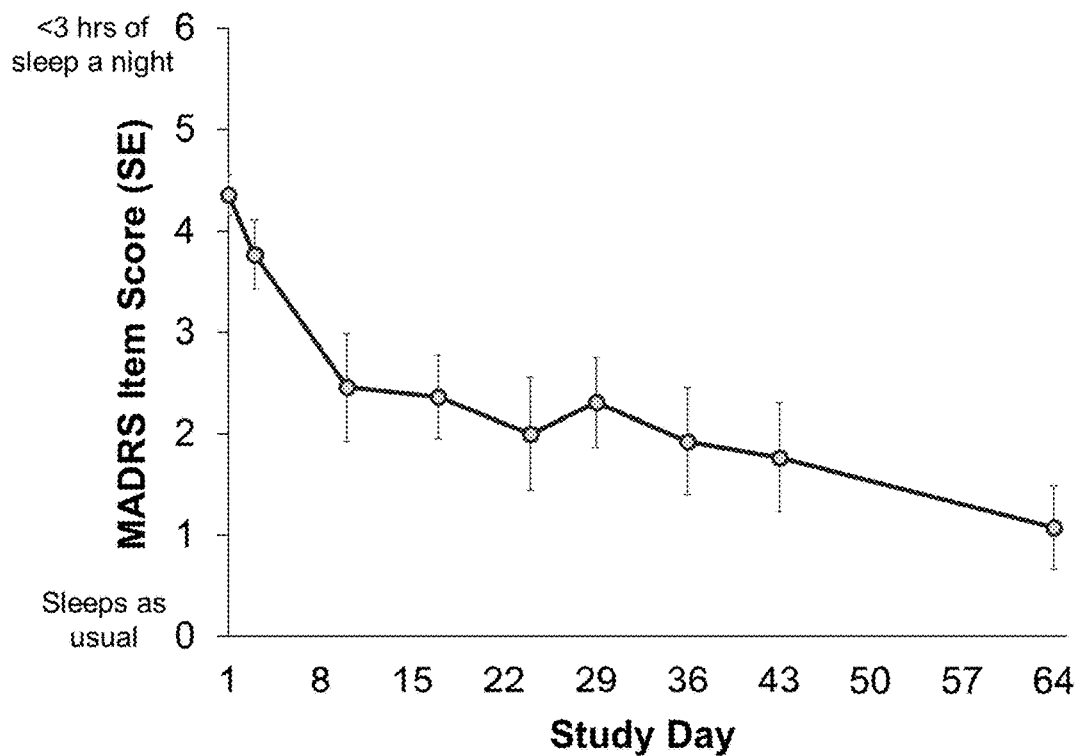

FIGS. 42A-42B: Change over time of the CAPS-5 Sleep Items (FIG. 42A) and the MADRS Sleep Item (FIG. 42B) for the Open-Label Study (IMPACT-1) of methylone.

Figure 43A:
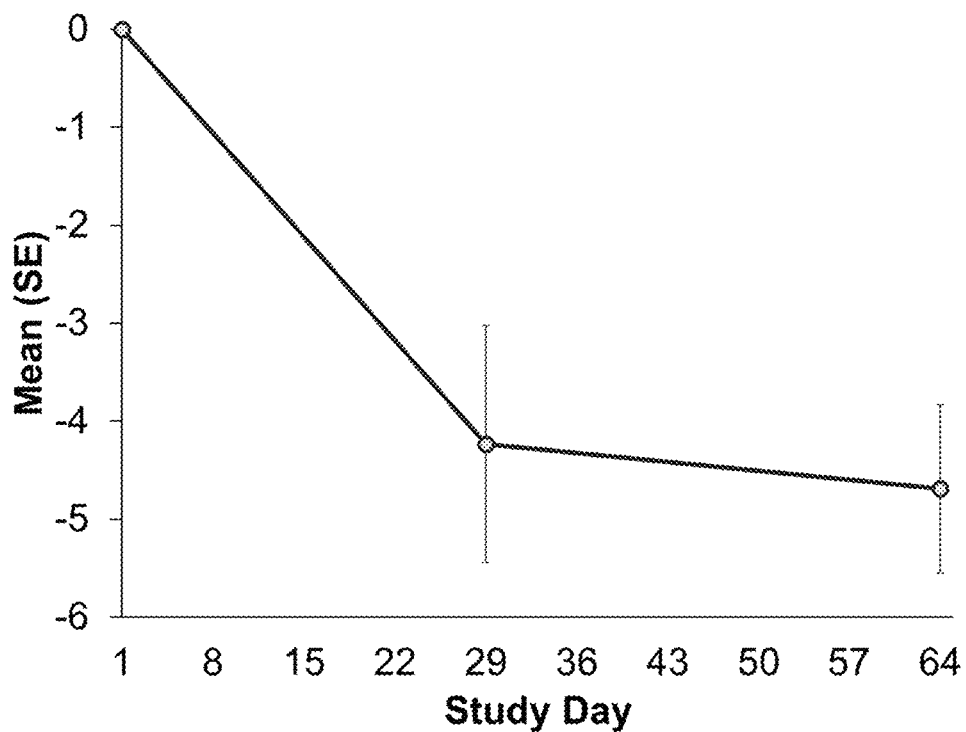
Figure 43B:
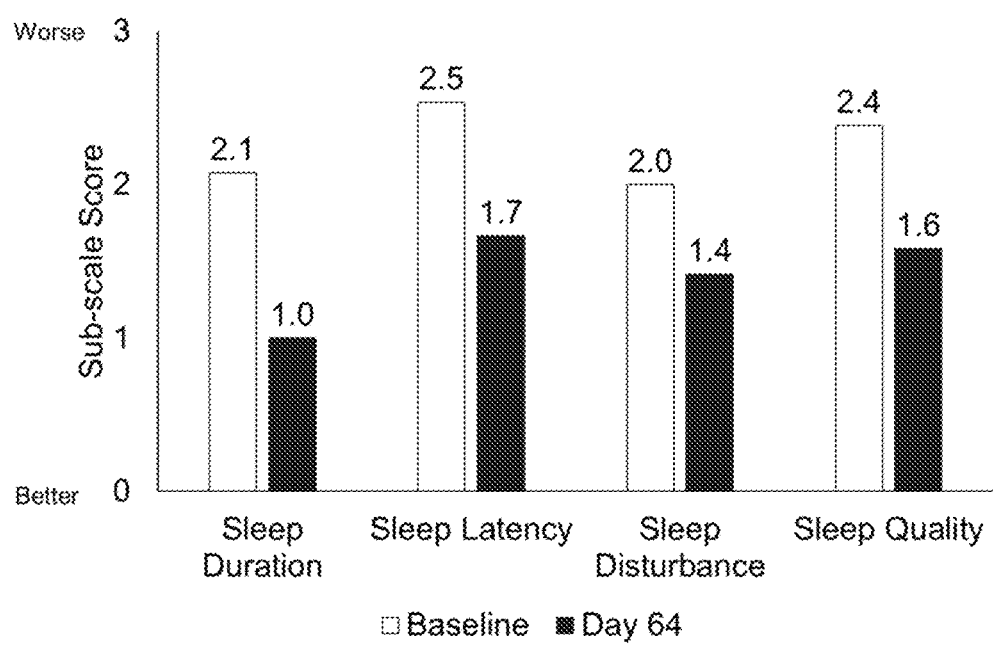

FIGS. 43A-43B: Change from baseline of the Pittsburgh Sleep Quality Index (PSQI) Total Score (FIG. 43A) and the PSQI Subscale Scores (FIG. 43B) for the Open-Label Study (IMPACT-1) of methylone to treat PTSD.

FIG. 44: Methylone induced neuroplasticity in vitro. Graph shows the length of the 20 longest neurites from cultured neurons stimulated by methylone or vehicle.

Figure 45:
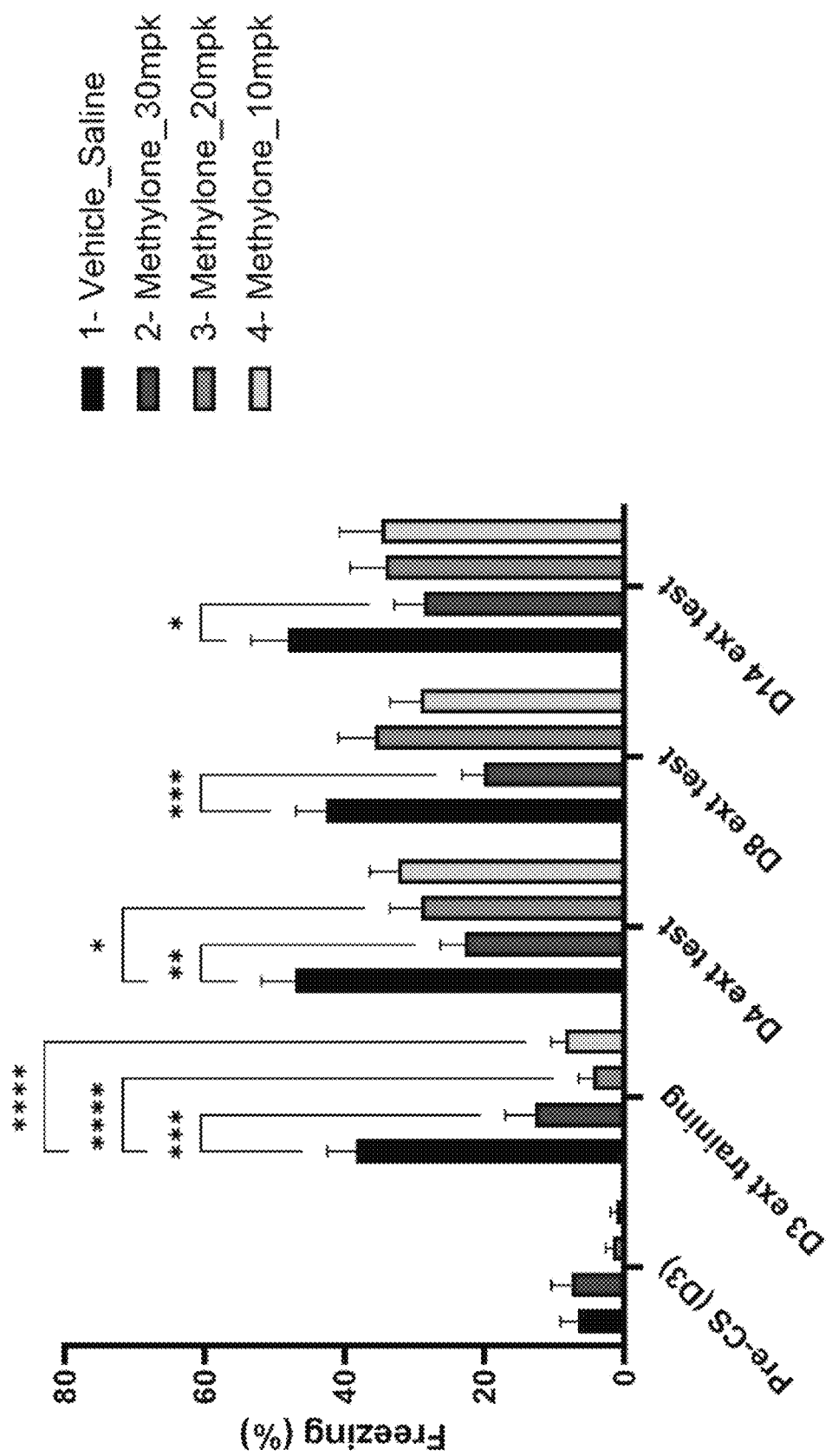

FIG. 45: Methylone showed rapid, robust and long-lasting improvement in fear extinction training and recall. The graph shows the percent time spent freezing during cue presentation before the tone was presented (pre-CS) and during extinction training on day 3 and during the extinction tests on days 4, 8, and 14. *p<0.05, p0.01, p<0.001, ****p<0.0001 compared to vehicle, N=15 per group.

DETAILED DESCRIPTION OF THE INVENTION

The present inventors identify methylone as a suitable agent for the treatment of CNS disorders. Methylone (3,4-methylenedioxy-N-methylcathinone; also known as "βk-MDMA") is a synthetic empathogenic cathinone and a close structural analog of MDMA, but with a >50% shorter half-life. There are no FDA-registered clinical trials of its efficacy or safety profile, after its placement into Schedule I restricted status by the United States DEA in 2010. Methylone and MDMA resemble amphetamines and are agonists of the 5-HT$_2$ family of serotonin receptors. In vitro release assays using rat brain synaptosomes reveal that methylone is a nonselective substrate for plasma membrane monoamine transporters and receptors.

Methylone acts as a mixed reuptake inhibitor/releasing agent, and compared to MDMA, has 3× lower affinity for the serotonin transporter, but similar affinity for the norepinephrine and dopamine transporters. This reduced serotonergic pathway predominance is one reason why its efficacy as an antidepressant is not expected. In addition, the "comedown" effects from amphetamines, including MDMA or synthetic cathinones like methylone, include intense depression and fatigue. Methylone produced a widespread depletion of 5-HT and the serotonin transporter 5-HTT levels in rats that resembles a depressed neurological state. Depression has also been reported in humans using methylone. Other adverse effects include anxiety, anorexia, dercalization/depersonalization, impaired short-term memory, psychosis, hallucinations, suicidal ideations, irritability, motivation suppression, thought deceleration, wakefulness, involuntary tremors, bruxism, jaw clenching, trismus, and unsteadiness of the hands and gait.

Taken together, the animal and human data do not point to a potential medical use for methylone as a treatment for CNS disorders, including depression and PTSD. It is unexpected that methylone—with low (est) 5-HT agonism in its class of synthetic cathinones—would be useful for the indications identified by the present inventors in patients with non-response, treatment-resistance, contraindications, or objections to current standard of care. This would include methylone administration either alone or in combination with an SSRI, TCA, MAOI, SNRI, SDNRI, or anxiolytics, e.g., benzodiazepines, β-blockers, alpha-blockers, and buspirone.

The present inventors find that methylone has mainstream potential as a CNS medication, including as an antidepressant or as a treatment for PTSD, or as an anxiolytic. Methylone has advantages compared to current therapies and others in development: better efficacy to safety ratio, faster-acting effect profile, fewer drug-drug interactions, more effective combination therapy, more frequent adjunct in individual or group psychotherapy. Methylone also causes fewer side effects after longer sessions or chronic usage, unlike symptoms of SSRI tolerance as efficacy wears off for a large proportion of patients. SSRI tolerance symptoms include fatigue, loss of motivation, weariness, sleep disorders, restless leg syndrome, irritability, and depressive moods.

The present inventors further identify 2C-B (2,5-dimethoxy-4-bromophenethylamine), as a suitable agent to treat and provide symptom relief in Somatic Symptom Disorders (SSD), Depressive Disorders, PTSD, and other Central Nervous System (CNS) diseases—but especially Fibromyalgia, a syndrome of widespread musculoskeletal pain accompanied by fatigue, sleep, memory and mood disorder symptoms. Fibromyalgia treatments, such as the SNRIs duloxetine and milnacipran, are often outweighed by their potential harms, and only a minority of fibromyalgia patients might experience substantial symptom relief without adverse events.

2C-B is a psychoactive phenethylamine reported to have limited efficacy as a 5-HT$_{2A}$ receptor partial agonist, yet we postulate that it is useful in 5-HT$_{2A}$ implicated pathophysiology. In vitro and in vivo models suggest it acts as a mixed 5-HT$_{2A}$ antagonist, and a 5-HT$_{2B}$ and 5-HT$_{2C}$ partial agonist—receptors which are particularly expressed on apical dendrites of neocortical pyramidal cells in layer V. It is a Schedule 1 drug due to its unfavorable characteristics and potential for abuse, as numerous hospitalizations have been tied to 2C-B ingestion via toxicology studies.

Human Open-Label Studies in experienced drug users who self-administered 2C-B, varying in dose from 10 to 20 mg, found no serious adverse effects. At doses higher than 20 mg, 2C-B users report more euphoria, kaleidoseope vision, and distorted perception.

Chronic psychiatric disorders often share a common core of intractable symptoms that respond favorably to psychoactive medicines, via complex pharmacological effects that may be further modulated by psychotherapy. Patients experience multiple co-occurring symptoms that are related to each other, have independent or concurrent temporal dimensions or gradings of severity, and may have shared underlying mechanisms. Clusters can also be considered "symptom endophenotypes" which cut across syndromes and disorders via neurobiological correlates of brain circuits and neurotransmitters.

Without wishing to be bound by theory, the inventors hypothesize that 2C-B—via an acute, somatically-transformative phenomenology and durable psychoactive pharmacological and physiological effect profile—has a compelling neurobiological rationale to treat SSD, depression, anxiety, PTSD and comorbid conditions. SSDs including Fibromyalgia are often diagnoses of exclusion, with chronic somatic symptoms of indeterminate biological or medical cause. The named entities in the DSM-5 under SSD are illness anxiety disorder/hypochondriasis, functional neurological/conversion disorder, pain disorder (under which fibromyalgia is classified), body dysmorphic disorder, and somatoform disorder "not otherwise specified." They are often comorbid with Mood & Affective disorders, which can include a mood disturbance cluster, and a neuropsychological discomfort cluster. Fibromyalgia patients can be successfully treated with 2C-B at a lower dose range from 1-24 mg, and in combination with other psychoactive medications for CNS disorders.

The present inventors further identify MBDB (N-methyl-1-(1,3-benzodioxol-5-yl)-2-aminobutane) as a suitable agent to treat and provide symptom relief in a wide range of anxiety disorders, or as an antidepressant. Animal and human data do not point to a potential medical use for MBDB as a treatment for CNS disorders, or otherwise. Experimental drug users who self-administered MBDB under supervision in a controlled setting, varying in dose from 100 to 300 mg, found no serious adverse effects. In summary, MBDB can be used as an anxiolytic, and this treatment effect can be reliably evaluated using measures such as the GAD-7 or the Generalized Anxiety Disorder Severity Scale (GADSS).

In one aspect, provided herein are methods of treating and/or preventing a neuropsychiatric illness and/or ameliorating a symptom thereof in a subject in need thereof, comprising administering a therapeutically effective amount of methylone (3,4-methylenedioxy-N-methylcathinone) or a pharmaceutical composition thereof to the subject. In some embodiments, the methylone dose ranges from 0.08-4 mg/kg. In some embodiments, the methylone dose ranges from 0.8-5 mg/kg. In some embodiments, the methylone dose ranges from 0.8-30 mg/kg. In some embodiments, the methylone dose ranges from 5-250 mg. In some embodiments, the methylone dose is less than 50 mg. In some embodiments, the methylone dose ranges from 5-50 mg. In some embodiments, the methylone dose is less than 25 mg. In some embodiments, the methylone dose ranges from 5-25 mg. In some embodiments, the methylone dose ranges from 50-350 mg. In some embodiments, the methylone dose ranges from 50-500 mg. In some embodiments, the methylone dose ranges from 50-1,000 mg. In some embodiments, the methylone is administered weekly. In some embodiments, the methylone is administered more frequently than weekly (e.g., daily). In some embodiments, the methylone is administered less frequently than weekly. In some embodiments, an initial dose of methylone (e.g., 50-500 mg) is administered, which is then boosted 30 minutes-4 hours later by administering a second methylone dose (e.g., an additional 25-250 mg of methylone). In some embodiments, the methylone is administered, e.g., as a single dose or according to the foregoing dosing schedule, once a week or twice or more times per week (up to daily dosing) or two or three times a day. In some embodiments, the methylone is administered as an extended release or sustained release formulation, for example, to achieve a dosing regimen disclosed herein and releasing 50 mg to 1 g on a set schedule to patients according to the indication(s) being treated in those patients. In some embodiments, the subject is suicidal. In some embodiments, the neuropsychiatric illness is treatment-resistant. In some embodiments, the methylone is used in combination with an additional therapy for the neuropsychiatric illness. In some embodiments, the additional therapy is psychotherapy. In some embodiments, the additional therapy comprises administering one or more additional psychoactive agents to the subject. In some embodiments, the additional psychoactive agents are selected from the group consisting of selective-serotonin reuptake (SSRIs), tricyclic antidepressants (TCAs), monoamine oxidase inhibitors (MAOIs), serotonin-norepinephrine reuptake inhibitors (SNRIs), serotonin-norepinephrine-dopamine reuptake inhibitors (SDNRIs), and anxiolytic agents.

In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is post-traumatic stress disorder (PTSD). In some embodiments, the neuropsychiatric illness is acute stress disorder. In some embodiments, the neuropsychiatric illness is Fibromyalgia. In some embodiments, the neuropsychiatric illness is a mood disorder. In some embodiments, the neuropsychiatric illness is an anxiety disorder. In some embodiments, the neuropsychiatric illness is an eating disorder. In some embodiments, the neuropsychiatric illness is a Personality Disorder (PD). In some embodiments, the Personality Disorder is selected from the group consisting of Borderline Personality Disorder (BPD), Avoidant Personality Disorder (AvPD), Antisocial Personality Disorder (AsPD), Schizotypal Personality Disorder, Other Anxiety and Panic producing Disorders, Specific personality disorders, Impulse disorders, Gender identity disorders, Paraphilias, Other sexual disorders, Other disorders of adult personality and behavior, Unspecified disorder of adult personality and behavior, Personality and behavioral disorders due to known physiological conditions. In some embodiments, the subject with the PD also has a Depressive Disorder. In some embodiments, the neuropsychiatric illness is a substance use disorder (SUD), such as an opioid use disorder (OUD).

In some embodiments, the pharmaceutical composition comprises a pharmaceutically acceptable salt of methylone. In some embodiments, the pharmaceutical composition comprises an enantiomer of methylone. In some embodiments, the pharmaceutical composition comprises an isotopologue and/or an isotopomer of methylone. In some embodiments, the pharmaceutical composition comprises a solvate (e.g., a hydrate) of methylone. In some embodiments, the pharmaceutical composition comprises a prodrug of methylone. In some embodiments, the pharmaceutical composition comprises a polymorph of methylone.

In another aspect, provided herein are methods of treating and/or preventing a neuropsychiatric illness and/or ameliorating a symptom thereof in a subject in need thereof, comprising administering a therapeutically effective amount of 2C-B (4-Bromo-2,5-dimethoxyphenethylamine) to the subject. In some embodiments, the 2C-B dose ranges from 0.08-4 mg/kg. In some embodiments, the 2C-B dose ranges from 0.8-5 mg/kg. In some embodiments, the 2C-B dose ranges from 0.8-30 mg/kg. In some embodiments, the 2C-B dose ranges from 5-250 mg. In some embodiments, the 2C-B dose is less than 50 mg. In some embodiments, the 2C-B dose ranges from 5-50 mg. In some embodiments, the 2C-B dose is less than 25 mg. In some embodiments, the 2C-B dose ranges from 5-25 mg. In some embodiments, the 2C-B dose ranges from 50-350 mg. In some embodiments, the 2C-B dose ranges from 50-500 mg. In some embodiments, the 2C-B dose ranges from 50-1,000 mg. In some embodiments, the 2C-B is administered weekly. In some embodiments, the 2C-B is administered more frequently than weekly (e.g., daily). In some embodiments, the 2C-B is administered less frequently than weekly. In some embodiments, an initial dose of 2C-B is administered (e.g., 50-500 mg), which is then boosted 30 minutes-4 hours later by administering a second 2C-B dose (e.g., an additional 25-250 mg of 2C-B). In some embodiments, the 2C-B is administered, e.g., as a single dose or according to the foregoing dosing schedule, once a week or twice or more per week (up to daily dosing) or two or three times a day. In some embodiments, the 2C-B is administered as an extended release or sustained release formulation, for example, to achieve a dosing regimen disclosed herein and releasing 50 mg to 1 g on a set schedule to patients according to the indication(s) being treated in those patients.

In some embodiments, the neuropsychiatric illness is a Somatic Symptom Disorders. In some embodiments, the Somatic Symptom Disorder is selected from the group consisting of Illness Anxiety Disorder, Conversion Disorder (Functional Neurological Symptom Disorder), Psychological Factors Affecting Other Medical Conditions, Factitious Disorder, Other Specified Somatic Symptom and Related Disorder, Unspecified Somatic Symptom and Related Disorder, and combinations thereof. In some embodiments, the neuropsychiatric illness is Fibromyalgia. In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is post-traumatic stress disorder (PTSD). In some embodiments, the neuropsychiatric illness is acute stress disorder. In some embodiments, the neuropsychiatric illness is a mood disorder. In some embodiments, the neuropsychiatric illness is an anxiety disorder. In some embodiments, the neuropsychiatric illness is an eating disorder. In some embodiments, the subject is suicidal. In some embodiments, the neuropsychiatric illness is treatment-resistant. In some embodiments, the 2C-B is used in combination with an additional therapy for the neuropsychiatric illness. In some embodiments, the additional therapy is psychotherapy. In some embodiments, the additional therapy comprises administering one or more additional psychoactive agents to the subject. In some embodiments, the additional psychoactive agents are selected from the group consisting of SSRIs, TCAs, MAOIs, SNRIs, SDNRIs, and anxiolytics. In some embodiments, the neuropsychiatric illness is a substance use disorder (SUD), such as an opioid use disorder (OUD).

In some embodiments, the pharmaceutical composition comprises a pharmaceutically acceptable salt of 2C-B. In some embodiments, the pharmaceutical composition comprises an enantiomer of 2C-B. In some embodiments, the pharmaceutical composition comprises an isotopologue and/or an isotopomer of 2C-B. In some embodiments, the pharmaceutical composition comprises a solvate (e.g., a hydrate) of 2C-B. In some embodiments, the pharmaceutical composition comprises a prodrug of 2C-B. In some embodiments, the pharmaceutical composition comprises a polymorph of 2C-B.

In another aspect, provided herein are methods of treating and/or preventing a neuropsychiatric illness and/or ameliorating a symptom thereof in a subject in need thereof, comprising administering a therapeutically effective amount of MBDB (N-methyl-1-(1,3-benzodioxol-5-yl)-2-aminobutane) to the subject. In some embodiments, the MBDB dose ranges from 0.08-4 mg/kg. In some embodiments, the MBDB dose ranges from 0.8-5 mg/kg. In some embodiments, the MBDB dose ranges from 0.8-30 mg/kg. In some embodiments, the MBDB dose ranges from 5-250 mg. In some embodiments, the MBDB dose is less than 50 mg. In some embodiments, the MBDB dose ranges from 5-50 mg. In some embodiments, the MBDB dose is less than 25 mg. In some embodiments, the MBDB dose ranges from 5-25 mg. In some embodiments, the MBDB dose ranges from 50-350 mg. In some embodiments, the MBDB dose ranges from 50-500 mg. In some embodiments, the MBDB dose ranges from 50-1,000 mg. In some embodiments, the MBDB is administered daily. In some embodiments, the MBDB is administered less frequently than daily (e.g., twice a week). In some embodiments, the MBDB is administered weekly. In some embodiments, the MBDB is administered less frequently than weekly. In some embodiments, an initial dose of MBDB is administered (e.g., 50-500 mg), which is then boosted 30 minutes-4 hours later by administering a second MBDB dose, e.g., an additional 25-250 mg of MBDB. In some embodiments, the MBDB is administered, e.g., as a single dose or according to the foregoing dosing schedule, once a week or twice or more per week (up to daily dosing) or two or three times a day. In some embodiments, the MBDB is administered as an extended release or sustained release formulation, for example, to achieve a dosing regimen disclosed herein and releasing 50 mg to 1 g on a set schedule to patients according to the indication(s) being treated in those patients.

In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder ((Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is an Anxiety Disorder. In some embodiments, the Anxiety Disorder is selected from the group consisting of Generalized anxiety disorder, Panic disorder, Panic attack, Phobic anxiety disorders, Illness Anxiety Disorder, dissociative, stress-related, somatoform other nonpsychotic mental disorders, acute stress reaction, transient adjustment reaction, neurasthenia, psychophysiologic disorders, Obsessive-compulsive disorder, Reaction to severe stress and adjustment disorders, Separation Anxiety Disorder, episodic paroxysmal anxiety, Selective Mutism, Specific Phobia, Social Anxiety Disorder (Social Phobia), Agoraphobia, Substance/Medication-Induced Anxiety Disorder, Anxiety Disorder Due to Another Medical Condition, Anxiety in pregnancy and childbirth, Anxiety in pregnancy antepartum (before childbirth), Anxiety postpartum, Animal type phobia, Arachnophobia, Other animal type phobia, Natural environment type phobia, Fear of thunderstorms, Fear of blood, Fear of injections and transfusions, Fear of other medical care, Fear of injury, Situational type phobia, Claustrophobia, Acrophobia, Other Unspecified Anxiety Disorder, Body Dysmorphic Disorder Hoarding Disorder Trichotillomania (Hair-Pulling Disorder) Excoriation (Skin-Picking), and combinations thereof. In some embodiments, the subject is suicidal. In some embodiments, the neuropsychiatric illness is treatment-resistant. In some embodiments, the neuropsychiatric illness is post-traumatic stress disorder (PTSD). In some embodiments, the neuropsychiatric illness is acute stress disorder. In some embodiments, the neuropsychiatric illness is Fibromyalgia. In some embodiments, the MBDB is used in combination with an additional therapy for the neuropsychiatric illness. In some embodiments, the additional therapy is psychotherapy. In some embodiments, the additional therapy comprises administering one or more additional psychoactive agents to the subject. In some embodiments, the additional psychoactive agents are selected from the group consisting of SSRIs, TCAs, MAOIs, SNRIs, SDNRIs, and anxiolytics. In some embodiments, the neuropsychiatric illness is a substance use disorder (SUD), such as an opioid use disorder (OUD).

In some embodiments, the pharmaceutical composition comprises a pharmaceutically acceptable salt of MBDB. In some embodiments, the pharmaceutical composition comprises an enantiomer of MBDB. In some embodiments, the pharmaceutical composition comprises an isotopologue and/or an isotopomer of MBDB. In some embodiments, the pharmaceutical composition comprises a solvate (e.g., a hydrate) of MBDB. In some embodiments, the pharmaceutical composition comprises a prodrug of MBDB. In some embodiments, the pharmaceutical composition comprises a polymorph of MBDB.

In another aspect, provided herein are methods of treating and/or alleviating pain in a subject in need thereof, comprising administering a therapeutically effective amount of methylone (3,4-methylenedioxy-N-methylcathinone) or a pharmaceutical composition thereof to the subject. In some embodiments, the methylone dose ranges from 0.08-4 mg/kg. In some embodiments, the methylone dose ranges from 0.8-5 mg/kg. In some embodiments, the methylone dose ranges from 0.8-30 mg/kg. In some embodiments, the methylone dose ranges from 5-250 mg. In some embodiments, the methylone dose is less than 50 mg. In some embodiments, the methylone dose ranges from 5-50 mg. In some embodiments, the methylone dose is less than 25 mg. In some embodiments, the methylone dose ranges from 5-25 mg. In some embodiments, the methylone dose ranges from 50-350 mg. In some embodiments, the methylone dose ranges from 50-500 mg. In some embodiments, the methylone dose ranges from 50-1,000 mg. In some embodiments, the methylone is administered weekly. In some embodiments, the methylone is administered more frequently than weekly (e.g., daily). In some embodiments, the methylone is administered less frequently than weekly. In some embodiments, an initial dose of methylone (e.g., 50-500 mg) is administered, which is then boosted 30 minutes-4 hours later by administering a second methylone dose (e.g., an additional 25-250 mg of methylone). In some embodiments, the methylone is administered, e.g., as a single dose or according to the foregoing dosing schedule, once a week or twice or more times per week (up to daily dosing) or two or three times a day. In some embodiments, the methylone is administered as an extended release or sustained release formulation, for example, to achieve a dosing regimen disclosed herein and releasing 50 mg to 1 g on a set schedule to patients according to the indication(s) being treated in those patients. In some embodiments, the methylone is used in combination with an additional therapy for pain. In some embodiments, the subject has acute pain, such as surgical and procedural pain, pain due to trauma/injury, or pain due to acute inflammatory processes. In some embodiments, the subject has chronic pain, such as cancer pain, neuropathic pain, fibromyalgia, osteoarthritis pain, or low back pain. In some embodiments, the pharmaceutical composition comprises a pharmaceutically acceptable salt of methylone. In some embodiments, the pharmaceutical composition comprises an enantiomer of methylone. In some embodiments, the pharmaceutical composition comprises an isotopologue and/or an isotopomer of methylone. In some embodiments, the pharmaceutical composition comprises a solvate (e.g., a hydrate) of methylone. In some embodiments, the pharmaceutical composition comprises a prodrug of methylone. In some embodiments, the pharmaceutical composition comprises a polymorph of methylone.

In another aspect, provided herein are methods of treating and/or alleviating pain in a subject in need thereof, comprising administering a therapeutically effective amount of 2C-B (4-Bromo-2,5-dimethoxyphenethylamine) to the subject. In some embodiments, the 2C-B dose ranges from 0.08-4 mg/kg. In some embodiments, the 2C-B dose ranges from 0.8-5 mg/kg. In some embodiments, the 2C-B dose ranges from 0.8-30 mg/kg. In some embodiments, the 2C-B dose ranges from 5-250 mg. In some embodiments, the 2C-B dose is less than 50 mg. In some embodiments, the 2C-B dose ranges from 5-50 mg. In some embodiments, the 2C-B dose is less than 25 mg. In some embodiments, the 2C-B dose ranges from 5-25 mg. In some embodiments, the 2C-B dose ranges from 50-350 mg. In some embodiments, the 2C-B dose ranges from 50-500 mg. In some embodiments, the 2C-B dose ranges from 50-1,000 mg. In some embodiments, the 2C-B is administered weekly. In some embodiments, the 2C-B is administered more frequently than weckly (e.g., daily). In some embodiments, the 2C-B is administered less frequently than weekly. In some embodiments, an initial dose of 2C-B is administered (e.g., 50-500 mg), which is then boosted 30 minutes-4 hours later by administering a second 2C-B dose (e.g., an additional 25-250 mg of 2C-B). In some embodiments, the 2C-B is administered, e.g., as a single dose or according to the foregoing dosing schedule, once a week or twice or more per week (up to daily dosing) or two or three times a day. In some embodiments, the 2C-B is administered as an extended release or sustained release formulation, for example, to achieve a dosing regimen disclosed herein and releasing 50 mg to 1 g on a set schedule to patients according to the indication(s) being treated in those patients. In some embodiments, the 2C-B is used in combination with an additional therapy for pain. In some embodiments, the subject has acute pain, such as surgical and procedural pain, pain due to trauma/injury, or pain due to acute inflammatory processes. In some embodiments, the subject has chronic pain, such as cancer pain, neuropathic pain, fibromyalgia, osteoarthritis pain, or low back pain. In some embodiments, the pharmaceutical composition comprises a pharmaceutically acceptable salt of 2C-B. In some embodiments, the pharmaceutical composition comprises an enantiomer of 2C-B. In some embodiments, the pharmaceutical composition comprises an isotopologue and/or an isotopomer of 2C-B. In some embodiments, the pharmaceutical composition comprises a solvate (e.g., a hydrate) of 2C-B. In some embodiments, the pharmaceutical composition comprises a prodrug of 2C-B. In some embodiments, the pharmaceutical composition comprises a polymorph of 2C-B.

In another aspect, provided herein are methods of treating and/or alleviating pain in a subject in need thereof, comprising administering a therapeutically effective amount of MBDB (N-methyl-1-(1,3-benzodioxol-5-yl)-2-aminobutane) to the subject. In some embodiments, the MBDB dose ranges from 0.08-4 mg/kg. In some embodiments, the MBDB dose ranges from 0.8-5 mg/kg. In some embodiments, the MBDB dose ranges from 0.8-30 mg/kg. In some embodiments, the MBDB dose ranges from 5-250 mg. In some embodiments, the MBDB dose is less than 50 mg. In some embodiments, the MBDB dose ranges from 5-50 mg. In some embodiments, the MBDB dose is less than 25 mg. In some embodiments, the MBDB dose ranges from 5-25 mg. In some embodiments, the MBDB dose ranges from 50-350 mg. In some embodiments, the MBDB dose ranges from 50-500 mg. In some embodiments, the MBDB dose ranges from 50-1,000 mg. In some embodiments, the MBDB is administered daily. In some embodiments, the MBDB is administered less frequently than daily (e.g., twice a week). In some embodiments, the MBDB is administered weekly. In some embodiments, the MBDB is administered less frequently than weekly. In some embodiments, an initial dose of MBDB is administered (e.g., 50-500 mg), which is then boosted 30 minutes-4 hours later by administering a second MBDB dose, e.g., an additional 25-250 mg of MBDB. In some embodiments, the MBDB is administered, e.g., as a single dose or according to the foregoing dosing schedule, once a week or twice or more per week (up to daily dosing) or two or three times a day. In some embodiments, the MBDB is administered as an extended release or sustained release formulation, for example, to achieve a dosing regimen disclosed herein and releasing 50 mg to 1 g on a set schedule to patients according to the indication(s) being treated in those patients. In some embodiments, the MBDB is used in combination with an additional therapy for pain. In some embodiments, the subject has acute pain, such as surgical and procedural pain, pain due to trauma/injury, or pain due to acute inflammatory processes. In some embodiments, the subject has chronic pain, such as cancer pain, neuropathic pain, fibromyalgia, osteoarthritis pain, or low back pain. In some embodiments, the pharmaceutical composition comprises a pharmaceutically acceptable salt of MBDB. In some embodiments, the pharmaceutical composition comprises an enantiomer of MBDB. In some embodiments, the pharmaceutical composition comprises an isotopologue and/or an isotopomer of MBDB. In some embodiments, the pharmaceutical composition comprises a solvate (e.g., a hydrate) of MBDB. In some embodiments, the pharmaceutical composition comprises a prodrug of MBDB. In some embodiments, the pharmaceutical composition comprises a polymorph of MBDB.

In another aspect, provided herein are methods of improving sleep in a subject in need thereof, comprising administering a therapeutically effective amount of methylone (3,4-methylenedioxy-N-methylcathinone) or a pharmaceutical composition thereof to the subject. In some embodiments, the methylone dose ranges from 0.08-4 mg/kg. In some embodiments, the methylone dose ranges from 0.8-5 mg/kg. In some embodiments, the methylone dose ranges from 0.8-30 mg/kg. In some embodiments, the methylone dose ranges from 5-250 mg. In some embodiments, the methylone dose is less than 50 mg. In some embodiments, the methylone dose ranges from 5-50 mg. In some embodiments, the methylone dose is less than 25 mg. In some embodiments, the methylone dose ranges from 5-25 mg. In some embodiments, the methylone dose ranges from 50-350 mg. In some embodiments, the methylone dose ranges from 50-500 mg. In some embodiments, the methylone dose ranges from 50-1,000 mg. In some embodiments, the methylone is administered weekly. In some embodiments, the methylone is administered more frequently than weekly (e.g., daily). In some embodiments, the methylone is administered less frequently than weekly. In some embodiments, an initial dose of methylone (e.g., 50-500 mg) is administered, which is then boosted 30 minutes-4 hours later by administering a second methylone dose (e.g., an additional 25-250 mg of methylone). In some embodiments, the methylone is administered, e.g., as a single dose or according to the foregoing dosing schedule, once a week or twice or more times per week (up to daily dosing) or two or three times a day. In some embodiments, the methylone is administered as an extended release or sustained release formulation, for example, to achieve a dosing regimen disclosed herein and releasing 50 mg to 1 g on a set schedule to patients according to the indication(s) being treated in those patients. In some embodiments, the methylone is used in combination with an additional therapy to improve sleep. In some embodiments, improvement in sleep comprises an improvement from baseline in the Pittsburgh Sleep Quality Index (PSQI) for the subject. In some embodiments, improvement in sleep comprises an improvement from baseline of sleep duration, and/or sleep latency, and/or sleep disturbance, and/or sleep quality. In some embodiments, the pharmaceutical composition comprises a pharmaceutically acceptable salt of methylone. In some embodiments, the pharmaceutical composition comprises an enantiomer of methylone. In some embodiments, the pharmaceutical composition comprises an isotopologue and/or an isotopomer of methylone. In some embodiments, the pharmaceutical composition comprises a solvate (e.g., a hydrate) of methylone. In some embodiments, the pharmaceutical composition comprises a prodrug of methylone. In some embodiments, the pharmaceutical composition comprises a polymorph of methylone.

In another aspect, provided herein are methods of treating a neuropsychiatric illness, and/or ameliorating a symptom thereof in a subject in need thereof, comprising administering to the subject a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a polymorph thereof and/or a prodrug thereof in a therapeutically effective amount that results in a plasma $C_{max}$ of methylone of 15-3,020 ng/ml in the subject. In some embodiments, the resulting plasma $C_{max}$ of methylone of 153-3,020 ng/mL in the subject. In some embodiments, the resulting plasma $C_{max}$ of methylone of 153-755 ng/mL in the subject. Also provided herein are methods of treating a neuropsychiatric illness, and/or ameliorating a symptom thereof in a subject in need thereof, comprising administering to the subject a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a polymorph thereof and/or a prodrug thereof in a therapeutically effective amount that results in a plasma $AUC_{0-24}$ of methylone of 104-25,350 ng·h/mL in the subject. In some embodiments, the resulting plasma $AUC_{0-24}$ of methylone of 1,042-25,350 ng·h/mL in the subject. In some embodiments, the resulting plasma $AUC_{0-24}$ of methylone of 104-6,340 ng·h/mL in the subject. In some embodiments, the subject is suicidal. In some embodiments, the neuropsychiatric illness is treatment-resistant. In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is post-traumatic stress disorder (PTSD). In some embodiments, the neuropsychiatric illness is acute stress disorder. In some embodiments, the neuropsychiatric illness is Fibromyalgia. In some embodiments, the neuropsychiatric illness is a mood disorder. In some embodiments, the neuropsychiatric illness is an anxiety disorder. In some embodiments, the neuropsychiatric illness is an eating disorder. In some embodiments, the neuropsychiatric illness is a Personality Disorder (PD). In some embodiments, the Personality Disorder is selected from the group consisting of Borderline Personality Disorder (BPD), Avoidant Personality Disorder (AvPD), Antisocial Personality Disorder (AsPD), Schizotypal Personality Disorder, Other Anxiety and Panic producing Disorders, Specific personality disorders, Impulse disorders, Gender identity disorders, Paraphilias, Other sexual disorders, Other disorders of adult personality and behavior, Unspecified disorder of adult personality and behavior, Personality and behavioral disorders due to known physiological conditions. In some embodiments, the subject with the PD also has a Depressive Disorder.

In another aspect, provided herein are methods of treating a neuropsychiatric illness, and/or ameliorating a symptom thereof in a subject in need thereof, comprising administering to the subject a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a polymorph thereof and/or a prodrug thereof in a therapeutically effective amount that results in a plasma $C_{max}$ of methylone of 98-994 ng/mL in the subject. In some embodiments, the resulting plasma $C_{max}$ of methylone of 210-882 ng/ml in the subject. In some embodiments, the resulting plasma $C_{max}$ of methylone of 322-770 ng/ml in the subject. In some embodiments, the resulting plasma $C_{max}$ of methylone of 434-658 ng/mL in the subject. In some embodiments, the resulting plasma $C_{max}$ of methylone of about 546 ng/ml in the subject. Also provided herein are methods of treating a neuropsychiatric illness, and/or ameliorating a symptom thereof in a subject in need thereof, comprising administering to the subject a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a polymorph thereof and/or a prodrug thereof in a therapeutically effective amount that results in a plasma $AUC_{0-24}$ of methylone of 47-10,983 ng·h/mL in the subject. In some embodiments, the resulting plasma $AUC_{0-24}$ of methylone of 1,414-9,616 ng·h/mL in the subject. In some embodiments, the resulting plasma $AUC_{0-24}$ of methylone of 2,781-8,249 ng·h/mL in the subject. In some embodiments, the resulting plasma $AUC_{0-24}$ of methylone of 4,148-6,682 ng·h/mL in the subject. In some embodiments, the resulting plasma $AUC_{0-24}$ of methylone of about 5,515 ng·h/mL in the subject. In some embodiments, the subject is suicidal. In some embodiments, the neuropsychiatric illness is treatment-resistant. In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is post-traumatic stress disorder (PTSD). In some embodiments, the neuropsychiatric illness is acute stress disorder. In some embodiments, the neuropsychiatric illness is Fibromyalgia. In some embodiments, the neuropsychiatric illness is a mood disorder. In some embodiments, the neuropsychiatric illness is an anxiety disorder. In some embodiments, the neuropsychiatric illness is an eating disorder. In some embodiments, the neuropsychiatric illness is a Personality Disorder (PD). In some embodiments, the Personality Disorder is selected from the group consisting of Borderline Personality Disorder (BPD), Avoidant Personality Disorder (AvPD), Antisocial Personality Disorder (AsPD), Schizotypal Personality Disorder, Other Anxiety and Panic producing Disorders, Specific personality disorders, Impulse disorders, Gender identity disorders, Paraphilias, Other sexual disorders, Other disorders of adult personality and behavior, Unspecified disorder of adult personality and behavior, Personality and behavioral disorders due to known physiological conditions. In some embodiments, the subject with the PD also has a Depressive Disorder.

For the methods provided herein, methylone (including stereoisomers, isotopologues and isotopomers thereof) concentrations may be measured and pharmacokinetic parameters may be calculated using any suitable techniques in the art. For example, plasma methylone (including stereoisomers, isotopologues and isotopomers thereof) concentrations may be measured using biological assays or chemical assays. Such techniques include, but are not limited to, liquid chromatography coupled to tandem mass spectrometry (LC-MS/MS), ultraviolet (UV) detection, fluorescence assays, liquid chromatography coupled with ultraviolet detection (LC-UV), and radio-immunoassays.

In another aspect, provided herein are methods of modulating neuroplasticity in a subject in need thereof, comprising administering to the subject a therapeutically effective amount of a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a prodrug thereof, and/or a polymorph thereof. In some embodiments, modulating neuroplasticity comprises increasing neuroplasticity in the subject. In some embodiments, the subject has a neuropsychiatric illness. In some embodiments, the neuropsychiatric illness is post-traumatic stress disorder (PTSD). In some embodiments, the neuropsychiatric illness is acute stress disorder. In some embodiments, the neuropsychiatric illness is a Depressive Disorder. In some embodiments, the neuropsychiatric illness is Fibromyalgia. In some embodiments, the neuropsychiatric illness is an anxiety disorder.

In another aspect, provided herein are methods of treating and/or preventing a neuropsychiatric illness and/or ameliorating a symptom thereof in a subject in need thereof, comprising administering to the subject a therapeutically effective amount of a serotonin-norepinephrine-dopamine reuptake inhibitor and releaser that lacks agonist or antagonist activity at the $5\text{-}HT_{2A}$ and $5\text{-}HT_{2B}$ receptors. In some embodiments, the serotonin-norepinephrine-dopamine reuptake inhibitor and releaser lacks agonist or antagonist activity at the 168 G-protein coupled receptors (GPCRs) set forth in Table 6. In some embodiments, the serotonin-norepinephrine-dopamine reuptake inhibitor and releaser has a $K_i$ for $5\text{-}HT_{2A}$ greater than or equal to 8 µM and a Ki for $5\text{-}HT_{2B}$ greater than or equal to 1 µM. In some embodiments, the serotonin-norepinephrine-dopamine reuptake inhibitor and releaser has reuptake inhibition ($IC_{50}$) of less than or equal to 3 µM at the serotonin transporter (SERT), and less than or equal to 1 µM at the norepinephrine transporter (NET), and less than or equal to 4 µM at the dopamine transporter (DAT); and $EC_{50}$ values for neurotransmitter release of less than or equal to 2 µM at the SERT, and less than or equal to 1 µM at the NET and less than or equal to 6 µM at the DAT. In some embodiments, the serotonin-norepinephrine-dopamine reuptake inhibitor and releaser has reuptake inhibition ($IC_{50}$) of less than or equal to 1 µM at the SERT), and less than or equal to 0.5 µM at the NET, and less than or equal to 3 µM at the DAT; and an $EC_{50}$ value for neurotransmitter release of greater than or equal to 2 µM at the DAT. In some embodiments, agonist or antagonist activity is determined using an in vitro β-arrestin based screen and a concentration of 1 µM of the serotonin-norepinephrine-dopamine reuptake inhibitor and releaser, and a threshold for agonist activity is less than 30% and a threshold for antagonist activity is less than 50%.

In some embodiments, agonist or antagonist activity is determined using an in vitro β-arrestin based screen and a concentration of 10 µM of the serotonin-norepinephrine-dopamine reuptake inhibitor and releaser, and a threshold for agonist activity is less than 30% and a threshold for antagonist activity is less than 50%. In some embodiments, the subject is suicidal. In some embodiments, the neuropsychiatric illness is treatment-resistant. In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is post-traumatic stress disorder (PTSD). In some embodiments, the neuropsychiatric illness is acute stress disorder. In some embodiments, the neuropsychiatric illness is Fibromyalgia. In some embodiments, the neuropsychiatric illness is a mood disorder. In some embodiments, the neuropsychiatric illness is an anxiety disorder. In some embodiments, the neuropsychiatric illness is an eating disorder. In some embodiments, the neuropsychiatric illness is a Personality Disorder (PD). In some embodiments, the Personality Disorder is selected from the group consisting of Borderline Personality Disorder (BPD), Avoidant Personality Disorder (AvPD), Antisocial Personality Disorder (AsPD), Schizotypal Personality Disorder, Other Anxiety and Panic producing Disorders, Specific personality disorders, Impulse disorders, Gender identity disorders, Paraphilias, Other sexual disorders, Other disorders of adult personality and behavior, Unspecified disorder of adult personality and behavior, Personality and behavioral disorders due to known physiological conditions. In some embodiments, the subject with the PD also has a Depressive Disorder. In some embodiments, the serotonin-norepinephrine-dopamine reuptake inhibitor and releaser is non-hallucinogenic and/or non-psychedelic and/or non-dissociative.

In some embodiments, the serotonin-norepinephrine-dopamine reuptake inhibitor and releaser is an enantiomer of methylone. In some embodiments, the serotonin-norepinephrine-dopamine reuptake inhibitor and releaser is an isotopologue and/or an isotopomer of methylone. In some embodiments, the serotonin-norepinephrine-dopamine reuptake inhibitor and releaser is a prodrug of methylone.

In another aspect, provided herein are methods for screening a compound to identify whether it is a potential therapeutic for a neuropsychiatric illness. In some embodiments, the methods comprise: (a) determining whether the compound is a serotonin-norepinephrine-dopamine reuptake inhibitor and releaser; and (b) measuring agonist and antagonist activity of the compound at the $5-HT_{2A}$ and $5-HT_{2B}$ receptors, wherein a determination that the compound is a serotonin-norepinephrine-dopamine reuptake inhibitor and releaser and that the compound lacks agonist or antagonist activity at the $5-HT_{2A}$ and $5-HT_{2B}$ receptors is indicative that the compound is a potential therapeutic for the neuropsychiatric illness. In some embodiments, the methods comprise: (a) determining whether the compound is a serotonin-norepinephrine-dopamine reuptake inhibitor and releaser; and (b) measuring agonist and antagonist activity of the compound at the 168 G-protein coupled receptors (GPCRs) set forth in Table 6, wherein a determination that the compound is a serotonin-norepinephrine-dopamine reuptake inhibitor and releaser and that the compound lacks agonist or antagonist activity at the 168 GPCRs is indicative that the compound is a potential therapeutic for the neuropsychiatric illness.

In some embodiments, agonist and antagonist activity is measured using an in vitro β-arrestin based screen and a concentration of 1 μM of the serotonin-norepinephrine-dopamine reuptake inhibitor and releaser, and a threshold for agonist activity is less than 30% and a threshold for antagonist activity is less than 50%. In some embodiments, agonist and antagonist activity is measured using an in vitro β-arrestin based screen and a concentration of 10 μM of the serotonin-norepinephrine-dopamine reuptake inhibitor and releaser, and a threshold for agonist activity is less than 30% and a threshold for antagonist activity is less than 50%. In some embodiments, the serotonin-norepinephrine-dopamine reuptake inhibitor and releaser has a $K_i$ for $5-HT_{2A}$ greater than or equal to 8 μM and a Ki for $5-HT_{2B}$ greater than or equal to 1 μM. In some embodiments, the serotonin-norepinephrine-dopamine reuptake inhibitor and releaser has reuptake inhibition ($IC_{50}$) of less than or equal to 3 μM at the serotonin transporter (SERT), and less than or equal to 1 μM at the norepinephrine transporter (NET), and less than or equal to 4 μM at the dopamine transporter (DAT); and $EC_{50}$ values for neurotransmitter release of less than or equal to 2 μM at the SERT, and less than or equal to 1 μM at the NET and less than or equal to 6 μM at the DAT. In some embodiments, the serotonin-norepinephrine-dopamine reuptake inhibitor and releaser has reuptake inhibition ($IC_{50}$) of less than or equal to 1 μM at the SERT), and less than or equal to 0.5 μM at the NET, and less than or equal to 3 μM at the DAT; and an $EC_{50}$ value for neurotransmitter release of greater than or equal to 2 μM at the DAT. In some embodiments, the serotonin-norepinephrine-dopamine reuptake inhibitor and releaser is non-hallucinogenic and/or non-psychedelic and/or non-dissociative.

In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is post-traumatic stress disorder (PTSD). In some embodiments, the neuropsychiatric illness is acute stress disorder. In some embodiments, the neuropsychiatric illness is Fibromyalgia. In some embodiments, the neuropsychiatric illness is a mood disorder. In some embodiments, the neuropsychiatric illness is an anxiety disorder. In some embodiments, the neuropsychiatric illness is an eating disorder. In some embodiments, the neuropsychiatric illness is a Personality Disorder (PD). In some embodiments, the Personality Disorder is selected from the group consisting of Borderline Personality Disorder (BPD), Avoidant Personality Disorder (AvPD), Antisocial Personality Disorder (AsPD), Schizotypal Personality Disorder, Other Anxiety and Panic producing Disorders, Specific personality disorders, Impulse disorders, Gender identity disorders, Paraphilias, Other sexual disorders, Other disorders of adult personality and behavior, Unspecified disorder of adult personality and behavior, Personality and behavioral disorders due to known physiological conditions. In some embodiments, the subject with the PD also has a Depressive Disorder.

In another aspect, provided herein are methods for screening whether a serotonin-norepinephrine-dopamine reuptake inhibitor and releaser is a potential treatment for pain. In some embodiments, the method comprises measuring agonist and antagonist activity of the serotonin-norepinephrine-dopamine reuptake inhibitor and releaser at the 5-HT$_{2A}$ and 5-HT$_{2B}$ receptors, wherein a lack of agonist or antagonist activity at the 5-HT$_{2A}$ and 5-HT$_{2B}$ receptors is indicative of a therapeutic for pain. In some embodiments, the methods comprise measuring agonist and antagonist activity of the serotonin-norepinephrine-dopamine reuptake inhibitor and releaser for the 168 G-protein coupled receptors (GPCRs) set forth in Table 6, wherein a lack of agonist or antagonist activity at the 168 GPCRs is indicative of a therapeutic for pain.

In some embodiments, agonist and antagonist activity is measured using an in vitro β-arrestin based screen and a concentration of 1 µM of the serotonin-norepinephrine-dopamine reuptake inhibitor and releaser, and a threshold for agonist activity is less than 30% and a threshold for antagonist activity is less than 50%. In some embodiments, agonist and antagonist activity is measured using an in vitro β-arrestin based screen and a concentration of 10 µM of the serotonin-norepinephrine-dopamine reuptake inhibitor and releaser, and a threshold for agonist activity is less than 30% and a threshold for antagonist activity is less than 50%. In some embodiments, the serotonin-norepinephrine-dopamine reuptake inhibitor and releaser has a K$_i$ for 5-HT$_{2A}$ greater than or equal to 8 µM and a Ki for 5-HT$_{2B}$ greater than or equal to 1 µM. In some embodiments, the serotonin-norepinephrine-dopamine reuptake inhibitor and releaser has reuptake inhibition (IC$_{50}$) of less than or equal to 3 µM at the serotonin transporter (SERT), and less than or equal to 1 µM at the norepinephrine transporter (NET), and less than or equal to 4 µM at the dopamine transporter (DAT); and EC$_{50}$ values for neurotransmitter release of less than or equal to 2 µM at the SERT, and less than or equal to 1 µM at the NET and less than or equal to 6 µM at the DAT. In some embodiments, the serotonin-norepinephrine-dopamine reuptake inhibitor and releaser has reuptake inhibition (IC$_{50}$) of less than or equal to 1 µM at the SERT), and less than or equal to 0.5 µM at the NET, and less than or equal to 3 µM at the DAT; and an EC$_{50}$ value for neurotransmitter release of greater than or equal to 2 µM at the DAT. In some embodiments, the serotonin-norepinephrine-dopamine reuptake inhibitor and releaser is non-halucinogenic and/or non-psychedelic and/or non-dissociative.

In another aspect, provided herein are oral dosage forms comprising methylone and a diluent/binder, a disintegrant, and a lubricant. In some embodiments, the oral dosage form further comprises a surfactant, for example sodium lauryl sulfate and/or Poloxamer 188. In some embodiments, the disintegrant is Croscarmellose Sodium. In some embodiments, the lubricant is magnesium stearate and/or sodium stearyl fumarate. In some embodiments, the diluent/binder is mannitol. In some embodiments, the oral dosage form is a capsule. In some embodiments, the methylone is methylone HCl. In some embodiments, the oral dosage comprises about 50 mg of methylone.

Diseases, conditions, and disorders listed herein are described in the Diagnostic and Statistical Manual of Mental Disorders (DSM-5) published by the American Psychiatric Association, or in International Classification of Diseases (ICD) published by the World Health Organization. A psychiatric illness, condition, disease or disorder includes, without limitation, the following, and all intermediate ICD-10 codes in the ranges defined:

F01-F09 Mental disorders due to known physiological conditions.

F01 Vascular dementia; F02 Dementia in other diseases classified elsewhere; F03 Unspecified dementia; F04 Amnestic disorder due to known physiological condition; F05 Delirium due to known physiological condition; F06 Other mental disorders due to known physiological condition; F07 Personality and behavioral disorders due to known physiological condition; F09 Unspecified mental disorder due to known physiological condition.

F10-F19 Mental and behavioral disorders due to psychoactive substance use

F10 Alcohol related disorders; F11 Opioid related disorders; F12 *Cannabis* related disorders; F13 Sedative, hypnotic, or anxiolytic related disorders; F14 Cocaine related disorders; F15 Other stimulant related disorders; F16 Hallucinogen related disorders; F17 Nicotine dependence; F18 Inhalant related disorders; F19 Other psychoactive substance related disorders. Caffeine-Related Disorders Caffeine Intoxication Caffeine Withdrawal Other Caffeine-Induced Disorders Substance-Related Disorder Non-Substance-Related Disorders Gambling Disorder Neurocognitive Disorders Delirium Other Specified Delirium Unspecified Delirium Major and Mild Neurocognitive Disorders Major Neurocognitive Disorder Mild Neurocognitive Disorder Major or Mild Neurocognitive Disorder Due to Alzheimer's Disease Major or Mild Frontotemporal Neurocognitive Disorder Major or Mild Neurocognitive Disorder With Lewy Bodies Major or Mild Vascular Neurocognitive Disorder Major or Mild Neurocognitive Disorder Due to Traumatic Brain Injury Substance/Medication-Induced Major or Mild Neurocognitive Disorder Major or Mild Neurocognitive Disorder Due to HIV Infection Major or Mild Neurocognitive Disorder Due to Prion Disease Major or Mild Neurocognitive Disorder Due to Parkinson's Disease Major or Mild Neurocognitive Disorder Due to Huntington's Disease Major or Mild Neurocognitive Disorder Due to Another Medical Condition Major or Mild Neurocognitive Disorder Due to Multiple Etiologies Unspecified Neurocognitive Disorder.

F20-F29 Schizophrenia, schizotypal, delusional, and other non-mood psychotic disorders F20 Schizophrenia; F21 Schizotypal disorder; F22 Delusional disorders; F23 Brief psychotic disorder; F24 Shared psychotic disorder; F25 Schizoaffective disorders; F28 Other psychotic disorder not due to a substance or known physiological condition; F29 Unspecified psychosis not due to a substance or known physiological condition.

F30-F39 Mood [affective] disorders

F30 Manic episode; F31 Bipolar disorder; F32 Major depressive disorder, single episode; F33 Major depressive disorder, recurrent; F34 Persistent mood [affective] disorders; F39 Unspecified mood [affective] disorder. Disruptive Mood Dysregulation Disorder, Persistent Depressive Disorder (Dysthymia) Premenstrual Dysphoric Disorder Substance/Medication-Induced Depressive Disorder Depressive Disorder Due to Another Medical Condition Other Specified Depressive Disorder Unspecified Depressive Disorder, Treatment-resistant depression.

F40-F48 Anxiety, dissociative, stress-related, somatoform other nonpsychotic mental disorders F40 Phobic anxiety disorders; F41 Other anxiety disorders; F42 Obsessive-compulsive disorder; F43 Reaction to severe stress, and adjustment disorders; F44 Dissociative and conversion disorders; F45 Somatoform disorders; F48 Other nonpsychotic mental disorders. Anxiety Disorders: Separation Anxiety Disorder Selective Mutism Specific Phobia Social Anxiety Disorder (Social Phobia) Panic Disorder Panic Attack (Specifier) Agoraphobia Generalized Anxiety Disorder Substance/Medication-Induced Anxiety Disorder Anxiety Disorder Due to Another Medical Condition Other Specified Anxiety Disorder Obsessive-Compulsive Disorder Body Dysmorphic Disorder Hoarding Disorder Trichotillomania (Hair-Pulling Disorder) Excoriation (Skin-Picking) Disorder Substance/Medication-Induced Obsessive-Compulsive and Related Disorder Obsessive-Compulsive and Related Disorder Due to Another Medical Condition Other Specified Obsessive-Compulsive and Related Disorder Unspecified Trauma- and Stressor-Related Disorders: Reactive Attachment Disorder Disinhibited Social Engagement Disorder Posttraumatic Stress Disorder Acute Stress Disorder Adjustment Disorders Other Specified Trauma- and Stressor-Related Disorder Unspecified Trauma- and Stressor-Related Disorder Somatic Symptom and Related Disorders: Somatic Symptom Disorder Illness Anxiety Disorder Conversion Disorder (Functional Neurological Symptom Disorder) Psychological Factors Affecting Other Medical Conditions Factitious Disorder Other Specified Somatic Symptom and Related Disorder Unspecified Somatic Symptom and Related Disorder Feeding and Eating Disorders: Pica Rumination Disorder Avoidant/Restrictive Food Intake Disorder Anorexia Nervosa Bulimia Nervosa Binge-Eating Disorder Other Specified Feeding or Eating Disorder Unspecified Feeding or Eating Disorder Sleep-Wake Disorders: Insomnia Disorder Hypersomnolence Disorder Narcolepsy Breathing-Related Sleep Disorders Obstructive Sleep Apnea Hypopnea Central Sleep Apnea Sleep-Related Hypoventilation Circadian Rhythm Sleep-Wake Disorders Parasomnias Non-Rapid Eye Movement Sleep Arousal Disorders Sleepwalking Sleep Terrors Nightmare Disorder Rapid Eye Movement Sleep Behavior Disorder Restless Legs Syndrome Substance/Medication-Induced Sleep Disorder Other Specified Insomnia Disorder Unspecified Insomnia Disorder Other Specified Hypersomnolence Disorder Unspecified Hypersomnolence Disorder Other Specified Sleep-Wake Disorder Unspecified Sleep-Wake Disorder Sexual Dysfunctions: Delayed Ejaculation Erectile Disorder Female Orgasmic Disorder Female Sexual Interest/Arousal Disorder Genito-Pelvic Pain/Penetration Disorder Male Hypoactive Sexual Desire Disorder Premature (Early) Ejaculation Substance/Medication-Induced Sexual Dysfunction Other Specified Sexual Dysfunction Unspecified Sexual Dysfunction Gender Dysphoria Gender Dysphoria Other Specified Gender Dysphoria Unspecified Gender Dysphoria F50-F59 Behavioral syndromes associated with physiological disturbances and physical factors F50 Eating disorders; F51 Sleep disorders not due to a substance or known physiological condition; F52 Sexual dysfunction not due to a substance or known physiological condition; F53 Mental and behavioral disorders associated with the puerperium, not elsewhere classified; F54 Psychological and behavioral factors associated with disorders or diseases classified elsewhere; F55 Abuse of non-psychoactive substances; F59 Unspecified behavioral syndromes associated with physiological disturbances and physical.

F60-F69 Disorders of adult personality and behavior

F60 Specific personality disorders; F63 Impulse disorders; F64 Gender identity disorders; F65 Paraphilias; F66 Other sexual disorders; F68 Other disorders of adult personality and behavior; F69 Unspecified disorder of adult personality and behavior.

Disruptive, Impulse-Control, and Conduct Disorders: Oppositional Defiant Disorder Intermittent Explosive Disorder Conduct Disorder Antisocial Personality Disorder Pyromania Kleptomania Other Specified Disruptive, Impulse-Control, and Conduct Disorder Unspecified Disruptive, Impulse-Control, and Conduct Disorder Personality Disorders General Personality Disorder Cluster A Personality Disorders Paranoid Personality Disorder Schizoid Personality Disorder Schizotypal Personality Disorder Cluster B Personality Disorders Antisocial Personality Disorder Borderline Personality Disorder Histrionic Personality Disorder Narcissistic Personality Disorder Cluster C Personality Disorders Avoidant Personality Disorder Dependent Personality Disorder Obsessive-Compulsive Personality Disorder Other Personality Disorders Personality Change Due to Another Medical Condition Other Specified Personality Disorder Unspecified Personality Disorder Conditions for Further Study Attenuated Psychosis Syndrome Depressive Episodes With Short-Duration Hypomania Persistent Complex Bereavement Disorder Gaming Disorder Neurobehavioral Disorder Associated With Prenatal Alcohol Exposure Suicidal Behavior Disorder Nonsuicidal Self-Injury F70-F79 Intellectual disabilities F70 Mild intellectual disabilities; F71 Moderate intellectual disabilities; F72 Severe intellectual disabilities; F73 Profound intellectual disabilities; F78 Other intellectual disabilities; F79 Unspecified intellectual disabilities F80-F89 Pervasive and specific developmental disorders F80 Specific developmental disorders of speech and language; F81 Specific developmental disorders of scholastic skills; F82 Specific developmental disorder of motor function; F84 Pervasive developmental disorders; F88 Other disorders of psychological development; F89 Unspecified disorder of psychological development. Neurodevelopmental Disorders Intellectual Disabilities Intellectual Disability (Intellectual Developmental Disorder) Global Developmental Delay Unspecified Intellectual Disability (Intellectual Developmental Disorder) Communication Disorders Language Disorder Speech Sound Disorder (previously Phonological Disorder) Childhood-Onset Fluency Disorder (Stuttering) Social (Pragmatic) Communication Disorder Unspecified Communication Disorder Autism Spectrum Disorder Autism Spectrum Disorder Attention-Deficit/Hyperactivity Disorder Attention-Deficit/Hyperactivity Disorder Other Specified Attention-Deficit/Hyperactivity Disorder Unspecified Attention-Deficit/Hyperactivity Disorder Specific Learning Disorder Specific Learning Disorder Motor Disorders Developmental Coordination Disorder Stereotypic Movement Disorder Tic Disorders Tourette's Disorder Persistent (Chronic) Motor or Vocal Tic Disorder Provisional Tic Disorder Other Specified Tic Disorder Unspecified Tic Disorder Other Neurodevelopmental Disorders Other Specified Neurodevelopmental Disorder Unspecified Neurodevelopmental Disorder F90-F98 Behavioral and emotional disorders with onset usually occurring in childhood and adolescence.

F90 Attention-deficit hyperactivity disorders; F91 Conduct disorders; F93 Emotional disorders with onset specific to childhood; F94 Disorders of social functioning with onset specific to childhood and adolescence; F95 Tic disorder; F98 Other behavioral and emotional disorders with onset usually occurring in childhood and adolescence.

As used herein, a neurologic illness, condition, disease or disorder includes, without limitation, the following, and all intermediate ICD-10 codes in the ranges defined:

G00-G09 Inflammatory diseases of the central nervous system
G00 Bacterial meningitis, not elsewhere classified; G01 Meningitis in bacterial diseases classified elsewhere; G02 Meningitis in other infectious and parasitic diseases classified elsewhere; G03 Meningitis due to other and unspecified causes; G04 Encephalitis, myelitis and encephalomyelitis; G05 Encephalitis, myelitis and encephalomyelitis in diseases classified elsewhere; G06 Intracranial and intraspinal abscess and granuloma; G07 Intracranial and intraspinal abscess and granuloma in diseases classified elsewhere; G08 Intracranial and intraspinal phlebitis and thrombophlebitis; G09 Sequelae of inflammatory diseases of central nervous system. Adding the exclusions: certain conditions originating in the perinatal period (P04-P96) certain infectious and parasitic diseases (A00-B99) complications of pregnancy, childbirth and the puerperium (O00-O9A) congenital malformations, deformations, and chromosomal abnormalities (Q00-Q99) endocrine, nutritional and metabolic diseases (E00-E88) injury, poisoning and certain other consequences of external causes (S00-T88) neoplasms (C00-D49) symptoms, signs and abnormal clinical and laboratory findings, not elsewhere classified (R00-R94).

G10-G14 Systemic atrophies primarily affecting the central nervous system
G10 Huntington's disease; G11 Hereditary ataxia; G12 Spinal muscular atrophy and related syndromes; G13 Systemic atrophies primarily affecting central nervous system in diseases classified elsewhere; G14 Postpolio syndrome G20-G26 Extrapyramidal and movement disorders
G20 Parkinson's disease; G21 Secondary parkinsonism; G23 Other degenerative diseases of basal ganglia; G24 Dystonia; G25 Other extrapyramidal and movement disorders; G26 Extrapyramidal and movement disorders in diseases classified elsewhere G30-G32 Other degenerative diseases of the nervous system
G30 Alzheimer's disease; G31 Other degenerative diseases of nervous system, not elsewhere classified; G32 Other degenerative disorders of nervous system in diseases classified elsewhere G35-G37 Demyelinating diseases of the central nervous system
G35 Multiple sclerosis; G36 Other acute disseminated demyelination; G37 Other demyelinating diseases of central nervous system G40-G47 Episodic and paroxysmal disorders
G40 Epilepsy and recurrent seizures; G43 Migraine; G44 Other headache syndromes; G45 Transient cerebral ischemic attacks and related syndromes; G46 Vascular syndromes of brain in cerebrovascular diseases; G47 Sleep disorders G50-G59 Nerve, nerve root and plexus disorders
G50 Disorders of trigeminal nerve; G51 Facial nerve disorders; G52 Disorders of other cranial nerves; G53 Cranial nerve disorders in diseases classified elsewhere; G54 Nerve root and plexus disorders; G55 Nerve root and plexus compressions in diseases classified elsewhere; G56 Mononeuropathies of upper limb; G57 Mononeuropathies of lower limb; G58 Other mononeuropathies; G59 Mononeuropathy in diseases classified elsewhere. Adding the exclusions: current traumatic nerve, nerve root and plexus disorders, nerve by body region neuralgia NOS (M79.2) neuritis NOS (M79.2), peripheral neuritis in pregnancy (O26.82), radiculitis NOS (M54.1)

G60-G65 Polyneuropathies and other disorders of the peripheral nervous system
G60 Hereditary and idiopathic neuropathy; G61 Inflammatory polyneuropathy; G62 Other and unspecified polyneuropathies; G63 Polyneuropathy in diseases classified elsewhere; G64 Other disorders of peripheral nervous system; G65 Sequelae of inflammatory and toxic polyneuropathies G70-G73 Diseases of myoneural junction and muscle
G70 Myasthenia gravis and other myoneural disorders; G71 Primary disorders of muscles; G72 Other and unspecified myopathies; G73 Disorders of myoneural junction and muscle in diseases classified elsewhere.

G80-G83 Cerebral palsy and other paralytic syndromes
G80 Cerebral palsy; G81 Hemiplegia and hemiparesis; G82 Paraplegia (paraparesis) and quadriplegia (quadriparesis); G83 Other paralytic syndromes.

G89-G99 Other disorders of the nervous system
G89 Pain, not elsewhere classified; G90 Disorders of autonomic nervous system; G91 Hydrocephalus; G92 Toxic encephalopathy; G93 Other disorders of brain; G94 Other disorders of brain in diseases classified elsewhere; G95 Other and unspecified diseases of spinal cord; G96 Other disorders of central nervous system; G97 Intraoperative and postprocedural complications and disorders of nervous system, not elsewhere classified; G98 Other disorders of nervous system not elsewhere classified; G99 Other disorders of nervous system in diseases classified elsewhere.

As used herein, "treatment resistant depression" (TRD) is a shorthand signifier for all related terms, approaches to management, etc., defined here as including but not limited to: non-responder depression, treatment refractory depression, partial response depression, optimization strategy, switching strategy, combination strategy, augmentation strategy, bupropione, mirtazapine, mianserine, lithium, thyroid hormones, second generation antipsychotics (SGA), dopamine agonists, lamotrigine, psychostimulants, dextromethorphan, dextrorphan, ketamine, omega-3 fatty acids, pindolol, sex steroids, and glucocorticoid agents. Management approaches include treatment strategies such as: (1) switching from an ineffective antidepressant to a new antidepressant from a similar or different class; (2) combining a current antidepressant regimen with a second antidepressant from a different class; and (3) augmenting a current antidepressant regimen with a second agent not thought to be an antidepressant itself.

As used herein, the terms "reduce," "decrease," "lessen" and similar terms mean a decrease of at least about 10%, about 15%, about 20%, about 25%, about 35%, about 50%, about 75%, about 80%, about 85%, about 90%, about 95%, about 97%, or more.

As used herein, the terms "improve," "increase," "enhance," and similar terms indicate an increase of at least about 10%, about 15%, about 20%, about 25%, about 50%, about 75%, about 100%, about 150%, about 200%, about 300%, about 400%, about 500%, or more.

As used herein, the terms "binds" or "binding" or grammatical equivalents, refer to compositions having affinity for each other. "Specific binding" is where the binding is selective between two molecules. A particular example of specific binding is that which occurs between an antibody and an antigen. Typically, specific binding can be distinguished from non-specific when the dissociation constant (KD) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

Reference to a psychoactive compound provided herein (e.g., methylone) is meant to include pharmaceutically acceptable salts, stereoisomers, tautomers, isotopologues and isotopomers, hydrates, or solvates thereof, as well as all amorphous and polymorph forms.

The term "prodrug" refers to a precursor or derivative form of a pharmaceutically active substance that can be activated or converted (e.g., enzymatically) into a more active parent form.

Many psychoactive compounds, including methylone, useful in the compositions and methods described herein have at least one stereogenic center in their structure. This stereogenic center may be present in an R or an S configuration, the R and S notation is used in correspondence with the rules described in *Pure Appl. Chem.* (1976) 45:11. The disclosure contemplates all stereoisomeric forms such as enantiomeric and diastereoisomeric forms of the compounds, salts, solvates, hydrates, tautomers, prodrugs, or mixtures thereof (including all possible stereoisomer mixtures).

A psychoactive compound provided herein (e.g., methylone, 2C-B, or MBDB) may be isotopically enriched and comprise stable isotopes of hydrogen, carbon, nitrogen, and oxygen in amounts greater than their natural abundance. For example, one or more carbon atoms may be enriched with 13C in an amount greater than about 1.1% (e.g., 1.2-1.5%, 1.5-2%, 2-10%, or more than 10%). One or more nitrogen atoms may be enriched with 15N in an amount greater than about 0.4% (e.g., 0.5-1%, 1-2%, 2-10%, or greater than 10%). Likewise, one or more oxygen atoms may be enriched with 16O in an amount greater than about 0.24% (e.g., 0.25-0.5%, 0.5-1%, 1-2%, 2-10%, or greater than 10%). The term "deuterated" refers to a compound or substituent in which one or more protium (1H) atom(s) is/are replaced by one or more deuterium atom(s) and in which the abundance of deuterium at each deuterated position of the compound is higher than the natural abundance of deuterium, which is about 0.015%. For example, in a deuterated psychoactive compound provided herein (e.g., methylone), the abundance of deuterium at each deuterated position of the compound is higher than 10%, 20%, 30%, 40%, 50%, 60%, 70% or 80%, preferably higher than 90%, 95%, 96% or 97%, even more preferably higher than 98% or 99% at said position(s).

In one embodiment, a variety of other therapeutic agents may find use for administration with the compositions and methods provided herein.

The psychoactive compounds provided herein may be used for various therapeutic purposes. In one embodiment, the compounds are administered to a subject to treat a neuropsychiatric illness. In one embodiment, the compounds are administered to a subject to treat pain. A subject for the purposes of the compositions and methods provided herein includes humans and other animals, preferably mammals and most preferably humans. Thus, the compounds provided herein have both human therapy and veterinary applications. In another embodiment the subject is a mammal, and in yet another embodiment the subject is human. By "condition" or "disease" herein are meant a disorder that may be ameliorated by the administration of a pharmaceutical composition comprising the compounds provided herein.

Methods and compositions described herein can be used for prophylaxis, as well as amelioration of signs and/or symptoms of a neuropsychiatric illness. The terms "treating" and "treatment" used to refer to treatment of a neuropsychiatric illness in a subject include: preventing, inhibiting or ameliorating the neuropsychiatric illness in the subject, as well as reducing or ameliorating a sign or symptom of the neuropsychiatric illness. Treatment goals may incorporate endpoints such as improvement in DSM-5 severity scales, to measure if resilience and quality of life are enhanced, with engagement of positive cognitive valence systems, and corresponding reduction in negative valence.

Provided herein are methods of treating and/or preventing a disease or condition, such as a neuropsychiatric illness, and/or ameliorating a symptom thereof in a subject in need thereof comprises administering to the subject an effective amount of a psychoactive compound or composition provided herein. In some embodiments, the psychoactive compositions or compounds used in the methods of treating neuropsychiatric illnesses (e.g., PTSD, acute stress disorder, an anxiety disorder, or a depressive disorder) are non-hallucinogenic. In some embodiments, the psychoactive compositions or compounds used in the methods of treating neuropsychiatric illnesses (e.g., PTSD, acute stress disorder, an anxiety disorder, or a depressive disorder) are non-psychedelic. In some embodiments, the psychoactive compositions or compounds used in the methods of treating neuropsychiatric illnesses (e.g., PTSD, acute stress disorder, an anxiety disorder, or a depressive disorder) are non-dissociative. In some embodiments, the psychoactive compositions or compounds used in the methods of treating neuropsychiatric illnesses (e.g., PTSD, acute stress disorder, an anxiety disorder, or a depressive disorder) are non-hallucinogenic, non-psychedelic and non-dissociative.

In some embodiments, the psychoactive compositions or compounds (e.g., methylone) rapidly treat a neuropsychiatric illness (e.g., PTSD, acute stress disorder, an anxiety disorder, or a depressive disorder) with the methods provided herein. In some embodiments, a rapid treatment comprises a therapeutic effect that is observable or statistically significant less than one month after the first dose or the beginning of a dosing schedule of a psychoactive composition or compound. In some embodiments, a rapid treatment comprises a therapeutic effect that is observable or statistically significant less than three weeks after the first dose or the beginning of a dosing schedule of a psychoactive composition or compound. In some embodiments, a rapid treatment comprises a therapeutic effect that is observable or statistically significant less than two weeks after the first dose or the beginning of a dosing schedule of a psychoactive composition or compound. In some embodiments, a rapid treatment comprises a therapeutic effect that is observable or statistically significant within ten days of the first dose or the beginning of a dosing schedule of a psychoactive composition or compound. In some embodiments, a rapid treatment comprises a therapeutic effect or statistically significant that is observable within one week of the first dose or the beginning of a dosing schedule of a psychoactive composition or compound. In some embodiments, a rapid treatment comprises a therapeutic effect that is observable or statistically significant within six days of the first dose or the beginning of a dosing schedule of a psychoactive composition or compound. In some embodiments, a rapid treatment comprises a therapeutic effect that is observable or statistically significant within five days of the first dose or the beginning of a dosing schedule of a psychoactive composition or compound. In some embodiments, a rapid treatment comprises a therapeutic effect that is observable or statistically significant within four days of the first dose or the beginning of a dosing schedule of a psychoactive composition or compound. In some embodiments, a rapid treatment comprises a therapeutic effect that is observable or statistically significant within three days of the first dose or the beginning of a dosing schedule of a psychoactive composition or compound. In some embodiments, a rapid treatment comprises a therapeutic effect that is observable or statistically significant within two days of the first dose or the beginning of a dosing schedule of a psychoactive composition or compound. In some embodiments, a rapid treatment comprises a therapeutic effect that is observable or statistically significant within one day of the first dose or the beginning of a dosing schedule of a psychoactive composition or compound.

In some embodiments, the psychoactive compositions or compounds (e.g., methylone, 2C-B, or MBDB) durably treat a neuropsychiatric illness (e.g., PTSD, acute stress disorder, an anxiety disorder, or a depressive disorder) with the methods provided herein. In some embodiments, a durable treatment comprises a therapeutic effect that is observable or statistically significant one week or more after a dose or the conclusion of a dosing schedule of a psychoactive composition or compound. In some embodiments, a durable treatment comprises a therapeutic effect that is observable or statistically significant at least two weeks after a dose or the conclusion of a dosing schedule of a psychoactive composition or compound. In some embodiments, a durable treatment comprises a therapeutic effect that is observable or statistically significant at least three weeks after a dose or the conclusion of a dosing schedule of a psychoactive composition or compound. In some embodiments, a durable treatment comprises a therapeutic effect that is observable or statistically significant at least one month after a dose or the conclusion of a dosing schedule of a psychoactive composition or compound. In some embodiments, a durable treatment comprises a therapeutic effect that is observable or statistically significant at least six weeks after a dose or the conclusion of a dosing schedule of a psychoactive composition or compound.

In some embodiments, the psychoactive compositions or compounds (e.g., methylone, 2C-B, or MBDB) robustly treat a neuropsychiatric illness (e.g., PTSD, acute stress disorder, an anxiety disorder, or a depressive disorder) with the methods provided herein. In one embodiment, a robust treatment is remission of the neuropsychiatric illness. In one embodiment, a robust treatment comprises a therapeutic effect that is statistically significant over baseline. In some embodiments, the neuropsychiatric illness is PTSD, and robust treatment comprises an improvement from baseline in the Clinician-Administered PTSD Scale for DSM-5 (CAPS-5) score. In one embodiment, the robust treatment comprises an improvement from baseline of at least ten points in the CAPS-5 score. In another embodiment, the robust treatment comprises an improvement from baseline of at least five points in the CAPS-5 score. In another embodiment, the neuropsychiatric illness is a depressive disorder, and robust treatment comprises an improvement from baseline of at least ten points in the Montgomery-Åsberg Depression Rating Scale (MADRS) score. In one embodiment, the robust treatment comprises an improvement from baseline of at least ten points in the MADRS score. In another embodiment, the robust treatment comprises an improvement from baseline of at least five points in the MADRS score. In one embodiment, a robust treatment comprises an improvement from baseline of at least one point in Clinical Global Impression-improvement (CGI-I) score or in Clinical Global Impression-severity (CGI-S) score. In one embodiment, a robust treatment comprises an improvement from baseline of at least two points in CGI-I and/or CGI-S scores.

In some embodiments, the psychoactive compositions or compounds (e.g., methylone, 2C-B, or MBDB) rapidly and durably treat a neuropsychiatric illness (e.g., PTSD, acute stress disorder, an anxiety disorder, or a depressive disorder) with the methods provided herein. In some embodiments, the psychoactive compositions (e.g., methylone, 2C-B, or MBDB) or compounds rapidly and robustly treat a neuropsychiatric illness (e.g., PTSD, acute stress disorder, an anxiety disorder, or a depressive disorder) with the methods provided herein. In some embodiments, the psychoactive compositions (e.g., methylone, 2C-B, or MBDB) or compounds durably and robustly treat a neuropsychiatric illness (e.g., PTSD, acute stress disorder, an anxiety disorder, or a depressive disorder) with the methods provided herein. In some embodiments, the psychoactive compositions (e.g., methylone, 2C-B, or MBDB) or compounds rapidly, durably and robustly treat a neuropsychiatric illness (e.g., PTSD, acute stress disorder, an anxiety disorder, or a depressive disorder) with the methods provided herein.

In some embodiments, the psychoactive compositions or compounds (e.g., methylone, 2C-B, or MBDB) improves or reduces functional impairment in a subject having a neuropsychiatric illness (e.g., PTSD, acute stress disorder, an anxiety disorder, or a depressive disorder) with the methods provided herein. In some embodiments, the improvement or reduction in function impairment comprises an improvement from baseline in the Shechan Disability Scale (SDS) for the subject. In some embodiments, the improvement or reduction in function impairment comprises a reduction of the number of underproductive days and/or days lost for the subject.

In some embodiments, the psychoactive compositions or compounds (e.g., methylone, 2C-B, or MBDB) improves sleep in a subject having a neuropsychiatric illness (e.g., PTSD, acute stress disorder, an anxiety disorder, or a depressive disorder) with the methods provided herein. In some embodiments, the improvement in sleep comprises an improvement from baseline in the Pittsburgh Sleep Quality Index (PSQI) for the subject. In some embodiments, the improvement in sleep comprises an improvement from baseline of sleep duration, and/or sleep latency, and/or sleep disturbance, and/or sleep quality.

Methods and compositions described herein can be used for treatment or alleviation of pain in a subject. Treatment of pain includes but is not limited to: the treatment of acute pain, (e.g., surgical and procedural pain, pain due to trauma/injury, pain due to acute inflammatory processes) and/or the treatment of chronic pain (e.g., cancer pain, neuropathic pain, fibromyalgia, osteoarthritis pain, low back pain).

It is to be understood by one of skill in the art that the methods of treatment and/or prevention comprising administering a psychoactive compound provided herein to treat and/or prevent one or more indications as described herein also include: the use of a psychoactive compound provided herein in the manufacture of a medicament to treat and/or prevent one or more indications as described herein; and the use of a psychoactive compound provided herein to treat and/or prevent one or more indications as described herein.

In some embodiments, methods of treating and/or preventing a neuropsychiatric illness and/or ameliorating a symptom thereof in a subject in need thereof comprise administering to the subject a therapeutically effective dose of a psychoactive compound provided herein. In some embodiments, methods of treating and/or preventing a neuropsychiatric illness and/or ameliorating a symptom thereof in a subject in need thereof comprise administering to the subject a therapeutically effective dose of a psychoactive compound provided herein in a controlled environment, wherein the subject is provided with psychological support.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1% or ±0.5%, and still more preferably ±0.1% from the specified value, as such variations are appropriate to perform the disclosed methods.

Pharmaceutical compositions are contemplated for the psychoactive compounds and methods provided herein. Formulations of the compositions and methods provided herein are prepared for storage by mixing said compound having the desired degree of purity with optional pharmaceutically acceptable carriers, excipients or stabilizers, in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g., Zn-protein complexes); and/or non-ionic surfactants or polyethylene glycol (PEG). In another embodiment, the pharmaceutical compositions provided herein are in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. Formulations used for in vivo administration are preferably sterile. This is readily accomplished by filtration through sterile filtration membranes or other methods.

Pharmaceutically acceptable excipients for formulations of psychoactive compounds provided herein include, but are not limited to: diluents, e.g., microcrystalline cellulose, starch, mannitol, calcium hydrogen phosphate anhydrous or co-mixtures of silicon dioxide, calcium carbonate, microcrystalline cellulose and talc; disintegrants, e.g., sodium starch glycolate or croscarmellose sodium; binders, e.g., povidone, co-povidone or hydroxyl propyl cellulose; lubricants, e.g., magnesium stearate or sodium stearyl fumarate; glidants, e.g., colloidal silicon dioxide; and film coats, e.g., Opadry II white or PVA based brown Opadry II.

The psychoactive compounds provided herein may also be entrapped in microcapsules prepared by methods including, but not limited to, coacervation techniques, interfacial polymerization (e.g., using hydroxymethylcellulose or gelatin-microcapsules, or poly-(methylmethacylate) microcapsules), colloidal drug delivery systems (e.g., liposomes, albumin microspheres, microemulsions, nano-particles and nano-capsules), and macroemulsions. Sustained-release preparations may be prepared. Suitable examples of sustained-release preparations include semipermeable matrices of solid hydrophobic polymer, which matrices are in the form of shaped articles, e.g., films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers (which are injectable microspheres composed of lactic acid-glycolic acid copolymer and leuprolide acetate), and poly-D-(−)-3-hydroxybutyric acid) which is a microsphere-based delivery system composed of the desired bioactive molecule incorporated into a matrix of poly-DL-lactide-co-glycolide (PLG).

Administration of a pharmaceutical composition comprising a psychoactive compound provided herein, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. As is known in the art, pharmaceutical compositions may be formulated accordingly depending upon the manner of introduction.

In some embodiments, the pharmaceutical formulation is an oral dosage form. In some embodiments, the pharmaceutical formulation is a parenteral dosage form. In some embodiments, the pharmaceutical composition comprises a tablet. In some embodiments, the pharmaceutical composition comprises a capsule. In some embodiments, the pharmaceutical composition comprises a dry powder. In some embodiments, the pharmaceutical composition comprises a solution. In some embodiments, more than one dosage form is administered to the subject at substantially the same time. In some embodiments, the subject may be administered the entire therapeutic dose in one tablet or capsule. In some embodiments, the therapeutic dose may be split among multiple tablets or capsules.

In some embodiments, a dose of a psychoactive compound provided herein may be between about 1 mg to about 100 mg. For example, the dose may be about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. In some embodiments, the dose of a psychoactive compound provided herein is between about 0.1 mg to about 100 mg, about 1 mg to about 50 mg, or about 5 mg to about 30 mg. In some embodiments, the dose of a psychoactive compound provided herein is about 1 mg, about 10 mg, or about 25 mg. In some embodiments, the dose of a psychoactive compound provided herein is between about 0.001 mg to about 1 g. In some embodiments, the dose of a psychoactive compound provided herein is between about 100 mg to about 250 mg. In some embodiments, the dose of a psychoactive compound provided herein is about 25 mg.

In some embodiments, the psychoactive compound provided herein is administered daily. In some embodiments, the psychoactive compound is administered twice a day. In some embodiments, the psychoactive compound is administered three times a day. In some embodiments, the psychoactive compound is administered every other day. In some embodiments, the psychoactive compound is administered every third day. In some embodiments, the psychoactive compound is administered every fourth day. In some embodiments, the psychoactive compound is administered every fifth day. In some embodiments, the psychoactive compound is administered weekly. In some embodiments, the psychoactive compound is administered every other week. In some embodiments, the psychoactive compound is administered every third week. In some embodiments, the psychoactive compound is administered monthly.

In some embodiments, about 5 mg of the psychoactive compound is administered daily. In some embodiments, about 5 mg of the psychoactive compound is administered twice a day. In some embodiments, about 5 mg of the psychoactive compound is administered three times a day. In some embodiments, about 5 mg of the psychoactive compound is administered every other day. In some embodiments, about 5 mg of the psychoactive compound is administered every third day. In some embodiments, about 5 mg of the psychoactive compound is administered every fourth day. In some embodiments, about 5 mg of the psychoactive compound is administered every fifth day. In some embodiments, about 5 mg of the psychoactive compound is administered weekly. In some embodiments, about 5 mg of the psychoactive compound is administered every other week. In some embodiments, about 5 mg of the psychoactive compound is administered every third week. In some embodiments, about 5 mg of the psychoactive compound is administered monthly.

In some embodiments, about 25 mg of the psychoactive compound is administered daily. In some embodiments, about 25 mg of the psychoactive compound is administered twice a day. In some embodiments, about 25 mg of the psychoactive compound is administered three times a day. In some embodiments, about 25 mg of the psychoactive compound is administered every other day. In some embodiments, about 25 mg of the psychoactive compound is administered every third day. In some embodiments, about 25 mg of the psychoactive compound is administered every fourth day. In some embodiments, about 25 mg of the psychoactive compound is administered every fifth day. In some embodiments, about 25 mg of the psychoactive compound is administered weekly. In some embodiments, about 25 mg of the psychoactive compound is administered every other week. In some embodiments, about 25 mg of the psychoactive compound is administered every third week. In some embodiments, about 25 mg of the psychoactive compound is administered monthly.

In some embodiments, about 50 mg of the psychoactive compound is administered daily. In some embodiments, about 50 mg of the psychoactive compound is administered twice a day. In some embodiments, about 50 mg of the psychoactive compound is administered three times a day. In some embodiments, about 50 mg of the psychoactive compound is administered every other day. In some embodiments, about 50 mg of the psychoactive compound is administered every third day. In some embodiments, about 50 mg of the psychoactive compound is administered every fourth day. In some embodiments, about 50 mg of the psychoactive compound is administered every fifth day. In some embodiments, about 50 mg of the psychoactive compound is administered weekly. In some embodiments, about 50 mg of the psychoactive compound is administered every other week. In some embodiments, about 50 mg of the psychoactive compound is administered every third week. In some embodiments, about 50 mg of the psychoactive compound is administered monthly.

In some embodiments, about 100 mg of the psychoactive compound is administered daily. In some embodiments, about 100 mg of the psychoactive compound is administered twice a day. In some embodiments, about 100 mg of the psychoactive compound is administered three times a day. In some embodiments, about 100 mg of the psychoactive compound is administered every other day. In some embodiments, about 100 mg of the psychoactive compound is administered every third day. In some embodiments, about 100 mg of the psychoactive compound is administered every fourth day. In some embodiments, about 100 mg of the psychoactive compound is administered every fifth day. In some embodiments, about 100 mg of the psychoactive compound is administered weekly. In some embodiments, about 100 mg of the psychoactive compound is administered every other week. In some embodiments, about 100 mg of the psychoactive compound is administered every third week. In some embodiments, about 100 mg of the psychoactive compound is administered monthly.

In some embodiments, about 150 mg of the psychoactive compound is administered daily. In some embodiments, about 150 mg of the psychoactive compound is administered twice a day. In some embodiments, about 150 mg of the psychoactive compound is administered three times a day. In some embodiments, about 150 mg of the psychoactive compound is administered every other day. In some embodiments, about 150 mg of the psychoactive compound is administered every third day. In some embodiments, about 150 mg of the psychoactive compound is administered every fourth day. In some embodiments, about 150 mg of the psychoactive compound is administered every fifth day. In some embodiments, about 150 mg of the psychoactive compound is administered weekly. In some embodiments, about 150 mg of the psychoactive compound is administered every other week. In some embodiments, about 150 mg of the psychoactive compound is administered every third week. In some embodiments, about 150 mg of the psychoactive compound is administered monthly.

In some embodiments, about 200 mg of the psychoactive compound is administered daily. In some embodiments, about 200 mg of the psychoactive compound is administered twice a day. In some embodiments, about 200 mg of the psychoactive compound is administered three times a day. In some embodiments, about 200 mg of the psychoactive compound is administered every other day. In some embodiments, about 200 mg of the psychoactive compound is administered every third day. In some embodiments, about 200 mg of the psychoactive compound is administered every fourth day. In some embodiments, about 200 mg of the psychoactive compound is administered every fifth day. In some embodiments, about 200 mg of the psychoactive compound is administered weekly. In some embodiments, about 200 mg of the psychoactive compound is administered every other week. In some embodiments, about 200 mg of the psychoactive compound is administered every third week. In some embodiments, about 200 mg of the psychoactive compound is administered monthly.

In some embodiments, about 250 mg of the psychoactive compound is administered daily. In some embodiments, about 250 mg of the psychoactive compound is administered twice a day. In some embodiments, about 250 mg of the psychoactive compound is administered three times a day. In some embodiments, about 250 mg of the psychoactive compound is administered every other day. In some embodiments, about 250 mg of the psychoactive compound is administered every third day. In some embodiments, about 250 mg of the psychoactive compound is administered every fourth day. In some embodiments, about 250 mg of the psychoactive compound is administered every fifth day. In some embodiments, about 250 mg of the psychoactive compound is administered weekly. In some embodiments, about 250 mg of the psychoactive compound is administered every other week. In some embodiments, about 250 mg of the psychoactive compound is administered every third week. In some embodiments, about 250 mg of the psychoactive compound is administered monthly.

In some embodiments, an initial dose of a psychoactive compound provided herein is administered, which is then boosted 30 minutes-4 hours later by administering a second dose of the psychoactive compound. In one embodiment, the boosted dose is administered about 30 min after the initial dose. In one embodiment, the boosted dose is administered about 60 min after the initial dose. In one embodiment, the boosted dose is administered about 90 min after the initial dose. In one embodiment, the boosted dose is administered about 120 min after the initial dose. In one embodiment, the boosted dose is administered about 150 min after the initial dose. In one embodiment, the boosted dose is administered about 180 min after the initial dose. In one embodiment, the boosted dose is administered about 210 min after the initial dose. In one embodiment, the boosted dose is administered about 240 min after the initial dose.

In some embodiments, the boosted dose is 10% to 100% in amount of the initial dose. In some embodiments, the boosted dose is the same amount as the initial dose. In one embodiment, the boosted dose is about half of the amount of the initial dose. In one embodiment, this dosing schedule is performed daily. In one embodiment, this dosing schedule is performed twice a day. In one embodiment, this dosing schedule is performed three times a day. In one embodiment, this dosing schedule is performed every other day. In one embodiment, this dosing schedule is performed every third day. In one embodiment, this dosing schedule is performed every fourth day. In one embodiment this dosing schedule is performed every fifth day. In one embodiment, this dosing schedule is performed weekly. In one embodiment, this dosing schedule is performed every other week. In one embodiment, this dosing schedule is performed every third week. In one embodiment, this dosing schedule is performed monthly.

In some embodiments, a dose of a psychoactive compound provided herein may be between about 1 mg/kg to about 100 mg/kg. For example, the dose may be about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, the dose of a psychoactive compound provided herein is between about 0.1 mg/kg to about 100 mg/kg, about 1 mg/kg to about 50 mg/kg, or about 5 mg/kg to about 30 mg/kg. In some embodiments, the dose of a psychoactive compound provided herein is about 1 mg/kg, about 10 mg/kg, or about 25 mg/kg. In some embodiments, the dose of a psychoactive compound provided herein is between about 0.001 mg/kg to about 1 g/kg. In some embodiments, the dose of a psychoactive compound provided herein is in the range of about 100 mg/kg to about 250 mg/kg. In some embodiments, the dose of a psychoactive compound provided herein is about 25 mg/kg.

In some embodiments, the psychoactive compound provided herein is administered, e.g., as a single dose or one or more times per week (up to twice daily or even three times a days). In some embodiments, the psychoactive compound provided herein is administered according to a dosing schedule provided herein. In some embodiments, the psychoactive compound provided herein is administered as an extended release or sustained release formulation, for example, to achieve a dosing regimen disclosed herein and releasing 50 mg to 1 g on a set schedule to patients according to the indication(s) being treated in those patients.

The term "subject" refers to a mammal, including a human, in need of therapy for, or susceptible to, a condition or its sequelae. The subject may include dogs, cats, pigs, cows, sheep, goats, horses, rats, mice, and humans. The term "subject" does not exclude an individual that is normal in all respects.

In some embodiments, the subject is a male. In some embodiments, the subject is a female. In some embodiments, the female subject is pregnant or post-partum. The subject may be a geriatric subject, a pediatric subject, a teenage subject, a young adult subject, or a middle-aged subject. In some embodiments, the subject is less than about 18 years of age. In some embodiments, the subject is at least about 18 years of age. In some embodiments, the subject is about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 85-90, about 90-95, or about 95-100 years of age.

As used herein, the singular forms "a," "an," and "the" include plural references unless the context clearly dictates otherwise. For example, the term "a molecule" can also include a plurality of molecules.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Unless the context indicates otherwise, it is specifically intended that the various features described herein can be used in any combination.

Any patent, patent application publication, or scientific publication, cited herein, is incorporated by reference herein in its entirety.

The following examples are presented to illustrate preferred embodiments of the invention more fully. They should in no way be construed, however, as limiting the broad scope of the invention.

EXAMPLES

Example 1: Effects of Methylone, 2C-B, and MBDB on Fear Extinction Plasticity and Dendritic Architecture in Mice A key experimental research question is how the short half-life of a compound translates to long-term behavioral changes. One plausible mechanism is neural plasticity. In effect, administering psychoactive compounds may drive lasting modifications in neural architecture in the brain by strengthening or increasing the number of synaptic connections. Current evidence supporting this view, however, comes mostly from studies of cultured neurons. Still unknown is the extent to which neural plasticity is induced by psychoactive compounds in the mammalian brain, and whether synaptic remodeling occurs in brain regions implicated in neuropsychiatric disorders.

In this study, the effects of multiple psychoactive medicines are compared in a rodent in vivo model. Multiple conditions are tested, including 3 psychoactive compounds of interest (methylone, 2C-B, and MBDB), in both chronically exposed vs treatment naïve groups (e.g., imipramine, or other antidepressant/anxiolytic agents), a positive control (e.g., another antidepressant/anxiolytic agent), and a vehicle control (saline). The dose-response curves for the psychoactive compounds are characterized by measuring head-twitch response in mice. The plasticity-enhancing effects of administering a single dose of each compound on fear extinction behavior is also determined. Then, the longitudinal effects of administering a single dose of each compound on the density and turnover of dendritic spines is determined using 2-photon imaging microscopy (Shao L X et al. Neuron. 2021 Jun. 25: S0896-6273 (21) 00423-2. doi: 10.1016/j.neuron.2021.06.008.).

Determine Dose-Response Curves in C57BL/6J Mice

It is important to determine the dose range that is behaviorally relevant for mice. To construct a dose-response curve, head-twitch responses are quantified for a range of doses for the 3 psychoactive compounds (methylone, 2C-B, MBDB) in adult, 6-8 week-old C57BL/6J mice, with 40 mice tested per condition. Briefly, animals are placed in arenas inside a sound-attenuated cubicle. The arenas are illuminated with near-infrared lighting. Movements of the mice within all arenas are captured simultaneously by a ceiling-mounted, high-speed camera. Each animal receives an intraperitoneal injection of 1 of 5 doses of one of the compounds—with a dose range selected based on the literature. Mice are assigned randomly to groups. Videos are recorded for ~10 minutes after administration. In a subset of studies, videos are recorded for up to 2 hours to chart the time course. For analyses, head twitches are counted by an experimenter who is blind to the experimental condition. These experiments are used to inform the dose to be used for further studies.

Determine Effects of Methylone, MBDB, and 2C-B on Fear Extinction Plasticity

Neural plasticity may promote alterations in emotional learning. Fear extinction is a behavior in which repeated exposure to an associated fear learning stimulus can reduce the intensity of the fear response, and which may be related to the mechanism of action of these compounds in reducing anxiety or fear. It is not known to what extent novel phenethylamines may enhance fear extinction. Here, the rate of fear extinction is determined after administration of drug in 4 conditions (saline, methylone, 2C-B, MBDB) in adult mice, with 10 mice tested per condition. Briefly, each mouse receives tone-shock pairing (day 1) then on a subsequent day they receive a single administration of the compound (at dose informed by prior study) 30 minutes prior to re-exposure to the fear associated stimulus (day 2). On day 3, fear extinction learning is tested by re-exposing mice again to the associated tone in a fear conditioning apparatus. Fear extinction serves as a model for ameliorating anxiety- and fear-related behaviors in psychiatric disorders and may serve to identify separable behavioral effects from hallucinogenic effects. The circuit mechanisms of potential plasticity enhancement is subsequently addressed in two-photon imaging experiments.

Determine Long-Term Effects on Dendritic Remodeling

Although it has been shown that psychoactive compounds can promote neural plasticity, these experiments study how different compounds induce different degrees of structural remodeling. Here, dendritic spine turnover in medial frontal cortex is determined for 5 conditions (saline, ketamine, methylone, 2C-B, MBDB) in adult mice, with 5 mice tested per condition. Briefly, Thy 1-GFP-M transgenic mice are used, because a sparse subset of cortical pyramidal neurons expresses enhanced green fluorescent protein, allowing for visualization of their dendritic architecture. Each mouse receives a single administration of the compound (at the dose determined above; 10 mg/kg for ketamine). Using a two-photon microscope, dendritic spines in the distal apical tuft branches are imaged and are tracked for 7 sessions at −3, −1, 1, 3, 5, 7, and ~30 days from the day of administration. Imaging the same sets of spines longitudinally allows the determination of the number density of dendritic spines, and also the turnover dynamics including the rates of spine formation and elimination, as well as the fraction of newly formed spines that remain persistent indicating the maturation of a new functional synapse. These results provide data on multiple psychoactive compounds to demonstrate their suitability to treat neuropsychiatric illness.

Example 2: Zebrafish Models of Neuropsychiatric Illnesses

Because of their physiological (neuroanatomical, neuroendocrine, neurochemical) and genetic homology to mammals, robust phenotypes, and value in high-throughput genetic and chemical genetic screens, zebrafish are ideal for developing valid experimental models of major depression, anxiety, and pain disorders to discover novel therapeutics. Behavioral testing approaches, such as approach-avoidance, cognitive, and social paradigms, are available in zebrafish and are useful for identifying depression-like indices in zebrafish in response to physiological, genetic, environmental, and/or psychopharmacological alterations. In addition, the high sensitivity of zebrafish to commonly prescribed psychoactive drugs support the use of this model as a tool for pharmacological research and drug screening. Possessing a fully characterized genome, both adult and larval zebrafish are currently widely used for in vivo screening of various psychoactive medicines.

Zebrafish Reserpine-Induced Depression Model

As a specific inhibitor of monoamine transporters, reserpine is known to deplete monoamine neurotransmitters—confirmed with liquid chromatograph-mass spectrometer analysis—and cause decreased swimming distance and average velocity (hypoactivity), and reduced response to both visual and sound stimuli. Reserpine induces depression-like behavior both in adult zebrafish and in larvae; this is used as an assay for drugs affecting these despair-like states, such as methylone, 2C-B and MBDB. A camera algorithm, Histogram of Oriented Gradient (HOG), analyzes the depression and hypoactivity behavior of zebrafish shoaling to achieve accuracy that is not possible for the human observer.

Zebrafish Anxiety Disorder Models

Many behaviors including anxiety, fear, and stimuli dependent learning can be assessed as early as free-swimming larval stages, whereas social behavior like shoaling and directed aggression, develop with age. Several anxiety tests are done, sequentially or in combination, including an elevated plus maze, novel tank, light-dark box, and open-field test. Known anxiolytic drugs such as benzodiazepines are used as positive controls to assess a drug's effect on levels of diving and exploration behavior, thigmotaxis, hyperactive swimming, freezing, erratic swimming, or avoidance of bright area in adults (scototaxis) and dark area in larval fish.

Example 3: Rodent Models of Neuropsychiatric Illnesses

This Example presents rodent models for several neurological and psychiatric conditions that are used to demonstrate the efficacy of psychoactive compounds described herein. Primate and rodent models have been traditionally used to study cellular mechanisms and neural circuits of hallucinogenic drugs' action.

Depression: Forced Swim Test (FST)

The Forced Swim Test (FST) is a classic, and the most used preclinical behavioral assay to screen compounds with antidepressant-like activity and has high predictive and face validity (Porsolt et al. (1977) *Nature* 266:730; Borsini and Meli (1988) *Psychopharmacology* 94:147). The premise of the FST is that when rats are placed into a cylinder filled with water, they will initially try to escape, but over time will become immobile. This increased immobility reflects behavioral despair, modeling a depressive-like state. A broad range of antidepressant treatments has been shown to consistently reduce immobility time, with the observation that increases in swimming or climbing correlate with serotonergic or noradrenergic activity, respectively (Detke et al. (1995) *Psychopharmacology* 121:66).

Anxiety: Open Field Test (Time Spent in the Center Vs. Periphery)

This behavioral assay, also widely used as an anxiety paradigm, capitalizes on a rodent's innate fear of brightly lit open spaces, which are assumed to induce fear or anxiety. Rodents spend more time hugging the walls of the open field during the test, and these effects correlate to underlying brain regions and mechanisms.

Method: Consecutive beam breaks and/or video-tracking of time spent in the center versus periphery of the open field are measured. Also measured are parameters such as distance traveled and ambulatory activity (horizontal and vertical) for the duration of the test session.

Results: Anxiolytics such as diazepam increase time spent (and/or distance traveled) in the center of the open field independent of changes in locomotion, used as positive control to assess an agent's effect on these parameters.

Anxiety: Elevated Plus Maze

This behavioral assay, widely used as an anxiety paradigm, is based on unconditioned responses of rodents to a potentially dangerous environment: maze height, luminosity, and open space are assumed to induce fear or anxiety, and to correlate to underlying brain regions and mechanisms.

Method: Video-tracking of time spent in the open arms of the maze to the closed arms, for 5 min starting at the junction. Other ethological parameters include rears, dips, stretched-attend postures.

Results: Anxiolytics such as diazepam increase time spent in open arm activity (duration and/or entries) without decreasing locomotion is used as positive control to assess an agent's effect on these parameters.

Modified Geller Seifter Conflict Test

Rats are trained to lever-press for food under a multiple variable interval-fixed ratio (food; food+shock) schedule of reinforcement. This task generally exhibits good predictive validity for anxiolytic-like compounds, such as diazepam, which increase punished responding (i.e., antagonize response suppression in the punished period). It also exhibits selectivity for anxiolytics, with apparently no effects in other classes and can assess MBDB's anxiolytic effect with a positive control such as Bupropion.

Fibromyalgia: Reserpine-Induced Myalgia Model

Reserpine (1 mg/kg/s.c.) is administered for 3 days to mimic chronic widespread pain and complex symptoms.

Method: Duloxetine (30 mg/kg, p.o.) is administered 60 min before a vonFrey test, in which filaments of different sizes are touched to the rat hindpaw and the filament size that elicits paw withdrawal is recorded.

Results: Reserpine significantly reduces the paw withdrawal threshold in the vonFrey test and decreases the amount of 5-hydroxytryptamine, dopamine, and norepinephrine in the cerebral cortex. It also increases malondialdehyde and nitric oxide and reduces glutathione contents in brain tissue. Duloxetine reverses reserpine-induced fibromyalgia, as assessed by the measured parameters.

Fibromyalgia: Acid-Saline Model

Allodynia, hyperalgesia, and other associated fibromyalgia-like symptomologies are rapidly induced via acid injection (pH 4.0). Once induced, animals display a hypersensitivity to mechanical and visceral stimulation. Symptoms last a minimum of 14 days post-induction, allowing for evaluation over time, and comparisons with vehicle and positive control (e.g., buprenorphine).

Example 4: Methylone Case Series

This Example is based on a case series of 32 narratives for methylone administered orally in single or multiple dosing sessions by a clinical psychologist in an outpatient therapy setting. The case series is composed of two datasets (Cohort 1 and Cohort 2):

Cohort 1:4 case narratives in a healthy population providing information on safety and tolerability of methylone administered in a single dosing session.

Cohort 2:28 case narratives providing efficacy and safety information from consecutive patients with a diagnosis of interest (PTSD or MDD) with baseline assessments. Cohort 2 was evaluated for efficacy post-dosing using the Clinical Global Impression-severity (CGI-S) at baseline and Clinical Global Impression-improvement (CGI-I), as described in more detail below, compared to baseline CGI-S established prior to first methylone dosing. CGI-S scale was also evaluated in a subset of patients from Cohort 2 post-treatment. Cohort 2 was evaluated for any observed or reported safety events following a single dosing session.

Clinical Global Improvement Scale

Clinical Global Impressions (CGI) scale includes 2 components: CGI-S ("severity") and CGI-I ("improvement").

CGI-S guidelines
1=Normal—not at all ill, symptoms of disorder not present past seven days
2=Borderline mentally ill—subtle or suspected pathology
3=Mildly ill—clearly established symptoms with minimal, if any, distress or difficulty in social and occupational function
4=Moderately ill—overt symptoms causing noticeable, but modest, functional impairment or distress; symptom level may warrant medication
5=Markedly ill—intrusive symptoms that distinctly impair social/occupational function or cause intrusive levels of distress
6=Severely ill—disruptive pathology, behavior and function are frequently influenced by symptoms, may require assistance from others
7=Among the most extremely ill patients—pathology drastically interferes in many life functions; may be hospitalized CGI-I Guidelines
1=Very much improved—nearly all better; good level of functioning; minimal symptoms; represents a very substantial change
2=Much improved—notably better with significant reduction of symptoms; increase in the level of functioning but some symptoms remain
3=Minimally improved—slightly better with little or no clinically meaningful reduction of symptoms. Represents very little change in basic clinical status, level of care, or functional capacity
4=No change—symptoms remain essentially unchanged
5=Minimally worse—slightly worse but may not be clinically meaningful; may represent very little change in basic clinical status or functional capacity
6=Much worse—clinically significant increase in symptoms and diminished functioning
7=Very much worse—severe exacerbation of symptoms and loss of functioning Results Baseline Demographics: Demographics for Cohorts 1 and 2 are presented in Table 1.

TABLE 1

| Baseline Demographics | | | | | |
|---|---|---|---|---|---|
| | Cohort 1 N = 4 | Cohort 2 N = 28 | PTSD N = 20 | MDD N = 8 | Total N = 32 |
| Sex | | | | | |
| Male (n, %) | 3 (75) | 12 (43) | 8 (40) | 4 (50) | 15 (47) |
| Female (n, %) | 1 (25) | 16 (57) | 12 (60) | 4 (50) | 17 (53) |
| Race | | | | | |
| Caucasian | 4 (100) | 26 (93) | 18 (95) | 8 (100) | 30 (94) |
| Asian | 0 | 2 (7) | 2 (5) | 0 | 2 (6) |
| Age | | | | | |
| Mean | 42.5 | 45.9 | 46.9 | 43.3 | 45.4 |
| Median | 41 | 47 | 43 | 48 | 45 |
| IQR | 56 | 21.5 | 20.5 | 29 | 23.3 |
| Min, Max | 28, 60 | 22, 78 | 25, 78 | 22, 76 | 22, 78 |
| Range | 32 | 56 | 53 | 54 | 56 |

TABLE 1-continued

Baseline Demographics

|  | Cohort 1 N = 4 | Cohort 2 N = 28 | PTSD N = 20 | MDD N = 8 | Total N = 32 |
|---|---|---|---|---|---|
| Age population | | | | | |
| 18-<65 years | 4 (100) | 24 (86) | 17 (85) | 7 (88) | 28 (88) |
| ≥65 years | 0 | 4 (14) | 3 (15) | 1 (13) | 4 (13) |

Abbreviations:
CGI-S = Clinical Global Impression-Severity;
IQR = Interquartile range;
Max = Maximum;
MDD = Major Depressive Disorder;
Min = Minimum;
PTSD = Post Traumatic Stress Disorder Cohort 1 is composed of 4 healthy adult subjects (3 males and 1 female) ranging in age from 28 to 60 years who were administered methylone in a single administration in either a group setting (3 subjects) or individually (1 subject). Cohort 1 tended to have a higher proportion of male subjects who were younger, and all were Caucasian. Prior experience with methylone was unknown in two subjects and confirmed in the other two subjects (one male and one female).

Cohort 2 is composed of 28 patients with PTSD or MDD treated in an outpatient setting. Note that one of the patients included in the MDD population had a primary diagnosis of bipolar disorder type I. Overall, males and females were well represented within Cohort 2 and showed similar proportions within the PTSD and MDD subsets.

The age population exceeded 85% for ages 18 to <65 years of age overall and in the subsets for PTSD and MDD with a small subset of elderly patients (≥65 years of age) in the overall data set and the PTSD and MDD subsets. The overall age range for Cohort 2 was wide ranging from 22 to 78 years (mean 45.9 years) with similar distribution among the PTSD and MDD subsets.

Cohort 2 Baseline Disease Characteristics
Primary Diagnosis

Overall, the majority [20 of the 28 patients, (71%)] of the patients included in Cohort 2 had a primary diagnosis of PTSD and 29% had a primary diagnosis of MDD or bipolar disorder (7 MDD; 1 bipolar). However, 10 of the 20 patients (50%) with PTSD also had a secondary diagnosis of MDD or depression (6 MDD; 4 depression) with 64.2% overall having a primary or secondary diagnosis of MDD or depression.

Prior/Concomitant Therapies

For the PTSD subset of Cohort 2, the most common prior/concomitant therapies reported for 2 patients or more in descending order were SSRIs (14 patients), talk therapy (7 patients), breath work (4 patients), cognitive and behavioral therapy and antidepressant unspecified (4 patients each). The majority of patients had discontinued their respective therapies prior to the initial methylone dosing session. Within the PTSD subset, 5 patients had concomitant therapy with SSRIs or other antidepressant classes and 4 of these patients had magnitude of improvement CGI 1 or 2. The treatment regimens were as follows:
fluoxetine 20-40 mg
fluoxetine (dose unspecified)
fluoxetine and bupropion (doses unspecified)
escitalopram (dose unspecified)
bupropion (dose unspecified)
    Lamotrigine (dose unspecified) discontinued after first of 6 sessions.

The patient had a quasi-psychedelic experience, but not specified at which session this occurred, as described below in more detail.

For the MDD subset of Cohort 2, the most common prior/current therapies reported for 2 patients or more in descending order were SSRIs (3 patients), talk therapy (3 patients each) psychotherapy (2 patients) and antiepileptics (2 patients). The majority of patients had discontinued their respective therapies prior to the initial methylone dosing session. Only a single patient had concomitant therapies at the time of methylone dosing with unspecified doses of escitalopram, clonazepam, lamotrigine and propranolol which were tapered after the fifth of 10 methylone sessions. Magnitude of improvement was CGI-I 2 and no safety events were reported.

Baseline Disease Severity

Baseline disease severity (CGI-S) for Cohort 2 is shown in Table 2 and FIG. 2. Baseline CGI-S ranged from 4 to 7 and 85.7% of patients had baseline CGI-S 5 or 6 with similar proportion in both the PTSD and MDD subsets.

TABLE 2

Cohort 2 Baseline Disease Severity by CGI-S

| CGI-S | PTSD N = 20 | MDD N = 8 | Total N = 28 |
|---|---|---|---|
| 4 | 2 | 1 | 3 |
| 5 | 11 | 2 | 13 |
| 6 | 5* | 5 | 10* |
| 7 | 2* | 0 | 2* |

Abbreviations:
CGI-S = Clinical Global Impression-Severity;
MDD = Major Depressive Disorder;
PTSD = Post Traumatic Stress Disorder
*One patient included in category "6" had baseline CGI-S "6+" and one patient in category 7 has baseline CGI-S "6 or 7"

Baseline Symptom Inventory

Figure 1:
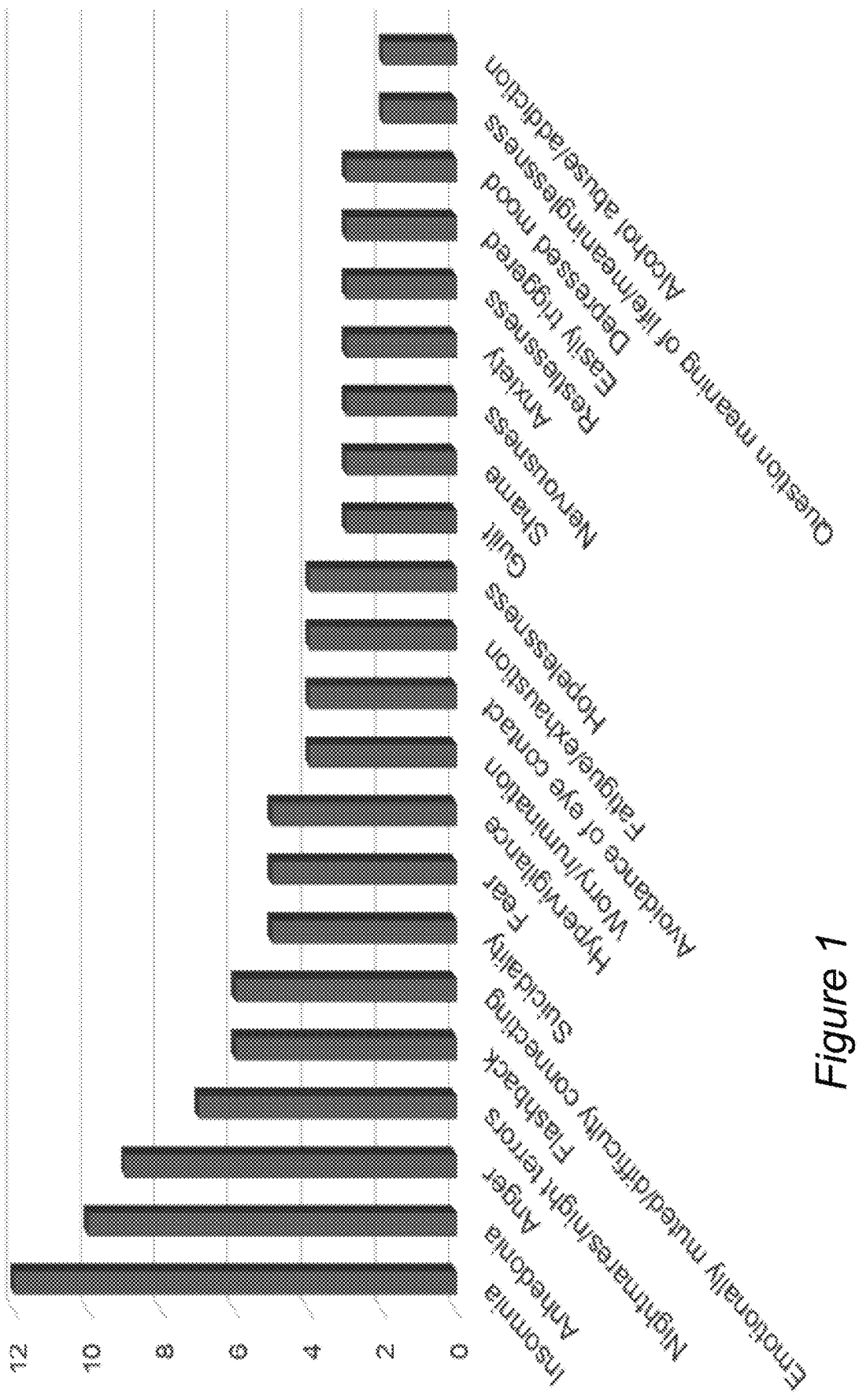
FIG. 1 shows the baseline symptom inventory for symptoms occurring in 2 or more of the 28 patients included in Cohort 2 of Example 4.

FIG. 1 shows the baseline symptom inventory for symptoms occurring in 2 or more of the 28 patients included in Cohort 2. The most common symptoms included insomnia (12 patients), anhedonia (10 patients), anger (9 patients) and nightmare/night terrors (7 patients).

Methylone Dose and Regimen
Cohort 1

The 3 males in Cohort 1 were dosed in a group setting during a single session with a total methylone dose of 790 mg administered as a regimen of methylone 280 mg followed by booster doses of 190 mg, 190 mg and 130 mg. For the one female healthy volunteer, the total dose was 870 mg administered as methylone 250 mg followed by booster doses of 220 mg, 200 mg, and 200 mg.

Cohort 2

Only sessions that included methylone dosing were counted as dosing sessions. Some patients were noted to continue group therapy with methylone beyond the sessions noted but the magnitude of improvement by CGI-I as compared to baseline was assessed following the methylone dosing sessions.

In two cases, one as an initial session, and one as a second session, MDMA was administered as a single agent. In one case with repeat methylone dosing sessions, the initial session included administration of 3 grams of mushrooms 30 minutes after methylone dosing.

Single sessions occurred for 8 of the 28 cases with no booster in two of these cases. In the remainder of the cases, multiple sessions occurred, and booster doses were used in all or some of the remaining patients (26 cases reports) with multiple booster doses used in some or all of the sessions in 15 patients. Methylone total dose at each session had a minimum range of 100 mg to 690 mg and a maximum range of 180 mg to 1020 mg. Maximum total dose for each session exceeded 500 mg [methylone dose plus booster dose(s)] in only four sessions in 3 patients. The methylone dose ranged from 100 to 270 mg and the booster dose(s) had a total cumulative dose that ranged from 50 mg to 880 mg but only exceeded 370 mg in two sessions in two patients. Individual methylone booster doses had a minimum range of 50 mg to 240 mg and a maximum range of 80 mg to 250 mg.

Safety
Cohort 1

For all 4 subjects in Cohort 1, no adverse effects or after-effects were observed or reported. All 3 males were noted to be able to walk, make tea and had no signs of inebriation.

Cohort 2

In a majority of cases included in Cohort 2 (25 of 28 cases; 89.3%), methylone dosing was well tolerated and no safety events were reported. One case report included an adverse event of increased anxiety following 117 mg MDMA administered in the first session that did not include methylone and occurred prior to any methylone dosing at subsequent sessions and did not recur with methylone dosing at 130 mg total dose (80 mg+50 mg booster). In 3 patients (all≥65 years of age), adverse events were reported following methylone dosing as follows:

I. Case Report A:
   75-year-old male with primary diagnosis of PTSD and medical history of atrial fibrillation and a pacemaker developed lightheadedness during the fifth session using methylone 150 mg and 150 mg booster (highest dose administered) when coming down from the medicine. The event was not considered severe and did not require intervention. Previous total doses ranged from 100-250 mg. There was a negative rechallenge (i.e., repeat methylone dosing) with administration of an unknown dose at home.

II. Case Report B:
   70-year-old male with primary diagnosis of PTSD and secondary diagnosis of depression administered methylone 690 mg during a single session (200 mg followed by booster doses 250 mg and 240 mg) did not experience any adverse events during the session but reported adverse events of sleeplessness and loss of appetite following the session, thought to be due to the simulant effects of methylone.

III. Case Report C:
   78-year-old male with primary diagnosis of PTSD and secondary diagnosis of anxiety with medical history of "well-regulated cardiovascular issues" administered methylone with a total dose at each session ranging from 100 to 300 mg (100-150 mg methylone with κ to 150 mg booster) over 5 sessions reported a quasi-psychedelic experience, but dose and further details were not provided. No intervention required.

Efficacy

As Cohort 1 consisted of healthy volunteers, efficacy is reported for Cohort 2 which consisted of PTSD and MDD patients.

Magnitude of Improvement
CGI-I and Time to Initial Improvement

Figure 3A:
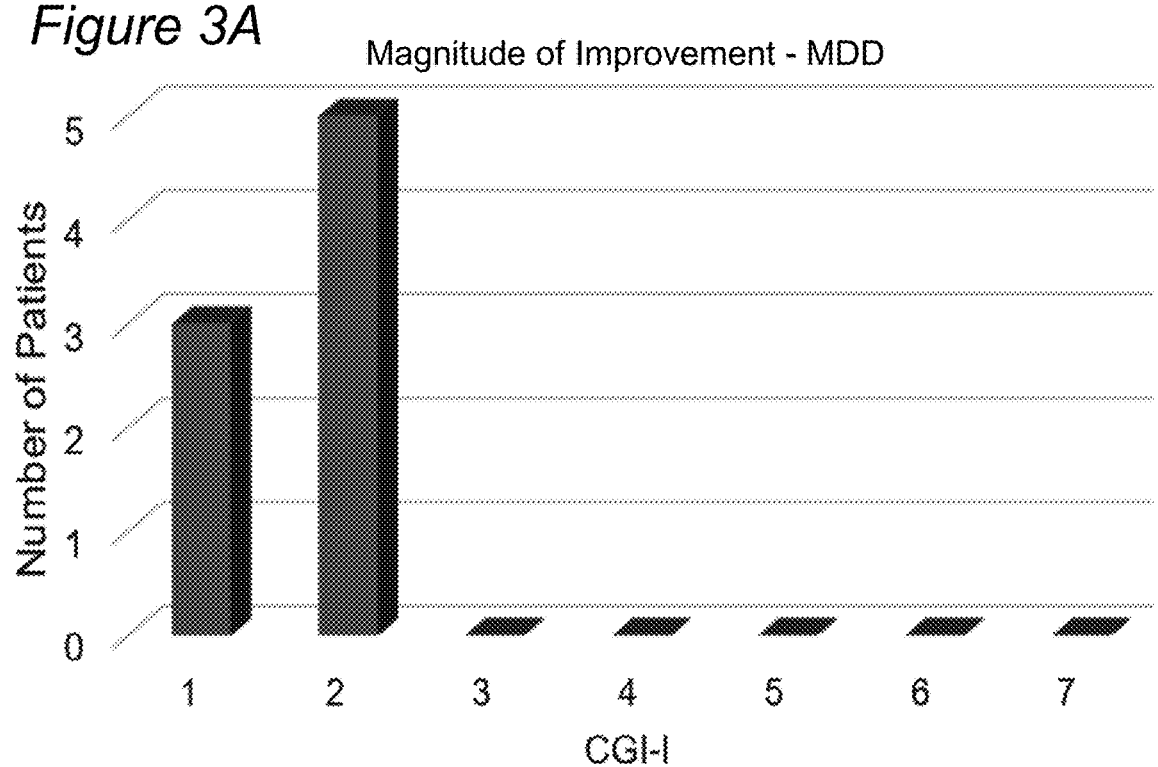
FIGS. 3A-3B show the Magnitude of Improvement in Cohort 2 for subjects in the (FIG. 3A) MDD subset and (FIG. 3B) PTSD subset.
Figure 3B:
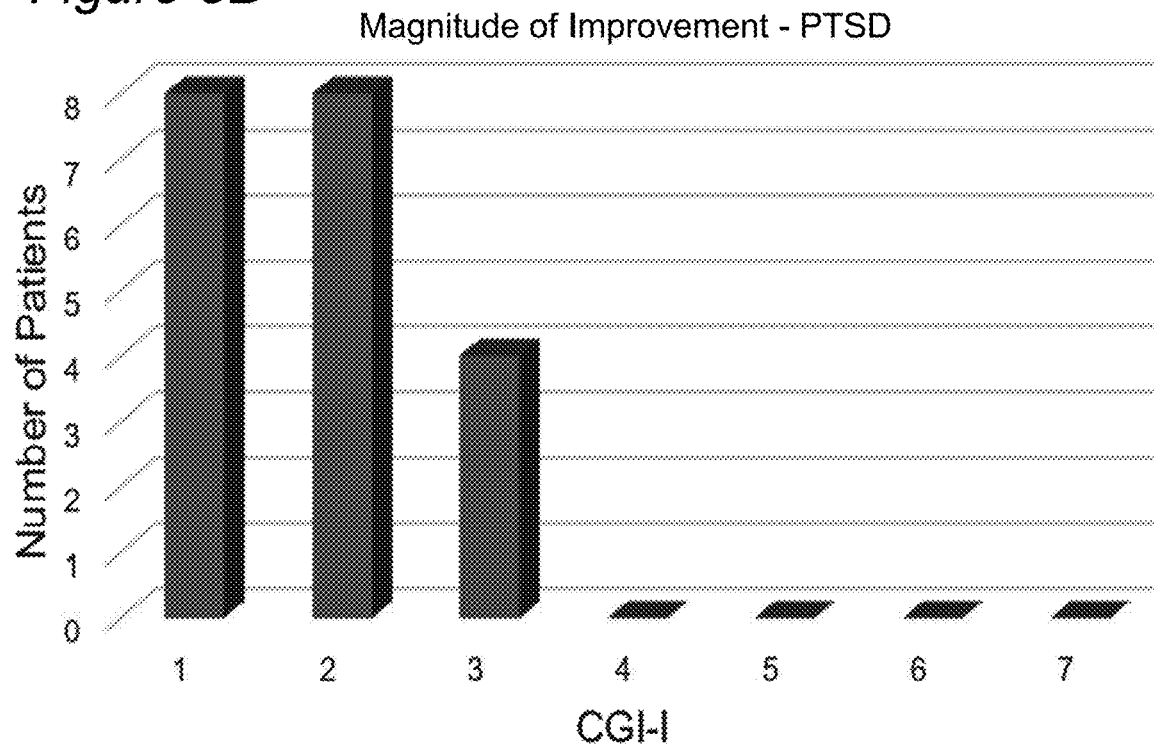

All patients achieved at least minimal improvement (CGI-3 or better) following treatment with methylone. The highest observed magnitude of improvement for the 28 cases included in Cohort 2 is shown in Table 3 and FIG. 3. CGI-I 1 or 2 was achieved in 86% of the patients [16/20 patients (80%) for the PTSD subset and 8/8 patients (100%) for the MDD subset] corresponding to "much improved" or "very much improved" compared to baseline CGI-S. Additionally, initial improvement was observed with the first methylone session in almost 90% of patients (25 of 28 patients). Two additional cases experienced initial improvement following the $2^{nd}$ and $3^{rd}$ sessions, respectively, and one case required 10+ sessions for initial improvement.

TABLE 3

Magnitude of Improvement

| CGI-I | Number of cases (N = 28) |
|---|---|
| 1 | 11* |
| 2 | 13 |
| 3 | 4 |
| 4 | 0 |
| 5 | 0 |
| 6 | 0 |
| 7 | 0 |

Abbreviations:
CGI-I = Clinical Global Impression-Improvement
*One case rated as CGI-I "1/2" and included in the category "1"

Durability of Response

Within the PTSD subset of Cohort 2, 16 of the case narratives included information on durability. One case reported no durable effect, and 15 case narratives reported a durable effect (6 months or greater in 12 of the cases, limited to 3 months in one case and unknown in 2 cases). In one of the cases with unknown length of durable response, the narrative stated that "the subject no longer qualified for the disease' following the $4^{th}$ methylone dosing session.

Within the MDD subset of Cohort 2, 6 of the 8 case narratives included information on durability. One case reported no durable effect, and the remaining 5 cases reported a durable effect which was noted to be 2 years in 2 patients, 5 years in 1 patient and unknown in 2 patients but reported as "stable after 13 sessions" in 1 patient and "sustained" in another patient.

Change in CGI-S

CGI-S post-treatment was only reported in 5 cases as shown in Table 4 including one patient noted to achieve a stable CGI-S 1. One case was noted to sometimes achieve CGI-S 1. In 5 additional case narratives that did not include post-treatment CGI-S scores, it was reported that patients no longer qualified for the diagnosis post-treatment and 5 of these cases achieved CGI-I 1.

TABLE 4

Maximum Change Post-treatment CGI-S

| Case ID # | Pre-treatment Baseline CGI-S | Best CGI-S | CGI-S max change from BL |
|---|---|---|---|
| 2 | 6 | 2 | −4 |
| 3 | 5 | 2* | −3 |
| 6 | 6 | 3 | −3 |
| 7 | 5 | 1 | −3 |
| 21 | 7 | 4 | −3 |

Conclusion

Overall methylone, administered in single or multiple sessions with single dosing and/or with booster dose(s) was well tolerated. No safety events were reported in healthy volunteers or adult patients age 18 or <65 years of age. Transient safety events were reported in 3 elderly patients which occurred at high dose or did not recur on rechallenge. One of these events included a quasi-psychedelic experience which occurs in ~5-6 of every 2,000 methylone administrations.

The majority of patients in the PTSD subset (90%) and MDD subset (88%) had baseline CGI-S of 5 or greater ("markedly" or "severely" μl) with 2 of the PTSD patients in the severest category of CGI-S 7 (i.e., amongst the "most severely ill patients"). Despite this, Cohort 2 had a magnitude of improvement of 1 or 2 in 86% of patients overall [16/20 patients (80%) for the PTSD subset and 8/8 patients (100%) for the MDD subset] corresponding to "much improved" or "very much improved" compared to baseline CGI-S.

Example 5: Clinical Evidence for the Use of Methylone in the Treatment of PTSD: A Case Series with Long-Term Follow-Up PTSD is a debilitating, and often chronic, psychiatric disorder characterized by a constellation of symptoms including intrusive memories, distressing dreams, dissociative reactions, physiological reactivity to and avoidance of trauma-related stimuli, negative cognition and mood, lassitude, increased arousal, impaired sleep, cognitive dysfunction, irritability, risk-taking behavior, and clinically significant distress and impairment in functioning. It is estimated that 70% of the world population have been exposed to trauma and, though resilience is the norm rather than the exception, approximately 6% of trauma-exposed individuals develop PTSD. The estimated prevalence of PTSD is 20% following interpersonal violence, 25% in combat-exposed military veterans, 50% in rape survivors, and as high as 86% among certain refugee groups. PTSD is a well-established risk factor for suicide, increasing suicide risk 6 to 29-fold above the general population.

Available pharmacotherapy options are limited. Selective serotonin reuptake inhibitors (SSRIs) represent the first-line pharmacological treatment; paroxetine and sertraline are the only FDA-approved medications for treating PTSD. However, despite their established efficacy, these treatments are sub-optimal. They are slow-acting antidepressants (SAADs) with a delayed onset of action—most patients do not show significant effects until at least 4 weeks (and often up to 8 weeks) of continuous treatment. This latency period is decidedly troubling, as it significantly increases the risk for suicide and self-harm as well as for other potentially destructive behaviors. Even when optimally delivered, 40% of the patients do not respond to SSRIs, and only about 20% to 30% achieve remission, and the magnitude of the difference from placebo ranges from 10% to 20%. The rates of non-response or partial response to these medications among individuals with chronic and complex PTSD such as military veterans, are comparable or worse to those of the civilian patient population. Furthermore, many who are classified as 'treatment-responders' remain symptomatic and continue to lead restricted lives.

Trauma-focused psychotherapy also shows some efficacy in treatment of PTSD and is often the first-line intervention selected, given the known limitations in pharmacotherapy. Prolonged Exposure (PE) and Cognitive Processing Therapy (CPT) are the gold standard treatments, but access to appropriately trained therapists is limited and effective therapy requires a willingness on the part of the patients to expose themselves to trauma-related memories and to experience the attendant distress. The attrition rate among gold-standard psychotherapy outcome studies ranges from 17% to 55.8%, and nonresponse can be as high as 50%. Regardless of treatment modality, troubling symptoms often persist even in patients classified as treatment responders. The efficacy gap may also be particularly significant among Veterans treated in Veterans Affairs (VA) Medical Center settings, perhaps due, at least in part, to the complexity of these patients, whom often have significant psychiatric and medical comorbidities and repeated chronic trauma exposures. There is thus an urgent need to identify rapidly acting novel strategies to treat PTSD, delineate the mechanisms underlying treatment effects, and, critically, establish baseline markers that can predict therapeutic response.

Recently, several placebo-controlled clinical trials have demonstrated an acute and enduring beneficial clinical effect in PTSD, as measured by the Clinician-Administered PTSD Scale for DSM-5 (CAPS-5), after administration of two to three doses of methylenedioxymethamphetamine (MDMA) with manualized psychotherapy. These robust enduring clinical effects were recently replicated in a large Phase 3 clinical trial. A second Phase 3 clinical trial is currently underway, and a favorable clinical outcome could place MDMA-assisted psychotherapy on track for FDA approval.

3,4-methylenedioxy-N-methylcathinone (methylone; also known as MDMC, βk-MDMA, and M1) is a rapid acting empathogen (RAE) structurally related to MDMA. An observational-naturalistic study compared the acute pharmacological and physiological effects of orally administered methylone and MDMA in healthy participants with a history of prior exposure to both compounds. While the compounds may be mechanistically similar, methylone produced less intense prototypical psychostimulant and empathogenic effects, including lessened euphoria, inebriation, stimulant-like effects, and changes in cognitive and body perception, with increased sociability relative to MDMA. The notable differences in acute pharmacological effects could be explained in part by differences in serotonin (5-HT) receptor affinity. Methylone has significantly lower affinity for $5\text{-HT}_{2A}$ than MDMA and has partial agonist activity at the $5\text{-HT}_{1A}$ receptor, which MDMA does not. Methylone also has weaker antagonistic effects on $5\text{-HT}_{2C}$ relative to MDMA, which has partial agonistic activity. Methylone also inhibits or reverses the monoamine reuptake transporters for dopamine, norepinephrine, and serotonin, which increases extracellular concentrations of these neurotransmitters.

This Example presents a more detailed analysis of 21 patients from the previous Example (the 20 patients from the PTSD subset discussed in the previous Example plus one patient from that Example who was mischaracterized and was subsequently determined to have a primary diagnosis of PTSD) with a primary diagnosis of PTSD, with a range of psychiatric comorbidities, who were treated clinically with methylone in an outpatient setting. The patients were not given structured psychotherapy in conjunction with methylone treatment, which differs from recent studies of MDMA that emphasize the importance of a manualized psychedelic-assisted psychotherapy model. These characteristics, together with methylone's short duration of action and less dramatic acute psychological and physiological effects, make it an attractive agent for clinical use in the treatment of PTSD.

Materials and Methods

Archival clinical data was obtained from 21 patients with a primary diagnosis of PTSD who received at least one oral methylone administration as part of specialty care in an outpatient psychiatric setting. No protected health information was disclosed, and no consent was obtained from patients for use of their archival data. Case narratives were systematically compiled from data collected as part of routine clinical work. Diagnoses were confirmed by an experienced clinician using semi-structured interviews. Baseline symptom severity was evaluated using the Clinical Global Impressions Scale-Severity (CGI-S). Symptom improvement was evaluated using the Clinical Global Impressions Scale-Improvement (CGI-I) following dosing. Patients were evaluated for any observed or reported safety events following their methylone dosing session(s). Because these case narratives were examined retrospectively from routine clinical care records, and not gathered prospectively in a research study, more specific validated rating scales for assessing PTSD symptoms were not available. Additionally, follow-up varied, with the length of follow-up ranging from one week (Case 2) to 15 years (Case 16).

TABLE 5

Demographic Data, Clinical Characteristics, and Response to Treatment

| ID | Age (years)/ Sex (M/F) | Comorbidities | Prior Treatments | Concomitant Medications | Total Methylone Dose Range Across all Sessions (mg) | # Observed Dosing Sessions | Duration Treatment | Baseline CGI-S | Peak CGI-I (Time since baseline CGI-S ) |
|---|---|---|---|---|---|---|---|---|---|
| 2 | 62/M | Bipolar II; GAD; SCZ; Insomnia; SI | Psychotherapy; psychiatric therapy; olanzapine; quetiapine; venlafaxine; Opiates | lamotrigine; lurasidone HCl; clonazepam; amphetamine, dextroamphetamine, propranolol | 550 | 1 | 1 session | 7 | 1 (1 week) |
| 3 | 75/M | Parkinson's Disease; Cardiovascular diagnosis; Atrial fibrillation; Pacemaker | CBT, Breath work, hypnosis, unspecified SSRIs | — | 100 to 300 | 5 | >18 months | 5 | 1 (11 months) |
| 4 | 49/M | MDD; GAD; Social phobia; SI; Insomnia | Talk therapy; CBT; experiential therapy (ketamine); fluoxetine | — | 250 to 620 | 4 | 10 months | 7 | 1 (10 months) |
| 5 | 54/M | Eating disorder (UNSP); Insomnia | Talk therapy; CBT; support group; SSRI (escitalopram) | Escitalopram | 150 to 350 | 3 | 11 months | 5 | 3 (11 months) |
| 6 | 38/F | MDD; BPD; SI | Residential clinical therapy including group therapy; breath therapy; talk therapy | — | 400 to 500 | 4 | 2 years | 6 | 1 (16 months) |
| 7 | 52/F | GAD | ~5 years talk therapy 2 experiential treatments each lasting 4 weeks (hug and scream + primal therapy) | — | 150 to 410 | 6 | 1-2 months | 5 | 1 (1 month) |
| 8 | 46/F | N/A | Unspecified SSRIs | — | 230 | 1 | 1 session | 4 | 2 (1st session) |
| 9 | 25/F | MDD; GAD; SI | fluoxetine <60 mg | — | 360 | 1 | 1 session | 6 | 1 (1st session) |
| 10 | 70/M | MDD | Unspecified SSRIs | — | 690 | 1 | 1 session | 5 | 2 (1st session |

TABLE 5-continued

Demographic Data, Clinical Characteristics, and Response to Treatment

| ID | Age (years)/ Sex (M/F) | Comorbidities | Prior Treatments | Concomitant Medications | Total Methylone Dose Range Across all Sessions (mg) | # Observed Dosing Sessions | Duration Treatment | Baseline CGI-S | Peak CGI-I (Time since baseline CGI-S) |
|---|---|---|---|---|---|---|---|---|---|
| 11 | 33/F | MDD; GAD; binge eating disorder; SI | Talk therapy; CBT; holotropic breathwork; somatic experiencing; inpatient treatment; unspecified SSRIs | Fluoxetine | 310 to 460 | 3 | 5 months | 6 | 1 (5 months) |
| 12 | 78/M | UNSP anxiety disorder; Insomnia | Unspecified antidepressants | bupropion* lamotrigine | 100 to 300 | 5 | 2 years | 5 | 2 (2 months) |
| 13 | 40/M | MDD; anxiety disorder; SI; Insomnia | Wellbutrin; unspecified SSRIs, psychotropics and unspecified narcoleptic | Unspecified SSRI | 330 | 1 | 1 session | 5 | 2 (1st session) |
| 14 | 36/F | Insomnia | Unspecified sleep medication | — | 220 | 1 | 1 session | 5 | 1 (1st session) |
| 15 | 38/F | Substance addiction; SI; insomnia | Detox for alcohol and narcotic abuse; couples counseling; unspecified SSRIs | — | 470 | 1 | 1 session | 6 | 2 (1st session) |
| 16 | 28/M | MDD; UNSP Personality disorder | Holotropic breathwork; weekly therapy; unspecified SSRIs | — | 310 to 1020 | unknown | 3 years with a gap of 15 years, then 2 years | 6 | 3 (2-3 days after each session, but relapsed soon after) |
| 17 | 38/F | N/A | Unspecified SSRIs | — | 300 to 330 | 12+ | 1.5-2 years | 4 | 3 (after 10 sessions, >1 year) |
| 18 | 25/M | N/A | | Unspecified psychotropic | 150 | 1 | 1 session | 5 | 3 (1st session) |
| 19 | 58/F | MDD; UNSP Anxiety | Several inpatient treatments; weekly therapy sessions; unspecified SSRI combination therapy | — | 250 to 400 | 5 | 10 months | 5 | 2 (8 months) |
| 20 | 59/F | MDD | Talk therapy; meditation, unspecified SSRIs, recreational psychedelics | — | 180 to 400 | 3 | 9 months | 5 | 1 (9 months) |
| 21 | 58/F | MDD; UNSP anxiety; social phobia; SI | Prior inpatient treatment; multiple psychiatric modalities; Multiple Medications | — | 100 | 1 | 1 session | 7 | 2 (1st session) |

TABLE 5-continued

Demographic Data, Clinical Characteristics, and Response to Treatment

| ID | Age (years)/ Sex (M/F) | Comorbidities | Prior Treatments | Concomitant Medications | Total Methylone Dose Range Across all Sessions (mg) | # Observed Dosing Sessions | Duration Treatment | Baseline CGI-S | Peak CGI-I (Time since baseline CGI-S) |
|---|---|---|---|---|---|---|---|---|---|
| 22 | 38/F | N/A | Inpatient treatment; unspecified SSRI | — | 250 to 360 | 4 | 3.5 years | 5 | 2 (1 year) |

*Case 12: Based on the case narrative, it is unknown if bupropion was a prior or concomitant medication.
Abbreviations:
BPD: Borderline personality disorder;
CBT: cognitive behavioral therapy;
F: female;
GAD: generalized anxiety disorder;
M: male;
MDD: major depressive disorder;
NR: not reported;
PTSD: posttraumatic stress disorder;
SCZ: Schizophrenia;
SSRI: selective serotonin reuptake inhibitor;
SNRI: serotonin-norepinephrine reuptake inhibitor;
SI: suicidal ideation;
UNSP: unspecified Results Methylone produced acute and enduring improvements in both PTSD and depression symptoms, without any notable lasting adverse effects. Clinical data are presented in Table 5. Twelve patients (57%) were female; 19 (90%) were White. The mean age was 47.6 years (range: 25 to 78). Baseline CGI-S scores ranged between 4 and 7 for all 21 patients (i.e., moderately to severely ill; see FIG. 4). Six patients (28.6%) were on concomitant SSRI or other psychotropic therapy at the time of methylone dosing. This is notable because recent trials of MDMA in PTSD have required that patients be on no other psychotropic medications, as SSRI antidepressants have been shown to attenuate the therapeutic effects of MDMA due to substrate competition. All patients were experiencing debilitating symptoms despite past and/or ongoing psychological and pharmacological treatment. Prior therapies included: SSRIs/SNRIs (n=14; 66.7%), supportive unstructured therapy (n=8; 38%), structured cognitive and behavioral therapy (n=4; 19%), and unspecified antidepressant therapy (n=3; 14.3%).

Figure 4B:
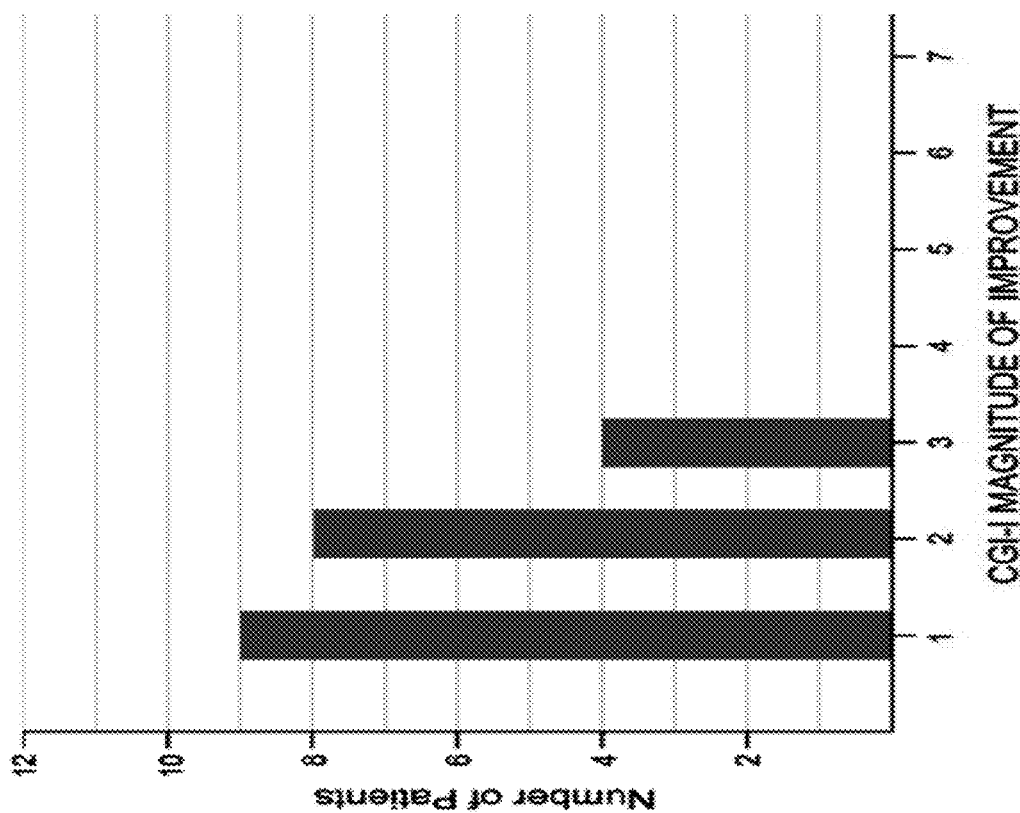
FIGS. 4A-4B show the (FIG. 4A) Baseline Disease Severity and (FIG. 4B) Magnitude of Improvement for the patients of Example 5.
Figure 4A:
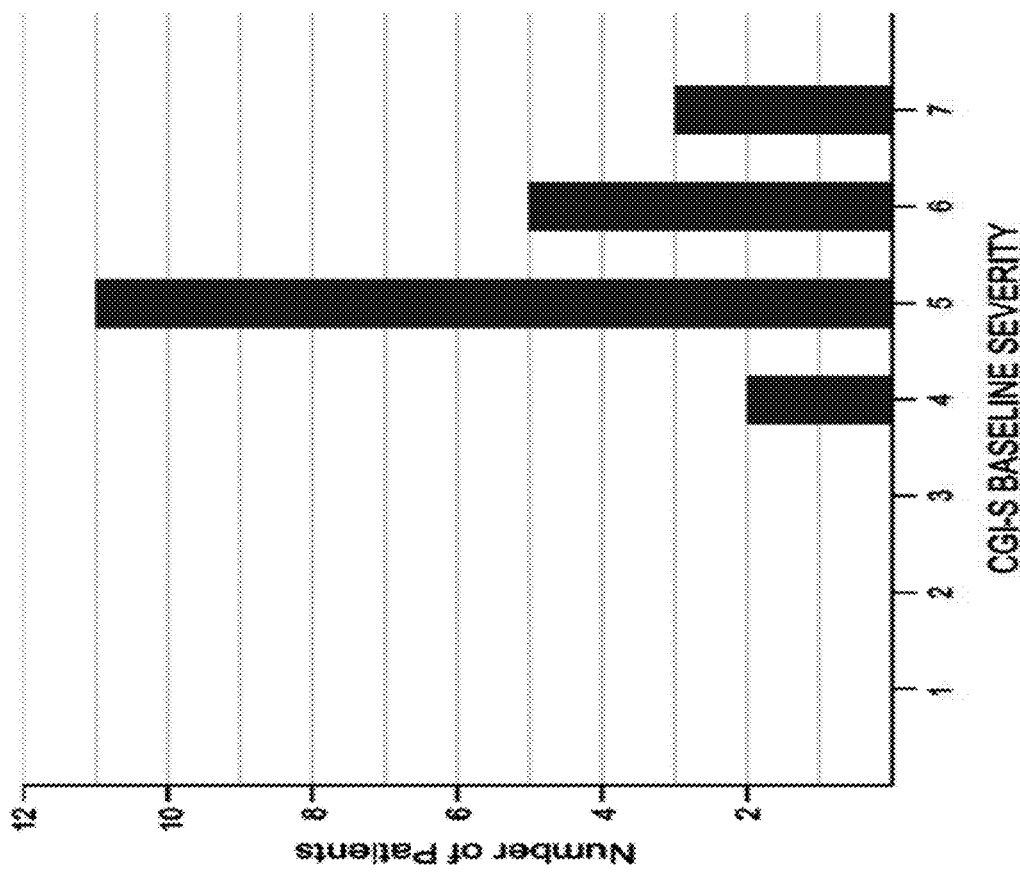

All 21 patients achieved at least minimal improvement (CGI-I 1, 2 or 3) following methylone treatment, with 17 achieving a CGI-I of 1 (very much improved, 9 patients) or 2 (much improved, 8 patients; see FIG. 4). This trend was observed even for patients who received only a single dose of methylone (n=9), where 8 patients (89%) achieved CGI-I scores of 1 or 2. For patients with multiple methylone dosing sessions (n=12), initial improvement was noted after the initial session in 83% (n=10) of the patients; one additional patient experienced improvement after the second session.

Information on durability of the clinical effect was captured for 17 of 21 patients. One individual reported no durable effect (i.e., symptom severity returned to baseline almost immediately), and 16 reported a durable effect (>six months in 11 patients) and one patient each reported a sustained effect of three months, two months, and one week respectively. In one of the four case narratives that did not include durability information, the patient "no longer qualified for the disease (i.e., PTSD)" following the 4th methylone dosing session (10 months after baseline assessment), as determined by the treatment team.

Dosing summary: Methylone was administered orally. Other medications were not changed during methylone treatment. In many cases, an additional, booster dose of methylone was administered 1 hour after the initial dose to extend the therapeutic window and optimize clinical response. In several cases, treatment was continued, and, in some cases, the dose was further escalated in later sessions (see Table 5). Booster doses were included for 19 patients in one or more of the sessions. Starting doses were between 100 and 270 mg, and these as well as booster doses were selected based on clinical judgement.

Safety: Methylone was generally well tolerated, and no patients discontinued treatment due to adverse events. A total of four adverse events were noted in three of the 21 patients (two in one patient); none were considered severe, and none required medical intervention. A 75-year-old male with a medical history of stable atrial fibrillation (with a pacemaker) and Parkinson's Disease developed lightheadedness around the end of his fifth session using methylone, at a total dose of 300 mg (150 mg followed by booster dose of 150 mg, which was the highest dose administered for this patient). This symptom resolved quickly, and the individual was feeling well upon discharge with no other adverse effects. A 70-year-old male administered methylone 690 mg during a single dosing session (200 mg followed by booster doses of 250 mg and 240 mg) did not experience any adverse events during the session but reported sleeplessness and loss of appetite the night following the session. These symptoms had resolved by the following day. A 78-year-old male reported a flashback-like experience during one treatment session. This patient participated in 5 dosing sessions with a total methylone dose at each session ranging from 100 to 300 mg.

Patient reports: A 62-year-old male patient with treatment-refractory PTSD (ID=Case 2 in Table 5) who received methylone in conjunction with ongoing treatment with SSRI noted after the first dosing session that "[his] problems are seemingly disappearing, and maybe more in the head than actual . . . [and that] the treatment with methylone is like a new 'window into hope' that makes the idea of suicide foolish and unnecessary." Following a rapid and sustained reduction in PTSD symptoms after a single methylone session, he expressed interest in tapering off his SSRI as it was no longer needed. Another patient, a 52-year-old female patient with treatment-refractory PTSD and comorbid generalized anxiety disorder (ID=Case 7 in Table 5) described one session as "the healing of the inner little girl." She expressed the recognition that "PTSD isn't going to rule [her] life anymore. [She is] there for that inner child, and she communicated with [her], and [they] have healed [their PTSD]."

Discussion

In this case series of patients with a primary diagnosis of PTSD, with a high rate of comorbidity and prior treatment attempts, methylone produced rapid symptom improvement, as measured by CGI-I. The majority (90%) had baseline CGI-S of 5 or greater ("markedly" or "severely" μl), with 3 patients in the category of CGI-S of 7 (i.e., amongst the "most severely ill patients"). The majority (81%) of patients achieved scores per CGI-I corresponding to "much improved" or "very much improved" (FIG. 4). These effects are similar to those seen in recent controlled clinical trials of MDMA in conjunction with manualized psychotherapy for PTSD, in which rapid and robust improvements were observed in severely ill, complex, and treatment-resistant patients.

Methylone was well-tolerated over a broad dose range (100 to 1,020 mg), with one to ten administrations. A few adverse events were reported in three older patients, age 70 and over; these were mild and required no intervention. No patients discontinued methylone treatment because of adverse events. Notably, none of these adverse events occurred in patients receiving concomitant SSRI therapy.

Strengths and Limitations: This is the first report of methylone administration in patients with PTSD. This case series provides evidence that methylone has utility in the pharmacological treatment of PTSD. However, these data have certain limitations. These participants were treated clinically; data for this report were collected retrospectively from review of clinical records. Dosing and follow-up were variable and there was no randomization, control, or blinding to treatment condition. Further, the sample lacks diversity and ongoing psychotherapy and medication adjustment during the variable follow-up period may have influenced clinical course. A strength of this report is the complexity of the sample, which aids in generalizability. Despite these limitations, these case narratives in a complex patient population constitute the first clinical evidence for the efficacy of methylone to treat PTSD.

Methylone has not received the same cultural or clinical attention as MDMA, perhaps due to its milder and shorter psychopharmacological effects (e.g., euphoria, empathogenic effects). However, these "softer" effects may be particularly helpful for some patients who are not appropriate for treatment with the more intense acute psychological and physiological effects of MDMA.

Example 6: Methylone in the FST: Implications for Depression, Anxiety, and PTSD

In this Example, whether methylone could produce a fast-acting antidepressant-like effect in the rat FST was investigated and the prototypical selective serotonin reuptake inhibitor (SSRI) fluoxetine was used as an antidepressant control.

Methods

Animals: Male Sprague Dawley rats (Charles River Laboratories) weighing 180-200 g on arrival, were used for this study which took place at Melior Discovery (Exton, PA). Rats acclimated to their home cages for at least one week before testing, were maintained in a controlled environment on a 12 h light/dark cycle, with no more than 2 rats per cage. Animals received ad libitum access to food and water and were assigned randomly to treatment groups. Animal use and procedures were in accordance with established protocols approved by the IACUC committee, Melior Standard Operation Procedures (SOP), and Transcend Therapeutics.

Forced Swim Test (EST): In the FST trial, rats were placed in a circular plexiglass container filled with water, with no means of escape. Water temperature was maintained at 22-25° C. and changed for every animal. After an acclimation period, rats were timed for inactivity (failure to struggle), activity, swim time and climbing time. Day 1 consisted of a 15 min acclimation trial, and Day 2 (24 h later) consisted of the 5 min test. A time sampling procedure was employed where animals were observed every 5 sec and scored for immobility, swimming, or climbing. Fluoxetine (10 mg/kg, IP, Sigma Aldrich) or 0.9% sterile saline vehicle (vehicle 3× group) were administered 23.5, 5, and 1 h before testing in the FST. Methylone (5, 10, 15, 20, and 30 mg/kg, IP; Cayman Chemical) or 0.9% saline vehicle (vehicle 1× group) were administered 30 min prior to FST testing. For oral administration, rats were administered a single dose of methylone (15 mg/kg) 2 hours before FST testing. The experimenter was blinded to treatment.

Binding Studies: Radioligand binding was performed using standard protocols using [$^3$H]citalopram, [$^3$H]WIN35428, and [$^3$H]nisoxetine for serotonin (5HT), dopamine (DA), and norepinephrine (NE) transporters, respectively. Radiolabeled 5HT, NE, and DA uptake and release studies in rat brain synaptosomes were conducted using standard protocols.

Statistical Analysis: Data for each parameter of the test (immobility, swimming, or climbing) is expressed as the mean±SEM. Differences between groups were determined by one-way ANOVA and post-hoc Tukey's test with a p-value of less than 0.05 indicating statistically significant differences.

Results and Conclusions

Figure 5:
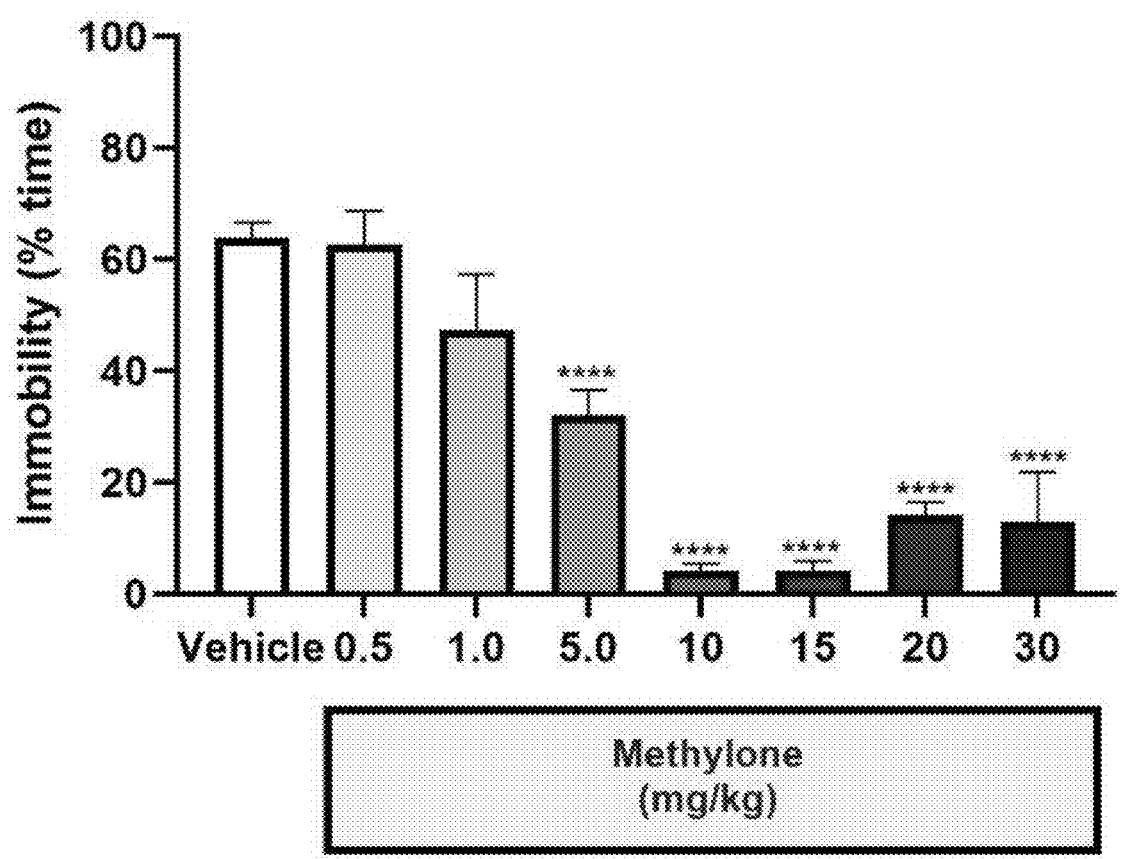
FIG. 5: Methylone has a rapid, robust antidepressant-like effect in the forced swim test (FST). Rats were given methylone or vehicle intraperitoneally (IP) 30 min before testing in the FST. Less immobility indicates stronger antidepressant-like activity. Methylone significantly reduced immobility at doses of 5, 10, 15, 20, and 30 mg/kg. **** $p<0.001$ vs. vehicle, N=6-16 per group.

A single dose of methylone produced a robust, dose-dependent and fast-acting antidepressant-like response in the rat FST (FIG. 5). Notably, 2-3 injections of an SSRI antidepressant are generally required to elicit a behavioral response in the FST, as observed in a fluoxetine control group in the current study that received 3 doses of fluoxetine prior to testing. However, rats treated with a single dose of methylone 30 minutes before testing in the FST showed highly significant reductions in immobility (FIG. 5). Notably, a single dose of methylone (5, 10, 15, 20, and 30 mg/kg, IP) administered 30 min prior to testing significantly reduced immobility compared to rats receiving saline vehicle. Mid and high doses of methylone significantly increased swimming. Climbing was only increased at the lowest dose of methylone, reflecting recruitment of noradrenergic receptor activity at this dose level.

The magnitude of the effect of mid (15 mg/kg) and high (30 mg/kg) doses of methylone (99% and 96% reductions)

was notably greater than fluoxetine (56%). These data also demonstrate that methylone out-performs other psychedelic drugs. Previous reports of ketamine administration show 30% (Hibicke et al. (2020) *ACS Chem. Neurosci* 11:864), 25-55% (Yang et al. (2013) *Ups J Med Sci* 118:3), or 60% (Tizabi et al. (2012) *Neuroscience* 213:72) reductions in immobility (reviewed by Weston et al. (2021) *Frontiers in Psychiatry* 12: 659052). LSD and psilocybin have been shown to reduce immobility in the FST by 38% and 67%, respectively (Hibicke, 2020). MDMA (5 or 10 mg/kg) has been reported to reduce immobility by 45% and 78% in Sprague Dawley rats, respectively (Majumder et al. (2011) *Behav Pharmacol* 22:758) but had a more robust effect in Flinders Sensitive Line rats, a genetic model for depression (45% and 93%, respectively, id.). Binding studies confirmed methylone binding at the 5HT, NE, and DA transporters.

Similarly for oral administration, rats administered a single dose of methylone (15 mg/kg, PO) 2 hours before FST testing also showed a significant antidepressant-like effect of methylone compared to vehicle controls (FIG. 37).

Figure 6:
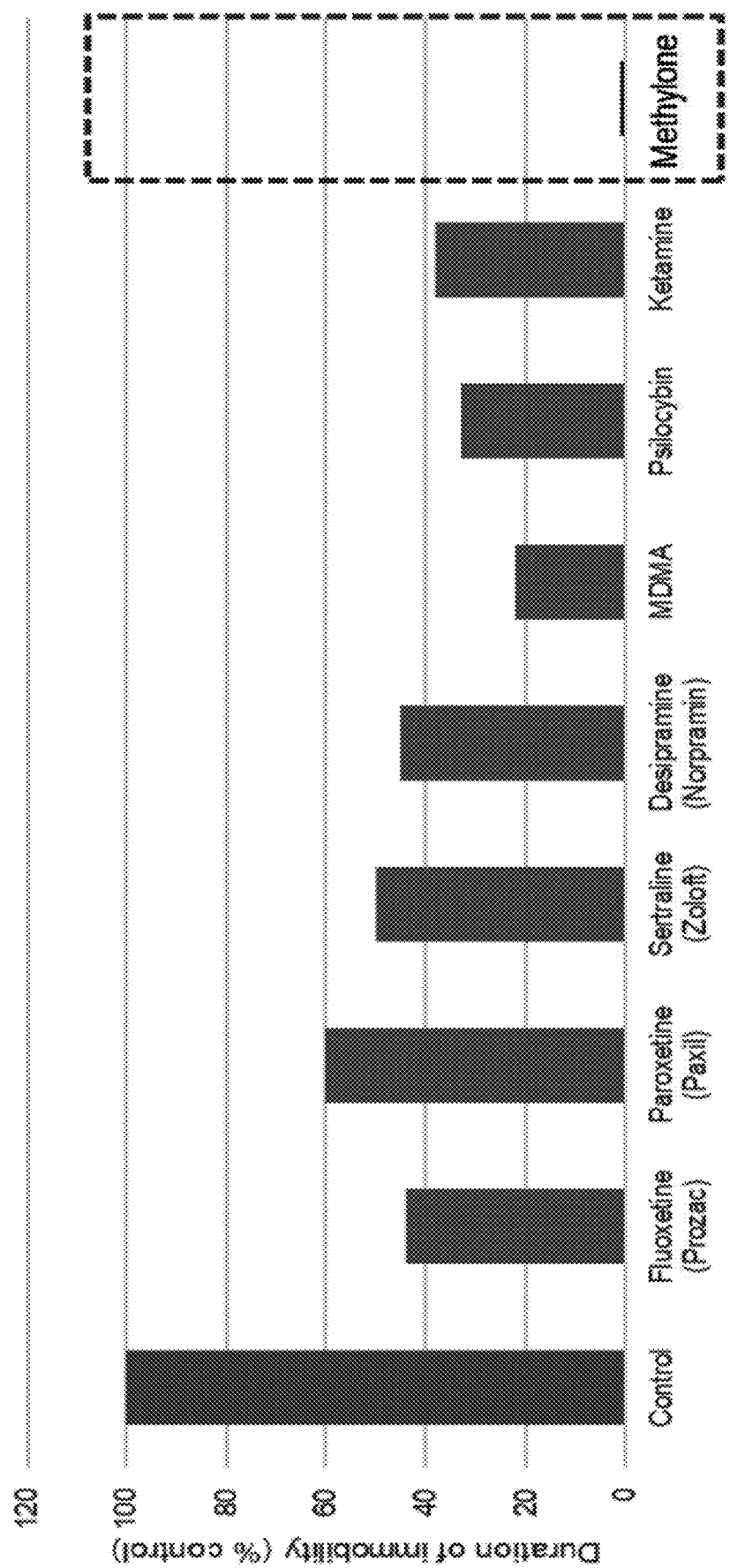
FIG. 6: Methylone outperforms other antidepressants in the Forced Swim Test.

In summary, methylone produced a more robust antidepressant-like response than the SSRI fluoxetine in the FST, a canonical behavioral assay with well-established specificity and selectivity for antidepressant drugs. The magnitude of methylone's effect in this test also surpassed that of other psychedelics and antidepressants tested in wild-type rats in the literature (FIG. 6). Despite its structural similarity to MDMA, methylone shows distinct effects on monoamine transporter binding, uptake and release.

Taken together, these results show the utility of methylone in the treatment of depression and other CNS disorders where antidepressants are efficacious, including but not limited to post-traumatic stress disorder (PTSD), mood disorders, anxiety disorders, obsessive compulsive disorder (OCD), and fibromyalgia.

Example 7: 2C-B in the FST: Implications for Depression, Anxiety, and PTSD

In this Example, whether 2C-B could produce a fast-acting antidepressant-like effect in the rat Forced Swim Test (FST) was investigated and the prototypical selective serotonin reuptake inhibitor (SSRI) fluoxetine was used as an antidepressant control.

Methods

Animals: Male Sprague Dawley rats (Charles River Laboratories) weighing 180-200 g on arrival, were used for this study which took place at Melior Discovery (Exton, PA). Rats acclimated to their home cages for at least one week before testing, were maintained in a controlled environment on a 12 h light/dark cycle, with no more than 2 rats per cage. Animals received ad libitum access to food and water and were assigned randomly to treatment groups. Animal use and procedures were in accordance with established protocols approved by the IACUC committee, Melior Standard Operation Procedures (SOP), and Transcend Therapeutics.

Forced Swim Test: In the FST trial, rats were placed in a circular plexiglass container filled with water, with no means of escape. Water temperature was maintained at 22-25° C. and changed for every animal. After an acclimation period, rats were timed for inactivity (failure to struggle), activity, swim time and climbing time. Day 1 consisted of a 15 min acclimation trial, and Day 2 (24 h later) consisted of the 5 min test. A time sampling procedure was employed where animals were observed every 5 sec and scored for immobility, swimming, or climbing. Fluoxetine (10 mg/kg, IP, Sigma Aldrich) or 0.9% sterile saline vehicle (vehicle 3× group) were administered 23.5, 5, and 1 h before testing in the FST. 2C-B (2.5, 10, or 20 mg/kg, IP, Cayman Chemical) or 0.9% saline vehicle (vehicle 1× group) were administered 30 min prior to FST testing. The experimenter was blinded to treatment.

Statistical Analysis: Data for each parameter of the test (immobility, swimming, or climbing) is expressed as the mean±SEM. Differences between groups were determined by one-way ANOVA and post-hoc Tukey's test with a p-value of less than 0.05 indicating statistically significant differences.

Results and Conclusions

Figure 7C:
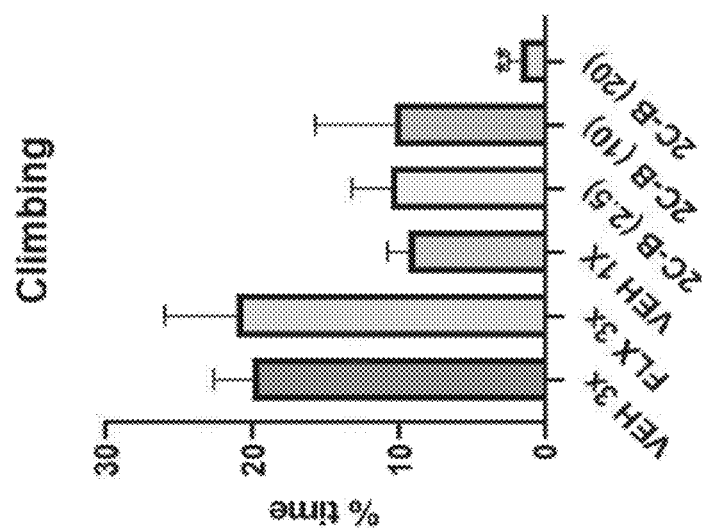
FIGS. 7A-7C: 2C-B has a fast-acting antidepressant-like effect in the Forced Swim Test (FST). Quantification of time spent (FIG. 7A) immobile ($F_{(5, 34)}=17.73$, $p<0.0001$), (FIG. 7B) swimming ($F_{(5, 34)}=16.49$, $p<0.0001$) or (FIG. 7C) climbing ($F_{(5, 34)}=4.984$, $p<0.001$) during a 5-min rat FST. Rats were subjected to a 15 minute swim 24 h before testing. Fluoxetine (10 mg/kg, IP) was administered 1, 5, and 23.5 h before testing. 2C-B (2.5, 10, 20 mg/kg, IP) was administered 30 min before testing. All data are presented as means+/−SEM. One-way ANOVA and post-hoc Tukey's test. $p<0.01$ vs. vehicle 1× group; **$p<0.0001$ vs.
Figure 7B:
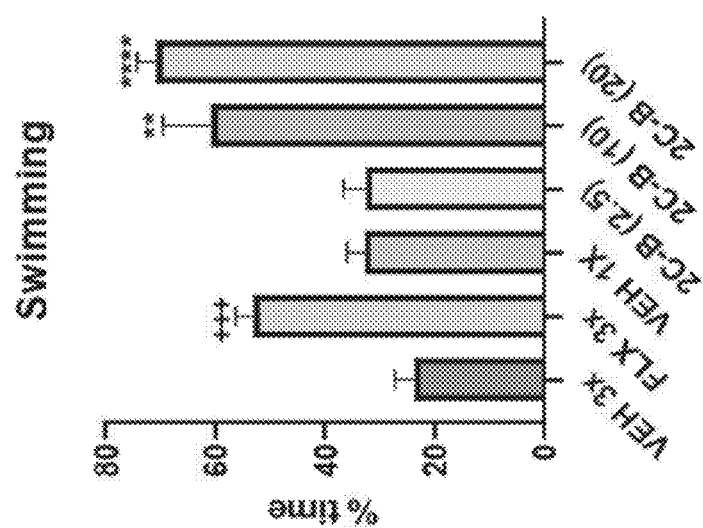
Figure 7A:
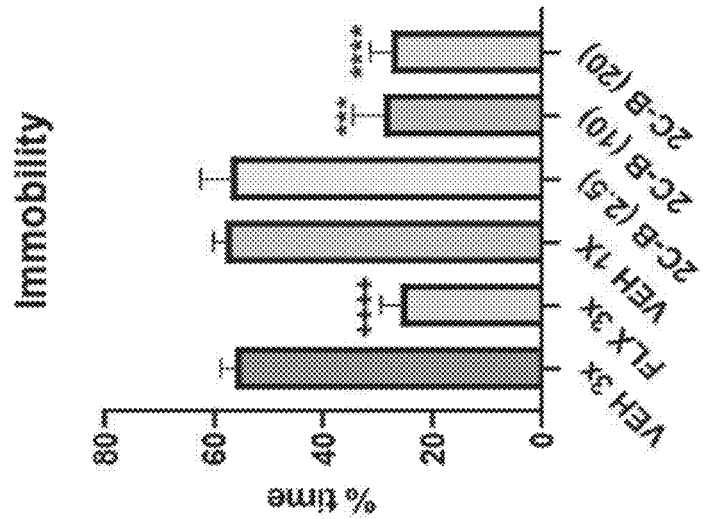

A single mid- or high-dose injection of 2C-B produced a fast-acting antidepressant-like response in the rat FST, while there was no effect at the lowest dose (FIG. 7). Typically, 2-3 injections of an SSRI antidepressant are required to elicit a behavioral response in the FST, as demonstrated by the fluoxetine control group in the current study that received 3 doses of fluoxetine prior to testing (FIG. 7). It is notable that rats receiving a single dose of 2C-B 30 minutes before testing in the FST showed a statistically significant reduction in immobility (FIG. 7A) and accompanying significant increase in swimming (FIG. 7B), consistent with serotonergic activity. The magnitude of the effect of both mid- and high-doses of 2C-B (50% and 53%, respectively) were almost identical to the fluoxetine control group (56%). Climbing was significantly decreased only in the high-dose group receiving 2C-B (FIG. 7C), but the interpretation of this result is unclear.

In summary, 2C-B produced a faster acting antidepressant-like response that is comparable in magnitude to the SSRI fluoxetine in the FST, a canonical behavioral assay with well-established specificity and selectivity for antidepressant drugs. These results show the utility of 2C-B in the treatment of depression and other CNS disorders where antidepressants are efficacious, including but not limited to post-traumatic stress disorder (PTSD), anxiety disorders, obsessive compulsive disorder (OCD), and fibromyalgia.

Example 8: Prior Selective Serotonin Reuptake Inhibitor (SSRI) Treatment does not Interfere with Efficacy of Methylone in the Rat Forced Swim Test Example 6 shows that Methylone produces a rapid, robust dose-dependent antidepressant-like effect in the Forced Swim Test (FST), greater in magnitude than any other antidepressant tested in this model. Selective serotonin reuptake inhibitors (SSRIs) are a first-line treatment for a variety of Central Nervous System (CNS) disorders including post-traumatic stress disorder (PTSD), Major Depressive Disorder (MDD), anxiety disorders, obsessive compulsive disorder (OCD), and fibromyalgia. MDMA-assisted psychotherapy is in clinical trials for the treatment of PTSD, with the caveat that SSRIs inhibit the efficacy of the MDMA-assisted therapy (Feduccia et al. (2021) *Psychopharmacology* 238:581). If a patient requires MDMA-assisted therapy, they will need to stop taking their SSRI treatment. Since SSRIs require a tapered withdrawal period over many weeks, it could take a significant period of time off medication before a patient could begin MDMA treatment. This poses both logistical and safety risks for the most severely affected individuals with PTSD. Since SSRIs prevent the clinical efficacy of MDMA-assisted psychotherapy, in this Example, whether prior administration of the prototypical SSRI fluoxetine affected the behavioral response to Methylone in the FST was investigated.

Methods

Animals: Male Sprague Dawley rats (Charles River Laboratories) weighing 180-200 g on arrival, were used for this study which took place at Melior Discovery (Exton, PA). Rats acclimated to their home cages for at least one week before testing, were maintained in a controlled environment on a 12 h light/dark cycle, with no more than 2 rats per cage. Animals received ad libitum access to food and water and were assigned randomly to treatment groups. Animal use and procedures were in accordance with established protocols approved by the IACUC committee, Melior Standard Operation Procedures (SOP), and Transcend Therapeutics.

Figure 8B:
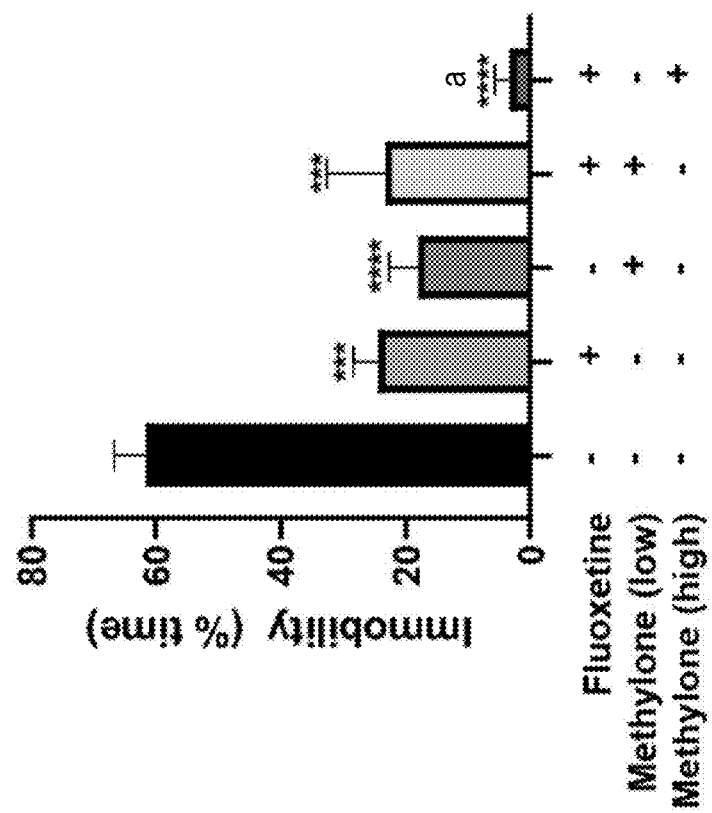
Figure 8A:
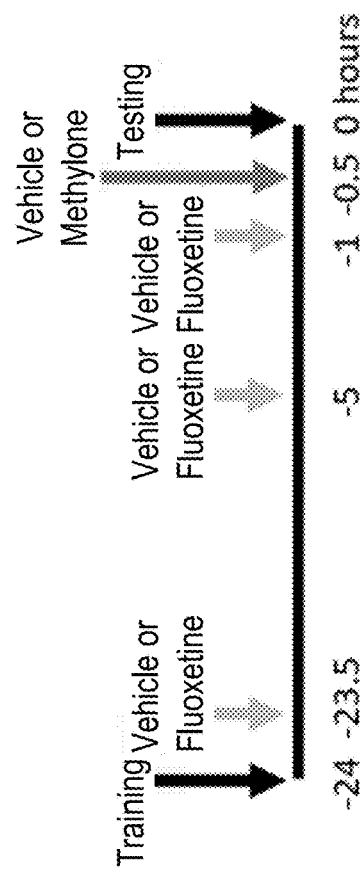
Figure 8D:
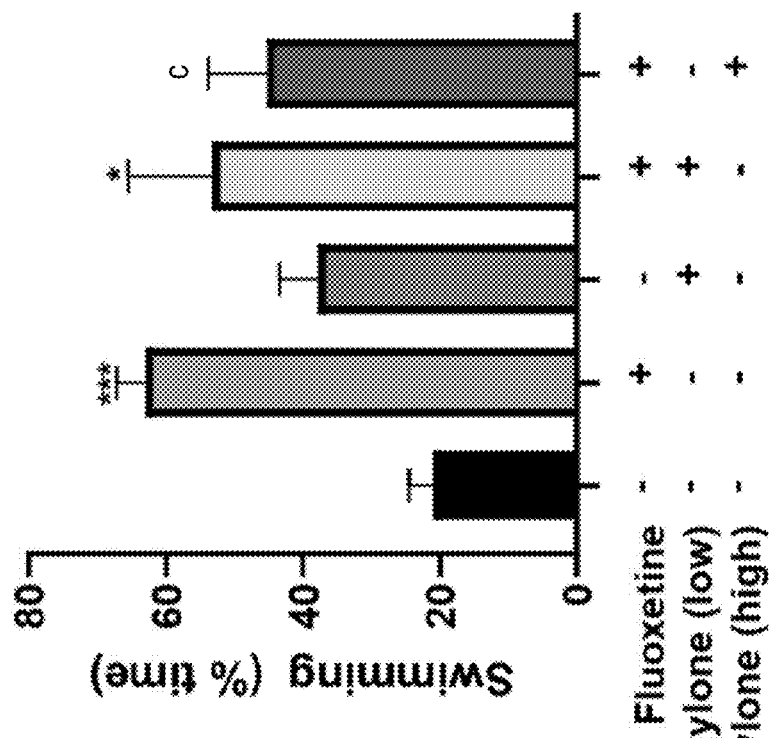

Drug Treatment: Fluoxetine (10 mg/kg, IP, Sigma Aldrich) or 0.9% sterile saline vehicle were administered 23.5, 5, and 1 h before testing in the FST. Methylone (5 or 15 mg/kg, IP; Cayman Chemical) or 0.9% saline vehicle were administered 30 min prior to FST testing (FIG. 8A). Control animals received fluoxetine alone, methylone alone, or saline vehicle. The lower dose of Methylone (5 mg/kg) was focused on because it produced a sub-maximal response in the FST, permitting the potential detection of changes in immobility that could occur in either direction.

Forced Swim Test: In the FST trial, rats were placed in a circular plexiglass container filled with water, with no means of escape. Water temperature was maintained at 22-25° C. and changed for every animal. After an acclimation period, rats were timed for inactivity (failure to struggle), activity, swim time and climbing time. The experimenter and scorer were blind to treatment group. Day 1 consisted of a 15 min acclimation trial, and Day 2 (24 h later) consisted of the 5 min test. A time sampling procedure was employed where animals were observed every 5 sec and scored for immobility, swimming, or climbing.

Statistical Analysis: Data for each parameter of the test (immobility, swimming, or climbing) is expressed as the mean±SEM. Differences between groups were determined by one-way ANOVA and post-hoc Tukey's test with a p-value of less than 0.05 indicating statistically significant differences.

Results and Conclusions

Three prior doses of fluoxetine had no effect on the immobility in response to a single dose of Methylone (62% reduced immobility vs. vehicle; FIG. 8B; $F_{(4,31)}$=17.05, p<0.0001). Consistent with the results of Example 6, fluoxetine and Methylone (5 mg/kg) both reduced immobility by 60% (p<0.001) and 71% (p<0.0001), respectively, compared to vehicle. Notably, combined treatment with a higher dose of Methylone (15 mg/kg) reduced immobility by 95% compared to vehicle (p<0.0001), which was consistent with Example 6.

Figure 8C:
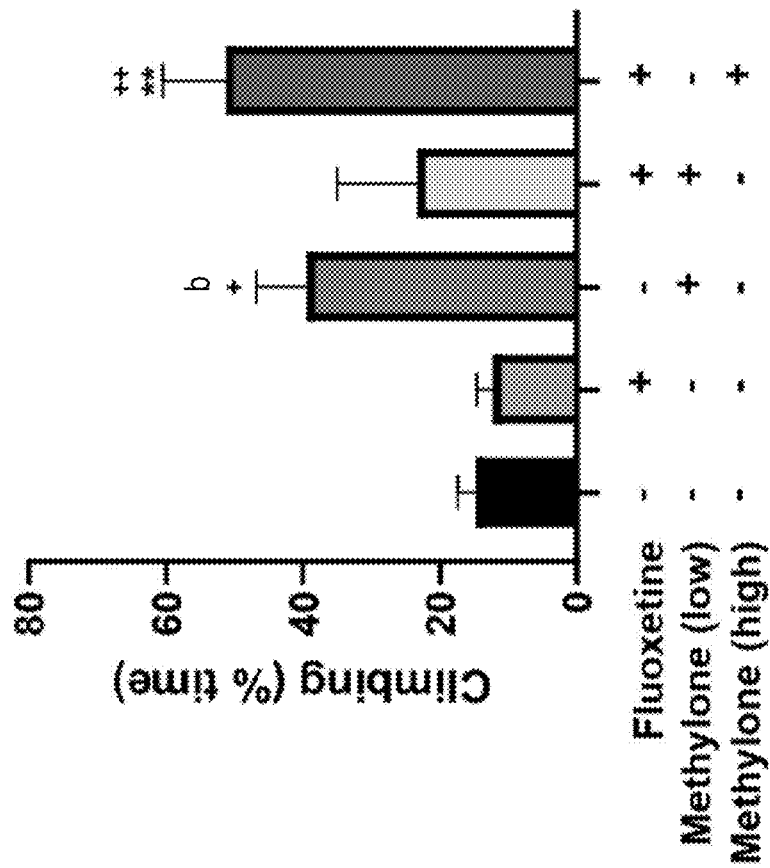

Methylone significantly increased climbing behavior (FIG. 8C; $F_{(4,31)}$=5.786, p<0.01) and fluoxetine significantly increased swimming behavior (FIG. 8D; $F_{(4,31)}$=6.063, p<0.01), consistent with noradrenergic and serotonergic activity, respectively.

In summary, prior treatment with an SSRI (fluoxetine) was investigated and does not affect the behavioral response to Methylone in the rat FST. These findings differentiate Methylone from MDMA and suggest that, unlike with MDMA, an SSRI does not interfere with Methylone's behavioral efficacy. Since SSRIs are the first-line treatment for many CNS disorders, including PTSD, these findings are particularly encouraging, as they suggest that patients could continue taking the SSRIs while taking Methylone potentially without concerns of reduced efficacy.

Example 9: Effects of Methylone, 2-CB and MBDB in a Mouse Model of Post-Traumatic Stress Disorder (PTSD)

Deficient fear extinction memory is a feature of PTSD in patients (Wicking et al. (2016) Neurobiology of Learning and Memory 136:116). SSRI antidepressants, similar to the two approved for the treatment of PTSD (i.e., paroxetine and sertraline), prevent fear memory generalization and enhance extinction (Pedraza et al. (2019) Transl Psychiatry 9:53). The enhancement of fear extinction might also underlie the beneficial effect of MDMA as a PTSD treatment (Feduccia & Mithocfer (2018) Progress in Neuro-Psychopharmacology & Biological Psychiatry 84 (Part A), 221-228).

Effective PTSD treatments facilitate the disassociation between a traumatic memory and the patient's fear response, making cues for the traumatic memory evoke less of a fear response. This is modeled in the mouse fear extinction paradigm (see FIG. 9A) which takes place over 3 days. On day 1 (fear conditioning), mice are trained to acquire a "traumatic memory," namely associating the conditioned stimulus (CS, tone) to the unconditioned stimulus (US, foot shock). On day 2 (extinction training), they are trained to forget the traumatic memory association by presenting the CS 6 times (with no US) in a novel environment. On day 3 (extinction recall), the mice are "asked" if that tone (CS) still elicits a fearful response, as measured by the time spent freezing when the tone is presented. Less time freezing means better extinction recall. Drugs that improve extinction recall reduce freezing time on day 3, and, therefore, show potential as a PTSD treatment.

Work with MDMA shows that after fear conditioning, administering MDMA (7.5 mg/kg) 30 minutes prior to extinction training enhances extinction recall measured as 35% reduced freezing compared to saline injected controls (Young et al. (2015) Transl Psychiatry 5: e634).

Using the experimental design depicted in FIG. 9A, the results show that methylone (30 mg/kg) significantly enhances fear extinction recall by nearly 60% compared to saline controls (FIG. 9B). Because effects on locomotor activity could confound the interpretation of these results, it is notable that there were no differences between groups in locomotion recorded for the duration of the testing session (FIG. 9C).

Using an experimental design like the one in FIG. 9A, MBDB was also tested in the fear extinction PTSD model. Mice given a single MBDB (5 mg/kg, IP) injection showed improved extinction acquisition on the first trial of extinction training on day 2 (FIG. 10A) and an accompanying small, but significant increase in locomotor activity on day 2 (FIG. 10B).

Example 10: Anxiolytic Effects of Methylone in the Open Field Test

The open field test (OFT) capitalizes on a rodent's innate fear of open spaces to assess anxiety-like behavior. More time spent in the center of an open field reflects an anxiolytic (anti-anxiety) effect.

A single methylone dose (5 or 15 mg/kg, IP) administered 30 minutes before testing significantly increases the time spent in the center of the open field compared to vehicle treated controls (FIG. 11A). Locomotor activity was also measured in the OFT. There was no effect of a 5 mg/kg methylone dose compared to vehicle controls, but a significant increase in locomotor activity with 15 or 30 mg/kg methylone doses (FIG. 11B).

Example 11: Lower Doses of Methylone Given More Frequently Mimic the Antidepressant-Like Effects of a Single Larger Dose in the Rat Forced Swim Test This study investigated whether repeated low-doses of methylone had an antidepressant-like effect in the Forced Swim Test (FST) and how those responses compared with single higher doses shown to have maximal effects in the FST. The results shed light on whether the robust antidepressant-like response to methylone is due to the $C_{max}$ or the AUC.

Methods: Male Sprague Dawley rats (Charles River Laboratories) weighing 180-200 g on arrival, were used. Rats acclimated to their home cages for at least one week before testing, were maintained in a controlled environment on a 12 h light/dark cycle, with no more than 2 rats per cage. Animals received ad libitum access to standard rodent chow and water and were assigned randomly to treatment groups.

Methylone HCl (2.5-15 mg/kg) was formulated in sterile saline vehicle before intraperitoneal administration. Control animals received saline vehicle. The dosing schedule and experimental design are found in FIG. 12A.

The FST was performed and scored by an experimenter blind to treatment group according to standard protocols and based on a "modified FST" procedure (Slattery and Cryan (2012) *Nat Protoc*, 7:1009). Briefly, rats were placed in a circular plexiglass container (29.2 cm diameter, 49.5 cm height) filled with water to a depth of 30 cm so rats could not support themselves by touching the bottom of the tank. Water was maintained at 22-25° C. and was changed for every animal. Day 1 (Training) consisted of a 15 min acclimation trial, and Day 2 (Testing, 24 h later) consisted of the 5 min test. A time sampling procedure was employed where animals were observed every 5 seconds for the duration of the test session (60 counts or 5 minutes) and scored for immobility (defined as the failure to struggle), swimming (defined as a circular movement around the tank), or climbing (defined as an upwards escape behavior). Data are expressed as the percent time spent immobile, swimming or climbing for the 5-minute testing session (e.g., the number of immobility counts divided by 60).

Results: FIG. 12B demonstrates that lower doses of methylone are as effective as larger single doses when dosed more frequently. This supports that lower ranges of $C_{max}$ and AUC would still show therapeutic benefit.

Single methylone doses from 5-30 mg/kg in rats (human equivalent doses of ~50-300 mg) have significant antidepressant-like effects in the rat forced swim test. A single 5 mg/kg methylone dose in the FST has a comparable effect to that of classic antidepressants like fluoxetine (PROZAC®). Methylone doses of 10 mg/kg or more are maximally effective in the FST, correlating with the rapid and robust clinical benefit on PTSD and depression symptoms.

Giving multiple lower doses (e.g., four 2.5 mg/kg doses in rat; human equivalent dose of 25 mg) also achieves significant antidepressant-like effects in the FST. This supports that giving lower doses of methylone, which would have lower associated PK parameters ($C_{max}$ and AUC) would still have therapeutic benefits, while potentially reducing side effects.

Example 12: Methylone Shows No Agonist/Antagonist Activity at 168 Different GPCRs in a β-Arrestin Based Screen To identify possible interactions with a selection of known GPCR or orphan GPCR targets, DiscoverX GPCR Arrestin was used to screen to investigate methylone's activity at 168 GPCRs. Using two concentrations of methylone (1 and 10 micromolar), agonist or antagonist activity at the receptors listed below was determined in an in vitro β-arrestin based screen.

Methods: PathHunter cell lines were expanded from freezer stocks according to standard procedures. Cells were seeded in a total volume of 20 μL into white walled, 384-well microplates and incubated at 37° C. for the appropriate time prior to testing.

For agonist determination, cells were incubated with sample to induce response. Intermediate dilution of sample stocks was performed to generate 5× sample in assay buffer. Five μL of 5× sample was added to cells and incubated at 37° C. or room temperature for 90 to 180 minutes. Vehicle concentration was 1%.

For antagonist determination, cells were preincubated with antagonist followed by agonist challenge at the $EC_{80}$ concentration. Intermediate dilution of sample stocks was performed to generate 5× sample in assay buffer. Five microliters of 5× sample was added to cells and incubated at 37° C. or room temperature for 30 minutes. Vehicle concentration was 1%. Five μL of 6× $EC_{80}$ agonist in assay buffer was added to the cells and incubated at 37° C. or room temperature for 90 or 180 minutes.

Assay signal was generated through a single addition of 12.5 or 15 μL (50% v/v) of PathHunter Detection reagent cocktail, followed by a one-hour incubation at room temperature. Microplates were read following signal generation with a PerkinElmer Envision™ instrument for chemiluminescent signal detection.

Compound activity was analyzed using CBIS data analysis suite (ChemInnovation, CA). For agonist mode assays, percentage activity was calculated using the following formula: % Activity=100%×(mean RLU of test sample−mean RLU of vehicle control)/(mean MAX control ligand−mean RLU of vehicle control).

For antagonist and negative allosteric mode assays, percentage inhibition was calculated using the following formula: % Inhibition=100%×(1−(mean RLU of test sample−mean RLU of vehicle control)/(mean RLU of EC80 control−mean RLU of vehicle control)).

Activation of a GPCR by a compound acting as an agonist will result in an increase in β-arrestin recruitment to the target GPCR. To determine if the compound potentially acting as an agonist, the activity should be >30%. Inhibition of GPCR activation by a compound acting as an antagonist of a ligand binding will result in a decrease in β-arrestin recruitment to the target GPCR. To determine if a compound is potentially acting as an antagonist to inhibit activation, >50% inhibition should be observed.

Results: As shown in Table 6, at concentrations of 1 and 10 micromolar, methylone did not meet criteria for agonist or antagonist activity at any of the 168 GPCRs tested. These data suggest that the activity of methylone is extremely specific for monoamine transporters SERT, DAT, and NET, and does not appear to interact with the selection of known GPCR or orphan GPCR targets in the β-arrestin based screen.

TABLE 6

Agonist/Antagonist activity of Methylone (1 or 10 μM) at 168 selected GPCRs.

| GPCR ID | Assay Mode | Conc(uM) | % Activity |
|---|---|---|---|
| ADCYAP1R1 | Agonist | 1 | −4 |
| ADORA3 | Agonist | 1 | −4.5 |
| ADRA1B | Agonist | 1 | −3.3 |
| ADRA2A | Agonist | 1 | −3.8 |
| ADRA2B | Agonist | 1 | −1 |
| ADRA2C | Agonist | 1 | −2.5 |
| ADRB1 | Agonist | 1 | −1.7 |
| ADRB2 | Agonist | 1 | 0 |
| AGTR1 | Agonist | 1 | 2.8 |
| AGTRL1 | Agonist | 1 | −0.9 |
| AVPR1A | Agonist | 1 | −0.6 |
| AVPR1B | Agonist | 1 | −1.2 |
| AVPR2 | Agonist | 1 | −0.9 |
| BDKRB1 | Agonist | 1 | −1.7 |
| BDKRB2 | Agonist | 1 | −3.6 |
| BRS3 | Agonist | 1 | 4.5 |
| C3AR1 | Agonist | 1 | −0.1 |
| C5AR1 | Agonist | 1 | −1 |
| C5L2 | Agonist | 1 | 8.4 |
| CALCR | Agonist | 1 | −0.3 |
| CALCRL-RAMP1 | Agonist | 1 | −2.6 |
| CALCRL-RAMP2 | Agonist | 1 | 0.1 |
| CALCRL-RAMP3 | Agonist | 1 | −2.2 |
| CALCR-RAMP2 | Agonist | 1 | 0.9 |
| CALCR-RAMP3 | Agonist | 1 | 7.9 |
| CCKAR | Agonist | 1 | 0.1 |
| CCKBR | Agonist | 1 | −1 |
| CCR1 | Agonist | 1 | −2.6 |
| CCR10 | Agonist | 1 | −2 |
| CCR2 | Agonist | 1 | −0.4 |
| CCR3 | Agonist | 1 | −6.7 |
| CCR4 | Agonist | 1 | −0.5 |
| CCR5 | Agonist | 1 | −0.1 |
| CCR6 | Agonist | 1 | −2.9 |
| CCR7 | Agonist | 1 | −3.4 |
| CCR8 | Agonist | 1 | −0.2 |
| CCR9 | Agonist | 1 | −0.5 |
| CHRM1 | Agonist | 1 | −9.1 |
| CHRM2 | Agonist | 1 | −0.2 |
| CHRM3 | Agonist | 1 | 6 |
| CHRM4 | Agonist | 1 | −5.8 |
| CHRM5 | Agonist | 1 | 7.2 |
| CMKLR1 | Agonist | 1 | −0.2 |
| CNR1 | Agonist | 1 | −0.4 |
| CNR2 | Agonist | 1 | 7 |
| CRHR1 | Agonist | 1 | 1.4 |
| CRHR2 | Agonist | 1 | 0.9 |
| CRTH2 | Agonist | 1 | −5.7 |
| CX3CR1 | Agonist | 1 | 0 |
| CXCR1 | Agonist | 1 | −0.5 |
| CXCR2 | Agonist | 1 | −0.2 |
| CXCR3 | Agonist | 1 | −0.2 |
| CXCR4 | Agonist | 1 | −4 |
| CXCR5 | Agonist | 1 | 2.5 |
| CXCR6 | Agonist | 1 | 0.3 |
| CXCR7 | Agonist | 1 | −1.3 |
| DRD1 | Agonist | 1 | −1.6 |
| DRD2L | Agonist | 1 | 0.1 |
| DRD2S | Agonist | 1 | 0 |
| DRD3 | Agonist | 1 | 2.2 |
| DRD4 | Agonist | 1 | −8 |
| DRD5 | Agonist | 1 | −0.1 |
| EBI2 | Agonist | 1 | 0.5 |
| EDG1 | Agonist | 1 | 0.1 |
| EDG3 | Agonist | 1 | −9.4 |
| EDG4 | Agonist | 1 | −2.2 |
| EDG5 | Agonist | 1 | −4.7 |
| EDG6 | Agonist | 1 | −1.7 |
| EDG7 | Agonist | 1 | 3 |
| EDNRA | Agonist | 1 | 0.3 |
| EDNRB | Agonist | 1 | 0.7 |
| F2R | Agonist | 1 | −2.5 |
| F2RL1 | Agonist | 1 | −0.6 |
| F2RL3 | Agonist | 1 | 4.3 |
| FFAR1 | Agonist | 1 | 1.7 |
| FPR1 | Agonist | 1 | 2.2 |
| FPRL1 | Agonist | 1 | −0.5 |
| FSHR | Agonist | 1 | −1 |
| GALR1 | Agonist | 1 | 0.8 |
| GALR2 | Agonist | 1 | 3.4 |
| GCGR | Agonist | 1 | −2.3 |
| GHSR | Agonist | 1 | −6.6 |
| GIPR | Agonist | 1 | −2.9 |
| ADCYAP1R1 | Antagonist | 1 | 13.6 |
| ADORA3 | Antagonist | 1 | 11.3 |
| ADRA1B | Antagonist | 1 | 17.9 |
| ADRA2A | Antagonist | 1 | −4.6 |
| ADRA2B | Antagonist | 1 | 8.5 |
| ADRA2C | Antagonist | 1 | −4.3 |
| ADRB1 | Antagonist | 1 | −0.8 |
| ADRB2 | Antagonist | 1 | 18.1 |
| AGTR1 | Antagonist | 1 | 3.3 |
| AGTRL1 | Antagonist | 1 | −3.3 |
| AVPR1A | Antagonist | 1 | −3 |
| AVPR1B | Antagonist | 1 | 9.8 |
| AVPR2 | Antagonist | 1 | −2.7 |
| BDKRB1 | Antagonist | 1 | 2.8 |
| BDKRB2 | Antagonist | 1 | 7.3 |
| BRS3 | Antagonist | 1 | 18.3 |
| C3AR1 | Antagonist | 1 | 2.5 |
| C5AR1 | Antagonist | 1 | 8.9 |
| C5L2 | Antagonist | 1 | 10 |
| CALCR | Antagonist | 1 | 5.4 |
| CALCRL-RAMP1 | Antagonist | 1 | 4.7 |
| CALCRL-RAMP2 | Antagonist | 1 | 19.1 |
| CALCRL-RAMP3 | Antagonist | 1 | −18.5 |
| CALCR-RAMP2 | Antagonist | 1 | −10.6 |
| CALCR-RAMP3 | Antagonist | 1 | −8.9 |
| CCKAR | Antagonist | 1 | −4.3 |
| CCKBR | Antagonist | 1 | −1.1 |
| CCR1 | Antagonist | 1 | −8.1 |
| CCR10 | Antagonist | 1 | 5.4 |
| CCR2 | Antagonist | 1 | 2 |
| CCR3 | Antagonist | 1 | −11.8 |
| CCR4 | Antagonist | 1 | 10 |
| CCR5 | Antagonist | 1 | 1.7 |
| CCR6 | Antagonist | 1 | 9.3 |
| CCR7 | Antagonist | 1 | −8.3 |
| CCR8 | Antagonist | 1 | 4.7 |
| CCR9 | Antagonist | 1 | 2.9 |
| CHRM1 | Antagonist | 1 | 15.8 |
| CHRM2 | Antagonist | 1 | −18.5 |
| CHRM3 | Antagonist | 1 | −5.5 |
| CHRM4 | Antagonist | 1 | 10.2 |
| CHRM5 | Antagonist | 1 | −8 |
| CMKLR1 | Antagonist | 1 | −0.2 |
| CNR1 | Antagonist | 1 | −3.5 |
| CNR2 | Antagonist | 1 | 3.6 |
| CRHR1 | Antagonist | 1 | 1.3 |
| CRHR2 | Antagonist | 1 | −2 |
| CRTH2 | Antagonist | 1 | 9 |
| CX3CR1 | Antagonist | 1 | −0.2 |
| CXCR1 | Antagonist | 1 | 12.1 |
| CXCR2 | Antagonist | 1 | −7.6 |
| CXCR3 | Antagonist | 1 | 4.5 |
| CXCR4 | Antagonist | 1 | 10.7 |
| CXCR5 | Antagonist | 1 | −4.3 |
| CXCR6 | Antagonist | 1 | 27.2 |
| CXCR7 | Antagonist | 1 | 14.1 |
| DRD1 | Antagonist | 1 | 6 |
| DRD2L | Antagonist | 1 | 1.1 |
| DRD2S | Antagonist | 1 | 3.6 |
| DRD3 | Antagonist | 1 | −12 |
| DRD4 | Antagonist | 1 | 8.4 |
| DRD5 | Antagonist | 1 | −5.9 |

TABLE 6-continued

Agonist/Antagonist activity of Methylone (1 or 10 μM) at 168 selected GPCRs.

| GPCR ID | Assay Mode | Conc(uM) | % Activity |
| --- | --- | --- | --- |
| EBI2 | Antagonist | 1 | 0.6 |
| EDG1 | Antagonist | 1 | 12.4 |
| EDG3 | Antagonist | 1 | 25.8 |
| EDG4 | Antagonist | 1 | −10.2 |
| EDG5 | Antagonist | 1 | −3.4 |
| EDG6 | Antagonist | 1 | 13.2 |
| EDG7 | Antagonist | 1 | 19.5 |
| EDNRA | Antagonist | 1 | −2.4 |
| EDNRB | Antagonist | 1 | 17.5 |
| F2R | Antagonist | 1 | −11.6 |
| F2RL1 | Antagonist | 1 | −26.8 |
| F2RL3 | Antagonist | 1 | −11.3 |
| FFAR1 | Antagonist | 1 | −7.9 |
| FPR1 | Antagonist | 1 | −4.9 |
| FPRL1 | Antagonist | 1 | 12.3 |
| FSHR | Antagonist | 1 | −11.8 |
| GALR1 | Antagonist | 1 | 7.1 |
| GALR2 | Antagonist | 1 | 7 |
| GCGR | Antagonist | 1 | −16 |
| GHSR | Antagonist | 1 | 25.8 |
| GIPR | Antagonist | 1 | −1 |
| GLP1R | Agonist | 1 | −0.3 |
| GLP2R | Agonist | 1 | −1.5 |
| GPR1 | Agonist | 1 | −0.5 |
| GPR103 | Agonist | 1 | 0.8 |
| GPR109A | Agonist | 1 | −8.7 |
| GPR109B | Agonist | 1 | 1 |
| GPR119 | Agonist | 1 | −5.8 |
| GPR120 | Agonist | 1 | −5.1 |
| GPR35 | Agonist | 1 | 2.2 |
| GPR92 | Agonist | 1 | −1.6 |
| GRPR | Agonist | 1 | 0 |
| HCRTR1 | Agonist | 1 | −0.1 |
| HCRTR2 | Agonist | 1 | 0.2 |
| HRH1 | Agonist | 1 | 3 |
| HRH2 | Agonist | 1 | −2.5 |
| HRH3 | Agonist | 1 | −3.4 |
| HRH4 | Agonist | 1 | 8.6 |
| HTR1A | Agonist | 1 | 0.8 |
| HTR1B | Agonist | 1 | 3.3 |
| HTR1E | Agonist | 1 | −3.5 |
| HTR1F | Agonist | 1 | −4.4 |
| HTR2A | Agonist | 1 | −0.1 |
| HTR2C | Agonist | 1 | 1.4 |
| HTR5A | Agonist | 1 | 13.6 |
| KISS1R | Agonist | 1 | −5.5 |
| LHCGR | Agonist | 1 | 0.4 |
| LTB4R | Agonist | 1 | −0.3 |
| MC1R | Agonist | 1 | −2.6 |
| MC3R | Agonist | 1 | −3.2 |
| MC4R | Agonist | 1 | −1.4 |
| MC5R | Agonist | 1 | −7.9 |
| MCHR1 | Agonist | 1 | 3.9 |
| MCHR2 | Agonist | 1 | −1.5 |
| MLNR | Agonist | 1 | −1.5 |
| MRGPRX1 | Agonist | 1 | −1.7 |
| MRGPRX2 | Agonist | 1 | 1.4 |
| MTNR1A | Agonist | 1 | −12.3 |
| NMBR | Agonist | 1 | 1.1 |
| NMU1R | Agonist | 1 | 1.3 |
| NPBWR1 | Agonist | 1 | 1.6 |
| NPBWR2 | Agonist | 1 | −0.3 |
| NPFFR1 | Agonist | 1 | −4.6 |
| NPSR1b | Agonist | 1 | −1.3 |
| NPY1R | Agonist | 1 | −2.2 |
| NPY2R | Agonist | 1 | −0.1 |
| NTSR1 | Agonist | 1 | −4.7 |
| OPRD1 | Agonist | 1 | −2 |
| OPRK1 | Agonist | 1 | −6.3 |
| OPRL1 | Agonist | 1 | −1.6 |
| OPRM1 | Agonist | 1 | 0.2 |
| OXER1 | Agonist | 1 | 3.2 |
| OXTR | Agonist | 1 | −0.6 |
| P2RY1 | Agonist | 1 | 2.2 |
| P2RY11 | Agonist | 1 | 0.5 |
| P2RY12 | Agonist | 1 | −1.5 |
| P2RY2 | Agonist | 1 | −2.1 |
| P2RY4 | Agonist | 1 | −3.3 |
| P2RY6 | Agonist | 1 | 4.5 |
| PPYR1 | Agonist | 1 | −1.7 |
| PRLHR | Agonist | 1 | −2.2 |
| PROKR1 | Agonist | 1 | −1.3 |
| PROKR2 | Agonist | 1 | −0.6 |
| PTAFR | Agonist | 1 | −1.3 |
| PTGER2 | Agonist | 1 | −1.4 |
| PTGER3 | Agonist | 1 | 4.5 |
| PTGER4 | Agonist | 1 | 2.8 |
| PTGFR | Agonist | 1 | 0.3 |
| PTGIR | Agonist | 1 | −4.4 |
| PTHR1 | Agonist | 1 | 0 |
| PTHR2 | Agonist | 1 | −0.6 |
| RXFP3 | Agonist | 1 | −7.6 |
| SCTR | Agonist | 1 | −2.6 |
| SSTR1 | Agonist | 1 | −5.3 |
| SSTR2 | Agonist | 1 | 0 |
| SSTR3 | Agonist | 1 | 0.7 |
| SSTR5 | Agonist | 1 | −2.4 |
| TACR1 | Agonist | 1 | −3.9 |
| TACR2 | Agonist | 1 | −1.9 |
| TACR3 | Agonist | 1 | 0.8 |
| TBXA2R | Agonist | 1 | −1.1 |
| TRHR | Agonist | 1 | −2 |
| TSHR(L) | Agonist | 1 | −1.2 |
| UTR2 | Agonist | 1 | 0.6 |
| VIPR1 | Agonist | 1 | 0.3 |
| VIPR2 | Agonist | 1 | −0.4 |
| GLP1R | Antagonist | 1 | 3.4 |
| GLP2R | Antagonist | 1 | 5.4 |
| GPR1 | Antagonist | 1 | 4.4 |
| GPR103 | Antagonist | 1 | 4.1 |
| GPR109A | Antagonist | 1 | 1.4 |
| GPR109B | Antagonist | 1 | −16.5 |
| GPR119 | Antagonist | 1 | 17.1 |
| GPR120 | Antagonist | 1 | 46.5 |
| GPR35 | Antagonist | 1 | 13.2 |
| GPR92 | Antagonist | 1 | −8 |
| GRPR | Antagonist | 1 | 0.7 |
| HCRTR1 | Antagonist | 1 | 2.3 |
| HCRTR2 | Antagonist | 1 | 6.4 |
| HRH1 | Antagonist | 1 | −18 |
| HRH2 | Antagonist | 1 | 7.1 |
| HRH3 | Antagonist | 1 | 9.5 |
| HRH4 | Antagonist | 1 | −11.6 |
| HTR1A | Antagonist | 1 | −5.2 |
| HTR1B | Antagonist | 1 | −9.5 |
| HTR1E | Antagonist | 1 | 7.6 |
| HTR1F | Antagonist | 1 | 14.4 |
| HTR2A | Antagonist | 1 | −7.9 |
| HTR2C | Antagonist | 1 | 21.1 |
| HTR5A | Antagonist | 1 | 9.8 |
| KISS1R | Antagonist | 1 | 28.7 |
| LHCGR | Antagonist | 1 | 13.8 |
| LTB4R | Antagonist | 1 | 3.5 |
| MC1R | Antagonist | 1 | 20.1 |
| MC3R | Antagonist | 1 | −5.7 |
| MC4R | Antagonist | 1 | −5.2 |
| MC5R | Antagonist | 1 | 1.7 |
| MCHR1 | Antagonist | 1 | −12.2 |
| MCHR2 | Antagonist | 1 | 2 |
| MLNR | Antagonist | 1 | 15.6 |
| MRGPRX1 | Antagonist | 1 | −6.5 |
| MRGPRX2 | Antagonist | 1 | 16.2 |
| MTNR1A | Antagonist | 1 | 30.8 |
| NMBR | Antagonist | 1 | 10.3 |
| NMU1R | Antagonist | 1 | −6.7 |
| NPBWR1 | Antagonist | 1 | 17.1 |
| NPBWR2 | Antagonist | 1 | −14.1 |
| NPFFR1 | Antagonist | 1 | 32 |
| NPSR1b | Antagonist | 1 | −10.6 |
| NPY1R | Antagonist | 1 | 0.2 |

TABLE 6-continued

Agonist/Antagonist activity of Methylone (1 or 10 μM) at 168 selected GPCRs.

| GPCR ID | Assay Mode | Conc(uM) | % Activity |
|---|---|---|---|
| NPY2R | Antagonist | 1 | 2.3 |
| NTSR1 | Antagonist | 1 | −0.7 |
| OPRD1 | Antagonist | 1 | −2.7 |
| OPRK1 | Antagonist | 1 | 11.8 |
| OPRL1 | Antagonist | 1 | 17.1 |
| OPRM1 | Antagonist | 1 | −8 |
| OXER1 | Antagonist | 1 | 2.9 |
| OXTR | Antagonist | 1 | 12.7 |
| P2RY1 | Antagonist | 1 | 14.5 |
| P2RY11 | Antagonist | 1 | 2.7 |
| P2RY12 | Antagonist | 1 | −14.8 |
| P2RY2 | Antagonist | 1 | 5.4 |
| P2RY4 | Antagonist | 1 | 15.1 |
| P2RY6 | Antagonist | 1 | 6.5 |
| PPYR1 | Antagonist | 1 | 9.5 |
| PRLHR | Antagonist | 1 | 17.8 |
| PROKR1 | Antagonist | 1 | 8.7 |
| PROKR2 | Antagonist | 1 | 2 |
| PTAFR | Antagonist | 1 | 2 |
| PTGER2 | Antagonist | 1 | 12.7 |
| PTGER3 | Antagonist | 1 | −6.2 |
| PTGER4 | Antagonist | 1 | 10.1 |
| PTGFR | Antagonist | 1 | 0.9 |
| PTGIR | Antagonist | 1 | 12.4 |
| PTHR1 | Antagonist | 1 | 2.2 |
| PTHR2 | Antagonist | 1 | −1 |
| RXFP3 | Antagonist | 1 | 23.1 |
| SCTR | Antagonist | 1 | 5.3 |
| SSTR1 | Antagonist | 1 | 32.4 |
| SSTR2 | Antagonist | 1 | −0.4 |
| SSTR3 | Antagonist | 1 | 13.2 |
| SSTR5 | Antagonist | 1 | 14.7 |
| TACR1 | Antagonist | 1 | 15.2 |
| TACR2 | Antagonist | 1 | 10 |
| TACR3 | Antagonist | 1 | −3.9 |
| TBXA2R | Antagonist | 1 | −5.5 |
| TRHR | Antagonist | 1 | −7.2 |
| TSHR(L) | Antagonist | 1 | 6.1 |
| UTR2 | Antagonist | 1 | −2.1 |
| VIPR1 | Antagonist | 1 | −0.7 |
| VIPR2 | Antagonist | 1 | −1.5 |
| ADCYAP1R1 | Agonist | 10 | −3 |
| ADORA3 | Agonist | 10 | −5.3 |
| ADRA1B | Agonist | 10 | −2.9 |
| ADRA2A | Agonist | 10 | −3.8 |
| ADRA2B | Agonist | 10 | 1.3 |
| ADRA2C | Agonist | 10 | 0.1 |
| ADRB1 | Agonist | 10 | −1.4 |
| ADRB2 | Agonist | 10 | −0.2 |
| AGTR1 | Agonist | 10 | −1 |
| AGTRL1 | Agonist | 10 | −1.5 |
| AVPR1A | Agonist | 10 | −0.5 |
| AVPR1B | Agonist | 10 | −1.1 |
| AVPR2 | Agonist | 10 | 1 |
| BDKRB1 | Agonist | 10 | −2.5 |
| BDKRB2 | Agonist | 10 | −2.9 |
| BRS3 | Agonist | 10 | −4.6 |
| C3AR1 | Agonist | 10 | 0 |
| C5AR1 | Agonist | 10 | −1.3 |
| C5L2 | Agonist | 10 | 12.9 |
| CALCR | Agonist | 10 | −0.2 |
| CALCRL-RAMP1 | Agonist | 10 | −0.2 |
| CALCRL-RAMP2 | Agonist | 10 | 2.8 |
| CALCRL-RAMP3 | Agonist | 10 | −2.2 |
| CALCR-RAMP2 | Agonist | 10 | 1.6 |
| CALCR-RAMP3 | Agonist | 10 | 7.1 |
| CCKAR | Agonist | 10 | −0.3 |
| CCKBR | Agonist | 10 | 1.5 |
| CCR | Agonist | 10 | 3.6 |
| CCR10 | Agonist | 10 | −1.8 |
| CCR2 | Agonist | 10 | −0.5 |
| CCR3 | Agonist | 10 | −7.6 |
| CCR4 | Agonist | 10 | −1.4 |
| CCR5 | Agonist | 10 | 0.3 |
| CCR6 | Agonist | 10 | −3.3 |
| CCR7 | Agonist | 10 | −3.7 |
| CCR8 | Agonist | 10 | −0.6 |
| CCR9 | Agonist | 10 | 0.2 |
| CHRM1 | Agonist | 10 | −8.5 |
| CHRM2 | Agonist | 10 | 0.2 |
| CHRM3 | Agonist | 10 | 6 |
| CHRM4 | Agonist | 10 | −6.2 |
| CHRM5 | Agonist | 10 | 8.7 |
| CMKLR1 | Agonist | 10 | −0.3 |
| CNR1 | Agonist | 10 | −2.7 |
| CNR2 | Agonist | 10 | 3.2 |
| CRHR1 | Agonist | 10 | 1.1 |
| CRHR2 | Agonist | 10 | 0.9 |
| CRTH2 | Agonist | 10 | −5 |
| CX3CR1 | Agonist | 10 | −0.4 |
| CXCR1 | Agonist | 10 | −0.1 |
| CXCR2 | Agonist | 10 | −2.6 |
| CXCR3 | Agonist | 10 | 1.6 |
| CXCR4 | Agonist | 10 | 7 |
| CXCR5 | Agonist | 10 | 1.4 |
| CXCR6 | Agonist | 10 | 0.3 |
| CXCR7 | Agonist | 10 | −0.8 |
| DRD1 | Agonist | 10 | −1.6 |
| DRD2L | Agonist | 10 | −0.7 |
| DRD2S | Agonist | 10 | 0.6 |
| DRD3 | Agonist | 10 | 2.3 |
| DRD4 | Agonist | 10 | −9.4 |
| DRD5 | Agonist | 10 | −0.2 |
| EBI2 | Agonist | 10 | −0.1 |
| EDG1 | Agonist | 10 | 0.4 |
| EDG3 | Agonist | 10 | −8.6 |
| EDG4 | Agonist | 10 | −2.1 |
| EDG5 | Agonist | 10 | −3.7 |
| EDG6 | Agonist | 10 | −0.3 |
| EDG7 | Agonist | 10 | 1.1 |
| EDNRA | Agonist | 10 | 1.4 |
| EDNRB | Agonist | 10 | −0.1 |
| F2R | Agonist | 10 | 0.2 |
| F2RL1 | Agonist | 10 | 3.8 |
| F2RL3 | Agonist | 10 | 7 |
| FFAR1 | Agonist | 10 | 4.5 |
| FPR1 | Agonist | 10 | 0.5 |
| FPRL1 | Agonist | 10 | 0.1 |
| FSHR | Agonist | 10 | −2.2 |
| GALR1 | Agonist | 10 | 0.6 |
| GALR2 | Agonist | 10 | 1.9 |
| GCGR | Agonist | 10 | −3 |
| GHSR | Agonist | 10 | −7.2 |
| GIPR | Agonist | 10 | −5.8 |
| ADCYAP1R1 | Antagonist | 10 | 12.5 |
| ADORA3 | Antagonist | 10 | 7.7 |
| ADRA1B | Antagonist | 10 | 20.6 |
| ADRA2A | Antagonist | 10 | 1.9 |
| ADRA2B | Antagonist | 10 | 6.3 |
| ADRA2C | Antagonist | 10 | 17.6 |
| ADRB1 | Antagonist | 10 | −1.2 |
| ADRB2 | Antagonist | 10 | 20.4 |
| AGTR1 | Antagonist | 10 | −1.4 |
| AGTRL1 | Antagonist | 10 | −4.1 |
| AVPR1A | Antagonist | 10 | 2.8 |
| AVPR1B | Antagonist | 10 | 3.5 |
| AVPR2 | Antagonist | 10 | −14.8 |
| BDKRB1 | Antagonist | 10 | 12.1 |
| BDKRB2 | Antagonist | 10 | −2.6 |
| BRS3 | Antagonist | 10 | 10.1 |
| C3AR1 | Antagonist | 10 | 0.3 |
| C5AR1 | Antagonist | 10 | 5 |
| C5L2 | Antagonist | 10 | 1.4 |
| CALCR | Antagonist | 10 | −4.4 |
| CALCRL-RAMP1 | Antagonist | 10 | 7 |
| CALCRL-RAMP2 | Antagonist | 10 | 7 |
| CALCRL-RAMP3 | Antagonist | 10 | −7.5 |
| CALCR-RAMP2 | Antagonist | 10 | −19.6 |
| CALCR-RAMP3 | Antagonist | 10 | −3.3 |
| CCKAR | Antagonist | 10 | −3.3 |

TABLE 6-continued

Agonist/Antagonist activity of Methylone (1 or 10 μM) at 168 selected GPCRs.

| GPCR ID | Assay Mode | Conc(uM) | % Activity |
|---|---|---|---|
| CCKBR | Antagonist | 10 | −2.4 |
| CCR1 | Antagonist | 10 | −16.6 |
| CCR10 | Antagonist | 10 | 2.6 |
| CCR2 | Antagonist | 10 | 4.9 |
| CCR3 | Antagonist | 10 | −4 |
| CCR4 | Antagonist | 10 | 9.5 |
| CCR5 | Antagonist | 10 | −0.5 |
| CCR6 | Antagonist | 10 | −1.6 |
| CCR7 | Antagonist | 10 | −3.4 |
| CCR8 | Antagonist | 10 | −0.3 |
| CCR9 | Antagonist | 10 | −9.9 |
| CHRM1 | Antagonist | 10 | 2 |
| CHRM2 | Antagonist | 10 | −7.4 |
| CHRM3 | Antagonist | 10 | 14.6 |
| CHRM4 | Antagonist | 10 | 6.7 |
| CHRM5 | Antagonist | 10 | −7.6 |
| CMKLR1 | Antagonist | 10 | −5.6 |
| CNR1 | Antagonist | 10 | −17.1 |
| CNR2 | Antagonist | 10 | −3.2 |
| CRHR1 | Antagonist | 10 | 0.6 |
| CRHR2 | Antagonist | 10 | −0.3 |
| CRTH2 | Antagonist | 10 | 8.9 |
| CX3CR1 | Antagonist | 10 | −6.1 |
| CXCR1 | Antagonist | 10 | 3.1 |
| CXCR2 | Antagonist | 10 | −1 |
| CXCR3 | Antagonist | 10 | −3.9 |
| CXCR4 | Antagonist | 10 | −4.2 |
| CXCR5 | Antagonist | 10 | −15.1 |
| CXCR6 | Antagonist | 10 | 12.6 |
| CXCR7 | Antagonist | 10 | 7.3 |
| DRD1 | Antagonist | 10 | 7.8 |
| DRD2L | Antagonist | 10 | 0.1 |
| DRD2S | Antagonist | 10 | −11.6 |
| DRD3 | Antagonist | 10 | −17.8 |
| DRD4 | Antagonist | 10 | 12.2 |
| DRD5 | Antagonist | 10 | −2.6 |
| EBI2 | Antagonist | 10 | −2.6 |
| EDG1 | Antagonist | 10 | 10.5 |
| EDG3 | Antagonist | 10 | 13.6 |
| EDG4 | Antagonist | 10 | −21 |
| EDG5 | Antagonist | 10 | −6.3 |
| EDG6 | Antagonist | 10 | 7.8 |
| EDG7 | Antagonist | 10 | 17.9 |
| EDNRA | Antagonist | 10 | −11.3 |
| EDNRB | Antagonist | 10 | 10.9 |
| F2R | Antagonist | 10 | −11.4 |
| F2RL1 | Antagonist | 10 | −16.2 |
| F2RL3 | Antagonist | 10 | −6.9 |
| FFAR1 | Antagonist | 10 | −13.8 |
| FPR1 | Antagonist | 10 | −11.4 |
| FPRL1 | Antagonist | 10 | 3.9 |
| FSHR | Antagonist | 10 | −8.4 |
| GALR1 | Antagonist | 10 | 6.8 |
| GALR2 | Antagonist | 10 | 1.5 |
| GCGR | Antagonist | 10 | −7.7 |
| GHSR | Antagonist | 10 | 9.1 |
| GIPR | Antagonist | 10 | −5.1 |
| GLP1R | Agonist | 10 | −0.1 |
| GLP2R | Agonist | 10 | −1 |
| GPR1 | Agonist | 10 | −0.7 |
| GPR103 | Agonist | 10 | 3.1 |
| GPR109A | Agonist | 10 | −4.3 |
| GPR109B | Agonist | 10 | 0.5 |
| GPR119 | Agonist | 10 | −2.2 |
| GPR120 | Agonist | 10 | −5.8 |
| GPR35 | Agonist | 10 | 2.5 |
| GPR92 | Agonist | 10 | −3.5 |
| GRPR | Agonist | 10 | −0.1 |
| HCRTR1 | Agonist | 10 | −0.1 |
| HCRTR2 | Agonist | 10 | 0.2 |
| HRH1 | Agonist | 10 | 2.5 |
| HRH2 | Agonist | 10 | −2.8 |
| HRH3 | Agonist | 10 | −3.7 |
| HRH4 | Agonist | 10 | 9 |
| HTR1A | Agonist | 10 | −0.1 |
| HTR1B | Agonist | 10 | 6.7 |
| HTR1E | Agonist | 10 | 0.2 |
| HTR1F | Agonist | 10 | −3 |
| HTR2A | Agonist | 10 | 1.4 |
| HTR2C | Agonist | 10 | 3.7 |
| HTR5A | Agonist | 10 | 13.9 |
| KISS1R | Agonist | 10 | −3.7 |
| LHCGR | Agonist | 10 | 0.4 |
| LTB4R | Agonist | 10 | −0.8 |
| MC1R | Agonist | 10 | −4.4 |
| MC3R | Agonist | 10 | −1.8 |
| MC4R | Agonist | 10 | −1.1 |
| MC5R | Agonist | 10 | −8.9 |
| MCHR1 | Agonist | 10 | 3.1 |
| MCHR2 | Agonist | 10 | −0.7 |
| MLNR | Agonist | 10 | −1 |
| MRGPRX1 | Agonist | 10 | −1.5 |
| MRGPRX2 | Agonist | 10 | 0.7 |
| MTNR1A | Agonist | 10 | −11.7 |
| NMBR | Agonist | 10 | 1.2 |
| NMU1R | Agonist | 10 | 2 |
| NPBWR1 | Agonist | 10 | −1.9 |
| NPBWR2 | Agonist | 10 | 1.3 |
| NPFFR1 | Agonist | 10 | −5.6 |
| NPSR1b | Agonist | 10 | 4.8 |
| NPY1R | Agonist | 10 | −4.9 |
| NPY2R | Agonist | 10 | 0.2 |
| NTSR1 | Agonist | 10 | −3.5 |
| OPRD1 | Agonist | 10 | −1.5 |
| OPRK1 | Agonist | 10 | −4.1 |
| OPRL1 | Agonist | 10 | −2.3 |
| OPRM | Agonist | 10 | 0.5 |
| OXER1 | Agonist | 10 | −3.7 |
| OXTR | Agonist | 10 | −0.5 |
| P2RY1 | Agonist | 10 | −4.1 |
| P2RY11 | Agonist | 10 | −0.3 |
| P2RY12 | Agonist | 10 | −2.5 |
| P2RY2 | Agonist | 10 | −2.7 |
| P2RY4 | Agonist | 10 | −4.1 |
| P2RY6 | Agonist | 10 | 2.4 |
| PPYR1 | Agonist | 10 | −1.2 |
| PRLHR | Agonist | 10 | −0.2 |
| PROKR1 | Agonist | 10 | −2.8 |
| PROKR2 | Agonist | 10 | −0.6 |
| PTAFR | Agonist | 10 | −2.6 |
| PTGER2 | Agonist | 10 | −3.1 |
| PTGER3 | Agonist | 10 | 1.9 |
| PTGER4 | Agonist | 10 | −1.4 |
| PTGFR | Agonist | 10 | −0.2 |
| PTGIR | Agonist | 10 | −2.3 |
| PTHR1 | Agonist | 10 | 0.1 |
| PTHR2 | Agonist | 10 | −0.5 |
| RXFP3 | Agonist | 10 | −8.7 |
| SCTR | Agonist | 10 | −1.4 |
| SSTR1 | Agonist | 10 | −7.4 |
| SSTR2 | Agonist | 10 | 0.7 |
| SSTR3 | Agonist | 10 | 0.3 |
| SSTR5 | Agonist | 10 | −1.3 |
| TACR1 | Agonist | 10 | −4.4 |
| TACR2 | Agonist | 10 | −3.3 |
| TACR3 | Agonist | 10 | 1.1 |
| TBXA2R | Agonist | 10 | −2.9 |
| TRHR | Agonist | 10 | −2.2 |
| TSHR(L) | Agonist | 10 | 0.7 |
| UTR2 | Agonist | 10 | 0 |
| VIPR1 | Agonist | 10 | 0.6 |
| VIPR2 | Agonist | 10 | −0.3 |
| GLP1R | Antagonist | 10 | −0.9 |
| GLP2R | Antagonist | 10 | 5.4 |
| GPR1 | Antagonist | 10 | 7.4 |
| GPR103 | Antagonist | 10 | 7 |
| GPR109A | Antagonist | 10 | −0.3 |
| GPR109B | Antagonist | 10 | −20.2 |
| GPR119 | Antagonist | 10 | −8.8 |
| GPR120 | Antagonist | 10 | 40.3 |

TABLE 6-continued

Agonist/Antagonist activity of Methylone (1 or 10 μM) at 168 selected GPCRs.

| GPCR ID | Assay Mode | Conc(uM) | % Activity |
|---|---|---|---|
| GPR35 | Antagonist | 10 | 7.3 |
| GPR92 | Antagonist | 10 | 5.8 |
| GRPR | Antagonist | 10 | −1.4 |
| HCRTR1 | Antagonist | 10 | 1.2 |
| HCRTR2 | Antagonist | 10 | 2.4 |
| HRH1 | Antagonist | 10 | −2.2 |
| HRH2 | Antagonist | 10 | 8.1 |
| HRH3 | Antagonist | 10 | 5.8 |
| HRH4 | Antagonist | 10 | −14 |
| HTR1A | Antagonist | 10 | −6.4 |
| HTR1B | Antagonist | 10 | −6.2 |
| HTR1E | Antagonist | 10 | 13.2 |
| HTR1F | Antagonist | 10 | 9.2 |
| HTR2A | Antagonist | 10 | −2.7 |
| HTR2C | Antagonist | 10 | 24.2 |
| HTR5A | Antagonist | 10 | 1.6 |
| KISS1R | Antagonist | 10 | 14.5 |
| LHCGR | Antagonist | 10 | 11.2 |
| LTB4R | Antagonist | 10 | −5.2 |
| EMC1R | Antagonist | 10 | 15.9 |
| EMC3R | Antagonist | 10 | 0.3 |
| EMC4R | Antagonist | 10 | −14 |
| MC5R | Antagonist | 10 | −6.3 |
| MCHR1 | Antagonist | 10 | −18.3 |
| MCHR2 | Antagonist | 10 | −4.5 |
| MLNR | Antagonist | 10 | 12.3 |
| MRGPRX1 | Antagonist | 10 | −10.2 |
| MRGPRX2 | Antagonist | 10 | 8.9 |
| MTNR1A | Antagonist | 10 | 7.8 |
| NMBR | Antagonist | 10 | 13.2 |
| NMU1R | Antagonist | 10 | −9.3 |
| NPBWR1 | Antagonist | 10 | 25.1 |
| NPBWR2 | Antagonist | 10 | −14 |
| NPFFR1 | Antagonist | 10 | 27.1 |
| NPSR1b | Antagonist | 10 | −7.6 |
| NPY1R | Antagonist | 10 | 5.4 |
| NPY2R | Antagonist | 10 | 2 |
| NTSR1 | Antagonist | 10 | −1.7 |
| OPRD1 | Antagonist | 10 | 3.5 |
| OPRK1 | Antagonist | 10 | 10.4 |
| OPRL1 | Antagonist | 10 | 13.2 |
| OPRM1 | Antagonist | 10 | −18 |
| OXER1 | Antagonist | 10 | 7.6 |
| OXTR | Antagonist | 10 | 6.9 |
| P2RY1 | Antagonist | 10 | 14.9 |
| P2RY11 | Antagonist | 10 | 6.6 |
| P2RY12 | Antagonist | 10 | −10.4 |
| P2RY2 | Antagonist | 10 | 1.8 |
| P2RY4 | Antagonist | 10 | 17.5 |
| P2RY6 | Antagonist | 10 | 2.6 |
| PPYR1 | Antagonist | 10 | 6.5 |
| PRLHR | Antagonist | 10 | 15.8 |
| PROKR1 | Antagonist | 10 | 3.3 |
| PROKR2 | Antagonist | 10 | −6.8 |
| PTAFR | Antagonist | 10 | −6.7 |
| PTGER2 | Antagonist | 10 | −4.4 |
| PTGER3 | Antagonist | 10 | −5.7 |
| PTGER4 | Antagonist | 10 | 4.3 |
| PTGFR | Antagonist | 10 | 0 |
| PTGIR | Antagonist | 10 | −21.5 |
| PTHR1 | Antagonist | 10 | −8.3 |
| PTHR2 | Antagonist | 10 | −0.2 |
| RXFP3 | Antagonist | 10 | 32.6 |
| SCTR | Antagonist | 10 | 2.5 |
| SSTR1 | Antagonist | 10 | 20.9 |
| SSTR2 | Antagonist | 10 | −4.2 |
| SSTR3 | Antagonist | 10 | 8 |
| SSTR5 | Antagonist | 10 | 5.7 |
| TACR1 | Antagonist | 10 | 8.9 |
| TACR2 | Antagonist | 10 | 9.1 |
| TACR3 | Antagonist | 10 | −14.3 |
| TBXA2R | Antagonist | 10 | −19.7 |
| TRHR | Antagonist | 10 | 2.8 |
| TSHR(L) | Antagonist | 10 | −6.6 |
| UTR2 | Antagonist | 10 | 4.2 |
| VIPR1 | Antagonist | 10 | 5.3 |
| VIPR2 | Antagonist | 10 | −2.6 |

Example 13: MBDB Produced a Rapid and Robust Antidepressant-Like Effect in the Forced Swim Test (FST)

MBDB is the α-ethyl analog of MDMA. This study tested whether MBDB had an antidepressant-like effect in the rat forced swim test (FST). The FST is a classic behavioral test that has been used for over 40 years to screen drugs with antidepressant-like effects. All classes of antidepressants, including serotonergic antidepressants, tricyclic antidepressants and even the more rapidly acting antidepressants like ketamine have been shown to reduce immobility in the FST, consistent with an antidepressant-like effect. Moreover, drugs that act on the serotonin and norepinephrine system increase swimming and climbing behaviors, respectively, in the FST. Therefore, those behaviors were also measured to glean insight into the underlying mechanism of the antidepressant-like behavioral response.

Methods: Male Sprague Dawley rats (Charles River Laboratories) weighing 180-200 g on arrival, were used. Rats acclimated to their home cages for at least one week before testing, were maintained in a controlled environment on a 12 h light/dark cycle, with no more than 2 rats per cage. Animals received ad libitum access to standard rodent chow and water and were assigned randomly to treatment groups.

MBDB (0.5-30 mg/kg) was formulated in sterile saline vehicle before intraperitoneal administration. Control animals received saline vehicle.

The FST was performed and scored by an experimenter blind to treatment group according to standard protocols and based on a "modified FST" procedure. Briefly, rats were placed in a circular plexiglass container (29.2 cm diameter, 49.5 cm height) filled with water to a depth of 30 cm so rats could not support themselves by touching the bottom of the tank. Water was maintained at 22-25° C. and was changed for every animal. Day 1 (Training) consisted of a 15 min acclimation trial, and Day 2 (Testing, 24 h later) consisted of the 5 min test. A time sampling procedure was employed where animals were observed every 5 seconds for the duration of the test session (60 counts or 5 minutes) and scored for immobility (defined as the failure to struggle), swimming (defined as a circular movement around the tank), or climbing (defined as an upwards escape behavior). Data are expressed as the percent time spent immobile, swimming or climbing for the 5-minute testing session (e.g., the number of immobility counts divided by 60).

Results: MBDB significantly reduced immobility ($p<0.0001$) at doses from 5-30 mg/kg (FIG. 13). These results suggest that MBDB has robust, fast-acting antidepressant-like activity.

Example 14: A Pilot Study to Assess the Use of Methylone in the Treatment of PTSD Methylone is a new and potentially effective treatment option for participants with PTSD. The purpose of this pilot study is to evaluate the safety, tolerability, and efficacy of methylone in adult participants with PTSD. The study is conducted in two parts. Part A is open-label enrolling up to 15 evaluable participants with PTSD. After completion of Part A, enrollment will begin for Part B, which is double-blind, placebo-controlled and enrolling up to 64 evaluable participants with PTSD.

Objectives and Endpoints: This is a two-part study with Part A focusing on safety as the primary objective and Part B focusing on efficacy as the primary objective. Therefore, each Part of the study has separate objectives and endpoints as presented in the tables below.

| Objective | Endpoints |
|---|---|
| Part A | |
| Primary | |
| To assess the safety and tolerability of oral methylone administered weekly over 4 weeks in participants with PTSD. | Incidence and severity of TEAEs. Incidence and severity of AESIs. Change in HR, SBP, DBP and temperature. Clinically significant changes in ECG. Changes from baseline in clinical laboratory parameters (clinical chemistry, haematology and urinalysis). |
| Secondary | |
| To assess the efficacy of methylone in treating PTSD symptoms. To assess the effect of methylone on sleep quality, functional disability, treatment satisfaction, quality of life, and physical function in participants with PTSD. | Mean change from baseline in CAPS-5 (total severity score assessed over 1 week) Mean change from baseline in the following scales: CGI-S MADRS SDS PCL-5 PGI-S BDI-II WEMWBS PSQI Percentage of participants with improvement on the following scales: PGI-C CGI-I |
| Exploratory | |
| To assess the acute and persisting subjective and physiological effects of methylone in participants with PTSD | MEQ-30 5D-ASC PTGI |
| Part B | |
| Primary | |
| To assess the efficacy of methylone in treating PTSD symptoms. | Mean change from baseline compared with placebo in CAPS-5. |
| Secondary | |
| To assess the effect of methylone compared to placebo on sleep quality, functional disability, treatment satisfaction, quality of life, and physical function in participants with PTSD. | Mean change from baseline compared with placebo in the following scales: CGI-S MADRS SDS PCL-5 PGI-S BDI-II WEMWBS PSQI Percentage of participants with improvement on the following scales: PGI-C CGI-I |
| To assess the safety and tolerability of oral methylone compared to placebo administered weekly over 4 weeks in participants with PTSD. | Incidence and severity of TEAEs Incidence and severity of AESIs Change in HR, SBP, DBP and temperature during each dosing session Clinically significant changes in ECG Changes from baseline in clinical laboratory parameters (clinical chemistry, haematology, and urinalysis) |

| Objective | Endpoints |
|---|---|
| Exploratory | |
| To assess the acute and persisting subjective and physiological effects of methylone in participants with PTSD | Effect of the following scales, compared with placebo:<br>PTGI<br>MEQ-30<br>5D-ASC |

Abbreviations:
5D-ASC = 5-Dimensional Altered State of Consciousness;
AE = adverse event;
AESI = adverse event of special interest;
BDI-II = Beck Depression Inventory-II;
DBP = diastolic blood pressure;
CAPS-5 = Clinician-Administered PTSD Scale for DSM-5;
CGI-I = Clinician Global Impression of Improvement;
CGI-S = Clinical Global Impression of Severity;
C-SSRS = Columbia Suicide Severity Rating Scale;
DBP = diastolic blood pressure;
ECG = electrocardiogram;
HR = heart rate;
MADRS = Montgomery-Åsberg Depression Rating Scale;
MEQ-30 = Mystical Experience Questionnaire - 30 Item;
PCL-5 = PTSD Checklist for DSM-5;
PGI-C = Patient Global Impression of Change;
PGI-S = Patient Global Impression of Severity;
PSQI = Pittsburgh Sleep Quality Index;
PTGI = Post-traumatic Growth Inventory;
PTSD = Post-traumatic stress disorder;
SDS = Sheehan Disability Index;
SBP = systolic blood pressure;
TEAEs = treatment-emergent adverse events;
WEMWBS = Warwick-Edinburgh Mental Wellbeing Scale.

Overall Design

Brief Summary: This is a two-part study to assess methylone for the management of the symptoms of PTSD. Part A is an open-label, non-controlled assessment in up to 15 evaluable participants with PTSD to assess early safety and efficacy and to confirm procedures included in the blinded portion (Part B) of the study. After completion of Part A, enrollment for Part B will begin in up to 64 participants. Part B is identical to Part A with the exception of the inclusion of a placebo arm in Part B.

The open-label treatment in Part A is:
  Methylone 150 mg, with a booster administration of 100 mg administered 90 (+10) minutes after the initial administration, during each dose session.

Part B is a randomized, double-blind, parallel-group, placebo-controlled assessment of methylone for the management of the symptoms of PTSD.

Enrollment includes up to 79 evaluable participants (up to 15 in Part A and up to 64 in Part B); in Part B, up to 40 evaluable participants are enrolled initially with an interim analysis to determine if a larger sample size is needed. There are 4 planned dose sessions for each participant. Participants in Part B are randomized 1:1 to the two study treatment arms and receive the randomized treatment at each of the weekly dose sessions for the study duration.

The two blinded study treatment arms in Part B are:
  Methylone 150 mg, with a booster administration of 100 mg administered 90 (+10) minutes after the initial administration, during each dose session.
  Matched placebo at each timepoint (initial+booster) during each dose session.

For each participant in Parts A and B, the study consists of:
  Screening Period (Day −28 to Day −4): Informed consent, eligibility assessment, and enrolment of eligible participants.
  Baseline/Preparatory Session (Day −3 to Day −1): Baseline assessments, confirmation of eligibility, and a preparatory psychoeducation session leading to enrolment confirmation.
  Treatment Period (Day 1 to Day 24): Four weekly dose sessions, with associated remote sessions. The dose sessions last at least 8 hours, or until all effects (physical and psychological) have resolved (whichever is longer). Each dose session is followed by a safety phone call 1 day after dosing and efficacy assessments 2 days after dosing. Each dosing period is video recorded for quality and training purposes. The videos may be reviewed to ensure the Mentor is adhering to the Mentor training.
  Follow-Up Period (Day 29 to Day 64): Follow-Up visits for safety and efficacy occur at 1, 2, 3 and 6 weeks post-final study drug administration. In addition, there are Mentor-Led Reflection Sessions 1, 2 and 3 weeks post-final study drug administration. Participants are contacted via telephone on Day 57 (±2 days) for Follow-Up.
  Discontinuations: Participants who discontinue prematurely are asked to return for an extra visit to duplicate the 6-week end-of-study (EOS) visit.

The expected duration of participation for each participant who completes all study visits, from Screening to the EOS visit, is up to 16 weeks.

Study Participants:
  Medically healthy adult participants aged between 18 to 65 years, inclusive. Participants must meet the diagnostic and statistical manual of mental disorders, fifth edition (DSM 5) criteria for current moderate to severe PTSD diagnosis with a symptom duration of at least 6 months at Screening, as assessed by the Mini International Neuropsychiatric Interview (MINI) 7.0.2, CAPS-5, and the Life Events Checklist for DSM-5 (LEC-5) and must have failed at least one treatment for PTSD (either psychotherapy or pharmacological treatment).

In addition, participants must not have a primary diagnosis of any other DSM-5 disorder, as assessed by the MINI Version 7.0.2, or have any history, physical or psychological symptoms, medication or other relevant findings that would make a participant unsuitable for the study based on the clinical judgement of study personnel.

Treatment Duration:

The treatment duration for both Parts A and B are the same: four weeks as weekly dosing (Day 1, Day 8 [±1 day], Day 15 [±1 day], and Day 22 [±1 day]).

Data Monitoring:

The objectives of the Data and Safety Monitoring Board (DSMB) are to review safety data (Parts A and B), review the interim analysis report and provide advice on the advisability of increasing the sample size for Part B.

DSMB meetings are scheduled to occur after 8 participants in Part A have completed the Day 29 Follow-Up visit, or EOS if the participant withdraws early (Safety Run-in Phase), and once at the conclusion of enrolment in Part A.

For Part B, DSMB meetings occur at intervals of approximately 20 participants (10 per treatment group). At least two DSMB meetings are scheduled. The first DSMB meeting, after 20 participants have completed the Day 29 Follow-Up visit, or EOS if the participant withdraws early, also includes an interim efficacy report to determine if the sample size is appropriate. have completed the Day 29 Follow-Up visit, or EOS if the participant withdraws early (sample size evaluation). A second DSMB meeting occurs after at least 40 participants have had the opportunity to complete the study, if more than 40 participants are anticipated to be enrolled. Ad hoc DSMB meetings can occur if needed.

The interim analysis focuses on the CAPS-5 data and is used for sample size assessment only. There are no stopping rules for either efficacy or futility.

Dose and Route of Administration:

Participants fast for 2 hours predose and until 2 hours after the initial administration during each dose session. Methylone (or matched placebo in Part B) is orally administered on Day 1, Day 8 (±1 day), Day 15 (±1 day) and Day 22 (±1 day). An initial administration of 150 mg methylone (or matched placebo in Part B) is given, followed by a booster administration of 100 mg methylone (or matched placebo in Part B) 90 (±10) minutes later.

Criteria for Evaluation:

Safety is assessed through adverse event (AE) reporting, monitoring AESIs, 12-lead ECG, vital signs, physical examinations and clinical laboratory evaluations; suicidal ideation and behavior is evaluated using the Columbia-Suicide Severity Rating Scale (C-SSRS).

Efficacy is assessed through several psychometric assessments and scales that assess PTSD symptoms and quality of life.

In addition, assessments are made of sleep quality, treatment satisfaction and psychedelic effects.

Statistical Analysis:

Safety parameters are listed and summarized using descriptive statistics for Parts A and B.

All efficacy endpoint data are listed for individual participants. All continuous efficacy endpoints are also summarized by descriptive statistics (n, arithmetic mean, standard deviation [SD], median, minimum, and maximum) by study part, overall, and by treatment (for Part B) and study period. All categorical efficacy endpoints are summarized by descriptive statistics (n, percentage).

For Part A, the change from baseline to each timepoint is presented along with a Paired t-test p-value.

A Mixed Model for Repeated Measures is fitted for select efficacy endpoints to analyze the difference between treatments for Part B. The model includes treatment as a fixed effect while visit and treatment by visit are a mixed effect. The baseline value is included (if applicable) as a covariate and participant as a random effect. The analysis uses an alpha of 0.1.

Example 15: Methylone Binds to the Serotonin Transporter (SERT) Differently than does MDMA MDMA binds the serotonin transporter (SERT) at its central site (i.e., where serotonin and serotonergic antidepressants bind) as well as at an allosteric site (Islas et al. (2021) *Heliyon* e07784; Islas & Scior (2022) *Molecules* 27:2977). Allosteric binding of MDMA to SERT was hypothesized to underlie its supraphysiological increased release and depletion of presynaptic serotonin as well as interference with SSRI antidepressants that has been described in patients and animal models (Feduccia et al. (2021) *Psychopharmacology* 238:581; Callaway et al. (1990) *J Pharmacol Exp Ther,* 254:456; Geyer (1994) *Neuropsychopharmacology* 10: 768S).

To test whether the methylone acts orthosterically or allosterically at the SERT, the uptake of serotonin (5HT) with a range of concentrations of [$^3$H]5HT was examined in the presence or absence of methylone. If high concentrations of [$^3$H]5HT override the effect of the methylone, that would indicate competitive (i.e., orthosteric) inhibition. In other words, methylone would produce a right shift in the $K_d$ (i.e., increase its value) but leave the $B_{max}$ unaffected. Three hot saturation curves were run with the [3H]5HT in the presence of two concentrations of methylone.

The results in FIG. 14 indicate that the interaction with methylone at the SERT is competitive, as the $K_d$ was right shifted by methylone. In addition, as the 5HT concentration was increased, methylone inhibition was overridden, and thus, there was no decrease in $B_{max}$.

The fact that methylone apparently binds only to the central site of the SERT, and not also allosterically like MDMA, could mechanistically explain why methylone does not deplete serotonin like MDMA (Baumann et al. (2012) *Neuropsychopharmacology* 37:1192) and suggests improved safety. These results could also shed light on why SSRI antidepressants interfere with the actions of MDMA (Feduccia et al. (2021) *Psychopharmacology* 238:581), and not with methylone (Warner-Schmidt et al. (2023) *Frontiers in Psychiatry*).

Example 16: Unlike MDMA, Methylone does not Bind to 5HT$_{2B}$ Receptors, which is a Positive Differentiator of Methylone in Terms of Cardiovascular Safety Agonists of serotonin 5HT$_{2B}$ receptors are strongly implicated in mediating drug-induced valvular heart disease. In fact, 5HT$_{2B}$ agonism is considered a toxicity signal in drug development (Cavero et al. (2014). *Journal of Pharmacological and Toxicological Methods* 69:150). MDMA has shown to be a non-selective agonist of 5HT$_{2B}$ receptors (Setola et al. (2003) *Molecular Pharmacology* 63:1223). In this Example, methylone was tested to determine whether it showed any affinity for the 5HT$_{2B}$ receptor by competitive radioligand binding.

Methods: Human serotonin $5HT_{2B}$ receptor membrane preparations were used to screen racemic methylone HCl and reference compound SB204741. Compounds were dissolved in DMSO (10 mM) and stored frozen at −20° C. On the day of the assay, compounds were thawed and diluted with assay buffer to 5× final maximal assay concentration (e.g., to 50 μM for a final assay concentration of 10 μM). Human serotonin $5HT_{2B}$ receptor membrane preparations were divided into aliquots. On the day of the assay, membranes were diluted at 1:200 in incubation buffer. Assays were carried out in 96-well plates in a final volume of 250 μL per well. To each well was added 150 μL membrane preparation, 50 μL test compound, non-specific compound, or buffer alone, as well as 50 μL radioligand. The plate was incubated at 35° C. for 90 minutes with gentle agitation. The incubation was stopped by vacuum filtration onto presoaked GF/C filters using a 96-well FilterMate™ harvester, followed by 5 washes with ice-cold wash buffer. Filters were then dried under a warm air stream, sealed in polyethylene, scintillation cocktail added, and the radioactivity counted in a Wallac® TriLux 1450 MicroBeta counter. For each concentration of drug, non-specific binding was subtracted from total binding to give specific binding. Data was fitted using the non-linear curve fitting routines in Prism® (Graphpad Software Inc) to determine $IC_{50}$. $K_i$ was subsequently calculated using the ChengPrusoff equation.

Results: As shown in FIG. 15, methylone did not show affinity for $5HT_{2B}$ receptors, with an $IC_{50}$=4285 nM and $K_i$=3749 nM. In contrast, MDMA and its metabolite MDA have reported $K_i$ values of 500 and 100 nM, respectively, which is 7.5-37 times greater affinity for the $5HT_{2B}$ receptor compared with methylone.

In short, these data strongly suggest that methylone offers improved cardiovascular safety compared with MDMA.

Example 17: Docking Study Demonstrates that Methylone does not Bind to 5HT2 Receptors Due to its Conformation and Steric Hindrance There are at least 13 different subtypes of serotonin receptors. Among them, serotonin $5HT_2$ receptor subtype activity has been linked to hallucinogenic effects ($5HT_{2A}$), cardiovascular toxicity ($5HT_{2B}$) and side effects of SSRI antidepressants ($5HT_{2C}$) in humans and animal models. Results obtained from a GPCR screen of methylone (Example 13 above) demonstrate that methylone had no agonist or antagonist activity at 138 different G-protein coupled receptors, including the 5HT2 receptors. Weak/no binding of methylone to $5HT_{2B}$ receptors has also been shown (Example 16 above). Docking analysis of methylone to 5-HT2 receptors ($5HT_{2A}$, $5HT_{2B}$ and $5HT_{2C}$) was used to understand the structural differences that might influence binding and to demonstrate that structural constraints of the methylone molecule prevent its binding to these three 5HT2 receptor subtypes.

Methods: The PDB structures used for docking into 2A, 2B, and 2C were 6A93, 5TVN, and 6BQG respectively. Standard preparation and docking were performed with MOE 2022.02 and evaluated for optimal binding pose. Both enantiomers were docked and the optimal isomer is shown in illustrations.

Results: This docking study demonstrates that methylone does not bind to 5HT2 receptors due to conformational issues and steric hindrance (FIG. 17). Methylone does not bind at $5HT_{2A}$, mostly due to conformational issues rather than steric reasons. At $5HT_{2B}$ and $5HT_{2C}$, methylone generates steric clashes (indicated by orange discs) and would not be expected to bind. These results provide additional evidence that methylone has a specific mechanism of action, acting on monoamine transporters with no off-target effects. Furthermore, these results support that methylone has no hallucinogenic activity, cardiovascular safety, and fewer possible side effects compared with other drugs used to treat PTSD and depression.

Example 18: RNA-Sequencing Study Shows Regulation of Genes in Key Brain Areas by Methylone Methylone binds to monoamine transporters and facilitates the release of norepinephrine (NE), serotonin (5HT), and dopamine (DA), but the downstream effects of these changes in key brain areas linked to PTSD and depression have not been investigated. It is these downstream effects (e.g., changes in gene expression) that drive functional changes in the brain that underlie the actions of methylone. Rats were dosed once with methylone (10 mg/kg, IP) or vehicle (saline) and sacrificed 8 hours later. Brains were removed and amygdala, frontal cortex, and hippocampus were dissected and subjected to RNA-sequencing. Results identified differentially expressed genes in these key brain areas linked to PTSD and depression. Using a cutoff of genes that were changed by >25% and had an adjusted p-value<0.1 vs. vehicle, 121 genes in the amygdala, 471 genes in the frontal cortex, and 12 genes in the hippocampus were identified that were differentially regulated by methylone (FIG. 18). Gene-ontology (GO) and pathway analysis revealed that the genes in the amygdala were linked to oligodendrocytes (suggesting changes in myelination and nerve conduction) and those in the frontal cortex were linked to functions like synaptic plasticity, learning and memory. There were too few genes changing in the hippocampus to identify GO terms. These results shed light on how methylone affects brain structure and function to exert its lasting behavioral and therapeutic effects.

Example 19: MBDB has Rapid-Acting, Robust Anxiolytic Effect, Increasing Time Spent in the Center of an Open Field To investigate whether MBDB has an anti-anxiety (anxiolytic) effect, rats were dosed with MBDB (0.5-30 mg/kg, IP) or vehicle (saline) and 30-minutes later were tested in the open field for 30 minutes. This anxiety test capitalizes on a rodents' innate fear of wide-open spaces and propensity to hug the walls when placed into the open field. Therefore, a drug that increases the time spent in the center of the open field has anxiolytic activity and predicts utility for treating anxiety in humans. As shown in FIG. 19, MBDB had a rapid-acting and robust anti-anxiety effect in the open field, significantly increasing time spent in the center by ~40% compared to control animals.

Example 20: Methylone for the Treatment for PTSD: Initial Results from an Open-Label Study (IMPACT-1)

Post-traumatic stress disorder (PTSD) is a serious debilitating disorder impacting approximately 13 million Americans each year. Suicide risk in PTSD is increased by at least 6-fold compared to the general population. Approximately half of people diagnosed with PTSD also have a diagnosis of major depressive disorder (MDD). Approved pharmacotherapies for PTSD treatment (sertraline and paroxetine)

have limited effectiveness. Less than 30% of patients treated with first-line pharmacotherapy achieve remission, which often takes many weeks to achieve. Thus, there is an urgent need for rapid-acting, non-hallucinogenic PTSD treatments.

Methylone is a rapid-acting neuroplastogen, which rapidly induces neuroplasticity gene expression (e.g., BDNF) in brain areas underlying pathophysiology of PTSD, depression, and anxiety. Well-characterized primary pharmacology. Monoamine transporters are primary site of action. No binding at $5HT_{2A}$ receptor, not hallucinogenic. Rapid, robust serotonin and norepinephrine release in the frontal cortex.

This Example presents initial results from a clinical study for the treatment of PTSD (IMPACT-1). The IMPACT-1 Study has two parts, an open-label study (Part A) and a placebo-controlled study (Part B), the study design is presented in FIG. 20. The demographics and baseline characteristics of the open-label study participants are provided in Table 7 below.

TABLE 7

Demographic and Baseline Characteristics (Safety Population)

| Characteristic | Unit | Methylone (N = 14) |
|---|---|---|
| Age Mean (range) | Years | 42.4 (23-65) |
| Sex (n, %) | Female | 10 (71.4) |
|  | Male | 4 (28.6) |
| Race (n, %) | White | 13 (92.9) |
|  | Not reported | 1 (7.1) |
| Duration of PTSD Mean (SD) | Months | 34.0 (32.96) |
| Baseline Scores Mean (range) | CAPS-5 | 47.8 (38-59) |
|  | MADRS | 30.8 (14-46) |

Methylone was administered once a week for 4 weeks. Each dose was given as an initial dose, followed by a second dose 90 minutes later. During the dosing session, participants were accompanied by a trained Mentor who provided non-directive support. After the 4-week treatment period, participants attended follow-up visits at 1, 2, 3, and 6 weeks following the last dose. Safety was assessed via standard measures including adverse events. PTSD symptoms were assessed via Clinician-Administered PTSD Scale for DSM-5 (CAPS-5), depressive symptoms were assessed via Montgomery-Åsberg Depression Rating Scale (MADRS). Anti-anxiety efficacy was evaluated using the Anxiety Sub-Scale of MADRS, namely, questions (Items 3, 4, 5, 6) that address four anxiety items (inner tension, reduced sleep, reduced appetite, concentration difficulties) Changes from baseline were analyzed using a paired t-test p-values.

Results: Table 8 below presents Treatment-Emergent Adverse Events (TEAE) observed in the Open-Label Study (IMPACT-1; Part A). The majority of TEAEs were transient and of mild severity. No drug-related SAEs occurred. There was one unrelated SAE that occurred (victim of assault) 20 days after the last dose.

TABLE 8

Treatment-Emergent Adverse Events in >1 Participants (Safety Population)

| Adverse Event | Methylone (N = 14) |
|---|---|
| Any AE | 78.6% |
| Headache | 42.9% |
| Decreased appetite | 28.6% |

TABLE 8-continued

Treatment-Emergent Adverse Events in >1 Participants (Safety Population)

| Adverse Event | Methylone (N = 14) |
|---|---|
| Non-cardiac chest pain | 21.4% |
| Fatigue | 21.4% |
| Bruxism | 14.3% |
| Dizziness | 14.3% |
| Hyperhidrosis | 14.3% |
| Influenza-like illness | 14.3% |
| Insomnia | 14.3% |
| Nasopharyngitis | 14.3% |

FIG. 21 plots mean Clinician-Administered PTSD Scale for DSM-5 (CAPS-5) scores in the Open-Label Study (IMPACT-1) over time and shows that methylone produced rapid and durable improvements. In particular, on Day 3, CAPS-5 scores decreased by 8.4 points, and by Day 10, CAPS-5 scores decreased by 23.3 points. In addition, 6 weeks after the last dose, CAPS-5 scores decreased by 36.2 points.

Similarly, FIG. 22A plots mean change from Baseline in Montgomery-Åsberg Depression Rating Scale (MADRS) scores over time for the Open-Label Study (IMPACT-1) and shows that methylone also produced rapid, robust, and durable improvements of depressive symptoms. In particular, on Day 3, MADRS scores decreased by 8.2 points, and by Day 10, MADRS scores decreased by 16.2 points. In addition, 6 weeks after the last dose, MADRS scores decreased by 21.4 points.

In addition, FIG. 22B plots mean change from Baseline in the Anxiety Sub-Scale of MADRS and shows that methylone also produced rapid, robust, and durable improvements in anxiety in humans. In particular, on Days 3, 10, 17, and 24, scores were reduced by 20%, 43%, 50%, and 57%, respectively. During the follow-up period, Days 29, 36, 43, and 64, scores continued to decrease by 56%, 66%, 64%, and 66%, respectively.

FIG. 23 plots response and remission based on CAPS-5 scores in the Open-Label Study (IMPACT-1) over time and shows high rates of response and remission occurred after methylone treatment. At Day 10, nearly 40% of participants achieved remission and at the end of the study remission was achieved in 61.5% of participants.

Conclusion: Methylone demonstrated rapid, robust, and durable effects on PTSD symptoms. PTSD symptom remission and response occurred rapidly after methylone treatment. Rapid improvement on depressive symptoms occurred concurrently with PTSD symptom improvement. Methylone was generally safe and well tolerated, the most common adverse event was headache.

Example 21: Methylone was Observed to Treat Chronic Pain in a Subject with PTSD

One of the subjects in the Open-Label Study (IMPACT-1; Part A) of Example 20 suffered from chronic pain for over ten years. The patient reported that methylone reduced pain across all areas. In particular, the patient reported a reduction in chronic pain from a 7-8 out of 10 and 8-9 out of 10, over many of the injury areas, to nearly no pain at all in some areas and in others down to 2-3 out of 10 (in the knees). The patient reported that his chronic migraine headache was gone with only a throbbing remaining in the temples.

Example 22: Evaluating the Effect of Methylone in a Chronic Pain Model

This Example presents a rat model to evaluate the benefit of methylone for fibromyalgia (FMA). A review of other animal models that may be used to evaluate the benefit of methylone for other forms of chronic pain and for pain pathologies are reviewed in Abboud et al. (2021) *Journal of Neuroscience Methods* 348:108997.

In this Example, male Sprague Dawley rats are tested in a behavioral model of FMA based on the protocol from Nakagura et al. (2009) *Pain* 146:26. This model uses three daily doses of reserpine (1 mg/kg, SC) or 0.5% acetic acid vehicle to reduce pain thresholds (i.e., increase pain perception) in the Von Frey Test (vFT, procedure outlined below). Animals are tested in the vFT on day −1 (baseline), day 4 (post-reserpine), and then pre-dose, 30, 60, 120, 240 minutes, 24 hours and 72 hours after methylone (test article), duloxetine (positive control/comparator) or vehicle injection (IP). This model has been validated using duloxetine as a positive control, demonstrating a significant increase in pain thresholds—corresponding to a reduction in perceived pain and consistent with its use as a treatment in FMA patients. Methylone increases pain thresholds, supporting its utility for treating chronic pain conditions.

Von Frey Test (vFT) procedure: Increasing pain thresholds in this test are consistent with a reduction in pain perception. Prior to the start of dosing, rats are tested for their baseline mechanical pain threshold. For von Frey measurements, animals are placed into wire bottom cubicles with opaque Plexiglas walls, allowing access to the underside of their paws. Animals are habituated to this environment for at least 30 minutes before the start of the von Frey filament application. Static allodynia is measured using Semmes-Weinstein von Frey filaments (Stoelting, Wood Dale, IL). Mechanical allodynia is tested by touching the plantar surface of the animals' left and right hind paws with von Frey filaments which deliver a calibrated amount of force. Each von Frey filament is presented perpendicularly to the plantar surface for approximately 6 seconds of constant application in either ascending or descending strength in a modified up-and-down method (Chaplan et al. (1994) *J Neurosci. Meth.* 53:55). Stimulation is presented at intervals of several seconds, allowing for apparent resolution of any behavioral responses to previous stimuli. A positive response is noted if the paw is sharply withdrawn. Flinching immediately upon removal of the hair is also considered a positive response. Ambulation is considered an ambiguous response, and, in such cases, the stimulus is repeated.

Results: Methylone has a beneficial effect in this rat fibromyalgia model and restores 'normal' pain thresholds in rats with pain sensitivity (FIG. 38). Rats were treated with reserpine for 3 days to induce pain sensitivity (+) or vehicle (−) to maintain the 'normal' pain threshold. Baseline paw withdrawal thresholds showed significant effect of reserpine vs. vehicle (not shown). On day 4, rats were given vehicle or methylone (15 mg/kg, IP) 30 min before testing in the vonFrey test for pain sensitivity. Methylone significantly increased paw withdrawal thresholds, consistent with a beneficial effect in this model of fibromyalgia.

Example 23: Evaluating the Effect of 2C-B in a Model for Fibromyalgia

This Example uses a rat model to show the benefit of 2C-B for fibromyalgia (FMA).

VonFrey measurements: Animals were placed into wire bottom cubicles with opaque Plexiglas walls, allowing access to the underside of their paws. Animals were habituated to this environment for at least 30 minutes before the start of the von Frey filament application. Static allodynia was measured using Semmes-Weinstein von Frey filaments (Stoelting, Wood Dale, IL). Mechanical allodynia (pain sensitivity) was tested by touching the plantar surface of the animals' left hind paws with von Frey filaments which deliver a calibrated amount of force. Each von Frey filament was presented perpendicularly to the plantar surface for approximately 6 seconds of constant application in either ascending or descending strength in a modified up-and-down method (Chaplan et al. (1994) *J Neurosci. Meth.* 53:55). Stimulation was presented at intervals of several seconds, allowing for apparent resolution of any behavioral responses to previous stimuli. A positive response was noted if the paw was sharply withdrawn. Flinching immediately upon removal of the hair was also considered a positive response. Ambulation was considered an ambiguous response, and the stimulus was repeated in such cases. Duloxetine (brand name: Cymbalta) was used here as a positive control, because it has shown benefit in this model and is a current treatment for fibromyalgia. The average hindpaw thresholds were determined 60-min post-injection.

Results are shown as means+/−SEM. Statistical analysis was performed using two-way ANOVA and posthoc Dunnett's multiple comparisons test. Differences were considered statistically significant when $p<0.05$.

Results: Results revealed a robust (maximal) and fast-acting effect of 2C-B at both doses (10 and 20 mg/kg) in this model of fibromyalgia (FIG. 16). 2C-B significantly and completely reversed reserpine-induced pain sensitivity in 100% of animals tested (9/9) Duloxetine also reversed pain sensitivity, but a maximal effect (i.e., a complete reversal of the increased pain sensitivity) was only observed in 44% of animals (4/9). These results show the therapeutic efficacy of 2C-B for fibromyalgia and other inflammatory pain conditions and suggest 2C-B outperforms duloxetine.

Example 24: Evaluating the Effect of 2C-B in a Model for Chemotherapy-Induced Peripheral Neuropathy (CIPN)

This Example uses a mouse model to show the benefit of 2C-B for chemotherapy-induced peripheral neuropathy (CIPN). CIPN is a painful condition that develops in cancer patients undergoing chemotherapy with platinum-based compounds, taxanes, *vinca* alkaloids, cpothilones, proteasome inhibitors and immunomodulatory drugs. The treatments can damage sensory, motor and autonomic neurons to cause CIPN, which results in significant reduction in function, quality of life, and often in cessation of therapy leading to increased mortality.

Cisplatin, a platinum-based chemotherapy agent has been used to reduce pain thresholds in a model of CIPN. Effects of acute (single higher dose) or sub-chronic (7 days repeated lower dose) 2C-B on pain thresholds were investigated in cisplatin-treated animals compared with vehicle or cisplatin-treated controls.

Methods: Male C57Bl/6 mice aged 12-16 weeks were used. Cisplatin (2.5 mg/kg) or vehicle was administered on days 1-5 and 11-15. Pain thresholds were tested in the VonFrey test at baseline (before first dose of cisplatin) and on day 6, 9, and 19 to monitor effects of cisplatin in the animals—and to ensure that pain thresholds significantly reduced.

Vehicle, sub-chronic 2C-B (5 mg/kg once daily days 17-23) or acute 2C-B (20 mg/kg once on day 17) was then administered IP (N=16-18/group). VonFrey testing took place on day 17 (30 min post-dose) and days 21 and 24 (pre-dose) to monitor the effects of 2C-B in cisplatin treated animals, compared with animals receiving cisplatin+vehicle or vehicle+vehicle.

For von Frey measurements, animals were placed into wire bottom cubicles with opaque Plexiglas walls, allowing access to the underside of their paws. Animals were habituated to this environment for at least 30 minutes before the start of the von Frey filament application. Static allodynia was measured using Semmes-Weinstein von Frey filaments (Stoelting, Wood Dale, IL). Mechanical allodynia was tested by touching the plantar surface of the animals' right and left hind paws with von Frey filaments which deliver a calibrated amount of force (0.07, 0.16, 0.4, 0.6. 1.0, 2.0, 4.0, 6.0 g). Each von Frey filament was presented perpendicularly to the plantar surface for approximately 6 seconds of constant application in either ascending or descending strength in a modified up-and-down method (Chaplan et al. (1994) *J Neurosci. Meth.* 53:55). Stimulation was presented at intervals of several seconds, allowing for apparent resolution of any behavioral responses to previous stimuli. A positive response was noted if the paw was sharply withdrawn. Flinching immediately upon removal of the hair was also considered a positive response. Ambulation is considered an ambiguous response, and, in such cases, the stimulus was repeated. To determine the 50% withdrawal threshold, testing was initiated with the 0.60 g fiber. The withdrawal responses were averaged and compared to the baseline measurement.

Data are presented as means+/−SEM. Differences between groups were determined by ANOVA and Fisher's LSD test using Graphpad Prism with an alpha threshold of 0.05.

Results

2C-B showed rapid, robust effects in this model of CIPN (FIG. 25). Increased pain thresholds in the VonFrey test indicate less pain sensitivity. Cisplatin significantly reduced pain thresholds, corresponding to increased pain sensitivity. Pain thresholds were significantly increased within 30 min of a single dose (5 or 20 mg/kg, IP) (F (3.62)=7.844, $p<0.001$, FIG. 25). Repeated doses of 5 mg/kg 2C-B resulted in sustained beneficial effect in this model.

Example 25: Pharmacokinetics (PK) of Methylone

Male SD rats were administered methylone HCl orally (15 mg/kg, PO), intraperitoneally (15 mg/kg, IP), intramuscularly (15 or 20 mg/kg, IM), or subcutaneously (15 or 20 mg/kg, SC). Plasma was collected 0.25, 0.5, 1-, 2-, 4-, and 8-hours post-dose. Plasma methylone concentrations were determined by LC-MS/MS and pharmacokinetic parameters were calculated using standard methods.

FIG. 24 shows the pharmacokinetic analysis of plasma in rats following oral (PO), intraperitoneal (IP), intramuscular (IM) or subcutaneous (SC) injection with methylone. The pharmacokinetic parameters are presented in Table 9 below:

TABLE 9

Pharmacokinetic parameters for methylone in rats by different administration routes

|  | PO (15 mg/kg) | IP (15 mg/kg) | IM (15 mg/kg) | IM (20 mg/kg) | SC (15 mg/kg) | SC (20 mg/kg) |
|---|---|---|---|---|---|---|
| Cmax (ng/ml) | 552 + 12 | 1246 + 38 | 5400 + 967 | 5917 + 763 | 3653 + 261 | 4320 + 519 |
| $T_{1/2}$ (hours) | 2.27 + 0.02 | 0.935 + 0.05 | 0.74 + 0.02 | 0.70 + 0.02 | 0.82 + 0.05 | 0.87 + 0.03 |
| $AUC_{0-inf}$ (ng * h/mL) | 2287 + 159 | 2589 + 817 | 4614 + 765 | 6367 + 1129 | 4333 + 314 | 5955 + 2173 |

In humans, a single ascending dose study has been conducted in healthy volunteers with doses ranging from 50 mg to 200 mg (Poyatos et al. (2022) *Int J Mol Sci,* 23:14636). Subjects received a single dose orally of methylone 50 mg, 100 mg, 150 mg or 200 mg, and pharmacokinetics (PK) samples were collected up to 24 hours post-dose.

Summary PK parameters are shown in Table 10A below. The PK appeared to be linear across oral doses of 50 mg to 200 mg. The time to reach maximum concentrations ($T_{max}$) was between 1-2 hours and the half-life was approximately 6-7 hours.

TABLE 10A

Observed Pharmacokinetic Parameters for Plasma Methylone in Humans

| Dose (Subjects) | 50 mg (N = 3) | 100 mg (N = 6) | 150 mg (N = 5) | 200 mg (N = 7) |
|---|---|---|---|---|
| $C_{max}$ (μg/L) | 151.2 (153.0, 18.9%) | 283.9 (303.6, 45%) | 340.2 (354.6, 30.7%) | 594.2 (603.6, 20.6%) |
| $T_{max}$ (hr)^ | 1.5 (1-2) | 2.5 (0.75-3) | 2 (1.5-4) | 2 (1-4) |
| $AUC_{10hr}$ (hr * μg/L) | 725 (725, 2.4%) | 1554 (1586, 23.1%) | 2153 (2236, 29.0%) | 3261 (3310, 17.9%) |
| $AUC_{24hr}$ (hr * μg/L) | 988 (989, 4.5%) | 2232 (2268, 20.4%) | 3165 (3349, 36.5%) | 4676 (4796, 23.2%) |
| $AUC_{inf}$ (hr * μg/L) | 1062 (1063, 6.9%) | 2410 (2444, 18.3%) | 3509 (3777, 42.2%) | 5116 (5267, 25.1%) |
| Half-life (hr) | 6.2 (6.3, 15%) | 6.0 (6.1, 23.3%) | 6.7 (6.8, 23.3%) | 6.5 (6.6, 15.1%) |

Data are presented at Geometric Mean (Mean, % CV)
^Median (Min – Max)

In order to predict the likely effect of adding a booster to an initial dose of methylone, a population pharmacokinetic (PK) model of methylone was developed based on the data from the dose-escalation study referenced above. This model was used to simulate methylone PK after various multiple dosing regimens.

Noncompartmental analysis (NCA) was performed within Phoenix WinNonlin (v8.3) to calculate summary PK parameters, including maximum concentration, time to maximum concentration, AUC, and half-life. Population PK modeling was performed within NONMEM (v.7.3). Raw data manipulation, and PK simulations were executed in R (v.4.2.0). Input data for population PK modeling was taken from the dose-escalation study referenced above.

The final population PK model was a one-compartment model with absorption lag time and linear clearance from the central compartment. Model parameters were estimated with sufficient precision. Goodness-of-fit plots indicated good agreement between model predictions and observed data with no substantial concentration or time-dependent trends. A combined additive plus proportional error model was used to account for residual error within the model. Between-subject variability was estimated for all PK parameters. Simulations were then performed using the final model to predict methylone PK after various multiple dose scenarios. For each scenario, the population PK model was used to simulate the PK of N=100 subjects. Summary PK parameters for the simulations are shown in Table 10B below. Table shows 95% confidence intervals in parentheses and shows calculated standard deviation (SD) values assuming N=100, as was used for the simulation.

TABLE 10B

Simulated Pharmacokinetic Parameters for Plasma Methylone

| Booster Time | 50 minutes | 60 minutes | 90 minutes | 120 minutes |
|---|---|---|---|---|
| Mean $C_{max}$ (μg/L) | 566 ± 120 (542-589) | 561 ± 120 (538-585) | 546 ± 112 (524-568) | 530 ± 102 (510-550) |
| Mean $AUC_{10hr}$ (hr * μg/L) | 3764 ± 760 (3615-3913) | 3745 ± 753 (3598-3893) | 3691 ± 732 (3548-3835) | 3634 ± 717 (3494-3775) |
| Mean $AUC_{24hr}$ (hr * μg/L) | 5533 ± 1385 (5261-5804) | 5528 ± 1380 (5257-5798) | 5515 ± 1367 (5247-5783) | 5502 ± 1355 (5237-5768) |

These data suggest that adding a booster will lead to an increased AUC, which is likely to provide a longer duration of biological action—but without increased intensity of the physiological responses. Of note, the predicted $C_{max}$ after the booster dose is 546.7 μg/L which is less than the observed $C_{max}$ of 594.2 μg/L after a single dose of methylone 200 mg.

Example 26: Pharmaceutical Composition of Methylone

In this Example, the physical and chemical compatibility of methylone drug substance, 50 mg with various commonly used solid dosage form excipients, as well as methylone active pharmaceutical ingredient (API) alone, was analyzed. Analyses were conducted at t=0, 2, 4 and 8 weeks for appearance, assay, and related substances for samples stored in closed vials at 25° C./60% RH and 40° C./75% RH. The excipients selected in this study meet USP/NF compendia where applicable and are listed in Table 11 below:

TABLE 11

List of excipients and ratios

| Functionality | Material | Trade Name | Grade | Manufacturer | Mixture Ratios (API: Excipients) |
|---|---|---|---|---|---|
| Fillers/Binders | Microcrystalline Cellulose | Avicel ® PH-101 | NF, Ph. Eur., JP | Dupont/IFF Nutrition & Biosciences | 1:10 |
| | Mannitol | Mannogem ® XL | USP, EP | SPI Pharma | 1:10 |
| Disintegrant | Croscarmellose Sodium | Ac-Di-Sol ® | NF, Ph. Eur., JP | Dupont/IFF Nutrition & Biosciences | 1:1 |
| | Crospovidone XL | Polyplasdone ™ XL | EP, USP, NF, JPE | Ashland | 1:1 |
| Surfactant | Sodium Lauryl Sulphate (SLS), Fine | Koliphor ® Fine | USP, NF, JP, Ph. Eur. | BASF | 10:1 |
| | Poloxamer 188 | Kolliphor ® P 188 | USP, NF, Ph. Eur., JPE | BASF | 10:1 |
| Glidant | Colloidal Silicon Dioxide | Aerosil ® 200 Pharma | USP, NF, EP, JP | Evonik | 10:1 |
| Lubricant | Magnesium Stearate | Hyqual ® non-bovine #5712 | BP, JP, EP, USP, NF | Mallinckrodt | 10:1 |
| | Sodium Stearyl Fumarate | Pruv ® | Ph Eur., NF, JPE | JRS Pharma | 10:1 |
| Capsule | Gelatin/Dyes | Colorista ® Capsule | N/A[1] | Colorcon | 10:1 |

[1]Individual components are USP, NF, Ph Eur, and/or JP.

Commonly used excipients in oral solid dosage forms were selected for excipient/API compatibility. The possible processes (blending, milling and dry granulation) followed for manufacturing of oral solid dosage forms were considered while shortlisting the excipients. The formulation will require a filler and binder, thus microcrystalline cellulose and mannitol can be used in dry granulation processing. The formulation may also need a disintegrant (croscarmellose sodium and crospovidone xl) irrespective of the manufacturing process followed. Sodium lauryl sulphate and poloxamer 188 may also be required as solubilizers to increase the solubility of the API. Colloidal silicon dioxide may be required in order to aid the flow properties of the blend and magnesium stearate or sodium stearyl fumarate may be used for lubrication. Colorista® capsules are also included to evaluate gelatin and dye in case a capsule dosage form is selected. The ratios of excipients to the API in the compatibility study are driven by possible formulations while taking into account the allowable quantity of each excipient taken from the database of FDA's inactive ingredient guide (IIG) available at www.accessdata.fda.gov/scripts/cder/iig/index.Cfm.

Excipient Compatibility Sample Mixtures: The excipients and API were dispensed individually by weight into 20 mL clear borosilicate (type I) glass vials to fill the appropriate weights as listed in Table 12. Table 12 lists mixtures of API with varied excipients and a stand-alone control sample of API alone. Each excipient mixture sample preparation was conducted using a clean spatula to mix the vial ingredients for 30-60 seconds. Each vial was properly labeled with the description and storage conditions. One vial was used for testing at the initial (t=0) time point. Three vials, closed, were placed at each storage condition to allow sampling at each time point and one vial, closed, was placed at each storage condition for overage.

TABLE 12

Excipient Compatibility Sample Mixtures

| Ingredients | Quantity to Dispense (mg) | | | | | | | | | | |
|---|---|---|---|---|---|---|---|---|---|---|---|
| Methylone | 50 | 50 | 50 | 50 | 50 | 50 | 50 | 50 | 50 | 50 | 50 |
| Microcrystalline Cellulose | | 500 | | | | | | | | | |
| Mannitol | | | 500 | | | | | | | | |
| Sodium Lauryl Sulphate (SLS), Fine | | | | 5 | | | | | | | |
| Poloxamer 188 | | | | | 5 | | | | | | |
| Croscarmellose Sodium | | | | | | 50 | | | | | |
| Crospovidone XL | | | | | | | 50 | | | | |
| Colloidal Silicon Dioxide | | | | | | | | 5 | | | |
| Magnesium Stearate | | | | | | | | | 5 | | |
| Sodium Stearyl Fumarate | | | | | | | | | | 5 | |
| Colorista ® Capsule | | | | | | | | | | | 5 |
| Sample ID | A | B | C | D | E | F | G | H | I | J | K |
| Total Weight, mg | 50 | 550 | 550 | 55 | 55 | 100 | 100 | 55 | 55 | 55 | 55 |
| No. of Vials | 9 | 9 | 9 | 9 | 9 | 9 | 9 | 9 | 9 | 9 | 9 |
| Storage Conditions | 25° C./60% RH closed, 40° C./75% RH closed | | | | | | | | | | |
| Time Points | Initial (t = 0), 2, 4 and 8 week, +1 vial as overage/condition | | | | | | | | | | |

Excipient Compatibility Sample Analysis: Each individual vial sampled at the requested time points was analyzed for the following parameters: (a) Appearance (Visual); Assay (HPLC); (c) Related Substances (HPLC).

The results of these studies through the last time point (8 weeks) are presented in Table 13 (Assay and Appearance) and Table 14 (Total Degradation Products) below:

TABLE 13

Methylone Excipient Compatibility Study (Assay and Appearance)

| Sample Description | Assay (% Recovery)/Appearance | | | | | | |
|---|---|---|---|---|---|---|---|
| | t = 0 | 2 Week 25° C./ 60% RH | 2 Week 40° C./ 75% RH | 4 Week 25° C./ 60% H | 4 Week 40° C./ 75% RH | 8 Week 25° C./ 60% RH | 8 Week 40 °C./ 75% RH |
| (A) Methylone | 100.6 | 99.7 | 99.0 | 100.3 | 99.6 | 98.2 | 100.3 |
| (B) Methylone + Microcrystalline Cellulose (Avicel ® PH-101) | 99.3 | 98.4 | 96.4 | 98.1 | 94.3 | 98.1 | 91.5 |
| (C) Methylone + Mannitol (Mannogem ® XL) | 101.6 | 100..0 | 98.7 | 100.2 | 99.8 | 101.0 | 98.2 |
| (D) Methylone + Sodium Lauryl Sulfate (Kolliphor ® SLS Fine) | 101.7 | 99.5 | 99.6 | 99.6 | 99.3 | 98.1 | 100.1 |
| (E) Methylone + Poloxamer (Kolliphor ® P 188) | 101.3 | 99.4 | 99.3 | 99.7 | 99.3 | 98.4 | 99.5 |
| (F) Methylone + Croscarmellose Sodium (Ac-Di-Sol ®) | 100.7 | 99.3 | 95.5 | 99.0 | 98.1 | 99.4 | 94.2 |
| (G) Methylone + Crospovidone (Polyplasdone ™ XL) | 99.0 | 99.3 | 98.8 | 99.6 | 96.9 | 97.6 | 96.9 |
| (H) Methylone + Colloidal Silicon Dioxide (Aerosil ® 200 Pharma) | 99.2 | 100.3 | 99.8 | 99.7 | 98.7 | 98.0 | 96.8 |
| (I) Methylone + Magnesium Stearate (Hyqual ®) | 99.2 | 99.3 | 100.4 | 99.3 | 99.3 | 98.1 | 99.4 |
| (J) Methylone + Sodium Stearyl Fumarate (PRUV ®) | 101.2 | 102.1 | 102.1 | 99.0 | 102.1 | 98.3 | 97.9 |
| (K) Methylone + Colorista ® Capsules | 101.4 | 99.6 | 99.8 | 102.3 | 99.7 | 100.5 | 98.4 |

TABLE 13-continued

Methylone Excipient Compatibility Study (Assay and Appearance)

| | | Assay (% Recovery)/Appearance | | | | | |
|---|---|---|---|---|---|---|---|
| Sample Description | t = 0 | 2 Week 25° C./ 60% RH | 2 Week 40° C./ 75% RH | 4 Week 25° C./ 60% H | 4 Week 40° C./ 75% RH | 8 Week 25° C./ 60% RH | 8 Week 40 °C./ 75% RH |
| Appearance | All Samples: off-white (light gray) powder | All Samples: off-white powder | All Samples: off-white powder | Sample IDs A to J: off-white powder Sample ID K: off-white powder with dark brown specs | Sample IDs A to J: off-white powder Sample ID K: off-white powder with dark brown specs | Sample IDs A to J: off-white powder Sample ID K: off-white powder with dark brown specs | Sample IDs A to J: off-white powder Sample ID K: off-white powder with dark brown specs |

TABLE 14

Methylone Excipient Compatibility Study (Total Degradation Products)

LOD ≥ 0.03%, LOQ ≥ 0.1%

| Sample Description | t = 0 | 2 Week 25° C. 60% RH | 2 Week 40° C. 75% RH | 4 Week 25° C. 60% RH % Area | 4 Week 40° C. 75% RH | 8 Week 25° C. 60% RH | 8 Week 40° C. 75% RH |
|---|---|---|---|---|---|---|---|
| Methylone (A) | <LOQ | <LOQ | <LOQ | <LOQ | 0.27 | <LOQ | 0.34 |
| Methylone + Microcrystalline Cellulose (Avicel ® PH-101) (B) | <LOQ | 0.39 | 2.99 | 0.95 | 5.87 | 1.63 | 8.89 |
| Methylone + Mannitol (Mannogem ® XL) (C) | <LOQ | <LOQ | 0.38 | <LOQ | 0.65 | <LOQ | 1.23 |
| Methylone + Sodium Lauryl Sulfate (Kolliphor ® SLS Fine) (D) | <LOQ | <LOQ | <LOQ | <LOQ | 0.39 | <LOQ | 0.74 |
| Methylone + Poloxamer (Kolliphor ® P 188) (E) | <LOQ | <LOQ | <LOQ | <LOQ | 0.62 | <LOQ | 1.12 |
| Methylone + Croscarmellose Sodium (Ac-Di-Sol ®) (F) | <LOQ | <LOQ | 0.31 | <LOQ | 0.47 | 0.14 | 1.71 |
| Methylone + Crospovidone (Polyplasdone ™ XL) (G) | <LOQ | <LOQ | 2.23 | 0.37 | 4.09 | 0.34 | 3.16 |
| Methylone + Colloidal Silicon Dioxide (Aerosil ® 200 Pharma) (H) | <LOQ | 0.10 | 0.87 | 0.31 | 1.75 | 0.42 | 2.16 |
| Methylone + Magnesium Stearate (Hyqual ®) (I) | <LOQ | <LOQ | 0.46 | 0.12 | 0.58 | <LOQ | 1.15 |
| Methylone + Sodium Stearyl Fumarate (PRUV ®) (J) | <LOQ | <LOQ | 0.12 | <LOQ | 0.14 | <LOQ | 0.43 |
| Methylone + Colorista ® Capsules (K) | <LOQ | 0.13 | 0.15 | <LOQ | 0.30 | <LOQ | 0.37 |

From the 4 week time point. 5 formulations were prepared, as indicated in Tables 15A-15B below, as direct blends (batches N3561-6 to N3561-14) using promising excipients from the compatibility study. Each direct blend was encapsulated into size 1 Swedish orange gelatin capsules using the FETON® encapsulator, targeting 300 mg fill/capsule. Capsules were tested for content uniformity and dissolution and the results for the batches of Table 15A are presented in Table 16 below. For the batches of Table 15B, shown below in the four tables below are % assay, % impurities and % moisture, 1M stability at 5° C., 25° C./60% RH, 40° C./75% RH. Results at release are shown for comparison.

TABLE 15A

| Material | Uses | N3561-6 | N3561-7 | N3561-8 mg/capsule | N3561-9 | N3561-10 |
|---|---|---|---|---|---|---|
| Methylone free base | API | 50.00 | 50.00 | 50.00 | 50.00 | 50.00 |
| Methylone HCl |  | 59.00 | 59.00 | 59.00 | 59.00 | 59.00 |
| Mannitol (MANTOGEM ® XL) | Diluent/ Binder | 232.00 | 230.20 | 230.20 | 230.20 | 230.20 |
| Sodium Lauryl Sulfate (KOLLIPHOR ®SLS Fine) | Surfactant |  | 1.80 |  | 1.80 |  |
| Poloxamer 188 (Kolliphor P 188) | Surfactant |  |  | 1.80 |  | 1.80 |
| Croscarmellose Sodium (AC-DI-SOL ®) | Disintegrant | 15.00 | 15.00 | 15.00 | 15.00 | 15.00 |
| Magnesium Stearate, USP (non-Bovine # 5712) | Lubricant | 3.00 | 30.00 | 3.00 |  |  |
| Sodium Stearyl Fumarate (PRUV ®) | Lubricant |  |  |  | 3.00 | 3.00 |
| Total |  | 300.0 | 300.0 | 300.0 | 300.0 | 300.0 |

TABLE 16

| | Batches | | | | |
|---|---|---|---|---|---|
| Number | N3561-6 | N3561-7 | N3561-8 % LC | N3561-9 | N3561-10 |
| 1 | 100.0 | 92.5 | 96.1 | 96.7 | 94.0 |
| 2 | 94.3 | 97.2 | 97.6 | 99.2 | 96.8 |
| 3 | 96.8 | 94.6 | 94.6 | 98.4 | 98.6 |
| 4 | 96.2 | 97.0 | 96.0 | 96.5 | 102.2 |
| 5 | 92.7 | 98.8 | 99.1 | 94.0 | 95.2 |
| 6 | 96.7 | 97.0 | 93.7 | 97.2 | 94.6 |
| 7 | 91.1 | 95.3 | 101.2 | 91.0 | 99.9 |
| 8 | 98.3 | 97.3 | 98.3 | 100.4 | 98.4 |
| 9 | 96.1 | 93.3 | 95.2 | 100.3 | 100.2 |
| 10 | 95.5 | 100.1 | 94.4 | 103.6 | 94.8 |
| Avg | 95.7 | 96.3 | 96.6 | 97.7 | 97.5 |
| % RSD | 2.7 | 2.5 | 2.5 | 3.6 | 2.9 |
| AV | 9.0 | 7.9 | 7.6 | 9.3 | 7.8 |

Acceptance Value (AV) Limit NMT 15.0

TABLE 15B

| Material | Uses | N3561-11 | N3561-12 mg/capsule | N3561-13 | N3561-14 |
|---|---|---|---|---|---|
| Methylone free base | API | 50.00 | 50.00 | 50.00 | 50.00 |
| Methylone HCl |  | 59.00 | 59.00 | 59.00 | 59.00 |
| Mannitol (MANTOGEM ® XL) | Diluent/ Binder | 223.00 | 222.82 | 221.20 | 221.02 |
| Sodium Lauryl Sulfate (KOLLIPHOR ®SLS Fine) | Surfactant | — | — | 1.80 | 1.80 |
| Poloxamer 188 (Kolliphor P 188) | Surfactant | — | — | — | — |
| Croscarmellose Sodium (AC-DI-SOL ®) | Disintegrant | 15.00 | 15.00 | 15.00 | 15.00 |
| Magnesium Stearate, USP (non-Bovine # 5712) | Lubricant | 3.00 | 3.00 | — | — |

TABLE 15B-continued

| Material | Uses | N3561-11 | N3561-12 | N3561-13 | N3561-14 |
|---|---|---|---|---|---|
| | | | mg/capsule | | |
| Sodium Stearyl Fumarate (PRUV ®) | Lubricant | — | — | 3.00 | 3.00 |
| Butylated Hydroxytoluene (BHT) | Antioxidant | — | 0.18 | — | 0.18 |
| Total | | 300.0 | 300.0 | 300.0 | 300.0 |

TABLE 17A

N3561-11

| | Release- 254 nm | | Stability Testing 280 nm | | | | | |
|---|---|---|---|---|---|---|---|---|
| | | | 1M- 5° C. | | 1M- 25 C./60% RH | | 1M- 40 C./75% RH | |
| | | | | Assay (n = 10) | | | | |
| | 93.2% | | 97.4 | | 97.8 | | 97.1 | |
| | RRT | Area % | RRT | Area % | RRT | Area % | RRT | Area % |
| Related Substances (n = 10) | 1.598 | 0.20% | 0.579 | 0.03 | 0.579 | 0.03 | 0.578 | 0.02 |
| | | | 1.598 | 0.06 | 1.598 | 0.07 | 1.598 | 0.11 |
| | | | 1.917 | 0.02 | 1.917 | 0.02 | 1.917 | 0.05 |
| Total Impurities (n = 10) | | 0.20% | | 0.11 % | | 0.12% | | 0.18% |
| % Moisture (n = 3) | | 0.2% | | 0.2% | | 0.2% | | 0.2% |

TABLE 17B

N3561-12

| | Release- 254 nm | | Stability Testing 280 nm | | | | | |
|---|---|---|---|---|---|---|---|---|
| | | | 1M-5° C. | | 1M- 25 C./60% RH | | 1M-40 C./75% RH | |
| | | | | Assay (n = 10) | | | | |
| | 93.2% | | 100.8% | | 100.0% | | 99.3% | |
| | RRT | Area % | RRT | Area % | RRT | Area % | RRT | Area % |
| Related Substances (n = 10) | 1.598 | 0.20% | 0.578 | 0.03% | | | | |
| | | | 1.598 | 0.10% | 1.598 | 0.11% | 1.598 | 0.15% |
| | | | 1.917 | 0.03% | 1.917 | 0.04% | 1.917 | 0.06% |
| | | | 3.658 | 0.03% | | | | |
| | | | 3.731 | 0.06% | 3.728 | 0.04% | | |
| Total Impurities (n = 10) | | 0.20% | | 0.25% | | 0.19% | | 0.21% |
| % Moisture (n = 3) | | 0.2% | | 0.2% | | 0.2% | | 0.2% |

TABLE 17C

N3561-13

| | Release- 254 nm | | Stability Testing 280 nm | | | | | |
|---|---|---|---|---|---|---|---|---|
| | | | 1M- 5° C. | | 1M- 25 C./60% RH | | 1M-40 C./75% RH | |
| | | | | Assay (n = 10) | | | | |
| | 93.2% | | 102.4% | | 100.3% | | 100.5% | |
| | RRT | Area % | RRT | Area % | RRT | Area % | RRT | Area % |
| Related Substances (n = 10) | 1.598 | 0.20% | 0.578 | 0.03% | | | | |
| | | | 1.598 | 0.03% | 1.598 | 0.04% | 1.598 | 0.09% |
| | | | | | | | 2.375 | 0.05% |
| Total Impurities (n = 10) | | 0.20% | | 0.06% | | 0.04% | | 0.14% |

TABLE 17C-continued

N3561-13

| | Release- 254 nm | Stability Testing 280 nm | | |
|---|---|---|---|---|
| | | 1M- 5° C. | 1M- 25 C./60% RH | 1M-40 C./75% RH |
| | | Assay (n = 10) | | |
| | 93.2% | 102.4% | 100.3% | 100.5% |
| | RRT    Area % | RRT    Area % | RRT    Area % | RRT    Area % |
| % Moisture (n = 3) | 0.2% | 0.2% | 0.2% | 0.2% |

TABLE 17D

N3561-14

| | Release- 254 nm 93.2% | Stability Testing 280 nm | | |
|---|---|---|---|---|
| | | 1M- 5° C. 97.7% | 1M- 25 C./60% RH 97.1% | 1M-40 C./75% RH 97.7% |
| | | Assay (n = 10) | | |
| | RRT    Area % | RRT    Area % | RRT    Area % | RRT    Area % |
| Related Substances (n = 10) | 1.598   0.20% | 0.578   0.03%<br>1.598   0.03%<br>3.604   0.05% | 0.578   0.03%<br>1.598   0.05%<br>3.604   0.05% | 1.598   0.11%<br>2.386   0.04%<br>3.602   0.04% |
| Total Impurities (n = 10) | 0.20% | 0.11% | 0.13% | 0.19% |
| % Moisture (n = 3) | 0.2% | 0.2% | 0.2% | 0.2% |

Example 27: Methylone is a Rapid-Acting Neuroplastogen with Less Off-Target Activity than MDMA Chronic antidepressant treatment increases neuroplasticity genes in the brain, corresponding to the time course of therapeutic benefit. It takes weeks of daily dosing with drugs like fluoxetine (brandname: Prozac) to increase brain expression of neurotrophic factors like brain-derived neurotrophic factor (BDNF) and associated modifications in synapses.

Rapid regulation of neuroplasticity-related gene expression in key brain areas may explain the persistent behavioral changes observed after methylone treatment. This Example tests this hypothesis in order to understand how a single dose of methylone could have rapid-acting and long-lasting behavioral effects in animals. Two brain areas in a well-characterized circuit underlying emotional learning that is known to be disrupted by PTSD, depression and anxiety were focused on. The effects of methylone were compared with MDMA to determine whether differences in their drug-induced gene expression profiles could help to explain the differences observed in behavioral and clinical experiences.

Materials and Methods

Animals: Male Sprague Dawley rats (Envigo) were used for binding, uptake and release assays and were kept at Gifford Bioscience, Ltd. (Birmingham, UK). The in-life portion of RNA-seq and immunohistochemistry studies were performed at WuXi Apptec (Cranbury, NY) using male Sprague Dawley rats (Hilltop). For all studies, rats weighed ~200 g at arrival and acclimated for at least 2-3 days before use. Animals were group housed in a light- and temperature-controlled environment (20 to 26° C.; 30 to 70% humidity; 12-hour light/dark cycle) with ad libitum access to standard rodent chow and water. All animal use and procedures were in accordance with established protocols approved by Gifford Bioscience IACUC and Standard Operating Procedures (SOP) or the WuXi Apptec IACUC committee and SOP, and Transcend Therapeutics.

Competitive Radioligand Binding: Binding was performed in SD rat brain lysates at Gifford Bioscience, Ltd (Birmingham, UK) according to standard protocols. Radioligands used were: [$^3$H]Citalopram (PerkinElmer NET1039250UC); [3H]Nisoxetine (PerkinElmer NET1084250UC); [$^3$H]WIN35428 (PerkinElmer NET1033250UC). Nonspecific compounds used were Citalopram (Tocris Bioscience 1427); JHW007 (Tocris Bioscience 4351); Nomifensine (Abcam ab146004). Test compounds used were methylone (Merck M-140) or MDMA (Merck M-103). Rat brains were dissected and tissue was homogenized in cold lysis buffer, centrifged at 100×g for 2 min and the supernatant was placed in a fresh tube. Supernatant was centrifuged at 13,000×g for 10 min at 4° C. to re-pellet the cell lysate. The pellet was resuspended in fresh wash buffer (50 mM Tris-HCl; 5 mM MgCl$_2$; 5 mM EDTA) and centrifuged a third time. The pellet was then resuspended in wash buffer containing 10% sucrose as a cryo-protectant, divided into aliquots (0.3 mL) and stored at −80° C. A sample of the homogenate was analyzed for protein content using the SIGMA® BCA assay. On the day of the assay, the membrane preparation was thawed, and the pellet resuspended in final assay buffer. Competition binding assays were carried out in 96-well polypropylene plates in a final volume of 250 μL per well. To each well was added 150 μL membranes, 50 μL of non-specific compound or buffer and 50 μL radioligand solution in buffer. The plate was incubated at 30° C. for 90 minutes with gentle agitation. The incubation was stopped by vacuum filtration onto presoaked (PBS buffer with PEI) GF/C filters using a 96-well FILTERMATE™ harvester, followed by 5 washes with ice-cold wash buffer. Filters were then dried under a warm air stream, sealed in polyethylene, scintillation cocktail added, and the radioactivity counted in a WALLAC® TriLux 1450 MicroBeta counter. For each concentration of drug, non-specific binding was subtracted from total binding to give specific binding. Data was fitted using the non-linear curve fitting routines in PRISM® (Graphpad Software Inc) to determine $IC_{50}$. $K_i$ was subsequently calculated using the Cheng-Prusoff equation.

Uptake Inhibition Assay: Studies were performed at Gifford Bioscience, Ltd (Birmingham, UK) according to standard protocols. Test and reference compounds [Methylone (Merck M-140), (±)-MDMA (Merck, M-103), Citalopram (Tocris Bioscience 1427), JHW007 (Tocris Bioscience 4351), Nomifensine (Abcam ab146004)] were dissolved in DMSO (10 mM) and stored frozen at −20° C. On the day of the assay, compounds were thawed and diluted with assay buffer to 5× final maximal assay concentration (e.g. 50 μM for a final assay concentration of 10 μM). Rat brain synaptosomes were isolated from Sprague Dawley rats (200-250 g). Brains were dissected and tissue was added to sucrose buffer (0.32 M), homogenized with a dounce-homogenizer and centrifuged at 100×g to remove cells and debris. Supernatant was collected and centrifuged 17,000×g for 10 minutes at 4° C. to pellet the synaptosomes. The pellet was resuspended in fresh assay buffer. Uptake assays were carried out in 96-well plates in a final volume of 250 μL per well. To each well was added 150 μL synaptosomes, 50 μL test or non-specific compound or buffer alone. The plate was incubated at 30° C. for 30 minutes with gentle agitation. 50 μL radiolabeled neurotransmitter ([$^3$H]5-HT (PerkinElmer, NET498001MC); [$^3$H]DA (PerkinElmer, NET673250UC); [$^3$H]NE (PerkinElmer, NET048250UC) in buffer was then added to each well to initiate the uptake. The plate was incubated 30° C. for a further five minutes with gentle agitation. The incubation was stopped by vacuum filtration onto presoaked (0.1% BSA in wash buffer) GF/C filters using a 96-well FILTERMATE™ harvester, followed by three washes with ice-cold wash buffer. Filters were then dried under a warm air stream, sealed in polyethylene, scintillation cocktail added, and the radioactivity counted in a WALLAC® TriLux 1450 MicroBeta counter. For each drug concentration, non-specific uptake was subtracted from total uptake to give specific uptake. Data was fitted using the non-linear curve fitting routines in PRISM® (Graphpad Software Inc) to determine $IC_{50}$.

Release Assay: Studies were performed at Gifford Bioscience, Ltd (Birmingham, UK) according to standard protocols. Test compounds and synaptosomes were prepared as described for uptake inhibition assays. Synaptosomes treated with [$^3$H]5-HT, [$^3$H]DA or [$^3$H]NE were loaded onto filter chambers containing GF/C filters and placed in a superfusion system. Oxygenated Krebs buffer was perfused through the chambers at a rate of 1.5 mL/minute at 35° C. using either an 8-channel or a 12-channel peristaltic pump. Trapped air bubbles were removed from the filters prior to collecting fractions to ensure an even flow over the synaptosomal bed. After a superfusion period of 45 minutes, 2 basal fractions were collected followed by 6 fractions following the addition of the test drug. In some instances, the fractions containing the test drug were followed by collection of four additional fractions with high potassium (30 mM) to depolarize the synaptosomes. Fractions were 2 ml each. Following collection, an aliquot of (0.25-0.30 mL) each fraction was transferred to a counting plate. After the addition of scintillation cocktail, radioactivity was counted using a WALLAC® TriLux 1450 MicroBeta counter. Once all fractions had been collected, the filters holding the synaptosomes were removed and dried under a stream of warm air. Scintillation cocktail was added, and the filters counted to determine residual radioactivity. Drug-evoked release of neurotransmitter was calculated by subtracting the average of the two basal fractions (collected prior to the drug addition), from the four fractions collected in the presence of drug. The drug-evoked release was then expressed as a percentage of the basal release. Potassium-evoked release was calculated by subtracting the average of two fractions collected prior to the addition of high KCl buffer from that in the two fractions following addition of high KCl buffer. Potassium-stimulated release was calculated as a percentage of basal release. The drug evoked release as a function of drug concentration plotted and the data fitted. Data was fitted using the non-linear curve fitting routines in PRISM® (Graphpad Software Inc).

GPCR Screen: Studies were done at Eurofins DiscoverX Corp (Fremont, CA) using the GPCRmax assay according to manufacturer's protocols. This assay uses enzyme fragment complementation with b-galactosidase as the functional reporter. When a GPCR is activated, b-galactosidase is recruited, and the reporter is detectable. GPCRmax offers a high-throughput screen of 168 GPCRs for agonist or antagonist activity. Briefly, PathHunter cell lines were propagated, seeded into 384-well microplates and incubated at 37° C. Cells were incubated with sample (methylone or MDMA at 1 mM or 10 mM concentrations or appropriate control compounds) for agonist or antagonist determination based on standard protocols and run in triplicate. Microplates were read following signal generation with a PerkinElmer ENVISION™ instrument for chemiluminescent signal detection. Compound activity was analyzed using CBIS data analysis suite (ChemInnovation, CA) to determine raw values (RLU). For agonist mode assay, percentage activity was calculated using the following formula: % Activity=100%× (mean RLU of test sample−mean RLU of vehicle control)/ (mean MAX control ligand−mean RLU of vehicle control). For antagonist mode assay, percentage inhibition was calculated using the following formula: % Inhibition=100%× (1−(mean RLU of test sample−mean RLU of vehicle control)/(mean RLU of $EC_{80}$ control−mean RLU of vehicle control)).

Docking: All calculations were performed with MOE 2022.02 using the Amber10 force field with Born solvation. Docking was used to examine potential ligand binding to receptors with experimentally determined structures. The process to prepare the crystallographic protein structures for modeling work as well as preparing the ligands for docking is described below. Protein preparation: In MOE, the Quick-Prep procedure was used to standardize and minimize the protein structure subject to tethers on the receptor to relax any strain in the structure while keeping it close to the experimental coordinates. This procedure also determines the ionization state of both protein sidechains and the ligand. After protein preparation, structures were superposed into a common reference frame to compare the binding modes of different ligands. Ligand preparation: In cases where there were two stereoisomers of a particular drug/ligand, each stereoisomer was treated separately for preparation and docking. Each ligand was first ionized at pH 7 with MOE's Wash function to produce the dominant species. This was followed by conformational generation using the stochastic search method to ensure complex ring systems were adequately sampled. All generated conformations were used as input for docking. Docking poses and the likelihood of binding were evaluated by a combination of MOE's GBVI/WSA dG docking score, ligand conformational strain, and similarity to related experimental structures.

RNA Sequencing: For RNA-seq, animals were treated with methylone (10 mg/kg, IP), MDMA (10 mg/kg, IP) or saline vehicle 24 h before sacrifice. Frontal cortex, hippocampus, and amygdala were rapidly dissected and frozen on dry ice. RNA extraction, library preparation, sequencing and analysis was done at Azenta Life Sciences (South Plainfield, NJ) as follows:

Extraction: Total RNA was extracted from fresh frozen tissue samples using RNeasy Plus Universal mini kit following manufacturer's instructions (Qiagen, Hilden, Germany).

Library Preparation with PolyA selection and Illumina Sequencing: RNA samples were quantified using Qubit 2.0 Fluorometer (Life Technologies, Carlsbad, CA, USA) and RNA integrity was checked using Agilent TapeStation 4200 (Agilent Technologies, Palo Alto, CA, USA). RNA sequencing libraries were prepared using the NEBNext Ultra RNA Library Prep Kit for Illumina using manufacturer's instructions (NEB, Ipswich, MA, USA). Briefly, mRNAs were initially enriched with Oligod (T) beads. Enriched mRNAs were fragmented for 15 minutes at 94° C. First strand and second strand cDNA were subsequently synthesized. cDNA fragments were end repaired and adenylated at 3'ends, and universal adapters were ligated to cDNA fragments, followed by index addition and library enrichment by PCR with limited cycles. The sequencing library was validated on the Agilent TapeStation (Agilent Technologies, Palo Alto, CA, USA), and quantified by using Qubit 2.0 Fluorometer (Invitrogen, Carlsbad, CA) as well as by quantitative PCR (KAPA Biosystems, Wilmington, MA, USA). The sequencing libraries were clustered on 5 lanes of a flowcell. After clustering, the flowcell was loaded on the Illumina instrument (4000 or equivalent) according to manufacturer's instructions. The samples were sequenced using a 2×150 bp Paired End (PE) configuration. Image analysis and base calling were conducted by the Control software. Raw sequence data (.bcl files) generated by the sequencer were converted into fastq files and de-multiplexed using Illumina's bcl2fastq 2.17 software. One mismatch was allowed for index sequence identification.

Data Analysis: After investigating the quality of the raw data, sequence reads were trimmed to remove possible adapter sequences and nucleotides with poor quality. The trimmed reads were mapped to the reference genome available on ENSEMBL using the STAR aligner v.2.5.2b. The STAR aligner is a splice aligner that detects splice junctions and incorporates them to help align the entire read sequences. BAM files were generated as a result of this step. Unique gene hit counts were calculated by using feature Counts from the Subread package v.1.5.2. Only unique reads that fell within exon regions were counted.

Pathway Analysis: Pathway analysis was performed on selected gene lists based on a statistical cutoff (0.32≥log 2FC≥0.32, padj≤0.1) using Metascape gene annotation and analysis resource.

Immunohistochemistry: The in-life portion of the study was conducted at WuXi Apptec (Cranbury, NJ). Sectioning and staining of brains took place at Neuroscience Associates (NSA, Knoxville, TN). Rats were treated with a single dose of methylone (10 mg/kg, IP), MDMA (10 mg/kg, IP), or vehicle and sacrificed 24 h later by transcardial perfusion with phosphate-buffered saline (PBS), followed by 4% paraformaldehyde (PFA). Brains were post-fixed in PFA before shipment to NSA for processing and staining. Hemisected brains were mounted, sectioned and stained using standard protocols with myelin-basic protein primary antibody (MBP SMI-99, 1:5000, Biolegend, San Diego, CA) and anti-mouse biotinylated secondary antibody (BA-2001, Vector Laboratories, Newark, CA). Slides were imaged using a Huron Digital Pathology TissueScope LE120 whole slide scanning system. 20× objective was used with a 0.4 µm/pixel resolution.

Statistical Analysis (excluding RNA-seq): Otherwise, data are presented as the mean±SEM. Differences between two groups were determined by unpaired t-test, differences between more than two groups were determined by one-way ANOVA and Fisher's LSD post-hoc test unless otherwise noted. A p-value<0.05 indicated statistical significance. All analyses were completed using Graphpad Prism software version 9.3.1 (San Diego, CA).

Results

Competitive radioligand binding studies at the serotonin (5HT), norepinephrine (NE) or dopamine (DA) transporters (SERT, NET and DAT, respectively), revealed that methylone is a less potent inhibitor of SERT than MDMA, demonstrated by a greater inhibition constant ($K_i$) ($K_i$=4.15 mM vs. 2.62 mM). Methylone showed more potent inhibition of NET ($K_i$=1.15 mM vs. 0.79 mM) and comparable inhibition of DAT ($K_i$=5.73 mM vs. 5.11 mM) compared with MDMA. Next, the effects of methylone or MDMA on uptake inhibition of radiolabeled 5HT, NE, and DA was assayed. Results revealed that methylone had four times greater effect on 5HT reuptake inhibition compared with MDMA and comparable effects on uptake inhibition of NE and DA, as shown in Table 17A below.

TABLE 17A

| Reuptake inhibition: $IC_{50}$ (µM) | | | |
|---|---|---|---|
| | SERT | NET | DAT |
| Methylone | 0.43 | 0.13 | 2.3 |
| MDMA | 1.8 | 0.12 | 2.5 |

TABLE 17B

| Neurotransmitter release: $EC_{50}$ (µM) | | | |
|---|---|---|---|
| | SERT | NET | DAT |
| Methylone | 0.62 | 0.33 | 4.79 |
| MDMA | 0.16 | 0.49 | 1.42 |

Drug-evoked neurotransmitter release of 5HT, NE or DA was also assayed. Results showed that methylone releases less DA, but similar amounts of 5HT and NE compared with MDMA (FIG. 26A-FIG. 26C) (DA effects: drug: F (1.4)= 9.932, p<0.05; concentration: $F_{(2,9)}$=28.66, p<0.0001). The calculated $EC_{50}$ values for neurotransmitter release are shown in Table 17B above. Together, these studies confirm that methylone and MDMA are monoamine uptake inhibitors and releasers, but their relative affinities for SERT, NET, and DAT differ.

MDMA binds to G-protein coupled receptors (GPCRs), including serotonin receptors (e.g., $5HT_{2A}$, $5HT_{2C}$) and adrenergic receptors (e.g., a1A, a2A). To determine whether methylone showed agonist or antagonist activity at GPCRs and to compare with effects of MDMA, methylone (1 or 10 mM) or MDMA (1 or 10 mM) were screened in the GPCRmax high-throughput screen of 168 GPCRs. Activity greater than 30% typically indicates agonist activity and inhibition greater than 50% indicates antagonist activity. Methylone (1 or 10 mM) had no significant agonist activity detected in this screen. The greatest activity detected was for $5HT_5A$ (13.9%), which was well below the 30% activity threshold. No significant effects were detected at the 1 mM concentration. In contrast, MDMA nearly reached the 30% activity cutoff for $5HT_{2A}$ and $5HT_{2C}$ receptor agonist activity (27.5 and 28.0%, respectively; FIG. 27A). MDMA effects on $5HT_{2A}$ and $5HT_{2C}$ agonist activity were significantly greater than methylone ($5HT_{2A}$: $F_{(3,8)}=354.8$, $p<0.0001$; $5HT_{2C}$: $F_{(3,8)}=255.6$, $p<0.0001$). No antagonist activity was detected for methylone (1 or 10 mM), but MDMA showed significant activity at the $5HT_{2C}$ receptor both in terms of reaching the activity threshold (52.2%; FIG. 27B) and statistically different from methylone ($5HT_{2A}$: $F_{(3,8)}=14.57$, $p<0.01$; $5HT_{2C}$: $F_{(3,8)}=47.64$, $p<0.0001$). Together these data suggest that methylone has no off-target activity at 168 GPCRs whereas MDMA shows some activity at serotonin receptors, consistent with previous reports.

Figure 28:
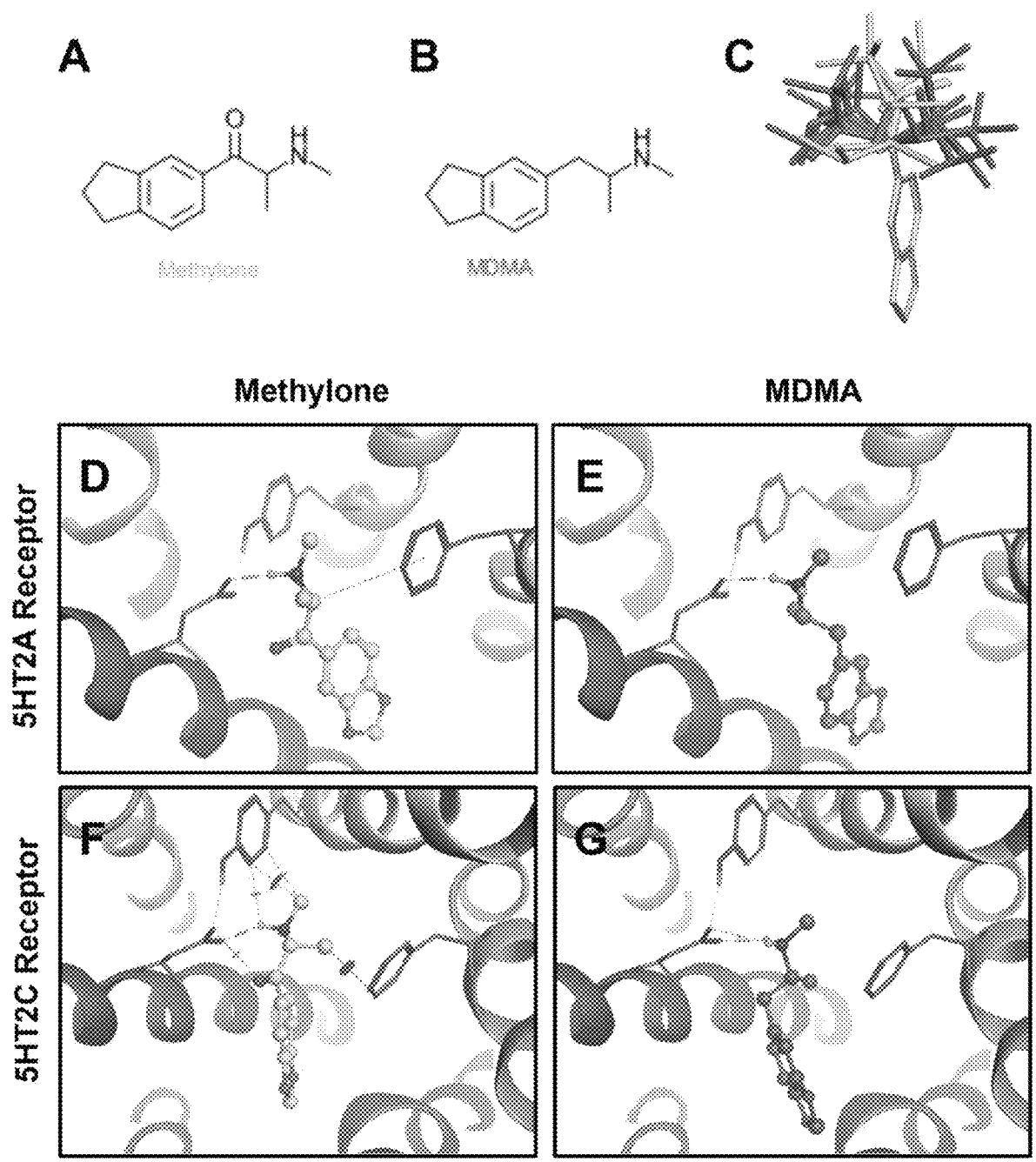

Methylone's chemical structure differs from MDMA only by a ketone group (FIGS. 28A-28B). To determine how differences between methylone and MDMA's structures may contribute to differences in binding to serotonin receptors, a docking study was performed to predict binding of methylone or MDMA to $5HT_{2A}$ or $5HT_{2C}$ receptors. The very similar chemical structures of MDMA and methylone might suggest similar binding characteristics. However, there are several important differences that can lead to major differences in potential binding to a given receptor. First, methylone contains a ketone carbonyl giving it a hydrogen bond acceptor that is not present in MDMA. This gives important physiochemical differences between the two molecules. For example, methylone will have a more polar surface area and it will also change the log P. Second, the carbonyl in methylone causes significant conformational differences compared with MDMA. Specifically, it is a difference in the torsional energy profile for a ketone to aromatic bond compared to a Csp3 to aromatic bond for MDMA. The diagram (FIG. 28C) shows low energy conformations generated for methylone (blue) or MDMA (purple) superimposed on the bicyclic ring system. Since there is better binding if a ligand binds in the low energy conformation, when MDMA fits a receptor, methylone would have to conform to the same shape as MDMA, which would cost energy and be less likely. Each molecule has different shapes with little to no overlap. Given subtle differences in receptor binding pocket shapes, the shape difference between MDMA and methylone could lead to very different binding profiles. In fact, results show that at the $5HT_{2A}$ receptor, MDMA fits well but methylone does not fit due to shape differences that cause strain energy (FIGS. 28D-28E). At the $5HT_{2C}$ receptor, which has a smaller binding pocket than $5HT_{2A}$, MDMA fits (FIG. 28G). However, due to the very different conformation of methylone, the docking algorithm cannot fit methylone into the binding pocket without generating steric clashes indicated by the orange disks (FIG. 28F). This is primarily due to methylone's different shape and as such, no binding would be expected. The docking study results align with the GPCR screen results and show that conformational differences between methylone and MDMA contribute to the differences in binding to off-target receptors.

The amygdala plays a central role in the brain's response to stress and is affected by CNS disorders like PTSD, MDD and anxiety. RNA-seq was used to determine how methylone or MDMA affected the amygdala, specifically to identify which genes and pathways were regulated within hours after a single dose, in order to shed light on methylone's mechanism of action. Differential expression (DE) analysis revealed genes significantly regulated by methylone (FIG. 29A) or MDMA (FIG. 29B) compared to vehicle-injected controls.

The number of genes significantly up- or downregulated by methylone or MDMA compared to vehicle were quantified and significantly more gene expression changes were induced by MDMA than methylone compared to vehicle controls (FIG. 29C). Both methylone and MDMA improve fear extinction, which is thought to underlie potential therapeutic benefit in PTSD. Therefore, it was hypothesized that genes changed by both methylone and MDMA reflected those linked to their therapeutic activity and drug-specific changes in gene expression underlie drug-specific and potentially off-target effects (FIG. 29D). Quantification of the number of significantly regulated genes revealed that nearly all the genes significantly regulated by methylone were also regulated by MDMA. However, 1313 additional genes were significantly regulated by MDMA only relative to vehicle (FIG. 29E).

To classify the list of MDMA-regulated genes and associate them with a particular phenotype, pathway or function, functional enrichment analysis was performed on the 774 downregulated (FIG. 30A) and 539 upregulated genes (FIG. 30B) in MDMA-treated animals. Among the significantly enriched terms were 'G alpha (q) signaling events' and 'Signaling by GPCR', consistent with changes in GPCR activity observed (FIG. 27A) and previously reported. Significantly enriched terms upregulated by MDMA only included receptor tyrosine kinase signaling, cellular response to stress, protein folding, orexin receptor pathway and cytokine signaling. Heatmaps generated to include the genes from protein folding (FIG. 30C), orexin receptor pathway (FIG. 30D) or cytokine signaling (FIG. 30E) enrichment lists show gene expression results from individual animals (N=6 per group) treated with vehicle, methylone or MDMA.

Methylone treatment did not significantly upregulate many genes in the amygdala (FIG. 29E), so functional enrichment analysis focused on downregulated genes by methylone (FIG. 31A) or MDMA (FIG. 31B). The most highly significantly enriched term was 'Ensheathment of neurons', reflected by the significant downregulation of myelin-associated genes by both methylone and MDMA (FIG. 31C).

Figure 32:
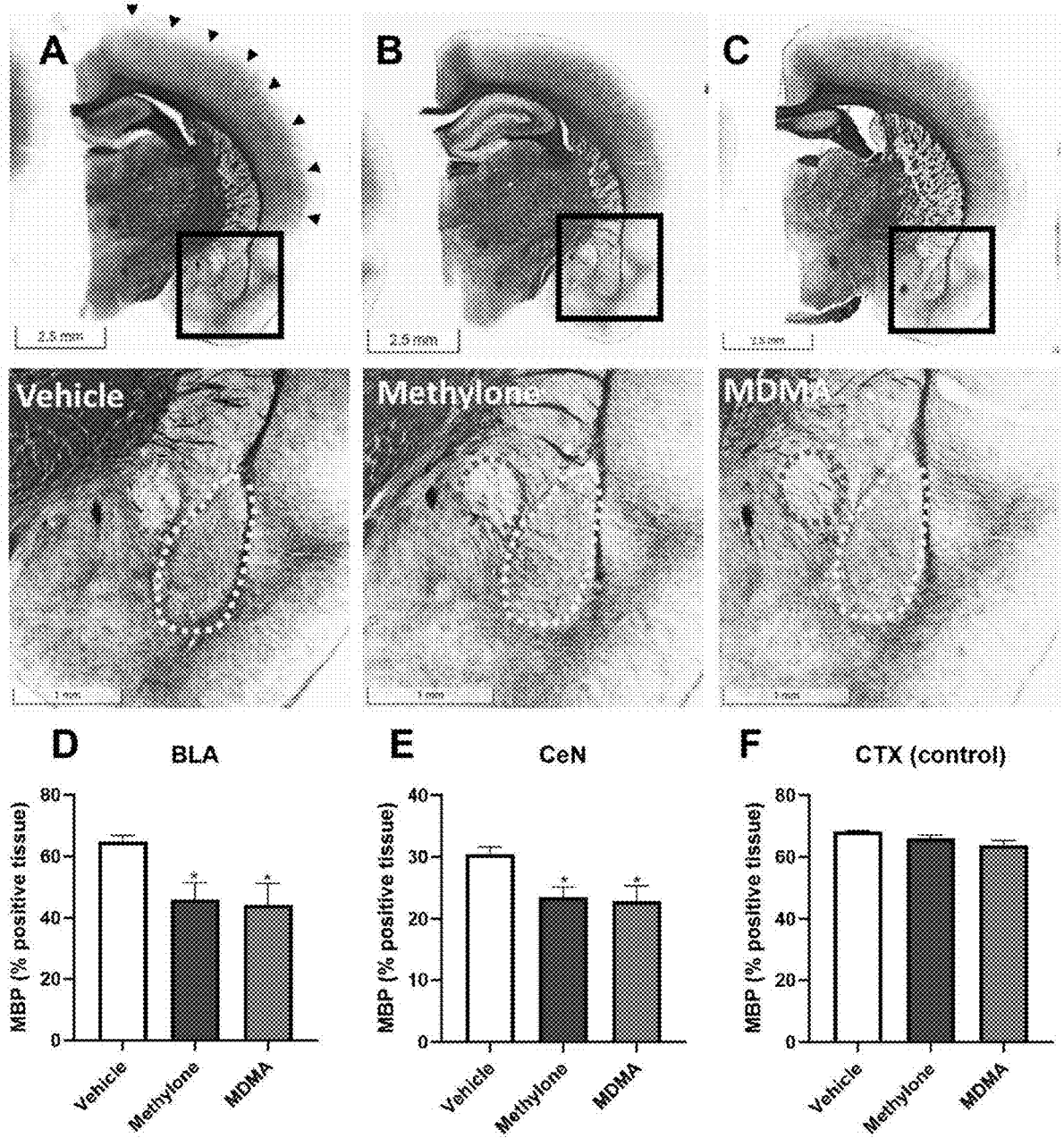

To confirm the results from functional enrichment analysis, levels of myelin basic protein (MBP) were assayed by immunohistochemistry in the amygdala of rats receiving methylone, MDMA, or vehicle (FIG. 32A-FIG. 32C). Results confirmed a significant reduction in MBP in the basolateral (FIG. 32D, $F_{(2,13)}=4.417$, $p<0.05$) and central nuclei of the amygdala (FIG. 32E, $F_{(2,13)}=4.062$, $p<0.05$) compared to vehicle. No change in MBP was observed in the cortex as a control (FIG. 32F, $F_{(2,13)}=3.776$, n.s.).

Figure 33:
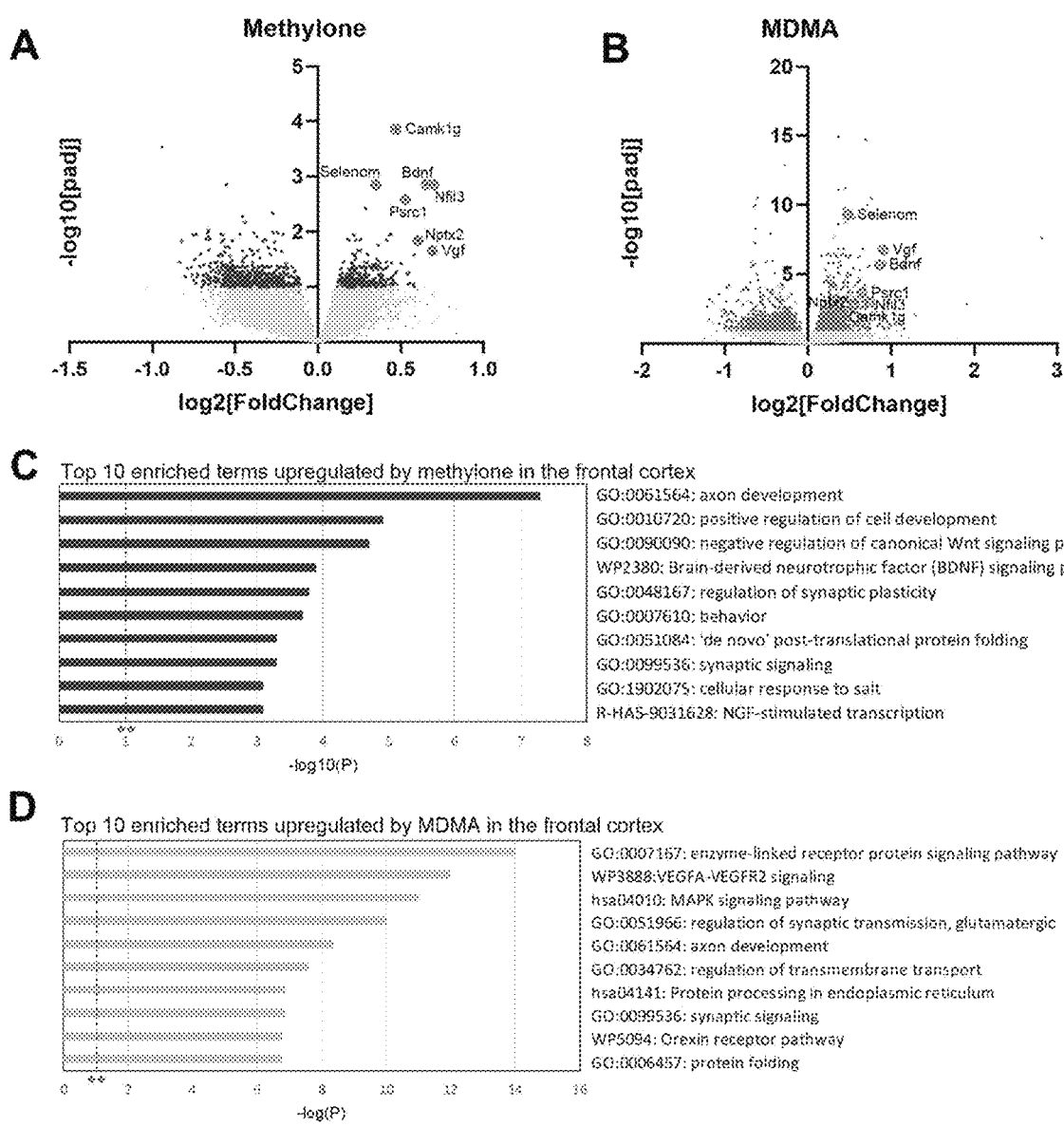

The prefrontal cortex shares strong connectivity with the amygdala and has been described as a critical substrate for fear conditioning and PTSD. Therefore, methylone and MDMA effects on gene expression in the frontal cortex was also investigated. Results of differential expression (DE) analysis show genes significantly regulated by methylone (FIG. 33A) or MDMA (FIG. 33B). Consistent with results obtained in the amygdala, MDMA significantly regulated ~72% more genes than methylone (825 vs. 480 genes) and 154 of those genes were regulated by both treatments. Notably, among the topmost significantly upregulated genes by methylone were Calcium/Calmodulin-dependent kinase I g (Camklg), selenoprotein N (Sclenom), brain-derived neurotrophic factor (BDNF), nuclear factor interleukin 3 related (Nfil3), proline and serine rich coiled-coil 1 (Psrc1), neuronal pentraxin-2 (Nptx2), and Vgf (non-acronymic), all of which are linked to neuroplasticity. Consistent with this, the top 10 most significant enrichment terms upregulated by methylone included almost exclusively terms linked to synaptic plasticity, cytogenesis and survival, and neurotrophin signaling (e.g., BDNF signaling pathway) (FIG. 33C). MDMA also regulated neuroplasticity genes (FIG. 33B), but the top 10 enriched terms differed slightly from those of methylone. Specifically, VEGFA-VEGFR2 signaling, MAPK signaling, protein processing in the endoplasmic reticulum, and protein folding were significantly upregulated (FIG. 33D). Orexin receptor pathway and protein folding were also top MDMA enrichment terms in the frontal cortex as observed in the amygdala (FIG. 33D, FIG. 31B). Together, these results point to changes in synaptic plasticity as a key step in the mechanisms of action of methylone and MDMA and to the specificity of methylone compared with MDMA.

Example 28: Methylone Shows No Hallucinogenic Activity in the Mouse Head-Twitch Response (HTR) Test Classic psychedelics are associated with hallucinations and dissociation, mediated at least in part by $5HT_{2A}$ receptor activity. In animals, these drugs also increase head-twitch response (HTR), a rapid head-shaking that depends on $5HT_{2A}$ receptor activation. Methylone releases serotonin but shows no agonist or antagonist activity at $5HT_{2A}$ receptors. There have been no reports of hallucinations following methylone administration in humans. Methylone was tested in HTR to evaluate whether indirect activity at $5HT_{2A}$ (i.e., via serotonin release) might increase HTR.

Methods

Head twitch response (HTR) was evaluated using C57BL/6J mice (ages 7-10 weeks). Mice were ear tagged at least three days after arrival to the animal facility and allowed to rest for at least three days before behavioral testing. Small magnets (SuperMagnetMan—N45 magnet 3 mm diameter, 0.5 mm thickness) were glued to car tags (Stoelting—La Pias Aluminum Ear Tags) at least two days before mice were car tagged. The experimental setup was adapted from Gonzales-Macso (de la Fuente Revenga et al., 2019) and Kwan (Jefferson et al., 2022; Savalia et al., 2021), including experimental apparatus and MATLAB code for analysis.

Doses were randomly assigned, and age-matched controls were injected with vehicle and randomly interspersed with drug conditions. At least three animals per sex were used for each drug dose and condition. If animals were used in multiple HTR experiments, experimental sessions took place at least one week apart. Two animals were run at a time. Immediately after i.p. injection of psychedelic or entactogen drug, animals were placed in separate plastic boxes within a larger chamber (Home Depot—28 in. W×32 in. H×21.5 in. D), and HTR was measured for 10 minutes. A small lamp was placed in the back of the larger chamber, and a high-speed camera (Basler-Aca 1920-155 μm) was suspended from the ceiling to record video of the animals in the plastic boxes. Between each recording, the plastic boxes were cleaned with 70% ethanol.

Results

As shown in FIG. 34, methylone had no effect on head-twitch behaviors at any dose tested, consistent with its lack of agonist/antagonist activity at $5HT_{2A}$ receptors and demonstrating that indirect effects on this receptor (e.g., via serotonin release) do not induce head-twitch behavior.

Example 29: Preclinical Testing of Methylone as a Therapeutic for Opioid Use Disorder This Example presents a mouse model to evaluate the benefit of methylone as a therapeutic for opioid use disorder (OUD).
Testing Methylone for Interactions with Oxycodone in Respiratory Depression.

Respiratory depression is a limiting safety factor for any therapeutic treatment for OUD. The experiments described below directly evaluate the effects of methylone on interaction with specific doses of oxycodone to test whether methylone can be safely used in the presence of oxycodone in both investigator and self-administered protocols.

Changes in respiratory rates in awake mice are observed to assess the development and changes in respiratory depression using pulse oximetry. The non-invasive MouseOx Plus system (Starr Life Sciences Corp) has been used extensively in both rat and mouse studies. C57BL6/J mice (10 mice per dose) are briefly anesthetized one day prior to the start of the experiment for hair removal around the collar area. The following day, baseline $SpO_2$ and respiratory rates are measured using the MouseOx Plus system with the CollarClip sensor. Mice are then pretreated with different doses methylone (0-30 mg/kg, IP) or vehicle 1 hour prior to oxycodone injections. Oxycodone is delivered in sequential doses (1.1, 1.1, 2.2, 4.5, and 9.0 mg/kg IP) every 17 min with respiratory rate being measured continuously with pulse oximetry. Any effects of methylone are repeated at the given dose to confirm and duplicate the result.

The intake, motivation and seeking of drugs define the addicted state. The ability of methylone to attenuate these components is evaluated in separate studies, with the first two taking advantage of an oxycodone self-administration paradigm in mice.
Testing Effects of Methylone on Self-Administration, Motivation, and Seeking of Oxycodone.

Effects on oxycodone intake: C57BL6/J mice are trained on oxycodone self-administration until stable intake>3 mg/kg/day for a minimum of two weeks. For testing of intake, the mice are pretreated with doses of methylone (0-30 mg/kg, IP) or vehicle approximately 1 hour prior to the 3-hour self-administration sessions, using a Latin Square Design. If effects are seen at a given dose, the same dose is retested in a new cohort of animals. This determines if methylone modifies ongoing oxycodone intake.

Effects of methylone on motivation for oxycodone intake: Here, the effects of methylone are evaluated using a progressive ratio task where animals must exponentially increase nosepokes across the session to receive the next reward. As the ratio of nosepoke:reward increases, mice cease to nosepoke and the number of rewards or pokes is recorded and represents the motivation for the drug. Whether treatment with methylone affects the number of rewards earned, or motivation, for oxycodone is evaluated. As in the previous study, C57BL6/J mice are trained on oxycodone self-administration until stable intake>3 mg/kg/day for a minimum of two weeks. The animals are then subjected to the progressive ratio task with increasing effort required to obtain each subsequent dose of oxycodone.

Effects on oxycodone seeking: Seeking using a conditioned place preference paradigm is evaluated using opioid conditioned place preference protocols. In brief, after baseline tests, the animals are injected alternately with either saline or oxycodone (5 mg/kg, IP) over 6 days, with placement on different compartments for 20 minutes. After this period, animals are injected with either saline or methylone before being placed in the middle chamber on the test day, and their movements recorded over 20 min to assess time spent in drug-paired side vs. saline-paired side. This reflects the strength of the drug-seeking behavior and the ability of methylone to attenuate this seeking.

Testing Methylone for Treatment of Oxycodone Dependence and Withdrawal.

A key component to OUD is the development of dependence and the severity of opioid withdrawal. Treating the withdrawal phase of OUD is a critical point in both emergency medicine contexts, as well as the first step toward transitioning to recovery and subsequent treatment. The effects of methylone on both the somatic (physical) signs of withdrawal, as well as on measures of the negative aversive state caused by opioid withdrawal, are assessed.

Determine effects of methylone on physical withdrawal from oxycodone: Somatic (physical) withdrawal is assessed by challenging opioid-dependent animals with mu-opioid receptor antagonists and assessing physical signs. An objective measurement of withdrawal severity has recently been developed using sensor-mediating recordings of jumps and oxycodone minipumps that produce more effective and robust states of dependence. The modified protocol yields more jumps with less variance. This protocol is used and methylone (0-30 mg/kg, IP) or vehicle is administered 1 hour before the injection of naloxone (1 mg/kg IP) and withdrawal is immediately assessed for 20 mins.

Determine effects of methylone on negative affective state of oxycodone withdrawal: Here, methylone is evaluated for effects on the development of negative emotional state during opioid withdrawal. This assay has been developed to better reflect withdrawal state that would be seen in humans. By using a lower dose of naloxone, the mice do not show signs of physical withdrawal (e.g., jumps), but instead are assessed for a negative state via a conditioned place aversion test. Attenuating this negative state reduces seeking and relapse to drugs of abuse.

For these studies, a lower dose of naloxone is used to produce an aversive state but with minimal somatic signs of withdrawal. This is assessed via conditioned place aversion (CPA) test in a three-chamber box. Two larger chambers, each with different wall colors (white and black) and different floors, are separated by a smaller middle chamber. Mice are first allowed to explore all chambers over 15 min (habituation), and the time spent in each chamber is monitored. Aversive pairing consists of treating each mouse with oxycodone (5 mg/kg, IP) 2 hours before, and either methylone (0-30 mg/kg, IP) or vehicle one hour before placing them in their "aversive side" chamber. Immediately before being placed in the chamber all mice receive naloxone (0.1 mg/kg, IP) to induce moderate withdrawal. Mice are confined to their designated chamber for 30 min. The next day all mice undergo a neutral pairing, consisting of saline treatment 2 hours prior, and vehicle 1 hour prior to placing them in their "neutral side" chamber for 30 min. This sequence of aversion and neutral pairing components are repeated for a total of 3 days of pairing for each condition. On test day, the mice receive no treatment and are allowed to freely move through all three chambers for 15 min. Aversion scores are calculated by subtracting the time spent in the aversive chamber on habituation day from their test day. A negative aversion score in the vehicle group reflects aversion from naloxone pairing.

Evaluating gene expression changes after methylone treatment: The neural mechanisms underlying the effects of entactogens are not known. It is very likely that changes in gene expression drive many of the persistent cellular and behavioral changes. While the focus of this Example is on behavioral outcomes, there are long-term advantages to understanding the molecular underpinnings of therapeutic effects. By identifying molecular pathways mediating methylone's effects, mechanisms of behavioral change and positive therapeutic outcomes are better understood. Here, the power of RNAseq to efficiently identify these pathways is leveraged. A separate cohort of animals (n=15 per group) is treated with 10 mg/kg methylone. The animals are then sacrificed after 24 hours and brains collected and frozen. The prefrontal cortex and nucleus accumbens are then dissected out and RNA isolated from these regions using RNAeasy kit (Qiagen). The RNA is sent for sequencing and analysis.

Example 30: Methylone for the Treatment of PTSD: Functional and Global Improvements from the Open-Label Portion of the IMPACT-1 Study Post-traumatic stress disorder (PTSD) is a debilitating psychiatric illness affecting approximately 12 million adults in the US each year. Functional impairment is common with PTSD, often resulting in significant impairments in daily life. Current treatment options for PTSD have limited effectiveness. Non-hallucinogenic compounds with rapid and sustained therapeutic benefits may be clinically useful and more accessible to patients, compared to classical psychedelics. Methylone is a non-hallucinogenic, rapid-acting neuroplastogen and the beta-ketone analog of MDMA. Both methylone and MDMA target monoamine transporters, but differences in affinity and a lack of off-target effects (vs. MDMA) produce distinctive pharmacological and subjective effects. Methylone is well-tolerated in healthy volunteers and shows positive clinical effects in a retrospective case series of patients with PTSD and depression. Methylone also has fast-acting, robust, and long-lasting anxiolytic and antidepressant-like activity in preclinical studies.

Methods: The IMPACT-1 study is a multi-center, two-part clinical trial. Part A has completed and was an open-label evaluation involving 14 participants with PTSD. Eligible participants are adults with severe PTSD (CAPS-5≥35) who had failed at least 1 prior treatment (pharmacotherapy and/or psychotherapy) for PTSD. Participants were treated with 4 doses of methylone given once a week for 4 weeks. Throughout each dosing session, participants were provided non-directive psychological support by a trained mental health practitioner. Following the 4-week treatment period, participants were followed for an additional 6 weeks to evaluate the durability of the therapeutic effect. PTSD symptom improvement was evaluated on the CAPS-5. Functioning was assessed via the 3 domains (school/work, family life, social life) of the Sheehan Disability Scale (SDS). Global improvement was measured by the CGI-I. Safety was assessed by monitoring adverse events, vital signs, and C-SSRS.

Results: On the CAPS-5, treatment with methylone resulted in a mean change from baseline of −8.4 points (p=0.002) after the first dose; the results were durable with a mean change from baseline of −36.2 points (p<0.001) at the end of study visit (6 weeks after the last dose). The overall SDS is presented as the mean of the 3 domains (Table 19 below).

TABLE 19

Baseline and End of Study SDS Scores

| SDS Domain | Baseline | Day 64 |
| --- | --- | --- |
| Mean Overall | 7.3 (1.72) | 3.1 (3.12) |
| Work/School | 6.4 (2.50) | 3.3 (3.78) |
| Social Life | 7.8 (1.54) | 3.2 (3.39) |
| Family Life | 7.1 (2.67) | 3.1 (3.45) |

At baseline, there was a high level of functional impairment (mean SDS total score: 7.3). Methylone treatment rapidly and durably improved functioning, and the improvements were consistent across each domain. After treatment with methylone, statistically significant improvements in functioning occurred after the first dose (mean change from baseline: −1.53; p=0.033) and were durable through the 6-week follow-up period (−4.26; p<0.0001) (FIG. 39A). By the end of study, >50% of participants having mild or no impairment, compared to >85% reporting markedly or extreme impairment at baseline (FIG. 39B).

In addition, methylone treatment improved the number of days underproductive and days lost (FIG. 40). At baseline, the mean number of days underproductive and lost were 4.7 and 2.6, respectively. At the end of the 4-week treatment period, methylone had reduced the number of days underproductive and lost by −3.3 and −2.0, respectively.

At baseline, the mean CGI-severity was 4.8, representing a moderate to markedly severe PTSD population (FIG. 41). By Day 10, two days after the 2nd dose, nearly 70% of participants were "much" or "very much" improved. At the end of the study, all participants were considered "much" or "very much" improved.

Conclusion: Methylone demonstrated rapid, robust, and durable improvements in functioning. Functional improvements were consistent across all domains (school/work, family life, social life). Productivity was improved after treatment with methylone, as noted by a reduction in the days lost and underproductive.

Example 31: Methylone for the Treatment of PTSD: Improvement in Sleep-Related Outcomes from the Open-Label Portion of the IMPACT-1 Study Post-traumatic stress disorder (PTSD) is a debilitating psychiatric illness affecting approximately 12 million adults in the US each year. Sleep disturbances with PTSD are common and typically include insomnia and nightmares. Poor sleep can worsen PTSD and result in additional health problems such as heart disease, high blood pressure, obesity, substance abuse, and stroke. Nightmares are often resistant to PTSD treatment and have been linked with a five-fold increase in suicidality; however, nightmares are often overlooked as a secondary symptom of PTSD. Existing medications (e.g., prazosin) have shown mixed results for treating nightmares, highlighting the need for new pharmacological options. Novel compounds with rapid and sustained therapeutic benefits may be clinically useful and more accessible to patients, compared to classical psychedelics. Methylone is a non-hallucinogenic, rapid-acting neuroplastogen and the beta-ketone analog of MDMA. Both methylone and MDMA target monoamine transporters, but differences in affinity and a lack of off-target effects (vs. MDMA) produce distinctive pharmacological and subjective effects. In preclinical studies, methylone has demonstrated significant benefit in a model of PTSD as well as fast-acting, robust, and long-lasting anxiolytic and antidepressant-like activity.

Methods: The IMPACT-1 study is a multi-center, two-part clinical trial. Part A was completed and was an open-label evaluation involving 14 participants with PTSD. Eligible participants were adults with severe PTSD (CAPS-5≥35) who had failed at least 1 prior PTSD treatment.

Participants were treated with 4 doses of methylone given once a week for 4 weeks. Following the 4-week treatment period, participants were followed for an additional 6 weeks to evaluate the durability of the therapeutic effect. Sleep-related improvements were evaluated on the CAPS-5 (including distressing dreams [item B2; scores range 0 to 4] and sleep disturbances [item E6; scores range 0 to 4]), the Pittsburgh Sleep Quality Index (PSQI; total scores range 0 to 21) and subscales, and the reduced sleep item of the Montgomery-Åsberg Depression Rating Scale (MADRS; scores range 0 to 6).

Results: On the CAPS-5 total severity score, treatment with methylone resulted in rapid, robust, and durable improvements (FIG. 21). At baseline on the CAPS-5, all participants had clinically significant Sleep Disturbances (item E6; mean score=3.3) and 79% had Distressing Dreams (item B2; mean score=2.2). After treatment with methylone, mean scores on Sleep Disturbances and Distressing Dreams decreased to 0.92 and 0.38, respectively, with absence of the symptom in 62% and 77% of participants, respectively (FIG. 42A). On the MADRS, Reduced Sleep at baseline was a mean of 4.3 points. After treatment with methylone, the mean score on Reduced Sleep was 1.08, with absence of the symptom in 62% of participants (FIG. 42B). On the PSQI, mean total scores at baseline were 13.5, indicating severe sleep disturbance (FIG. 43A). At the end of study (6 weeks after the last dose), PSQI total score improved by −4.0 points (mean score=9.4). Similar improvements were seen on the PSQI subscales (sleep duration, latency, disturbance, and quality) (FIG. 43B).

Conclusion: Treatment with methylone demonstrated rapid, robust, and durable effects on PTSD symptoms; including key PTSD-related sleep issues (sleep disturbances and disturbing dreams). Overall sleep, measured by MADRS and PSQI total score, was improved after treatment with methylone. Each of the PSQI subscales was consistently improved after treatment with methylone (sleep duration, latency, disturbance, and quality).

Example 32: An Evaluation of the Safety and Efficacy of Methylone for the Treatment of PTSD (IMPACT-2)

This study is designed to evaluate the safety and efficacy of methylone, when given as 3 doses of 150 mg once per week for 3 weeks. This study is intended to complement a study, which is evaluating the safety and efficacy of methylone when given weekly for 4 weeks at a dose of 150 mg, followed by a booster dose of 100 mg after 90 minutes. The rationale for conducting this study is to understand if a less frequent dosing (3 doses vs. 4 doses) without a booster dose will result in similar efficacy. Additionally, the removal of the booster dose allows for the duration of the dosing session to be shortened to 4 hours.

Objectives

Primary Objective: In Part A, the primary objective is to evaluate the preliminary efficacy and safety of three doses of methylone, separated by 1 week, in participants with PTSD. In Part B, the primary objective is to evaluate the efficacy and safety of three doses of methylone, separated by 1 week, compared to placebo, in participants with PTSD.

Secondary Objectives: In both Parts, the following endpoints are as follows used to evaluate efficacy:
CAPS-5 (total severity score; primary efficacy outcome measure)
PTSD Checklist for DSM-5 (PCL-5)
Montgomery-Åsberg Depression Rating Scale (MADRS).
Shechan Disability Scale (SDS)
Clinical Global Impression of Improvement (CGI-I)
Clinical Global Impression of Severity (CGI-S)
Patient Global Impression of Change (PGI-C)
Patient Global Impression of Severity (PGI-S)
Quick Inventory Depressive Symptoms (QIDS)
Pittsburgh Sleep Quality Index (PSQI)
Warwick-Edinburgh Mental Wellbeing Scale (WEMWBS)
Post-traumatic Growth Index (PTGI)

In both Parts, the following measures are used to evaluated safety:
Adverse events (AEs)
Vital signs (blood pressure [BP], heart rate, temperature)
Clinical labs (chemistry, hematology, urinalysis)
Columbia-Suicide Severity Rating Scale (C-SSRS)
Electrocardiogram (ECG)

Study Design

Overall Study Design and Plan

This is a two-part study to evaluate the safety and efficacy of methylone for the treatment of PTSD. Part A is an open-label assessment in up to 15 participants with PTSD, Part B is a randomized (1:1), double-blind, placebo-controlled assessment in up to 64 participants. FIGS. 35A and 35B are schematics for the experimental design of Part A and Part B, respectively. After completion of Part A, enrolment for Part B will begin.

The open-label treatment in Part A is:
Methylone 150 mg×3 doses, with each dose separated by 1 week.

The two blinded treatments for Part B are:
Methylone 150 mg×3 doses, with each dose separated by 1 week.
Placebo×3 doses, with each dose separated by 1 week Participants are adults (age 18 to 70, inclusive) who meet the Diagnostic and Statistical Manual of Mental Disorders, 5th Edition (DSM-5) criteria for current PTSD, with a symptom duration of at least 6 months at Screening. Eligible participants will have severe PTSD symptoms (based on a Clinician-Administered PTSD Scale for DSM-5 [CAPS-5] total severity score of ≥35 at Screening). Eligible participants will attend the following study visits:
Screening visit (Day −28 to Day −4): Informed consent and eligibility assessments.

Baseline/Preparatory Session (Day −3 to Day −1): Baseline assessments, confirmation of eligibility, and a preparatory psychoeducation session.

Treatment Period (3 weeks; Day 1 to Day 17): Each participant will receive a dose of study drug at Day 1, Day 8, and Day 15). For each dose, the participant will remain in clinic, with a qualified Mentor, for at least 4 hours after the dose, or until all effects (physical and psychological) have resolved (whichever is longer). Each dose session is followed by a safety phone call 1 day after dosing and efficacy assessments 2 days after dosing. Each dosing session may be video recorded for quality and training purposes. The videos may be reviewed to ensure the Mentor is adhering to the Mentor training.

Follow-Up Period (6 weeks following the final dose; Day 22 to Day 57): Following the final dosing session, follow-up visits will occur weekly. This will include: efficacy and safety assessments at 1, 2, 4, and 6 weeks post-final study drug administration, telephone contact at 3 and 5 weeks post-final study drug administration.

Planned enrolment includes up to 79 participants (up to 15 in Part A and up to 64 in Part B). Initially in Part B, 40 participants are studied; this may be increased to up to 64 based on an interim analysis that will assess the sample size. In Part B, participants are stratified based on selective serotonin reuptake inhibitor (SSRI)/selective norepinephrine reuptake inhibition (SNRI) use at Screening (e.g., participants undergoing tapering of SSRI/SNRI vs. those not receiving an SSRI/SNRI at Screening). In Part A, attempts are made to enroll<50% of participants requiring an SSRI/SNRI washout.

Discussion of Study Design: This two-part study is designed to assess the safety and efficacy of three dose sessions of methylone, with each dose separated by one week, in participants with PTSD. Part A is an open-label evaluation to confirm safety and preliminary efficacy of this methylone dose regimen as a PTSD treatment. Part B is a randomized, double-blind, placebo-controlled study to evaluate the efficacy and safety of methylone as a PTSD treatment. Double-blinding with use of placebo is included in Part B to permit a true assessment of the safety and tolerability of methylone and to evaluate its benefits and risks. This design also allows for an objective assessment of key safety issues such as suicidality, which can be part of the disease process (PTSD) rather than a side effect of treatment.

Also included are standard assessments to evaluate the safety and tolerability, such as vital signs, physical examination, 12-lead ECGs, clinical laboratory evaluations and AE collection. The battery of clinical outcome assessments to be performed are those routinely used to assess the severity of PTSD symptoms and functional impairment. These include observer-blinded assessments of PTSD severity and self-administered questionnaires that explore the participant's experience of life events. These questionnaires and scales are standardly used in clinical trials investigating psychoactive medications in similar patient populations.

Selection of Participants

Selection of Study Population and Diagnosis

Eligible participants will have PTSD and meet the below listed eligibility criteria and none of the exclusion criteria.

Inclusion Criteria

1. Male or female participants aged between 18 to 70 years, inclusive.
2. Participant meets the DSM-5 criteria for severe PTSD diagnosis, with a symptom duration of at least 6 months at Screening, as assessed by the CAPS-5.

3. Participant must have a CAPS-5 score of >35 at Screening.
4. Participant has failed at least one treatment for PTSD (either psychotherapy or pharmacological treatment).
5. Proficient in reading and writing in English language sufficient to complete questionnaires.
6. Free from any other clinically significant illness or disease that may adversely affect the safety of the participant, or, the integrity of the study (in the opinion of the Investigator and Medical Monitor).
7. Willing to refrain from taking any psychiatric medications or interventions during the study, unless provided by the Investigator. Note: No participant will be asked to discontinue potentially beneficial treatment in order to participate in this study.
8. Willing to provide a contact for emergencies.
9. Willing to be contacted via telephone for all necessary telephone visits.
10. Ability to swallow and retain oral medications.
11. Males who engage in sexual activity that has the risk of pregnancy must agree to use one of the following acceptable contraceptive methods and agree to not donate sperm throughout the study and for at least 90 days after the last dose of the study medication:
    a. Use of a double barrier method (male condom with a diaphragm or a cervical cap)
    b. Female use of hormonal contraceptives (as described below)
    c. Either partner is surgically sterilized (as described below)
    d. Abstinence, if consistent with the participants preferred and usual lifestyle
12. Females of childbearing potential* who are sexually active with a male partner must be willing to use one of the following acceptable contraceptive methods throughout the study and for at least 1 month after the last study drug administration.
    a. Hormonal contraceptives or intrauterine devices: at least 4 weeks before first dosing and must follow that product's package insert instructions including additional protection at times when hormonal contraceptive doses might be missed.
    b. Male condom with a diaphragm or cervical cap: consistent use for at least 21 days prior to the first dosing
    c. Sterile male partner: vasectomized for at least 6 months prior to the first dose.
    d. Abstinence, if consistent with the participants preferred and usual lifestyle A non-childbearing female is defined as:
Post-menopausal female (absence of menses for 12 months prior to drug administration, bilateral oophorectomy or hysterectomy with bilateral oophorectomy at least 6 months prior to drug administration); OR
Surgically sterile female (hysterectomy or tubal ligation at least 6 months prior to drug administration)
Women of childbearing potential (WOCBP; see Appendix 1) must have a negative highly sensitive urine pregnancy test at Screening, Baseline, and Day 1, and prior to dosing. If a urine test cannot be confirmed as negative (e.g., an ambiguous result), a serum pregnancy test is required to be confirmed as negative prior to dosing.
13. Agree to not participate in any other interventional clinical trials for the duration of this study.
14. Willing to provide written informed consent, which includes compliance with the requirements and restrictions listed in the consent form.
15. Is able to understand the procedures and study requirements and agrees to abide by the study restrictions and return for the required study assessments.

Exclusion Criteria
A participant is excluded from the study if they meet any of the following criteria:
1. Participant has a primary diagnosis of any other DSM-5 disorder, as assessed by the Mini International Neuropsychiatric Interview (MINI).
2. Participant has a body mass index (BMI)<18 kg/m2 or >40 kg/m2.
3. Participant is known to abuse illegal drugs or meets DSM-5 criteria for moderate or severe substance use disorder (mild substance use disorder may be allowed, after consultation with the sponsor, if use of the substance is unlikely to confound the study results) or has a positive urine test for illegal drugs at Screening, Baseline, or prior to dosing on Day 1. The Investigator must confirm the participant is not otherwise impaired prior to dosing on Day 1.
4. Known history of: Hepatitis B, Hepatitis C, or human immunodeficiency virus.
5. Participant smokes an average of >10 cigarettes and/or e-cigarettes per day.
6. Abnormal liver function tests (LFTs) at Screening defined as:
   a. AST, ALT or gamma-glutamyl transferase (GGT)>2× the ULN, OR,
   b. Total bilirubin levels>1.5× the ULN (participants with a diagnosis of Gilbert's syndrome with high unconjugated bilirubin are eligible provided they meet other LFT criteria).
7. Moderate to severe renal impairment at Screening, with an estimated glomerular filtration rate (eGFR) of ≤45 mL/min according to the Cockcroft-Gault equation.
8. Active suicidal ideation and/or intent within 2 months of Screening, indicated by a 'Yes' response to suicidal ideation question 4 or 5 on the C-SSRS.
9. Any history of suicidal behaviour within the last 5 years (excluding suicidal ideation):
   a. Medical history of suicide attempt, or
   b. 'Yes' response to the following suicidal behaviour questions on the C-SSRS: actual, interrupted, or aborted attempt.
10. Uncontrolled hypertension at Screening, defined as:
    a. SBP>140 mmHg, or
    b. DBP>90 mmHg.
    c. Resting heart rate at Screening of ≥90 bpm (mean of triplicate after 3 minutes rest).
11. Have any history, physical or psychological symptoms, medication or other relevant findings that would make a participant unsuitable for the study based on the clinical judgement of study personnel. This would include (but is not limited to):
    a. A need to continue active any psychotherapy or pharmacotherapy during the study period.
    b. Moderate or severe alcohol use disorder (as assessed by the MINI) OR the inability to refrain from alcohol use for 24 hours before Screening and each scheduled dose session.
    Note: Moderate alcohol use disorder in early remission is not exclusionary.

c. Medical or psychiatric condition that is incompatible with establishment of rapport with the Mentor, or safe exposure to study drug.
12. Prior treatment within the 90 days prior to Baseline, with:
    a. deep brain stimulation,
    b. vagus nerve stimulation,
    c. treatment with electroconvulsive therapy, or
    d. transcranial magnetic stimulation.
13. Use of a psychedelic (e.g., lysergic acid diethylamide [LSD], psilocybin, dimethyltryptamine [DMT], mescaline), or entactogens such as MDMA, within 12 months of Screening.
14. Use of prohibited concomitant medications or therapies.
15. Current or previous history of clinically significant cardiovascular/cerebrovascular conditions, including, but not limited to: Presence of underlying cardiovascular or cerebrovascular conditions where an acute rise in blood pressure would pose a clinical concern, including but not limited to, aneurysms or arteriovenous malformations, a history of cardiac or cerebral ischemia.
16. Any clinically significant abnormal 12-lead ECG findings at Screening, including, but not limited to:
    a. Resting QT interval corrected for heart rate using Fridericia's formula (QTcF)≥450 msec (≥470 msec for females) at Screening, or inability to determine QTcF interval.
    b. Presence of risk factors for Torsades de Pointes.
17. Any history of head injury with loss of consciousness for more than 30 minutes within 12 months of Screening.
18. Clinically relevant history of schizophrenia, psychotic disorder, bipolar disorder, delusional disorder, paranoid personality disorder, antisocial personality disorder, schizoaffective disorder, borderline personality disorder or panic disorder, as assessed by the MINI and SPQ (and SCID-5-PD, if needed).
19. Have a first-degree relative with:
    a. schizophrenia spectrum, OR
    b. other psychotic disorders (except substance/medication-induced or due to another medical condition), OR
    c. bipolar I disorder.
20. Participant has participated in a clinical study with an unapproved investigational medication within 3 months, or 5 half-lives (whichever is longer), prior to Screening.
21. Has an allergy or intolerance to any of the materials contained in the investigational formulations (methylone or placebo [Part B]).
22. Donation of blood or plasma of >400 mL within 3 months prior to Screening.
23. Family member of a member of the investigating team or Sponsor Treatments Methylone is provided in 50 mg capsules containing 59 mg (+5%) of methylone hydrochloride. Methylone hydrochloride is manufactured and encapsulated by Pisgah Labs, North Carolina. Methylone or placebo capsules are administered orally with water. A hand and mouth check is performed to ensure consumption of the medication. Capsules are administered on each treatment day as follows:

Part A
  Methylone 50 mg×3 capsules (total dose of 150 mg)
Part B
  Methylone 50 mg×3 capsules (total dose of 150 mg)
  OR
  Placebo×3 capsules Participants should have fasted (water only) for at least 2 hours prior to the dose and at least 2 hours after the dose. Water and clear fluids are encouraged up to a maximum fluid intake of 3 liters during the dosing session. A psychiatrist is available during each dose session for each participant.

Method of Assigning Participants to Treatment: During Part A, all participants will receive open-label methylone. In Part A, attempts are made to enroll<50% of participants requiring an SSRI/SNRI washout. During Part B, participants are randomly assigned, in a 1:1 ratio to receive methylone or placebo. Participants are stratified to treatment based on selective serotonin reuptake inhibitor (SSRI)/selective norepinephrine reuptake inhibition (SNRI) use at Screening (e.g., participants undergoing tapering of SSRI/SNRI vs. those not receiving an SSRI/SNRI at Screening).

Prohibited Medications: The following medications are prohibited within 14 days, or 5 half-lives, whichever is longer of Day 1:
  Selective serotonin reuptake inhibitor (SSRIs)
  Serotonin and norepinephrine reuptake inhibitors (SNRIs)
  Tricyclic/tetracyclic antidepressants
  Other medications to treat PTSD
  Lithium and other mood stabilizers
  Antipsychotics
  Stimulants
  Efavirenz
  Strong CYP2D6 inhibitors or inducers
  Serotonin-acting dietary supplements (such as 5 hydroxytryptophan or St. John's wort)

The following are restricted within 24 hours of a dosing session:
  Benzodiazepines
  Opioids
  Alcohol Lifestyle and Dietary Restrictions: Participants should agree to abstain from strenuous exercise for 24 hours prior to each dose session. Participants are also not allowed to operate any motor vehicle for at least 24 hours after each administration of study drug. Site staff should ensure participants have organised transport after discharge from the study site during the treatment period. The participants are also required to adhere to the following restrictions:
  Participants should abstain from alcohol for 24 hours prior to Screening and each dose session until after discharge from the study site.
  Participants should abstain from tobacco and nicotine-containing products for 2 hours prior to dosing until at least 8 hours after the administration on each dosing day.
  Participants should abstain from (methyl) xanthine- and caffeine-containing products for 2 hours before dosing until at least 8 hours after administration on each dosing day.
  Participants should have fasted (water only) for at least 2 hours prior to dosing and for at least 2 hours after the dose.
  Participants should refrain from consuming poppy seeds 48 hours prior to Screening and each dosing day (Days 1, 8, and 15) to avoid a positive result on the urine drug screen.

Study Procedures

Participants provide written informed consent before any study-related procedures are initiated, including cessation of prohibited concomitant therapy. If a participant misses a study visit for any reason, the visit should be rescheduled within the visit window specified below.

Study Periods, Visits, and Procedures

Screening (Day −28 to Day −4)

The following procedures are performed at Screening:
- Obtain written informed consent
- Review inclusion/exclusion criteria and confirm eligibility.
- Record demographics, medical history, substance use history, and concomitant medications/therapies. All prior CNS medications/therapies taken in the past 5 years should be recorded; all prior PTSD medications/therapies should be recorded, regardless of timeframe prior to Screening.
- Perform a complete physical exam (excluding breast and genitourinary examination) with review of body systems.
- Record vital signs (blood pressure, heart rate, respiratory rate and body temperature) after the participant has been seated or supine for at least 3 minutes.
- Measure height and weight.
- Perform urine drug screen.
- Perform 12-Lead ECG after participant has been in a seater or supine position for at least 3 minutes.
- Collect blood and urine samples for clinical laboratory tests and urine pregnancy test for WOCBP. Inconclusive urine pregnancy tests should be confirmed by a serum pregnancy test.
- Administer the following scales: CAPS-5 (Past Month), MINI, PCL-5, LEC-5, SPQ (and SCID-PD if needed).
  - The CAPS-5 (Past Month), MINI, and SCID-PD, if needed, are administered via telephone/video by a central rater and recorded for rater fidelity.
- Administer the C-SSRS.

Baseline/Preparatory Session (Day −3 to Day −1)
- Confirm eligibility.
- Record concomitant medications/therapies.
- Urine drug screen.
- Record vital signs (blood pressure, heart rate, respiratory rate and body temperature) after the participant has been seated or supine for at least 3 minutes.
- Administer the C-SSRS.
- Administer the following scales: CAPS-5 (Past Week), MADRS, CGI-S, PCL-5, QIDS, SDS, WEMWBS, PGI-S, PTGI, and PSQI.
  - The CAPS-5, MADRS and CGI-S are administered via telephone/video by a central rater and recorded for rater fidelity. The CAPS-5 is performed followed by MADRS and CGI-S.
  - The participant should complete the self-administered assessments: PCL-5, QIDS, SDS, WEMWBS, PGI-S, PTGI, and PSQI.
- Conduct the Preparatory Session following completion of all baseline assessments. Preparatory sessions should be conducted by a trained Mentor. Mentor will proactively provide the participant with an understanding of the anticipated experience following administration of an entactogen medication, like methylone. If needed, a second preparatory session may occur prior to the first dosing to ensure the participant is adequately prepared for the treatment period.

Treatment Period (Doses 1, 2, and 3)

Dose Session (Days 1, 8, and 15)

Pre-Dose:
- Confirm eligibility (Day 1)
- Review concomitant medications and AEs.
- Urine drug screen
- Urine pregnancy test (WOCBP only)
- Record vital signs (blood pressure, heart rate, respiratory rate and body temperature) after the participant has been seated or supine for at least 3 minutes. BP and HR are recorded approximately 10 minutes prior to study drug administration.
- Perform 12-Lead ECG after participant has been in a seated or supine position for at least 3 minutes approximately 10 minutes prior to study drug administration (after vital sign collection).
- Administer the C-SSRS Dosing Session:
- Randomize the participant in the IRT (Day 1—Part B only)
- Administer study drug and begin video recording of dosing session.
- Record BP and HR at 30-minute intervals post-dose until the end of the dose session. Note: a window of up to ±15 minutes for vital sign collection is acceptable. The collection of vital signs should not interfere with the participants therapeutic process and the collection window can be further extend, if needed, assuming that vital signs are collected at least once per hour.
- Record temperature at 60-minute intervals post-dose until the end of the dose session. Note: a window of up to ±15 minutes for temperature collection is acceptable.
- Perform 12-lead ECG at end of the dosing session.
- Record AEs and concomitant medications.

Discharge:
- Prior to discharge, the participant is encouraged to reflect on their experience.

Telephone Visit (Days 2, 9, and 16)
- Record AEs and concomitant medications
- Administer the C-SSRS Efficacy Assessments (Days 3, 10, and 17)

Note: If deemed appropriate, Day 3, Day 10, and Day 17 visits may be conducted remotely.
- Administer the following scales: CAPS-5 (Past Week), MADRS, CGI-S, CGI-I, PCL-5, QIDS, SDS, PGI-S, and PGI-C.
  - Clinical Scales: The CAPS-5, MADRS, CGI-S and CGI-I are conducted by a central rater via a telephone/video call and recorded for rater fidelity. The CAPS-5 is performed first followed by MADRS, CGI-S and CGI-I.
  - The participant should complete the self-administered assessments: PCL-5, QIDS, SDS, PGI-S, PGI-C, and BIQ (Part B; Day 17 only).

Follow-Up Period

Follow-Up Visits (Day 22, 29, and 43)

Note: if deemed appropriate, the Day 29 and 43 follow-up visits may be done remotely.
- Record AEs and concomitant medications
- Administer the following scales: CAPS-5 (Past Week), MADRS, CGI-S, CGI-I, PCL-5, QIDS, SDS, WEMWBS (Day 22 and Day 43 only), PGI-S, PGI-C, PTGI (Day 29 only), and PSQI (Day 29 only).
  - The CAPS-5, MADRS, CGI-S and CGI-I are conducted by a central rater via a telephone/video call and recorded for rater fidelity. The CAPS-5 is performed first followed by MADRS, CGI-S and CGI-I.

The participant should complete the self-administered assessments: PCL-5, SDS, QIDS, PGI-S, PGI-C, WEMWBS (Day 22 and 43 only), PTGI (Day 29 only), and PSQI (Day 29 only).
Administer the C-SSRS.
If the participant is in need of psychological support the Mentor is available to the participant.
On Day 22, the following should also be collected:
Vital signs
ECG
Clinical labs
Pregnancy test (for WOCBP)
Telephone Visit (Days 36 and 50)
Record AEs and concomitant medications
Administer the C-SSRS
End of Study (Day 57)
Record AEs and concomitant medications
Physical exam (excluding breast and genitourinary examination)
Record vital signs (blood pressure, heart rate, respiratory rate and body temperature) after the participant has been seated or supine for at least 3 minutes.
Perform 12-Lead ECG after participant has been in a seated or supine position for at least 3 minutes.
Collect blood and urine samples for clinical laboratory tests.
Urine pregnancy test for WOCBP.
Administer the C-SSRS.
Administer the following scales: CAPS-5 (Past Week), MADRS, CGI-S, CGI-I, PCL-5, QIDS, SDS, WEMWBS, PTGI, PSQI, PGI-S, and PGI-C.
   The CAPS-5, MADRS, CGI-S and CGI-I are conducted by a central rater via a telephone/video call and recorded for rater fidelity. The CAPS-5 is performed first followed by MADRS, CGI-S and CGI-I.
   The participant should complete the self-administered assessments: PCL-5, QIDS, SDS, WEMWBS, PSQI, PGI-S, PGI-C, and PTGI.
Provide Participant Exit Plan
Early Termination Visit
If the participant prematurely discontinues prior to the End of Study visit, an Early Termination Visit should be conducted and include the following assessments:
Record AEs and concomitant medications
Physical exam (excluding breast and genitourinary examination)
Record vital signs (blood pressure, heart rate, respiratory rate and body temperature) after the participant has been seated or supine for at least 3 minutes.
Perform 12-Lead ECG after participant has been in a seated or supine position for at least 3 minutes.
Collect blood and urine samples for clinical laboratory tests.
Urine pregnancy test for WOCBP.
Administer the C-SSRS.
Administer the following scales: CAPS-5 (Past Week), MADRS, CGI-S, CGI-I, PCL-5, QIDS, SDS, WEMWBS, PTGI, PSQI, PGI-S, and PGI-C.
   The CAPS-5, MADRS, CGI-S and CGI-I are conducted by a central rater via a telephone/video call and recorded for rater fidelity. The CAPS-5 is performed first followed by MADRS, CGI-S and CGI-I.
   The participant should complete the self-administered assessments: PCL-5, QIDS, SDS, WEMWBS, PSQI, PGI-S, PGI-C, and PTGI.
Provide Participant Exit Plan
Dosing Rooms
   During each dose session, each participant is in a comfortable, private space so they cannot see or interact with other individuals for the duration of their dose session. The space will have a quiet, calm atmosphere where they are comfortable talking about personal matters. The space will have ambient temperature controls and access to water. The participants are asked to remain in the dosing room for the 4-hour duration of the dose session or until all effects (physical and psychological) have resolved (whichever is longer).
Psychological Support
   Mentors are experienced healthcare providers with professional training and clinical experience in psychotherapy who are able to practice independently. The Mentor will provide the participant psychological support throughout their participation in the study. Each Mentor will undergo formal training prior to working with participants in this study. The same Mentor is present for all sessions with each participant. Their role is to provide unstructured psychological support as the participant explores their response to the medication. The Mentor is present throughout the dose session and a clinical staff member is intermittently available to collect safety assessments (e.g., vital signs); in addition, a trained psychiatrist is immediately available in case of acute psychotic events. The Mentor will not be involved in any medical, nursing, or other research activities.
   The psychological framework is focused on participant preparation for the dose session, and psychological support/reassurance during the dose session. If needed, the Mentor is available during the Follow-Up visits.
   During the Preparatory session, the Mentor will provide unstructured psychological guidance. This session will focus on psychoeducation about PTSD, possible physiological and psychological effects of methylone (including possible adverse and challenging effects), building safety for the therapeutic relationship, obtaining the background for the trauma and preparing the participant for dose sessions. Goals and expectations for the dose sessions will also be discussed.
   During each dose session, the Mentor will provide non-directive support of psychological well-being continuously during each dose session.
   During the early stages of the dose session, while the acute effects of methylone are active, the Mentor will provide reactive support and engaged listening. The Mentor will provide guidance if the participant falls into a negative pattern.
   At the end of each dose session, the Mentor will encourage the participant to reflect on their experience and on any strong emotions or thoughts they might have encountered.
   Each dosing session should be recorded. The videos are reviewed to ensure the Mentor is adhering to the Mentor training and to facilitate training of future Mentors.
Management of Psychological Events
   Drug-related adverse psychological events (e.g., psychotic symptoms) are not anticipated, but may occur during, or following, the dose sessions. The risk of such events occurring is minimised by the inclusion/exclusion criteria and the Preparatory Session. A psychiatrist is available throughout the dosing day to help support any psychological events.
   If medical intervention is required, diazepam (5 to 10 mg, orally), lorazepam (1 mg, orally or intramuscularly [IM]) or olanzapine (5 to 10 mg, orally or IM) may be administered, according to the clinical judgement of the responsible physician. Lorazepam and olanzapine should not be given at the same time due to the possibility of excessive sedation and cardiorespiratory depression. The participant should not be discharged from the clinic until the condition has stabilised.

Participants experiencing a psychological event related to dosing that requires an intervention will not receive further dosing. If psychological events arise after the participant has left the clinic, they are instructed to contact the site immediately. Based on the situation, =the most appropriate course of action is determined.

Assessments

Centrally-rated Assessments: All clinician-rated efficacy assessments are administered by a central rater via telephone or video call. Remote assessments assure that the assessor who is collecting the primary efficacy outcome measures will not witness dose sessions and the acute effects of methylone, which reduces bias and strengthens the study blind. The central ratings may be recorded to ensure quality ratings and rater fidelity across the central rater pool.

Clinician-Administered PTSD Scale for DSM-5 (CAPS-5): The CAPS-5 is 30-item structured interview. In addition to assessing the 20 DSM-5 PTSD symptoms, questions target the onset and duration of symptoms, subjective distress, impact of symptoms on social and occupational functioning, improvement in symptoms since a previous CAPS administration, overall response validity, overall PTSD severity and specifications for the dissociative subtype (depersonalization and derealization). The CAPS-5 also rates intrusion symptoms (intrusive thoughts or memories), avoidance, cognitive and mood symptoms, arousal and reactivity symptoms, duration and degree of distress. For each symptom, standardized questions and probes are provided.

The 'past month' version of the CAPS-5 is performed at Screening to confirm the diagnosis. The 'past week' version of the CAPS-5 is performed at each subsequent study visit.

Each CAPS-5 is administered by a central rater via telephone or video call.

Mini International Neuropsychiatric Interview (MINI): The MINI is a short, structured diagnostic interview that is compatible with DSM-5 and International Classification of Disease criteria for psychiatric disorders. Each module of the MINI consists of two or three questions where the answer is either 'Yes' or 'No', and a decision-tree logic is used to determine whether to ask additional questions. The PTSD, suicidality, and antisocial personality disorder modules of the MINI are not required to be administered as these are addressed via other scales. The MINI is administered by a central rater via telephone or video call.

Structured Clinical Interview for the DSM-5 Personality Disorders (SCID-5-PD)

The SCID-5-PD is a structured diagnostic interview to assess for DSM-5 personality disorders. In this study, only participants who endorse a positive response for paranoid personality disorder, antisocial personality disorder, or borderline personality on the SPQ is administered the relevant sections of the SCID-5-PD to assess for those personality disorders. The SCID-5-PD is administered by a central rater via telephone or video call.

Structured Interview Guide for the Montgomery-Asberg Depression Rating Scale (MADRS) (SIGMA): The SIGMA is a standardised version of the MADRS. The SIGMA maintains the original MADRS format, which is a 10-item clinician-rated, diagnostic questionnaire used to measure depression severity, with the exception that the first two items are reversed. Each item is measured on a 7-point scale, from 0 to 6. Higher total MADRS scores indicate more severe depression. Follow-up questions are also provided to clarify symptoms, if required. The MADRS is administered by a central rater via telephone or video call.

Clinician Global Impressions Scale-Severity (CGI-S): The CGI-S is designed to acquaint the participant's severity of symptoms with those of other people experiencing the same mental ailment. The CGI-S rates this severity on a 7-point scale, with (1) representing normal symptoms, meaning the participant is not ill, and (7) representing participants among the most severely ill. The rating (4) represents a participant that is defined a participant that is defined as moderately ill.

Two CGI-S's are evaluated, one CGI-S assessing the participants overall clinical status (focusing on their PTSD) and the second CGI-S assessing the participants depressive status. The CGI-S is administered by a central rater via telephone or video call.

Clinician Global Impressions Scale-Improvement (CGI-I): The CGI-I is a 7-point scale that requires the assessor to assess how much the participant's illness has improved or worsened relative to a baseline state prior to dosing. The CGI-I scale rates improvement with (1) representing a 'very much improved' participant to (7) representing a participant who has become 'very much worse' due to treatment. The rating (4) represents a participant displaying no change from the treatment.

Two CGI-I's are evaluated, one CGI-I assessing the participants overall clinical status (focusing on their PTSD) and the second CGI-I assessing the participants depressive status. The CGI-I is administered by a central rater via telephone or video call.

Participant-Completed Assessments: Psychometric assessments are administered in a neutral, non-leading manner to minimize the chance for bias.

PTSD Checklist for DSM-5 (PCL-5): The PCL-5 is a 20 item self-report measure that assesses the presence and severity of the 20 DSM-5 symptoms of PTSD. Participants are asked to rate each item from 0 ('not at all') to 4 ('extremely') to indicate the degree to which they have been affected by that particular symptom over the past week; the results are interpreted by a clinician.

Life Events Checklist for DSM-5 (LEC-5): The LEC-5 is a brief, 17-item self-report measure designed to screen for potentially traumatic events in a participant's lifetime, to facilitate the diagnosis of PTSD. It is a companion to the PCL-5 and is used to assess PTSD. The LEC-5 extended version is used.

Structured Clinical Interview for DSM-5 Screening Personality Questionnaire (SCID-5 SPQ): The SCID-5-SPQ is a self-report screening tool to assess for DSM-5 personality disorders. Participants are required to only complete questions specific for assessing personality disorders (paranoid personality disorder, antisocial personality disorder, or borderline personality). Participants who endorse a positive response for paranoid personality disorder, antisocial personality disorder, or borderline personality on the SPQ are administered the SCID-5-PD by the central rater for those personality disorders.

Sheehan Disability Scale (SDS): The SDS is a brief, 5-item self-report tool that assesses functional impairment in work, social life/leisure activities and family life/home responsibilities. The SDS is designed to measure the extent to which the three major domains in a participant's life are functionally impaired by psychiatric or medical symptoms.

Each domain is rated from 0 to 10, with a total score from 0 to 30, where 0 is unimpaired and 30 is highly impaired.

Patient Global Impression of Change (PGI-C): The PGI-C is a self-report tool to reflect a participant's belief about the efficacy of treatment. The PGI-C is a 7-point scale depicting a participant's rating of overall improvement. Participants rate their change from '1—Very much improved' through to '7—Very much worse'.

Patient Global Impression of Severity (PGI-S): The PGI-S is a self-report tool to measure disease severity. The PGI-S is a 5-point scale, ranging from '1—None', through to '5—Very severe'.

Warwick-Edinburgh Mental Wellbeing Scale (WEMWBS): The WEMWBS is a scale of 14 positively worded items for assessing a population's mental wellbeing. The items cover both physiological functioning aspects of mental wellbeing (including: optimism, autonomy, agency, curiosity, clarity of thought and positive relationships) and positive effect (feelings, including: confidence, feeling relaxed, cheerful, having the energy to spare). The scale has 5 response categories, summed to provide a single score.

Quick Inventory of Depressive Symptoms-Self Report (QIDS-SR): The QIDS-SR is a 16-item self-report measure a patient-rated scale, is an abbreviated version of the 30-item Inventory of Depressive Symptomatology (IDS) and is designed to assess the severity of depressive symptoms. The QIDS-SR-16 assesses criterion symptom domains to diagnose a major depressive episode. The QIDS-SR is used to assess the participant's depressive symptomatology over the past 7 days.

Patients report severity of symptoms on 10 items assessing sleep, feelings of sadness, appetite, weight change, concentration, self-regard, suicidality, general interest level, energy level, psychomotor retardation, and restlessness. Each item is scored on a 4-point scale with a score of 0 reflecting no symptoms and a score of 3 reflecting symptoms of maximum severity.

Pittsburgh Sleep Quality Index (PSQI): The PSQI is a measure of self-reported sleep quality and sleep disturbance. The PSQI contains 19 self-rated questions, which are combined to form 7 'component' scores, each of which has a range of 0 to 3 points. The 7 components of the PSQI are: subjective sleep quality, sleep latency, sleep duration, habitual sleep efficiency, sleep disturbances, use of sleeping medications and daytime dysfunction. The sleep component scores are summed to yield a total score ranging from 0 to 21, with a higher total score indicating worse sleep quality.

Post-Traumatic Growth Inventory (PTGI): The Post-Traumatic Growth Inventory measures the extent to which survivors of traumatic events perceive personal benefits, including changes in perceptions of self, relationships with others and philosophy of life, accruing from their attempts to cope with trauma and its aftermath. This 21-item scale includes factors of: new possibilities, relating to others, personal strength, spiritual change and appreciation of life.

Blinding Integrity Questionnaire (BIQ): The BIQ is a visual analog scale that is used to ascertain the degree of blinding; participants are asked to circle a number from 0 (Strongly believe they received Placebo) to 10 (Strongly believe they received active drug) indicating which treatment they believed they were administered during the dose sessions. The BIQ is administered during Part B only.

Clinical Safety Examinations

Safety assessments include the evaluation of treatment emergent adverse events (TEAEs), clinical laboratory tests, ECGs, vital sign measurements, and physical examinations.

Electrocardiogram: A 12-lead ECG is collected in triplicate, approximately 1 minute apart, within approximately 30 minutes predose and at the end of the dose session. 12-Lead ECGs should be obtained after the participant has rested in the supine position for at least 3 minutes. The ECG machine used should automatically calculate the HR and PR, QRS, QT and QTcF intervals.

Vital Signs and Temperature: Supine vital signs, including HR, BP, and temperature are collected after the participant has rested in the supine position for at least 3 minutes. Predose vital signs should be collected within 10 minutes predose. Blood pressure and HR are at 30-minute (±15 minute) intervals postdose administration until the end of the dose session.

Temperature is recorded predose and at 60-minute (±15 minute) intervals postdose until end of the dose session.

Physical Examination: A physical examination, including body weight and height (Screening only), and assessments of the head, eyes, ears, nose, throat, skin, neurological, lungs, cardiovascular system, abdomen, and lymph nodes are conducted.

Columbia-Suicide Severity Rating Scale (C-SSRS) The C-SSRS is used to assess suicide potential or tendency as a study entry criterion and monitored throughout the study. The C-SSRS is a semi-structured interview designed to assess the severity and intensity of suicidal ideation, suicidal behaviour and non-suicidal self-injurious behaviour over a specified time period. The measurement of suicidal ideation is based on five 'yes' or 'no' questions with accompanying descriptions arranged in order of increasing severity. If the participant answers 'yes' to either questions 1 or 2, the intensity of ideation is assessed in five additional questions related to frequency, duration, controllability, deterrents and reasons for the most severe suicidal ideation. Suicidal behaviour is assessed by asking questions categorising behaviours into actual, aborted and interrupted attempts; preparatory behaviour, and non-suicidal self-injurious behaviour.

If any item(s) on the C-SSRS are answered 'yes', the Investigator must review the participant's responses in order to (a) at the Screening visit and Baseline/Preparatory session to determine the participant's study eligibility and potential need for referral to a mental health professional, and (b) during the study evaluate the participant's need for appropriate medical management such as a referral to a mental health professional, or appropriateness of further study drug administration in consultation with the Medical Monitor and Sponsor.

A significant risk of suicide is defined as a 'yes' in answer to:

(a) questions 4 or 5 on the suicidal ideation section; or, (b) any questions on any item in the suicidal behaviour section At Screening, the C-SSRS is completed for the participant's lifetime history of suicidal ideation and behavior, along with a recent (2 month) recall period. At all other visits, the C-SSRS is completed with a recall period since the last visit.

Clinical Laboratory Test

Blood samples for analysis in the following laboratory tests are collected at the time points specified.

| | |
|---|---|
| Hematology | Hemoglobin, hematocrit, red blood cell (RBC) count, RBC indices (mean cell hemoglobin, mean corpuscular hemoglobin concentration, mean cell volume), platelet count (or estimate), and white blood cell count, including differential. |
| Serum Chemistry | Albumin, total bilirubin, direct bilirubin, total protein, calcium, alkaline phosphatase, alanine aminotransferase (ALT), aspartate aminotransferase (AST), gamma-glutamyl transpeptidase (GGT), blood urea, creatinine, glucose, sodium, potassium, bicarbonate, lactate dehydrogenase, phosphorus, and chloride. |
| Urinalysis | pH, specific gravity, protein, glucose, ketones, bilirubin, occult blood, nitrite, urobilinogen, and leucocyte esterase. Unless otherwise specified, microscopic examination is performed on abnormal findings. |
| Pregnancy Test | For all WOCBP. A urine pregnancy test is conducted at all timepoints as specified in the schedule of events. An inconclusive pregnancy test should be confirmed with a serum pregnancy test. |
| Urine Drug Screen | A urine drug screen (tests include but are not limited to amphetamines (including MDMA), benzodiazepines, cocaine, opiates,) is performed at screening and prior to dosing. |

Adverse Events

Definitions

Adverse Events

An AE is defined as any untoward medical occurrence in a participant administered a pharmaceutical product that does not necessarily have a causal relationship with the product. An AE can therefore be any unfavorable and unintended sign (including a new, clinically important abnormal laboratory finding), symptom, or disease, temporally associated with the product, whether or not related to the product.

Pre-existing diseases or conditions will not be considered AEs unless there is an increase in the frequency or severity, or a change in the quality, of the disease or condition. (Worsening of a pre-existing condition is considered an AE.)

Serious Adverse Event

A serious adverse event (SAE) is any untoward medical occurrence that at any dose:

Results in death.

Is life-threatening.
NOTE: The term "life-threatening" in the definition of "serious" refers to an event in which the participant was at risk of death at the time of the event; it does not refer to an event which hypothetically might have caused death if it were more severe.

Requires inpatient hospitalization or prolongation of existing hospitalization.
NOTE: Inpatient hospitalization is defined as 24 hours in a hospital or an overnight stay. An elective hospital admission to treat a condition present before exposure to the study drug, or a hospital admission for a diagnostic evaluation of an AE, does not qualify the condition or event as an SAE. Further, an overnight stay in the hospital that is only due to transportation, organization, or accommodation problems and without medical background does not need to be considered an SAE.

Results in persistent or significant disability/incapacity.

Is a congenital anomaly.
NOTE: A congenital anomaly in an infant born to a mother who was exposed to the study drug during pregnancy is an SAE. However, a newly diagnosed pregnancy in a participant who has received a study drug is not considered an SAE unless it is suspected that the study drug(s) interacted with a contraceptive method and led to the pregnancy.

Is an important medical event.
NOTE: Medical and scientific judgment should be exercised in deciding whether it is appropriate to consider other situations serious, such as important medical events that may not be immediately life-threatening or result in death or hospitalization but may jeopardize the participant or may require intervention to prevent 1 of the other outcomes listed in the definition above. Examples of such events are intensive treatment in an emergency room or at home for allergic bronchospasm, blood dyscrasias or convulsions that do not result in hospitalization, or development of drug dependency or drug abuse. The occurrence of malignant tumors is also to be considered serious Any clinically significant observations made during the visit will also be considered AEs.

Treatment-Emergent Adverse Events

An AE is defined as treatment emergent if the first onset or worsening is after an administration of study drug and not more than 7 days after the last dose. Any AEs that are deemed to be treatment related by the Investigators will always count as TEAEs. The primary safety assessments are based on TEAEs.

Evaluation of Adverse Events

Severity of Adverse Events

The clinical severity of an AE is classified as:

| | |
|---|---|
| Mild | Usually transient and may require only minimal treatment or therapeutic intervention. The event does not generally interfere with usual activities of daily living. |
| Moderate | Usually alleviated with additional specific therapeutic intervention. The event interferes with usual activities of daily living, causing discomfort but poses no significant or permanent risk of harm to the participant. |
| Severe | Interrupts usual activities of daily living, or significantly affects clinical status, or may require intensive therapeutic intervention. |

It is important to distinguish between severe AEs and SAEs. Severity is a classification of intensity whereas an SAE is an AE that meets serious criteria.

Seriousness

The investigator is to evaluate whether the AE meets serious criteria.

Action(s) Taken

Action(s) taken may consist of:

| | |
|---|---|
| Dose not changed | An indication that a medication schedule was maintained. |
| Drug interrupted | An indication that a medication schedule was modified by temporarily terminating a prescribed regimen of medication. |
| Drug withdrawn | An indication that a medication schedule was modified through termination of a prescribed regimen of medication. |
| Not applicable | Determination of a value is not relevant in the current context (eg, after the last dose). |
| Unknown | Not known, not observed, or not recorded. |

Outcome at the Time of Last Observation

The outcome, including Fatal, at the time of last observation is classified. Only select fatal as an outcome when the AE results in death. If more than 1 AE is possibly related to the participant's death, the outcome of death should be indicated for each such AE. Although "fatal" is usually an event outcome, events such as sudden death or unexplained death should be reported as SAEs.

Relationship to the Study Drug

The investigator will also assess the relationship (if any) between the AE and the study treatment (not related, unlikely, possibly, or probably). The investigator will use the following definitions to classify the relationship of an AE to study medication:

Not related: AEs which, after careful consideration, are clearly and undeniably because of extraneous causes (e.g. disease, environment);

Unlikely: This category can generally be considered applicable to those AEs which, after careful medical consideration at the time they are evaluated, are judged to be unrelated to the study drug. An AE may be considered unlikely to be related if or when at least two of the following criteria are fulfilled:
1) The event does not follow a reasonable temporal sequence from administration of the test drug;
2) The event could readily have been produced by the patient's clinical state, environmental or toxic factors, or other modes of therapy administered to the patient;
3) The event does not follow a known pattern of response to the test drug;
4) The event does not reappear or worsen when the drug is re-administered.

Possibly: This category applies to those AEs for which, after careful medical consideration at the time they are evaluated, a connection with the test drug administration appears unlikely, but cannot be ruled out with certainty. An AE may be considered possibly related if or when at least two of the following criteria are fulfilled:
1) The event follows a reasonable temporal sequence from administration of the drug;
2) The event could not readily have been produced by the patient's clinical state, environmental or toxic factors, or other modes of therapy administered to the patient;
3) The event follows a known pattern of response to the test drug.

Probably: This category applies to those AEs which, after careful medical consideration at the time they are evaluated, are felt with a high degree of certainty to be related to the test drug. An AE may be considered probably related if or when least three of the following criteria are fulfilled:
1) The event follows a reasonable temporal sequence from administration of the drug;
2) The event could not be reasonably explained by the known characteristics of the patient's clinical state, environmental or toxic factors, or other modes of therapy administered to the patient;
3) The event disappears or decreases on stopping or reducing the dose. There are important exceptions when an AE does not disappear upon discontinuation of the drug, but drug-relatedness clearly exists, e.g. bone marrow depression, fixed drug eruptions, tardive dyskinesia;
4) The event follows a known pattern of response to the test drug.

Treatment of Adverse Events

Adverse events that occur during the study are treated if necessary by established standards of care. If such treatment constitutes a deviation from the protocol, the participant may continue in the study after consultation with the investigator and medical monitor.

If AEs occur in a participant that are not tolerable, or for which continued administration of the study drug is not reasonable in view of the potential benefit to the participant, the investigator must decide whether to stop the study and/or treat the participant.

Follow-Up of Adverse Events

All AEs are followed (up to a maximum of 30 days after the participant's last visit in the study) to a satisfactory resolution, until it becomes stable, or until it can be explained by another known cause(s) (i.e., concurrent condition or medication) and clinical judgment indicates that further evaluation is not warranted. All findings relevant to the final outcome of an AE must be reported in the participant's medical record and recorded.

Data Safety Monitoring Board (DSMB)

The objectives of the DSMB are to review safety data (Part A and Part B), review the interim analysis report and provide advice on the advisability of increasing the sample size (Part B). The safety and tolerability data to be reviewed will include, at a minimum, AEs, 12-lead ECGs, vital signs, clinical laboratory evaluation results, and C-SSRS results, summarised by a non-voting Statistician. The interim analysis will focus on the CAPS-5 data and are used for sample size assessment only. There are no stopping rules for either efficacy or futility.

Statistics

Sample Size Determination

Approximately 15 participants are enrolled to evaluate the efficacy and safety of methylone. No formal sample size calculation was conducted. The sample size of up to 15 participants in the open-label study is based on medical and clinical considerations.

Sample size calculations for Part B assumes a treatment difference of 11 points on the CAPS-5 and a pooled standard deviation (SD) of 12, based upon a previously completed Phase 3 trial of MDMA as a treatment for PTSD. Assuming a treatment effect of 11 points and a pooled SD of 12 in this trial and an N of 20 evaluable participants in each treatment group, the trial should provide 80% power to detect such a difference. Evaluable participants are defined as participants who reach end-of-study assessment or withdrawal with appropriate close-out.

Part B of the study initially recruits up to 40 participants, but this might be increased up to 64 participants based on an interim analysis that assesses the sample size assumptions.

Analysis Populations

The following analysis populations are planned for this study:

Safety population—all participants who received at least one dose of study medication.

Modified Intent-to-treat (mITT) population—all participants who receive at least one dose of study drug and have an evaluable post-baseline efficacy parameter.

Per protocol population—all participants in the mITT population who received at least one dose of study drug and have no important major protocol deviations.

Statistical Analyses

Summary statistics are provided for the variables described in the following sections. For continuous variables, these statistics will typically include the number of subjects, mean, SD, median, minimum, and maximum. For categorical variables, these statistics will typically include the number and percentage of subjects in each category.

Study Subjects and Demographics

Disposition and Withdrawals: The disposition of subjects includes the number and percentage of subjects for the following categories: subjects enrolled, screen failures, subjects treated (safety population), subjects in each analysis population, and subjects discontinued from the study. The reasons for study discontinuation will also be summarized. Only one primary reason for study discontinuation is reported in the summary. However, all reasons are presented.

Protocol Deviations: Protocol deviations are classified and important protocol deviations are discussed in the clinical study report (CSR). All protocol deviations are presented in a data listing.

Demographics and Other Baseline Characteristics: Baseline demographic and clinical characteristics are summarized as percentages for categorical variables and as mean, SD, median, minimum and maximum for continuous measures.

Exposure and Compliance: The dose (mg) of study drug administered, the total number of doses of study drug, and the duration of treatment are provided.

Efficacy

Primary Efficacy Outcome Measure

The primary efficacy outcome measure is the change from baseline in the CAPS-5 total severity score. The primary efficacy endpoint is the change from baseline in CAPS-5 total severity score one week following the last dose. In addition, other secondary endpoints evaluate the effect of methylone on remission, response, and lack of diagnosis via the CAPS-5.

Secondary Efficacy Outcome Measures

Secondary efficacy outcome measures include the following:

MADRS, including change from baseline, remission and response rates.

SDS, including total score change from baseline, domain score change from baseline, response and remission rates.

PCL-5, including change from baseline, remission and response rates.

QIDS-SR-16, including change from baseline, remission and response rates.

CGI-I, percent of participants with "much or very much" improved.

CGI-S, change from baseline, and categorical changes from baseline.

PGI-C, percent of participants with "much or very much" improved.

PGI-S, change from baseline and categorical changes from baseline.

WEMWBS, change from baseline.

PSQI, change from baseline.

PTGI, change from baseline.

All continuous efficacy endpoints are also summarized by descriptive statistics (n, arithmetic mean, SD, median, minimum, and maximum). All categorical efficacy endpoints are summarized by descriptive statistics (n, percentage). All efficacy endpoint data are listed for individual participants.

Safety

Adverse Events

Adverse events are coded by system organ class (SOC) and preferred term using the Medical Dictionary for Regulatory Activities (MedDRA) reporting system.

The number and percentage of subjects with TEAEs are displayed by SOC and preferred term. Additionally, TEAEs are tabulated by severity and by relationship to the study drug. A listing of SAEs is provided if applicable.

Vital Signs: Descriptive summaries (mean, SD, median, minimum, and maximum) of actual values for all vital signs are presented and changes from pre-dose are calculated for systolic blood pressure, diastolic blood pressure, heart rate, and oral body temperature.

Clinical Laboratory Values: Descriptive summaries (mean, SD, median, minimum, and maximum) of actual values and changes from baseline are calculated for each laboratory value.

Electrocardiogram Values: Descriptive summaries (mean, SD, median, minimum, and maximum) of actual values and changes from baseline are calculated for each ECG parameter.

Physical Examination Findings: Physical examination data are presented in the listings.

C-SSRS: C-SSRS data, including item scores, suicidal ideation and suicidal behavior are listed for individual participants. Scores are summarized using descriptive statistics (n, arithmetic mean, SD, median, minimum and maximum) overall and by treatment for Part B and trial period.

Example 33: A Single, Ascending-Dose Evaluation of the Safety, Pharmacokinetics of Methylone in Healthy Subjects The primary aim of this open-label study is to evaluate the safety, pharmacokinetics (PK), and psychological effects (pharmacodynamics) of single, ascending doses of methylone in healthy subjects. Approximately 24 healthy volunteers are enrolled into one of four cohorts. FIG. 36 is a schematic of the experimental design of this study. The study is conducted as described in the Table below.

| Objectives | Primary objective: To evaluate the pharmacokinetics (PK) of different doses of methylone. |
|---|---|
| | Secondary objectives: |
| | To evaluate the safety of methylone. |
| | To evaluate the psychological effects (pharmacodynamics) of different doses of methylone. |
| | To evaluate the pharmacokinetics of the methylone, and its metabolites, in plasma and urine. |

| | |
|---|---|
| Study Design | This is an open-label, single, ascending dose study evaluating the PK and safety of methylone in healthy subjects. Approximately 24 healthy volunteers are enrolled into one of four cohorts. The cohorts are as follows;<br>Cohort 1: 50 mg methylone (n = 6)<br>Cohort 2: 100 mg methylone (n = 6)<br>Cohort 3: 150 mg methylone (n = 6)<br>Cohort 4: 200 mg methylone (n = 6)<br>Eligible subjects are confined to the clinical research unit (CRU) from Day −1 through at least 48-hours post-dose, or until the investigator confirms the subject is safe for discharge (eg, to drive and/or return to work). During the confinement period, subjects will receive a dose of methylone followed by 48 hours of intensive plasma PK sampling and 24-hour urine PK collection. Additionally, during the confinement period subjects will complete questionnaires related to the psychological effects of methylone (visual analog scales [VAS]), drug craving (Brief Substance Craving Scale [BSCS]), drug withdrawal (Physician Withdrawal Checklist - 20 item [PWC-20]), dissociation (Clinician Administered Dissociative States Scale-6 [CADSS-6]) and wellbeing (Warwick-Edinburgh Mental Wellbeing Scale [WEMWBS]). Subjects will return to clinic on Day 4 (1 day after discharge) and Day 10 (7 days after discharge) to assess for safety, wellbeing (via the WEMWBS) and drug craving/withdrawal (via the PWC-20 and BSCS).<br>Unique subjects are enrolled in each cohort. The study will begin enrolling Cohort 1. A Safety Monitoring Committee will review the safety data and confirm if it is safe to advance to the next cohort.<br>Safety assessments will include adverse event (AE) monitoring, vital signs, Columbia-suicide severity rating scale (C-SSRS, electrocardiograms (ECGs), and clinical labs.<br>Study Design<br>See FIG. 36<br>*Each cohort will enroll a unique group of 6 subjects |
| Test Treatment | Methylone hydrochloride, provided as capsules of 50 mg methylone.<br>All doses are given open-label. |
| Dosing Regimen | Approximately 24 subjects (6 per cohort) are enrolled to receive the following doses:<br>Cohort 1: 50 mg methylone (n = 6)<br>Cohort 2: 100 mg methylone (n = 6)<br>Cohort 3: 150 mg methylone (n = 6)<br>Cohort 4: 200 mg methylone (n = 6) |
| Pharmacokinetic Evaluation | Plasma Sampling. Plasma samples are collected for concentration analysis of methylone and its metabolites, at the following timepoints: 16 samples; pre-dose, 0.25, 0.5, 0.75, 1, 1.5, 2, 2.5, 3, 4, 6, 8, 12, 24, 36 and 48 hours post-dose<br>Urine Sampling. Urine is collected for 24 hours following the dose. Urine is collected in samples as follows: 0-4, 4-8, 8-12, and 12-24 hours following the dose.<br>Analytical Method. Plasma samples are analyzed for concentrations of methylone, MDC, and HMMC, using LC-MS/MS. Urine samples are analyzed for concentration of methylone MDC, and HMMC, using LC-MS/MS.<br>Pharmacokinetic Assessment.<br>The following plasma PK parameters are calculated on dosing days: $AUC_{0-24}$, $AUC_{0-t}$, $AUC_{0-inf}$, $C_{max}$, $T_{max}$, $K_{el}$, CL, $T_{1/2el}$, and $V_d$<br>Urine concentration results are presented descriptively. |
| Safety Evaluations | Safety is evaluated by the following assessments: Aes, vital signs (blood pressure [BP], heart rate, temperature, respiratory rate), clinical labs (chemistry, hematology, urinalysis), C-SSRS, and ECGs. |
| Psychological Assessments | On the dosing day, subjects will complete the following scales to assess subjective effects of methylone:<br>Bowdle visual analog scales (VAS) consisting of 13 questions - assessed at the following times:<br>pre-dose, 0.5, 1, 1.5, 2, 2.5, 3, 4, 6, 8, and 12 hours post-dose.<br>CADSS-6 - assessed at pre-dose, 1.5, 3, 6, and 12 hours post-dose.<br>WEMWBS - assessed at Baseline, Day 3 (prior to discharge) and on Day 10.<br>PWC-20 item - assessed at Baseline, Day 3 (prior to discharge), Day 4, and on Day 10.<br>BSCS - assessed at Baseline, Day 3 (prior to discharge), Day 4 and on Day 10. |
| Study Duration | The study is approximately 45 days in duration.<br>Screening period: up to 35 days<br>Confinement period: 3 days<br>Follow-up period: 7 days |
| Inclusion Criteria | A subject is eligible for study participation if they meet all of the following criteria:<br>1. Healthy adult male or female aged 25 to 55 inclusive, with BMI >18.0 and <32.0 $kg/m^2$, inclusive.<br>2. Normal (or abnormal that is not clinically significant in the opinion of the investigator) resting ECG.<br>3. Normal hematologic and hepatic function defined as liver function tests (LFTs) ≤ 1.5x ULN and determined by clinical lab results. Participants with a diagnosis of Gilbert's syndrome with high unconjugated bilirubin are eligible provided they meet other LFT criteria). Repeat test may be conducted at the discretion of the investigator.<br>4. Normal renal function, defined as >80 mL/min calculated using Cockcroft & Gault formula and determined by clinical lab results. Repeat tests may be conducted at the discretion of the investigator.<br>5. Ability to swallow and retain oral medication.<br>6. Females of childbearing potential* who are sexually active with a male partner must be willing to use one of the following acceptable contraceptive methods throughout the study and for at least 1 month after the last study drug administration.<br>Female subjects using a hormonal contraceptive or intrauterine device must have been doing so for at least 4 weeks before dosing and must follow that product's package insert instructions including additional protection at times when hormonal contraceptive doses might be missed.<br>Male condom with a diaphragm or cervical cap started at least 21 days prior to dosing<br>Sterile male partner (vasectomized for at least 6 months). |

| | |
|---|---|
| | *A non-childbearing female is defined as:<br>Post-menopausal female (absence of menses for 12 months prior to drug administration, bilateral oophorectomy or hysterectomy with bilateral oophorectomy at least 6 months prior to drug administration); OR<br>Surgically sterile female (hysterectomy or tubal ligation at least 6 months prior to drug administration)<br>7. Females must agree to refrain from ova donation during the study and for at least 90 days after the last dose of the study medication.<br>8. Males who engage in sexual activity that has the risk of pregnancy must agree to use one of the following acceptable contraceptive methods and agree to not donate sperm throughout the study and for at least 90 days after the last dose of the study medication:<br>Use of a double barrier method (male condom with a diaphragm or a cervical cap)<br>Female use of hormonal contraceptives (as described above in Inclusion Criteria #6)<br>Either partner is surgically sterilized (as described above in Inclusion #6)<br>9. Provides written informed consent to participate in the study<br>10. Is able to understand the procedures and study requirements and agrees to abide by the study restrictions and return for the required study assessments. |
| Exclusion Criteria | A subject is excluded from the study if they meet any of the following criteria:<br>1. Vital sign abnormalities (systolic blood pressure lower than 90 or over 140 mmHg, diastolic blood pressure over 90 mmHg, or heart rate less than 45 or over 90 bpm) at screening or prior to dosing. Vital signs may be repeated at investigator discretion.<br>2. Known hypersensitivity to methylone, MDMA, or other cathinone.<br>3. Positive urine drug screen at screening and/or Day −1. Repeat tests may be conducted at investigator discretion.<br>4. Participant smokes an average of >5 cigarettes and/or e-cigarettes per day and/or has a positive urine cotinine test at screening.<br>5. Use of any drugs known to induce or inhibit CYP2D6 within 30 days prior to study drug administration.<br>6. Use of medication within 14 days prior to dosing, with the exception of hormonal contraceptives and the occasional use of acetaminophen (up to 2 g daily).<br>7. Undergoing a current life stressor which could predispose the participant to a higher risk of the potential for addiction.<br>8. Family history of addiction.<br>9. Current mental illness such as depression, anxiety disorder, schizophrenia or other psychotic disorders.<br>10. Family history of psychosis or bipolar disorder.<br>11. Subjects with stable past depression or anxiety disorder more than 2 years at the discretion of Addiction Medicine Physician.<br>12. Borderline personality disorder or antisocial personality disorder.<br>13. Active suicidal ideation and/or intent within 12 months of Screening, indicated by a 'Yes' response to suicidal ideation question 4 or 5 on the C-SSRS OR any history of suicidal behavior.<br>14. Known history or presence of renal, pulmonary, gastrointestinal, dermatological, endocrine, musculoskeletal, neurological, psychiatric, hematological, or liver disease, unless judged not clinically significant by the investigator.<br>15. Known history or presence of cardiovascular disease. Including any cardiovascular or cerebrovascular conditions in which an acute rise in blood pressure would pose a clinical concern, including (but not limited to) aneurysms or arteriovenous malformations or a history of cardiac or cerebral ischemia.<br>16. Use of an investigational drug within 30 days (90 days for biologics) prior to dosing.<br>17. Donation of plasma within 7 days prior to dosing. Donation or loss of blood (excluding volume drawn at screening) of 50 mL to 499 mL of blood within 30 days, or more than 499 mL within 56 days prior to dosing.<br>18. Hemoglobin <115 g/L (males) and <105 g/L (females) at screening and/or Day −1. Repeat labs may be conducted at investigator discretion.<br>19. History of alcohol abuse disorder or regular use of alcohol within six months prior to the screening visit (more than 10 units of alcohol per week [1 Unit = 150 mL of wine, 360 mL of beer, or 45 mL of 40% alcohol]).<br>20. Use of MDMA or other recreational amphetamines within 3 months of screening.<br>21. History of substance abuse disorder in the opinion of the investigator.<br>22. Women who are pregnant or lactating.<br>23. Any reason which, in the opinion of the Investigator, would prevent the subject from participating in the study. |
| Concomitant Medications | Concomitant medications are not allowed during the study except for hormonal contraceptives and the occasional use of acetaminophen (up to 2 g daily).<br>Prescription and over-the-counter medications (including vitamins and herbal products), are not allowed 14 days prior to dosing and throughout the study.<br>Vaccines are not allowed within 14 days prior to dosing and throughout the study.<br>Drugs that inhibit or induce CYP2D6 are not allowed within 14 days prior to dosing and throughout the study. |
| Prohibited Foods and Beverages | The following foods/beverages are not allowed:<br>Within 14 days of dose until discharge:<br>Quinine containing products (e.g., tonic water) within 14 days of dose<br>Grapefruit products/Pomelo products/Seville orange products (including supplements containing Citrus aurantium or "bitter orange") within 14 days of dose<br>Within 24 hours prior to dose until discharge:<br>Xanthines, and caffeine containing products (e.g., coffee, tea, chocolate, Cola-products)<br>Consumption of alcohol-based products. |

| Populations | Safety population - all subjects who received at least one dose of study medication.<br>Pharmacokinetic population - all subjects who received at least one dose and for whom the pharmacokinetic profile can be adequately characterized. |
|---|---|
| Sample Size | Approximately 24 healthy subjects (6 per cohort) are enrolled to evaluate the PK, safety and psychological effects of methylone.<br>A sample size of 6 per cohort was selected based on feasibility. No formal sample size calculation was conducted. |
| Statistical Considerations | Descriptive statistics are used for all variables and all data listed by appropriate dose-level group. |

Example 34: Methylone Induced Neuroplasticity In Vitro

Neuroplasticity is defined as changes in the structure, connections and function of neurons, including neurite outgrowth. Methylone (10 µM) significantly increased neurite outgrowth in Sprague Dawley rat neurons in vitro. E18 cortical cultures were harvested and plated on culture dishes. Methylone (or vehicle) were applied on day 1 and cells were fixed and stained with βIII-Tubulin on day 3-4. Neurite length was measured using ImageJ software. The results in FIG. 44 show that methylone significantly increased the length of neurites by nearly 2-fold compared to vehicle treated neurons.

Example 35: Methylone Showed Rapid, Robust and Long-Lasting Improvement in Fear Extinction Training and Recall Methods: Cued fear conditioning was performed in C57BL/6J mice. On day 1, animals were placed in the chambers and presented with a training session (CS-US pairing). The training consisted of a 2-minute habituation followed by a 30-second, 80 dB tone; during the last 2 seconds of the tone animals received a 1 mA foot shock. This US-CS procedure occurred once for a total of one paired presentation of tone and shock. Freezing behavior (immobility) was recorded in 5-10-see intervals during the session. Percent baseline freezing behavior was determined in the 2-minute habituation period. On day 3, animals were placed in context B, in which tactile and odor cues differed from context A. Following a 2 minute acclimation period animals received 4×30 sec presentations of the CS (tone) in the absence of the US (footshock), with a 45 sec interval between presentations. Freezing was recorded in 5-10-sec intervals to measure baseline freezing response to the altered context, and freezing response to each tone cuc presentation. Animals were dosed with vehicle methylone (10, 20, or 30 mg/kg, IP) 30 min before extinction training on Day 3. On day 4 (Post-Extinction Testing in Drug-Free State), animals were placed in Context B. Following a 2 min acclimation period, animals received 4×30 sec extinction tone duration presentations of the CS (tone) in the absence of the US (footshock), with a 45 sec interval between presentations. Freezing was recorded in 5-10-sec intervals to measure baseline freezing response to the altered context, and freezing response to each tone cue presentation.

The results in FIG. 45 show that a 30 mg/kg (IP) dose of methylone had rapid, robust and long-lasting beneficial effect on fear extinction training and testing. Results were observed 30 min post-dose and persisted for at least 11-days post dose (day 14). All doses significantly improved fear extinction training on day 3. Doses of 20 and 30 mg/kg improved extinction recall on day 3 significantly, and there was a strong trend for an effect at 10 mg/kg. The 30 mg/kg dose had the most significant, persistent, long-lasting effect on fear extinction recall while 20 and 10 mg/kg dose effects also produced strong trends in the same direction. This dose is equivalent to ~15 mg/kg in a rat and ~150 mg in a human based on allometric dose scaling.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of treating a neuropsychiatric illness and/or ameliorating a symptom thereof in a human subject in need thereof, comprising administering to the subject a therapeutically effective amount of a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a prodrug thereof, and/or a polymorph thereof, wherein the neuropsychiatric illness is selected from a Depressive Disorder, post-traumatic stress disorder (PTSD), acute stress disorder, an Anxiety Disorder and/or Fibromyalgia.

2. The method according to claim 1, wherein methylone is administered in a dose of 5-250 mg.

3. The method according to claim 1, wherein methylone is administered in a dose of 50-1,000 mg.

4. The method according to claim 1, wherein methylone is administered weekly.

5. The method according to claim 1, wherein methylone is administered more frequently than weekly.

6. The method according to claim 1, wherein methylone is administered orally.

7. The method according to claim 1, wherein the neuropsychiatric illness is treatment-resistant.

8. The method according to claim 1, wherein the methylone is used in combination with an additional therapy for the neuropsychiatric illness.

9. The method according to claim 8, wherein the additional therapy comprises psychotherapy and/or administering one or more additional psychoactive agents to the subject.

10. A method of treating a neuropsychiatric illness, and/or ameliorating a symptom thereof in a human subject in need thereof, comprising administering to the subject a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a polymorph thereof, and/or a prodrug thereof in a therapeutically effective amount that results in a plasma $C_{max}$ of methylone of 98-994 ng/mL in the subject, wherein the neuropsychiatric illness is selected from a Depressive Disorder, post-traumatic stress disorder (PTSD), acute stress disorder, an Anxiety Disorder and/or Fibromyalgia.

11. A method of treating a neuropsychiatric illness, and/or ameliorating a symptom thereof in a human subject in need thereof, comprising administering to the subject a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a polymorph thereof and/or a prodrug thereof in a therapeutically effective amount that results in a plasma $AUC_{0-24}$ of methylone of 47-10,983 ng·h/mL in the subject, wherein the neuropsychiatric illness is selected from a Depressive Disorder, post-traumatic stress disorder (PTSD), acute stress disorder, an Anxiety Disorder and/or Fibromyalgia.

12. The method according to claim 1, wherein the pharmaceutical composition comprises methylone HCl.

13. The method according to claim 1, wherein the pharmaceutical composition comprises a polymorph of methylone.

14. The method according to claim 1, wherein the pharmaceutical composition comprises a polymorph of methylone HCl.

15. The method according to claim 10, wherein the pharmaceutical composition comprises methylone HCl.

16. The method according to claim 10, wherein the pharmaceutical composition comprises a polymorph of methylone.

17. The method according to claim 10, wherein the pharmaceutical composition comprises a polymorph of methylone HCl.

18. The method according to claim 11, wherein the pharmaceutical composition comprises methylone HCl.

19. The method according to claim 11, wherein the pharmaceutical composition comprises a polymorph of methylone.

20. The method according to claim 11, wherein the pharmaceutical composition comprises a polymorph of methylone HCl.

21. A method of treating post-traumatic stress disorder (PTSD) and/or ameliorating a symptom thereof in a human subject in need thereof, comprising administering to the subject a therapeutically effective amount of a pharmaceutical composition comprising methylone (3,4-methylenedioxy-N-methylcathinone) or a pharmaceutically acceptable salt thereof, and/or an enantiomer thereof, and/or an isotopologue thereof, and/or an isotopomer thereof, and/or a solvate thereof, and/or a prodrug thereof, and/or a polymorph thereof.

22. The method according to claim 21, wherein the pharmaceutical composition comprises methylone HCl.

23. The method according to claim 21, wherein the pharmaceutical composition comprises a polymorph of methylone.

24. The method according to claim 21, wherein the pharmaceutical composition comprises a polymorph of methylone HCl.

25. The method according to claim 21, comprising administering the pharmaceutical composition in a therapeutically effective amount that results in a plasma $C_{max}$ of methylone of 98-994 ng/mL in the subject.

26. The method according to claim 25, comprising administering the pharmaceutical composition in a therapeutically effective amount that results in a plasma $C_{max}$ of methylone of 322-770 ng/mL in the subject.

27. The method according to claim 26, comprising administering the pharmaceutical composition in a therapeutically effective amount that results in a plasma $C_{max}$ of methylone of 434-658 ng/mL in the subject.

28. The method according to claim 21, comprising administering the pharmaceutical composition in a therapeutically effective amount that results in a plasma $AUC_{0-24}$ of methylone of 47-10,983 ng·h/mL in the subject.

29. The method according to claim 28, comprising administering the pharmaceutical composition in a therapeutically effective amount that results in a plasma $AUC_{0-24}$ of methylone of 2,781-8,249 ng·h/mL in the subject.

30. The method according to claim 29, comprising administering the pharmaceutical composition in a therapeutically effective amount that results in or a plasma $AUC_{0-24}$ of methylone of 4,148-6,682 ng·h/mL in the subject.

* * * * *